United States Patent [19]

Nelson

[11] 4,073,808

[45] Feb. 14, 1978

[54] 2-DECARBOXY-2-AMINO-METHYL-PGA AND 9-DEOXY-9,10-DIDEHYDRO-PGD ANALOGS

[75] Inventor: Norman A. Nelson, Galesburg, Mich.

[73] Assignee: The Upjohn Company, Kalamazoo, Mich.

[21] Appl. No.: 719,055

[22] Filed: Aug. 30, 1976

Related U.S. Application Data

[63] Continuation-in-part of Ser. No. 645,276, Dec. 29, 1975, abandoned.

[51] Int. Cl.$^2$ .................... C07C 87/24; A61K 31/13; A61K 31/135
[52] U.S. Cl. .................... 260/563 R; 260/570.5 P; 260/570.5 CA; 424/325; 424/330
[58] Field of Search ........ 260/240 R, 563 R, 570.5 P, 260/570.5 CA; 424/320, 325

[56] References Cited

U.S. PATENT DOCUMENTS

| 2,166,971 | 7/1939 | Schmidt et al. ............. 260/563 R X |
| 3,228,831 | 1/1966 | Nicholson et al. ............. 424/320 X |
| 3,647,804 | 3/1972 | Rynbrandt et al. ............. 424/320 X |
| 3,852,296 | 12/1974 | Viterbo et al. ............... 260/563 R X |
| 3,954,741 | 5/1976 | Schaaf et al. ..................... 260/240 R |
| 3,987,085 | 10/1976 | Yankee .............................. 260/240 R |
| 3,987,087 | 10/1976 | Bundy ........................... 260/240 R X |

*Primary Examiner*—Daniel E. Wyman
*Assistant Examiner*—Thomas A. Waltz
*Attorney, Agent, or Firm*—Robert A. Armitage

[57] ABSTRACT

Prostaglandin analogs wherein the C-2 carboxy is replaced by an aminomethyl or (substituted amino)methyl are disclosed along with intermediates useful in their preparation and processes for their preparation. These analogs are useful for the same pharmacological purposes as the prostaglandins.

11 Claims, No Drawings

2-DECARBOXY-2-AMINO-METHYL-PGA AND 9-DEOXY-9,10-DIDEHYDRO-PGD ANALOGS

CROSS REFERENCE TO RELATED APPLICATIONS

This application is a continuation-in-part of abandoned copending application Ser. No. 645,276, filed Dec. 29, 1975 now abandoned.

BACKGROUND OF THE INVENTION

This invention provides novel compositions of matter. This invention further provides novel processes for producing these compositions of matter. This invention further provides novel chemical intermediates useful in the above process.

Particularly this invention provides novel analogs of some of the known prostaglandins which differ from corresponding known prostaglandins in that they are substituted at C-2 by an aminomethyl or a substituted aminomethyl in contrast to prostaglandins which are substituted at C-2 with a carboxyl.

The known prostaglandins include the PGE compounds, e.g. prostaglandin $E_1$ (PGE$_1$), prostaglandin $E_2$ (PGE$_2$), prostaglandin $E_3$ (PGE$_3$), and dihydroprostaglandin $E_1$ (dihydro-PGE$_1$).

The known prostaglandins include PGF$_\alpha$ compounds, e.g. prostaglandin $F_{1\alpha}$ (PGF$_{1\alpha}$), prostaglandin $F_{2\alpha}$ (PGF$_{2\alpha}$), prostaglandin $F_{3\alpha}$ (PGF$_{3\alpha}$), and dihydroprostaglandin $F_{1\alpha}$ (dihydro-PGF$_{1\alpha}$).

The known prostaglandins include PGF$_\beta$ compounds, e.g. prostaglandin $F_{1\beta}$ (PGF$_{1\beta}$), prostaglandin $F_{2\beta}$ (PGF$_{2\beta}$), prostaglandin $F_{3\beta}$ (PGF$_{3\beta}$), and dihydroprostaglandin $F_{1\beta}$ (dihydro-PGF$_{1\beta}$).

The known prostaglandins include PGA compounds, e.g. prostaglandin $A_1$ (PGA$_1$), prostaglandin $A_2$ (PGA$_2$), prostaglandin $A_3$ (PGA$_3$), and dihydroprostaglandin $A_1$ (dihydro-PGA$_1$).

Each of the above mentioned known prostaglandins (PG's) is a derivative of prostanoic acid which has the following structure and carbon atom numbering

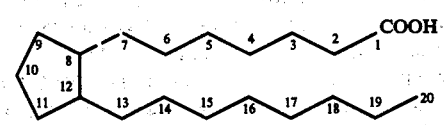

See, for example, Bergstrom et al., Pharmacol. Rev. 20, 1 (1968), and references cited therein. A systematic name for prostanoic acid is 7-[(2$\beta$-octyl)-cyclopent-1$\alpha$-yl]heptanoic acid.

PGE$_1$ has the following structure:

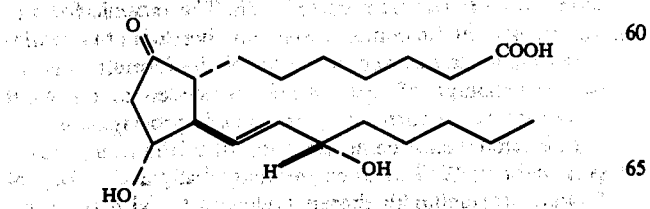

PGE$_2$ has the following structure:

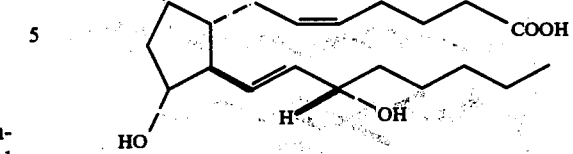

PGE$_3$ has the following structure:

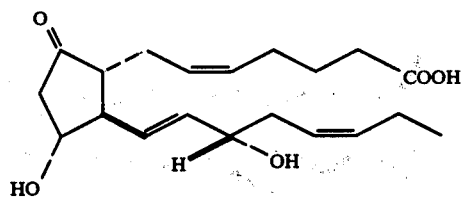

Dihydro-PGE$_1$ has the following structure:

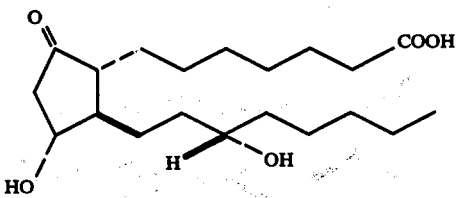

PGF$_{1\alpha}$ has the following structure:

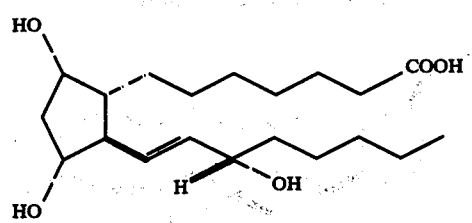

PGF$_{2\alpha}$ has the following structure:

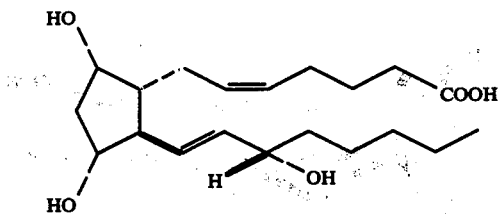

PGF$_{3\alpha}$ has the following structure:

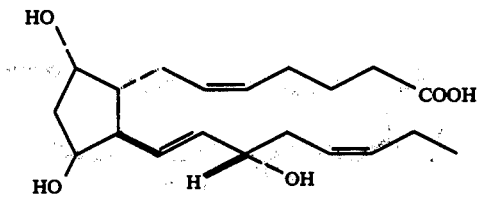

Dihydro-PGF$_{1\alpha}$ has the following structure:

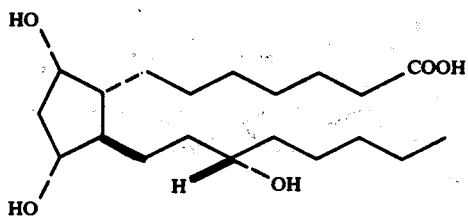

PGF$_{1\beta}$ has the following structure:

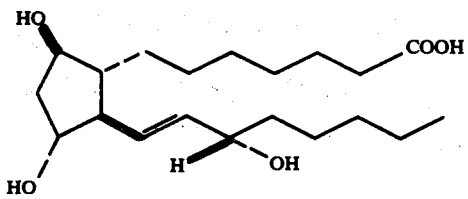

PGF$_{2\beta}$ has the following structure:

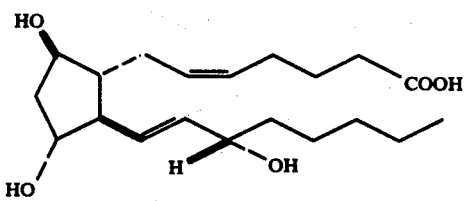

PGF$_{3\beta}$ has the following structure:

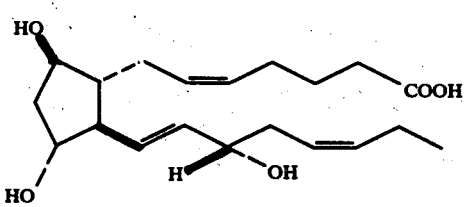

Dihydro-PGF$_{1\beta}$ has the following structure:

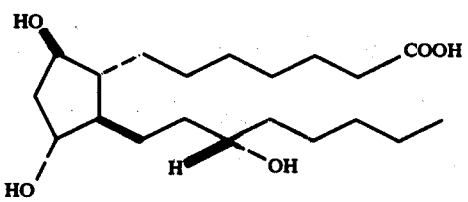

PGA$_1$ has the following structure:

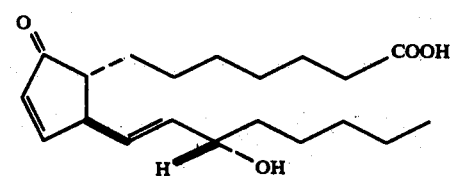

PGA$_2$ has the following structure:

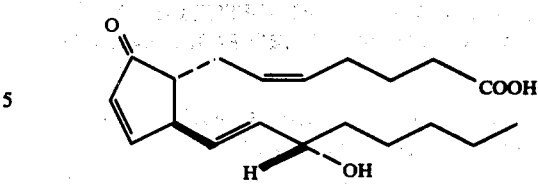

PGA$_3$ has the following structure:

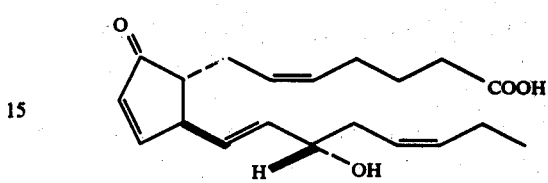

Dihydro-PGA$_1$ has the following structure:

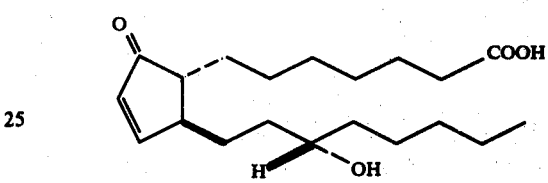

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines (∼) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins. Expressions such as C-2, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammalian tissues, for example, sheep vesicular glands, swine lung, or human seminal plasma, from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin.

For convenience hereinafter, use of the term, prostaglandin or "PG" will mean the optically active form of that prostaglandin thereby referred to with the same absolute configuration as PGE$_1$ obtained from mammalian tissues. When reference to the racemic form of one of those prostaglandins is intended, the word "racemic" or "dl" will precede the prostaglandin name.

The term "prostaglandin-type" (PG-type) product, as used herein, refers to any cyclopentane derivative herein which is useful for at least one of the same pharmacological purposes as the prostaglandins, as indicated herein.

The term prostaglandin-type intermediate, as used herein, refers to any cyclopentane derivative useful in preparing a prostaglandin-type product.

The formulas, as drawn herein, which depict a prostaglandin-type product or an intermediate useful in preparing a prostaglandin-type compound, each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type products.

The term "prostaglandin analog", as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type product herein, the term prostaglandin analog refers to the compound of that formula or a mixture comprising that compound and the enantiomer thereof.

The various PG's named above, their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein.

For the PGE compounds these biological responses include:

a. stimulating smooth muscle (as shown by tests, for example, on guinea pig ileum, rabbit duodenum, or gerbil colon);

b. affecting lipolytic activity (as shown by antagonism of epinephrine induced release of glycerol from isolated rat fat pads);

c. inhibiting gastric secretion and reducing undesirable gastrointestinal effects from systematic administration of prostaglandin synthetase inhibitors;

d. controlling spasm and facilitating breathing in asthmatic conditions;

e. decongesting nasal passages;

f. decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);

g. affecting the reproductive organs of mammals as labor inducers, abortifacients, cervical dilators, regulators of the estrus, and regulators of the menstrual cycle; and h. accelerating growth of epidermal cells and keratin in animals.

For the PGF$_\alpha$ compound these biological responses include:

a. stimulating smooth muscle (as shown by tests on guinea pig ileum, rabbit duodenum, or gerbil colon);

b. inhibiting gastric secretion and reducing undesirable gastrointestinal effects from systemic administration of prostaglandin synthetase inhibitors;

c. decongesting nasal passages;

d. decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and e. affecting the reproductive organs of mammals as labor inducers, abortifacients, cervical dilators, regulators of the estrus, and regulators of the menstral cycle.

For the PGF$_\beta$ compounds these biological response include:

a. stimulating smooth muscle (as shown by tests on guinea pig ileum, rabbit duodenum, or gerbil colon);

b. inhibiting gastric secretion and reducing undesirable gastrointestinal effects from systematic administration of prostaglandin synthetase inhibitors;

c. controlling spasm and facilitating breathing in asthamatic conditions;

d. decongesting nasal passages;

e. decreasing blood platelet adhesion (as shown by platelet to glass adhesiveness) and inhibiting blood platelet aggregation and thrombis formation induced by various physical stimuli (e.g., arterial injury) or chemical stimuli (e.g., ADP, ATP, serotinin, thrombin, and collagen); and f. affecting the reproductive organs of mammals as labor inducers, abortifacients, cervical dilators, regulators of the estrus, and regulators of the menstrual cycle.

For the PGA compounds these biological responses include:

a. stimulating smooth muscle (as shown by tests on guinea pig ileum, rabbit duodenum, or gerbil colon);

b. inhibiting gastric secretion and reducing undesirable gastrointestinal effects from systematic administration of prostaglandin synthetase inhibitors;

c. controlling spasm and facilitating breathing in asthmatic conditions;

d. decongesting nasal passages; and e. increasing kidney blood flow.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The compounds so cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50$\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The prostaglandins so cited above as useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg. to about 500 µg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin in synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally.

It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex, and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experienced the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other antiasthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The prostaglandins so cited above as useful in mammals, including man, as nasal decongestants are used for this purpose, in a dose range of about 10 µg. to about 10 mg. per ml. of a pharmacologically suitable liquid vehicle or as an aerosol spray, both for topical application.

The prostaglandins so cited above as useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The prostaglandins so cited above as useful in place of oxytocin to induce labor are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but no so old that regular menstruation has ceased. For that purpose the prostaglandin is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively the prostaglandin is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals, include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1-100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range of 10 to 1000 $\mu$g. per kg. of body weight or by intravenous infusion at a dose in the range of 0.1 to 20 $\mu$g. per kg. of body weight per minute until the desired effect is obtained. Subsequent doses are given by intravenous, intramuscular, or subcutaneous injection or infusion in the range of 0.05 to 2 mg. per kg. of body weight per day.

The compounds so cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg. per ml. of the prostaglandin pound. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

Certain prostaglandin-type compounds, related to those of the present invention, are known in the prior art. See E. J. Corey, et al., J. Am. Chem. Soc. 90, 3245 (1968) which discloses 9-amino-11,15-bis(tetrahydropyranyl)-trans-13-prostanoic acid and U.S. Pat. No. 3,835,179 which discloses certain 15-amino-PG-type compounds.

SUMMARY OF THE INVENTION

This invention provides novel prostaglandin analogs, esters of these analogs, and pharmacologically acceptable salts of these analogs.

This invention further provides novel processes for preparing these analogs.

This invention further provides novel chemical intermediates useful in the preparation of these analogs.

In particular this specification discloses and expressly claims as part of the present invention:

a prostaglandin analog of the formula

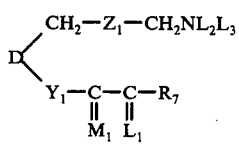

where D is

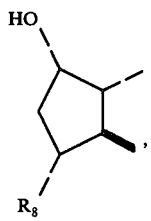

-continued

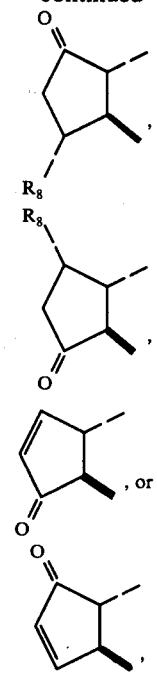

wherein $R_8$ is hydrogen or hydroxy;
wherein $L_1$ is

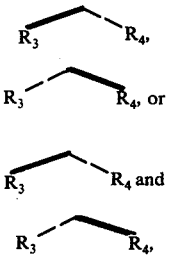

a mixture of wherein $R_3$ and $R_4$ are hydrogen, methyl, or fluoro, being the same or different, with the proviso that one of $R_3$ and $R_4$ is methyl only when the other is hydrogen or methyl;

wherein $L_2$ and $L_3$ are hydrogen, alkyl of one to 4 carbon atoms, inclusive, or —$COOR_1$, wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted one, 2, or 3 chloro or alkyl of one to 3 carbon atoms, inclusive; being the same or different, with the proviso that nor more than one of $L_2$ and $L_3$ is —$COOR_1$;

wherein $M_1$ is

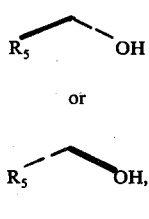

wherein $R_5$ is hydrogen or methyl; wherein $R_7$ is
1. —$(CH_2)_m$—$CH_3$,
2. —cis—CH=CH—$CH_2CH_3$,

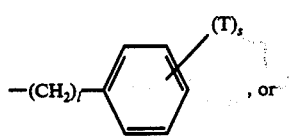   (3)

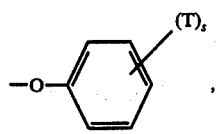   (4)

wherein 1 is zero to three, inclusive, wherein m is one to 5, inclusive, s is zero, one, 2, or 3 and T is chloro, fluoro, trifluoromethyl, alkyl of one to 3 carbon atoms or alkoxy of one to 3 carbon atoms, the various T's being the same or different, with the proviso that not more than two T's are other than alkyl; wherein $Y_1$ is
1. trans—CH=CH—
2. cis—CH=CH—,
3. —CH$_2$CH$_2$—, or
4. —C≡C—; and wherein $Z_1$ is
1. cis—CH=CH—CH$_2$—(CH$_2$)$_g$—CH$_2$—,
2. cis—CH=CH—CH$_2$—(CH$_2$)$_g$—CF$_2$—,
3. cis—CH$_2$—CH=CH—(CH$_2$)$_g$—CH$_2$,
4. —(CH$_2$)$_3$—(CH$_2$)$_g$—CH$_2$—,
5. —(CH$_2$)$_3$—(CH$_2$)$_q$—CF$_2$—,
6. —CH$_2$—O—CH$_2$—(CH$_2$)$_g$—CH$_2$—,
7. —(CH$_2$)$_2$—O—(CH$_2$)$_g$—CH$_2$—,
8. —(CH$_2$)$_3$—O—(CH$_2$)$_g$—,

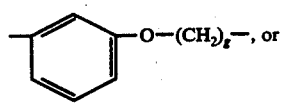   (9)

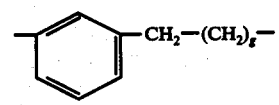   (10)

wherein g is zero, one, two, or three; and the pharmacologically acceptable acid addition salts thereof when $X_1$ is CH$_2$NL$_2$L$_3$.

Within the scope of the novel prostaglandin analogs described in this specification there are represented above a. PGD-type compounds when    is

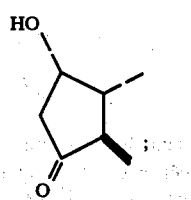

b. PGE-type compounds when    is

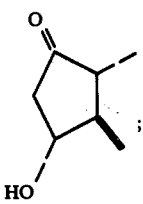

c. PGF$_\alpha$-type compounds when    is

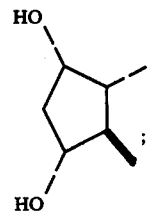

d. PGF$_\beta$-type compounds when    is

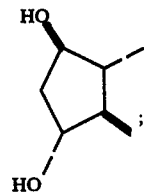

e. 9-deoxy-PGD-type compounds when    is

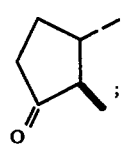

f. 11-deoxy-PGE-type compounds when    is

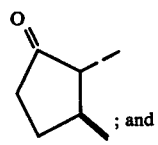    ; and g. 11-deoxy-PGF$_\alpha$-type compounds when    is

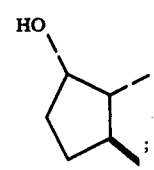

h. 11-deoxy-PGF$_\beta$-type compounds when    is

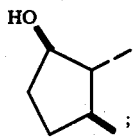

i. 9-deoxy-9,10-didehydro-PGD-type compounds when    is

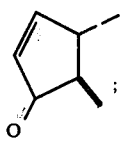

and j. PGA-type compounds when is

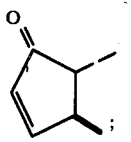

Those prostaglandin analogs herein wherein $Z_1$ is cis—CH=CH—CH$_2$—(CH$_2$)$_g$—CH$_2$— or cis—CH=CH—CH$_2$—(CH$_2$)$_g$—CF$_2$— are named as "PG$_2$" compounds. The latter compounds are further characterized as "2,2-difluoro" PG-type compounds. When g is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are referred to as C-2a and C-2b, counting from the C-2 to the C-3 position. When g is zero, these compounds are characterized as "2-nor", wherein the C-2 carbon atom is construed as missing. Accordingly, the C-3 carbon atom is construed as being attached to the C-1 carbon atom.

Further when $Z_1$ is —(CH$_2$)$_3$—(CH$_2$)$_g$—CH$_2$— or —(CH$_2$)$_3$—(CH$_2$)$_g$—CF$_2$, wherein g is as defined above, the compounds so described are "PG$_1$" compounds. When g is zero, 2 or 3, the "2-nor";"2a-homo" or "2a,2b-dihomo" compounds are described as is discussed in the preceding paragraph.

When $Z_1$ is —CH$_2$—O—CH$_2$—(CH$_2$)$_g$—CH$_2$— the compounds so described are named as "5-oxa-PG$_1$" compounds. When g is zero, 2 and 3, the compounds so described are "2-nor", "2a-homo", or "2a,2b-dihomo" compounds, respectively, as discussed above.

When $Z_1$ is —(CH$_2$)$_2$—O—(CH$_2$)$_g$—CH$_2$—, wherein g is as defined above, the compounds so described are named as "4-oxa-PG$_1$" compounds. When g is zero, 2, or 3, the compounds so described are additionally characterized as "2-nor", "2a-homo", or "2a,2b-dihomo" compounds, respectively, as is discussed above.

When $Z_1$ is —(CH$_2$)$_3$—O—(CH$_2$)$_g$—, wherein g is as defined above, the compounds so described are named as "3-oxa-PG$_1$" compounds. When g is zero, 2, or 3, the compounds so described are further characterized as "2-nor", "2a-homo", or "2a,2b-dihomo" compounds, respectively, as is discussed above.

When $Z_1$ is cis—CH$_2$—CH=CH—(CH$_2$)$_g$—CH$_2$—, wherein g is as defined above, the compounds so described are named "cis-4,5-didehydro-PG$_1$" compounds. When g is zero, 2, or 3, the compounds so described are further characterized as "2-nor", "2a-homo", or "2a,2b-dihomo" compounds, respectively, as discussed above.

For the novel compounds of this invention wherein $Z_1$ is

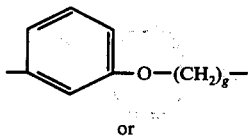

or

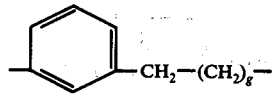

there are described, respectively, 3-oxo-3,7-inter-m-phenylene-4,5,6-trinor or 3,7-inter-m-phenylene-4,5,6-trinor-PG-type compounds, when g is 1. When g is zero, 2, or 3, the above compounds are additionally described as "2-nor", "2a-homo", or "2a,2b-dihomo" PG-type compounds, respectively.

The novel prostaglandin analogs of this invention which contain a cis—CH=CH—, CH$_2$CH$_2$— or —C≡C— moiety at the C-13 to C-14 position, are accordingly, referred to as "cis-13", "13,14-dihydro" or 13,14-didehydro compounds respectively.

Each of the novel PG-anaogs herein contains an aminomethyl or substituted aminomethyl substituent at C-2 in place of the carboxyl. Accordingly, each of these PG analogs is named as a "2-decarboxy-2-(optionally substituted) aminomethyl" compound. For example when $L_2$ is -COOCH$_3$ and $L_3$ is methyl, the compounds so defined are characterized as "2-decarboxy-2-(carbomethoxmethyl)aminomethyl" compounds.

When $R_7$ is —(CH$_2$)$_m$—CH$_3$, wherein m is as defined above, the compounds so described are named as "19,29-dinor", "20-nor", "20-methyl", or "20-ethyl" compounds when m is When $R_7$ is

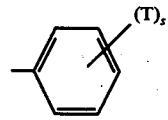

wherein T and s are as defined above, and neither $R_3$ nor $R_4$ is methyl, the compounds so described are named as "16-phenyl-17,1,19,20-tetranor" compounds, when s is zero. When s is one, 2, or 3, the corresponding compounds are named as "16-(substituted phenyl)-17,18,19,20-tetranor" compounds. When one and only one of $R_3$ and $R_4$ is methyl or both $R_3$ and $R_4$ are methyl, the corresponding compounds wherein $R_7$ is as defined in this paragraph are named as "16-phenyl or 16-(substituted phenyl)-18,19,20-trinor" compounds or "16-methyl-16-phenyl or 16-(substituted phenyl)-18,19,20-trinor" compounds, respectively.

When $R_7$ is

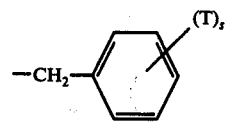

wherein T and s are s defined above, the compounds so described are named as "17-phenyl-18,19,20-trinor" compounds, when s is 0. When s is one, 2, or 3, the corresponding compounds are named as "17-(substituted phenyl)-18,19,20-trinor" compounds.

When R₇ is

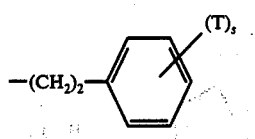

wherein T and s are s defined above, the compounds so described are named as "18-phenyl-19,20-dinor" compounds, when s is 0. When s is one, 2, or 3, the corresponding compounds are named as "18-(substituted phenyl)-19,20-dinor" compounds.

When R₇ is

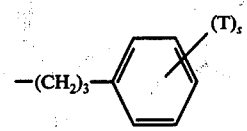

wherein T and s are as defined above, the compounds so described are named as "19-phenyl-20-nor" compounds, when s is 0. When s is one, 2, or 3, the corresponding compounds are named as "19-(substituted phenyl)-20-nor" compounds.

When R₇ is

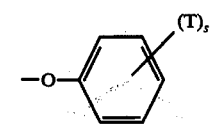

wherein T and s are as defined above, and neither R₃ nor R₄ is methyl, the compounds so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds. When one and only one of R₃ and R₄ is methyl or both R₃ and R₄ are methyl, then the corresponding compounds wherein R₇ is as defined in this paragraph are named as "16-phenoxy or 16-(substituted phenoxy)-18,19,20-trinor" compounds or "16-methyl-16-phenoxy or 16-(substituted phenoxy)-18,19,20-trinor" compounds, respectively.

When R₇ is cis—CH=CH—CH₂—CH₃, the compounds so described are "PG₃" or "cis-17,18-didehydro" compounds depending on whether Z₁ is cis—CH=CH—(CH₂)ₐ—C(R₂)₂, wherein R₂ is hydrogen or fluoro, or another moiety, respectively.

When at least one of R₃ and R₄ is not hydrogen then (except for the 16-phenyl 16-phenoxy compounds discussed above) there are described the "16-methyl" (one and only one of R₃ and R₄ is methyl), "16,16-dimethyl" (R₃ and R₄ are both methyl), "16-fluoro" (one and only one of R₃ and R₄ is fluoro), "16,16-difluoro" (R₃ and R₄ are both fluoro) compounds. For those compounds wherein R₃ and R₄ are different, the prostaglandin analogs so represented certain an asymmetric carbon atom at C-16. Accordingly, two epimeric configurations are possible: (16S)" and "(16R)". Further, there is described by this invention the C-16 epimeric mixture: "(16RS)".

When R₅ is methyl, the compounds so described are named as "15-methyl" compounds.

Some formulas of 13-cis-cyclopentane derivatives described hereinafter contain a moiety of the formula:

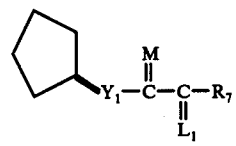

wherein the cyclopentane ring is variously substituted, wherein M is variously defined according to the subscripts provided herein; wherein L₁ and R₇ is as defined above; and wherein Y₁ is cis—CH=CH—. Optionally the above formula is depicted with one or both of L₁ and M above the carbon atom to which it is attached, e.g. as follows:

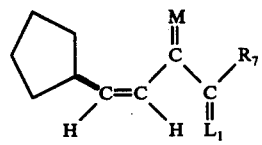

When the above representation is employed, it is hereby defined to indicate the following convention with respect to the representation of the cis-13 double bond:

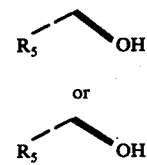

Further in employing this convention whn M is, for example,

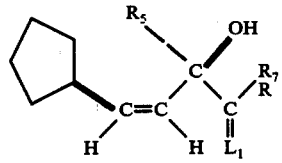

then the corresponding representations:

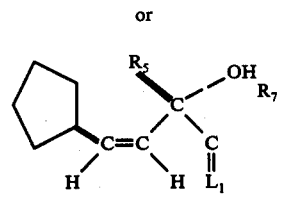

are intended, respectively. Accordingly all the formulas herein which represent 13-cis cyclopentane derivatives are depicted by the same convention as that for the cis-13-PGE₁ when drawn as follows:

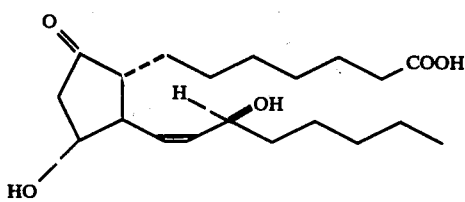

Thus, by this convention the (15S)-hydroxy of cis-13-PGE₁ is in the beta configuration.

cis-13-PG-type compounds as drawn herein which have an hydroxy or methoxy at C-15 in the alpha configuration are of the opposite relative stereochemical configuration at C-15 as that of cis-13-PGE₁, and are therefore named as "15-epi" compounds. When the beta hydroxy configuration is present, no special designation of this sterochemistry is provided.

Accordingly, 2-decarboxy-2-aminomethyl-15-epi-16,16-difluoro-cis-13-PGD₂ is depicted herein as follows:

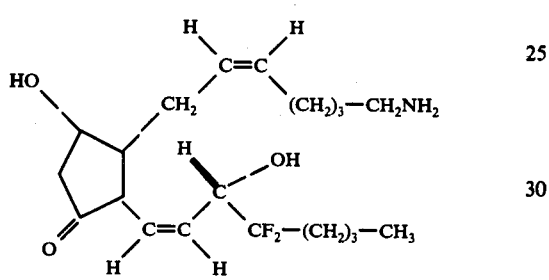

Alternate representations of cis-13-PGE₁ affect the depiction at C-15 as an alpha or beta hydroxy. Thus, by a representation contrary to the instant convention, cis-13-PGE₁ appears as follows:

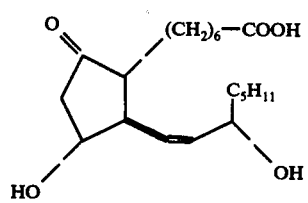

Accordingly, care must be taken to consistently draw the formulas of cis-13-PG-type compounds herein such that the C-15 carbon atom is properly represented, i.e., all cis-13-15-epi-PG's are of the 15α-hydroxy configuration.

13,14-Trans or saturated cyclopentane derivatives which contain the moiety.

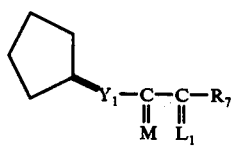

wherein the cyclopentane ring is variously substituted, wherein M is variously defined according to the subscripts provided herein; wherein L₁ and R₇ are as defined above; and wherein Y₁ is trans-CH=CH— or —CH₂CH₂—; indicate the following convention with respect to the representation of the C-13 to C-14 moiety;

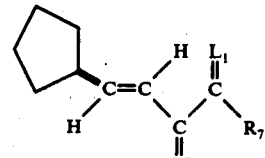

or

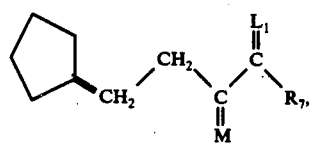

respectively. Likewise in employing this convention when M is, for example

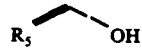

or

then the corresponding representation for the trans-13:

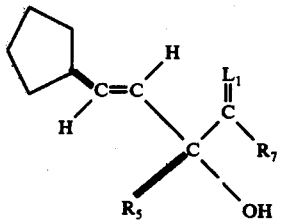

or

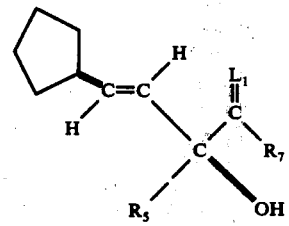

and the 13,14-saturated:

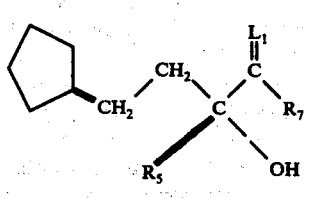

or

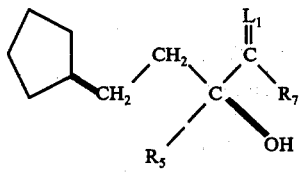

are intended, respectively. Accordingly all the formulas herein which represent trans-13 or 13,14-saturated cyclopentane derivatives are depicted by the same convention as that for PGE$_1$ when drawn as above, i.e.,

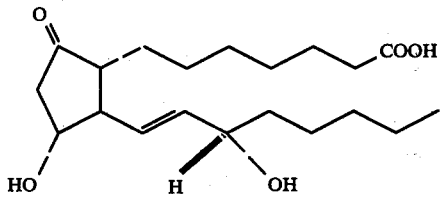

Thus, for all trans-13 or 13,14-dihydro-PGE-type compounds, as drawn herein the 15α-hydroxy configuration corresponds to the relative C-15 sterochemical configuration of PGE$_1$ as obtained from mammalian tissues. No special designation of the C-15 stereochemistry is provided in naming these compounds. For compounds of the opposite stereochemical configuration at C-15 (i.e., 15β-hydroxy), the descrition "15-epi" will be employed.

For a general description of the nomenclature employed herein see N. A. Nelson, J. Med. Chem. 17, 911 (1974).

Examples of alkyl of one to 12 carbon atoms, inclusive, are mthyl, ethyl, propyl, butyl pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butyl cyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4,dichlorophenyl, 2,4,6-trichlorophenyl, p-tolyl, n-tolyl, o-tolyl, p-ethylphenyl, p-tertbutylphenyl, 2,5-dimethylphenyl, 4chloro-2-methylphenyl, and 2,4-dichloro-3-methylphenyl.

Examples of

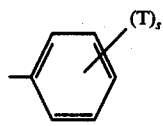

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)-ethylphenyl, 2-ethyl-p-tolyl, 4ethyl-o-tolyl, 5-ethyl-m-tolyl, (o-, m-, or p-)propylphenyl, 2-propyl-(o-, m-, or p-)tolyl, 4-isopropyl-2,6-xylyll, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-) tolyl, 4-fluoro-2,5-xylyl, (2,4-, 2,5-, 2,6-, 3,4-, or 3,5-)difluorophenyl, (o-, m-, or p-)-chlorophenyl), 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl), o-, m-, or p-trifluoromethylphenyl, (o-, m-, or p-)methoxyphenyl, (o-, m-, or p-)ethoxyphenyl, (4- or 5-)chloro-2-methoxyphenyl, and 2,4-dichloro(5- or 6-)methylphenyl.

The novel prostaglandin analogs of this invention correspond to the prostaglandins described above, in that the novel prostaglandin analogs exhibit prostaglandin-like activity.

Specifically the PGE- and 11-deoxy-PGE-type compounds of this invention correspond to the PGE compounds described above, in that these novel PGE- and 11-deoxy-PGE-type compounds are useful for ech of the above-described purposes for which the PGE compounds are used, and are used in the same manner as the PGE compounds, as described above.

The PGF$_\alpha$ and 11-deoxy-PGF$_\alpha$-type compounds of this invention correspond to the PGF$_\alpha$ compounds described above, in that these novel PGF$_\alpha$ and 11-deoxy-PGF$_\alpha$-type compounds are useful for each of the above-described purposes for which the PGF$_\alpha$ compounds are used, and are used in the same manner as the PGF$_\alpha$ compounds, as described above.

The PGD-, 9deoxy-PGD-, and 9,10-didehydro-9-deoxy-PGD-type compounds of this invention corresponding to the PGE or PGF$_\alpha$ compounds described above, in that these novel PGD-, 9-deoxy-PGD-, or 9-deoxy-9,10-didehydro-PGD-type compounds are useful for each of the above-described purposes for which either the PGE or PGF$_\alpha$ compounds are used, and are used in the same manner as the PGE or PGF$_\alpha$ compounds, as described above.

The PGA-type compounds of this invention correspond to the PGA compounds described above. In that these novel PGA-type compounds are useful for each of the above described purposes for which the PGA compounds are used, and are used in the same manner as the PGA compounds, as described above.

The prostaglandins described above, are all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmalogical purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, bucally, or rectally in those cases wherein the corresponding prostaglandin is effective only by the intravenous, intramuscular, or subcutaneous injection or infusion methods of administration indicated above as uses of these prostaglandins. These alternate routes of administration are advantageous because they facilitate maintaining uniform levels of these compounds in the body with fewer, short, or smaller doses, and make possible self-administration by the patient.

Accordingly, the novel prostaglandin analogs of this invention are administered in various ways for various purposes; e.g., intravenously, ntramuscularly, subcutaneously, orally, intravaginally, rectally, bucally, sublingually, topically, and in the form of sterile implants for prolonged action. For intravenous injection or infusion, sterile aqueous isotonic solutions are preferred. For subcutaneous or intramuscular injection, sterile solutions or suspensions are used. Tablets, capsules, and liquid preparation such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The novel PG analogs of this invention used for the purposes described above in free hydroxy form or also in the form wherein the hydroxy moities are transformed to lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds.

To obtain the optimum combination of biological response specificity, potency, and duration of activity, certain compounds within the scope of this invention are preferred as discussed below.

Especially preferred are those compounds which satisfy two or more of the preferences herein. Further, the preferences herein are expressly intended to describe the preferred compounds within the scope of any generic formula of novel prostaglandin analogs disclosed herein. Thus, for example the preferences herein describe preferred compounds within the scope of each formula of a prostaglandin analog provided in the Tables hereinafter.

In another aspect of the interpretation the preferences, herein, the various prostaglandin cyclopentane ring structures as employed herein are each representative of a particular "parent structure" which is useful in naming and categorizing the novel prostaglandin analogs disclosed herein. Further, where a formula depicts a genus of PG analogs disclosed herein evidencing a single cyclopentane ring structure, then each corresponding genus of PG analogs evidencing one of the remaining cyclopentane ring structures cited herein for novel prostaglandin analogs is intended to represent an equally preferred genus of compounds. Thus, for example, for each genus of $PGF_\alpha$-type products depicted by a formula herein, the corresponding genera of PGD-, PGE-, and 11-deoxy-$PGF_\alpha$-type products are equally preferred embodiments of the invention as the genus of $PGF_\alpha$-type products.

Finally, where subgeneric grouping of PG analogs of any cyclopentane ring structure are described herein, then the corresponding subgeneric groupings of PG analogs of each of the remaining cyclopentane ring structures are intended to represent equally preferred embodiments of the present invention.

It is preferred that in the carboxy-terminated side chain, g be one or 3; it is especially preferred that g be one, i.e, the chain is of the neutral chain length of the prostaglandins. Further when $R_7$ is $-(CH_2)_m-CH_3$, it is preferred that m be 3. For those compounds wherein $R_7$ is

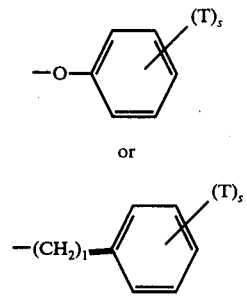

it is preferred that s and 1 be zero or one and T is chloro, fluoro, or trifluoromethyl.

For those compounds wherein at least one of $R_3$ and $R_4$ is methyl or fluoro, it is preferred that $R_5$ be hydrogen. For those compounds wherein $R_5$ is methyl, it is preferred that $R_3$ and $R_4$ both be hydrogen. For those compounds wherein $R_7$ is

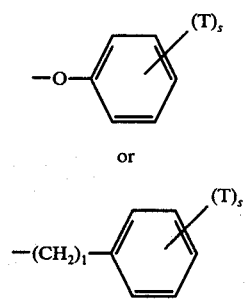

it is preferred that $R_3$ and $R_4$ be hydrogen.

For those compounds wherein an oxa is substituted for a methylene (i.e., —O— for —$CH_2$—), it is preferred that such substitution occur at C-5, in preference to C-4 and C-3, and when g is zero and $L_2$ and $L_3$ are hydrogen or alkyl, that such substitution not be present at C-3.

It is further preferred that the 15-hydroxy be of the alpha configuration, i.e., that the hydroxy be in the 15-epi configuration for the novel cis-13-PG analogs as drawn herein and not be in the 15-epi configuration when non-cis-13-PG analogs are considered.

Finally for those PG analogs with a carbonyl-containing cyclopentane ring, it is especially preferred that one of $L_2$ and $L_3$ be —$COOR_1$, so as to impart stability to products thusly obtained.

The Charts herein describe methods whereby the novel prostaglandin analogs disclosed herein are prepared.

With respect to the charts below:

T, g, and s are as defined above; M is one or two.

$R_1$ is as defined above.

$R_2$ is hydrogen or fluoro. $R_{53}$ is hydrogen or methyl.

$R_3$, $R_4$, $R_5$, and $R_7$ are as defined above.

$R_8$ is hydrogen or hydroxy.

$R_9$ is acyl protecting group.

$R_{10}$ is a blocking group.

$R_{16}$ is hydrogen or $-OR_9$; $R_{18}$ is hydrogen or $-OR_{10}$.

$R_{22}$ and $R_{26}$ are hydrocarbyl, e.g. alkyl, cycloalkyl, aralkyl, and the like. Preferably $R_{22}$ and $R_{26}$ are alkyl, being most preferably lower alkyl (e.g., methyl or ethyl).

$R_{51}$ is $R_{30}$-$SO_2$, wherein $R_{30}$ is alkyl, cycloalkyl, aralkyl, phenyl, or phenyl substituted with alkyl or halogen. Preferably $R_{30}$ is methyl or p-tolyl.

$R_{55}$ and $R_{56}$ are alkyl of one to 4 carbon atoms, inclusive, being the same or different, or when taken together represent a group of the formula Chart A

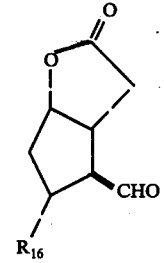
XXI

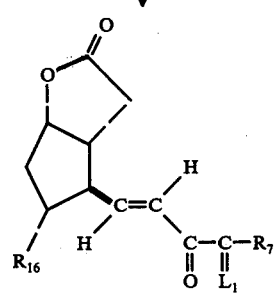
XXII

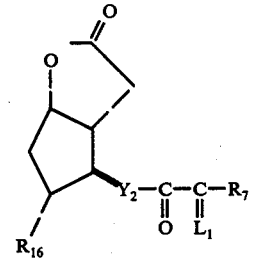
XXIII

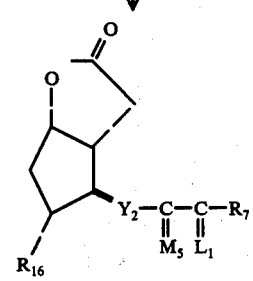
XXIV

Chart A-continued
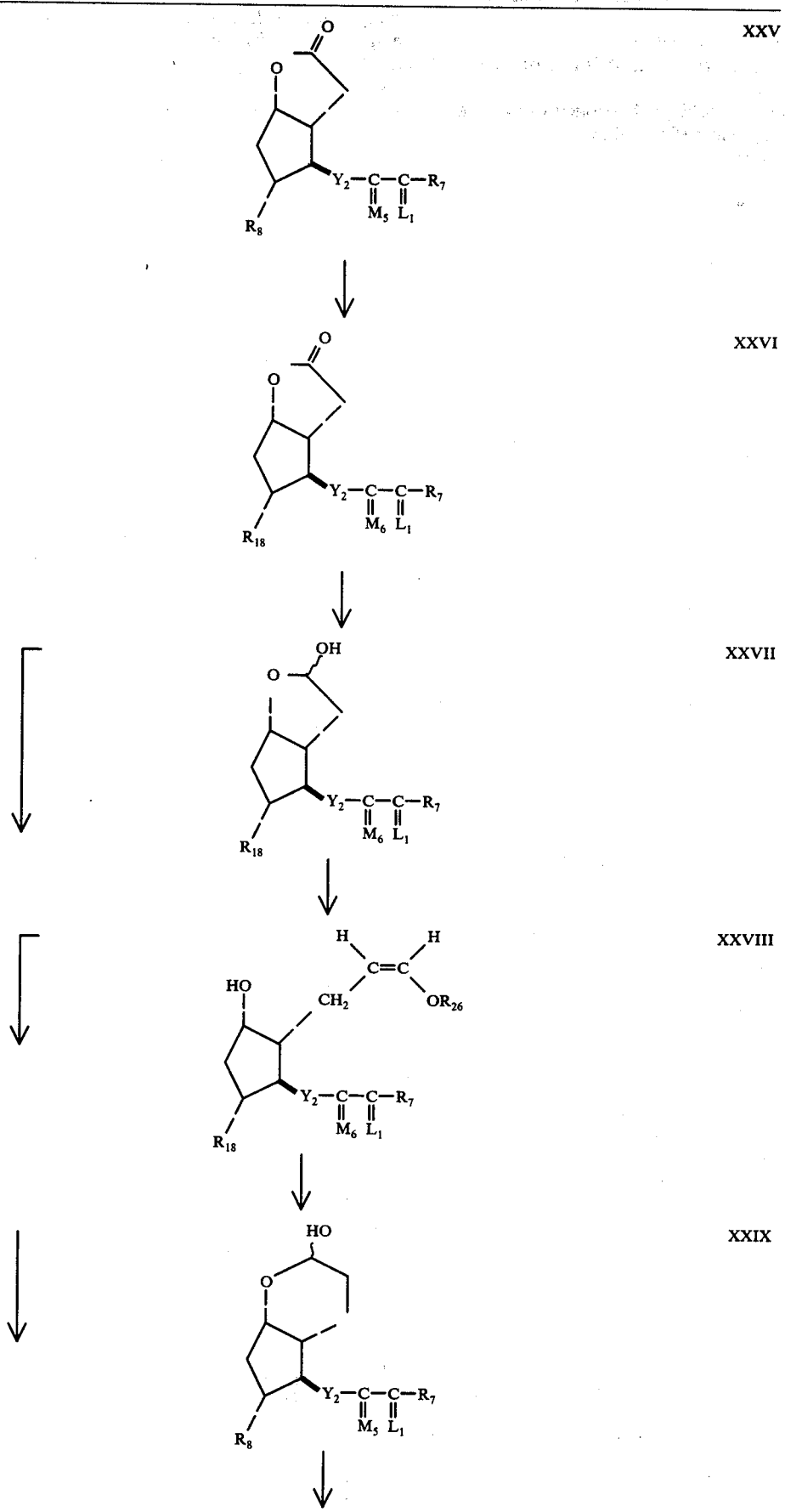

Chart A-continued
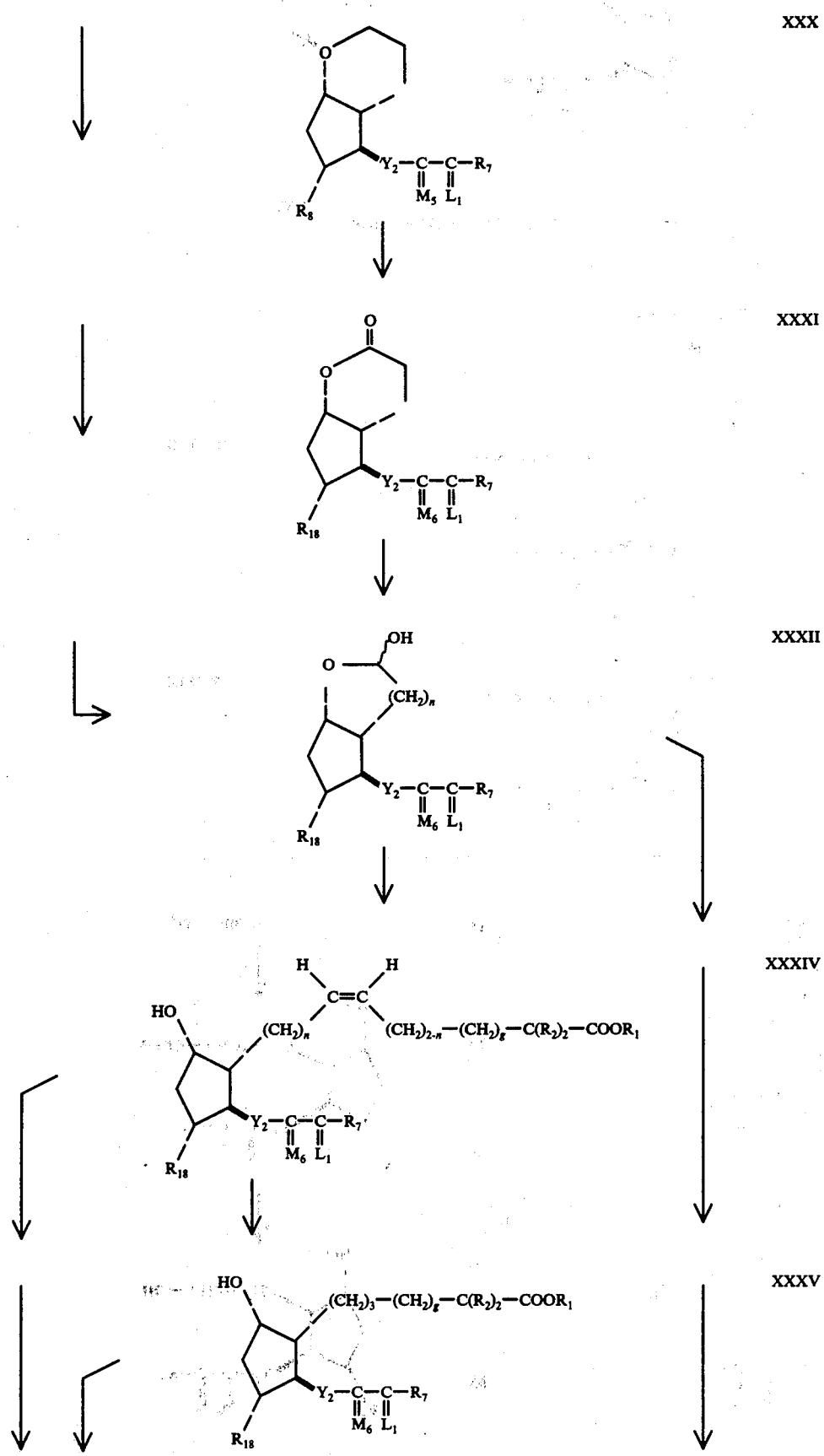

Chart A-continued
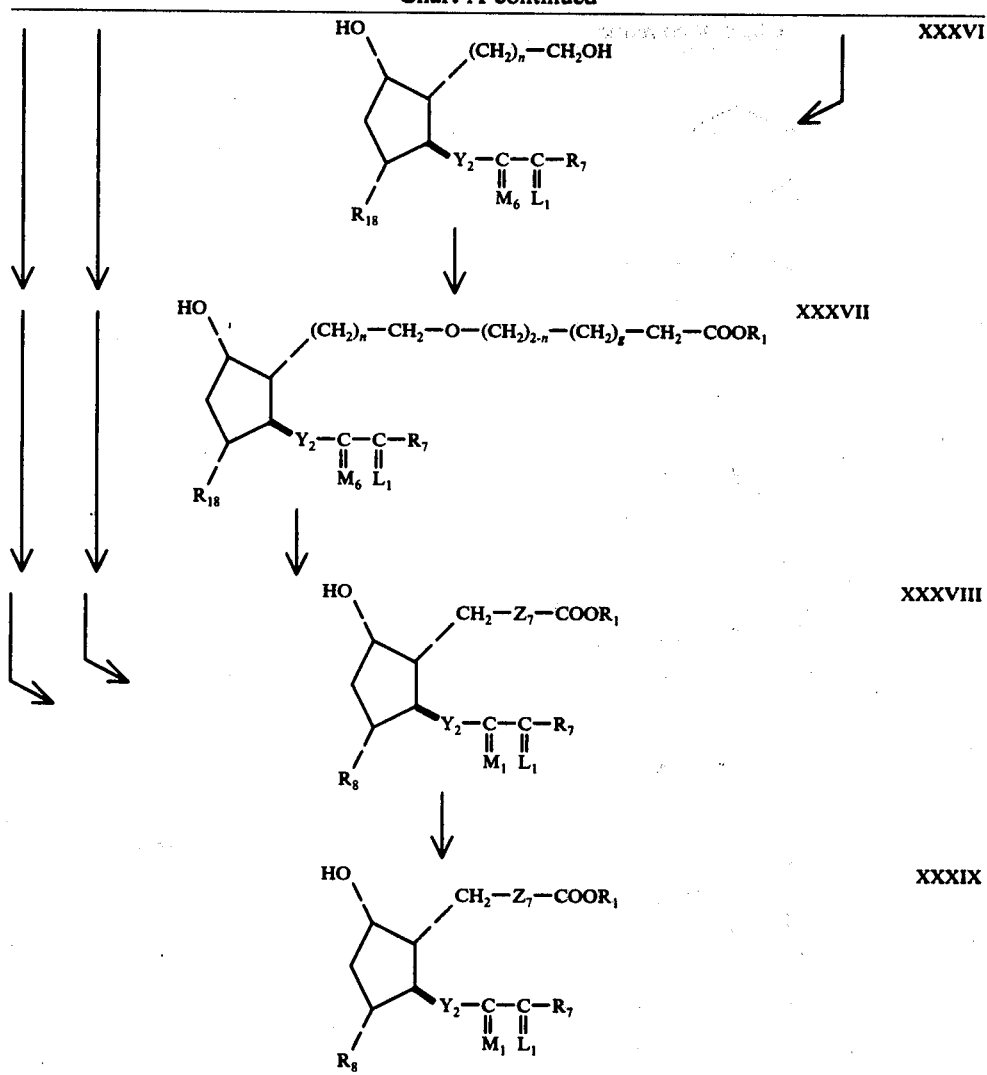
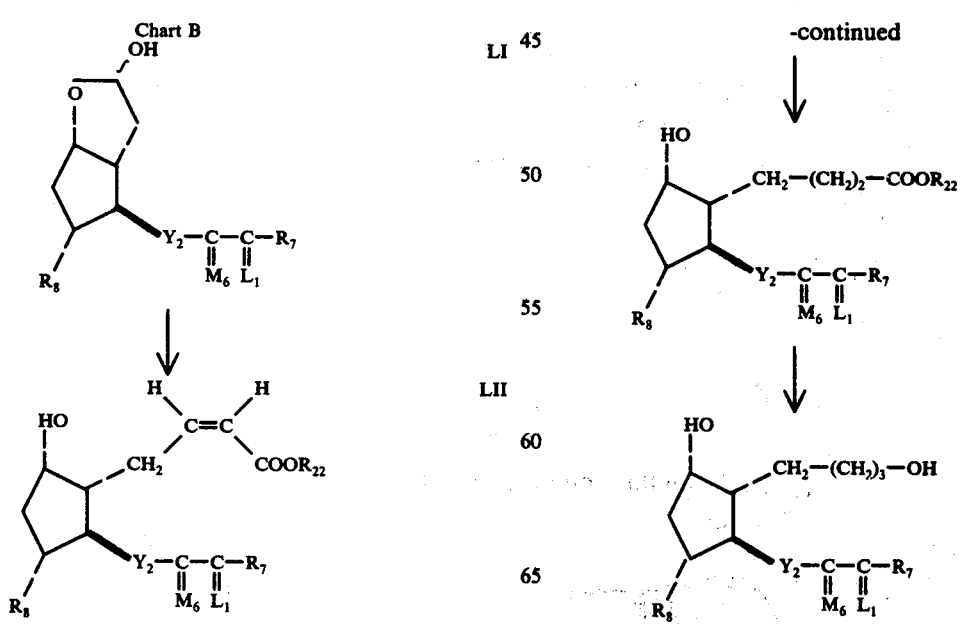

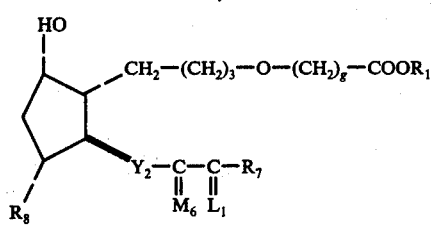
LV
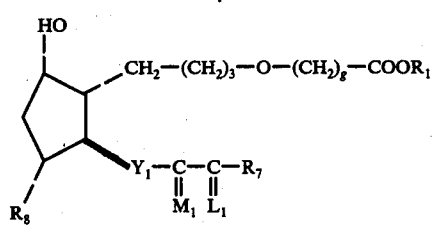
LVI
Chart C
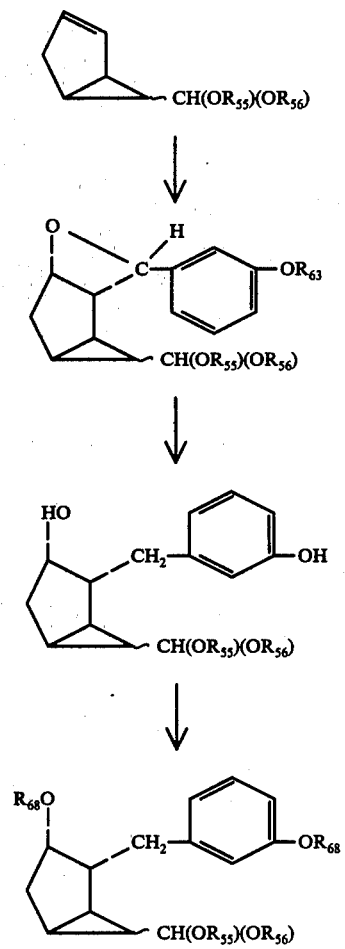
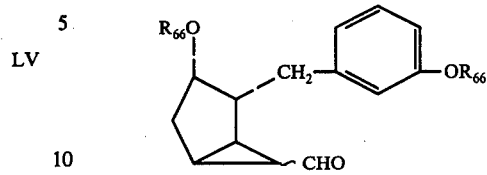
LXV
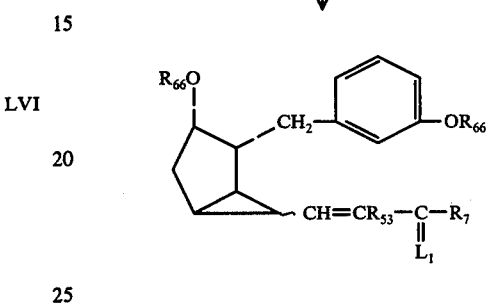
LXVI
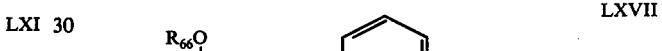
LXVII
LXVIII
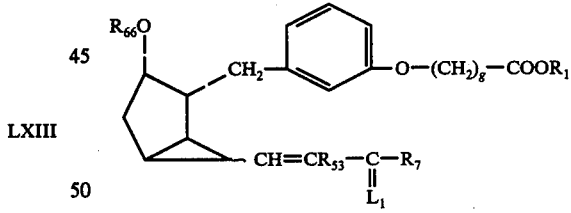
LXIX
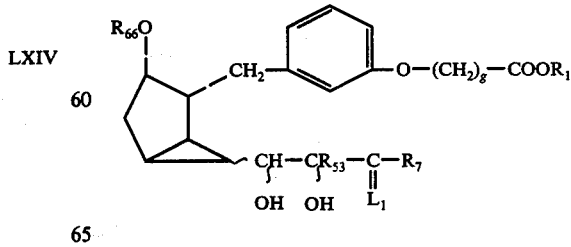

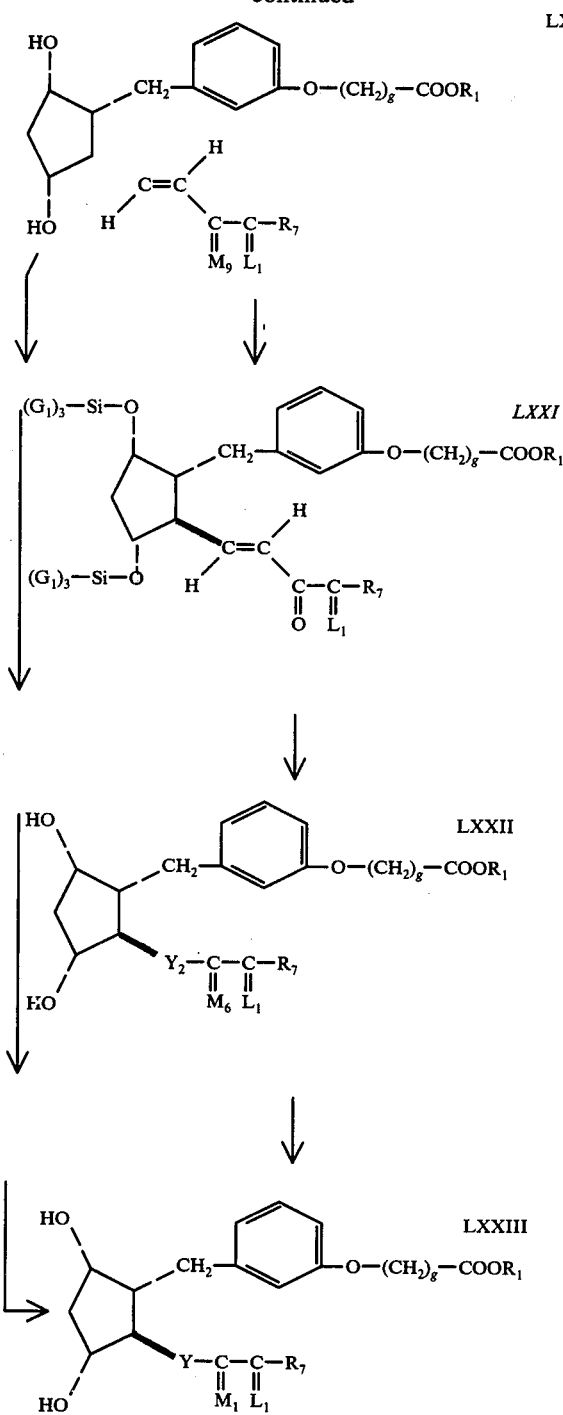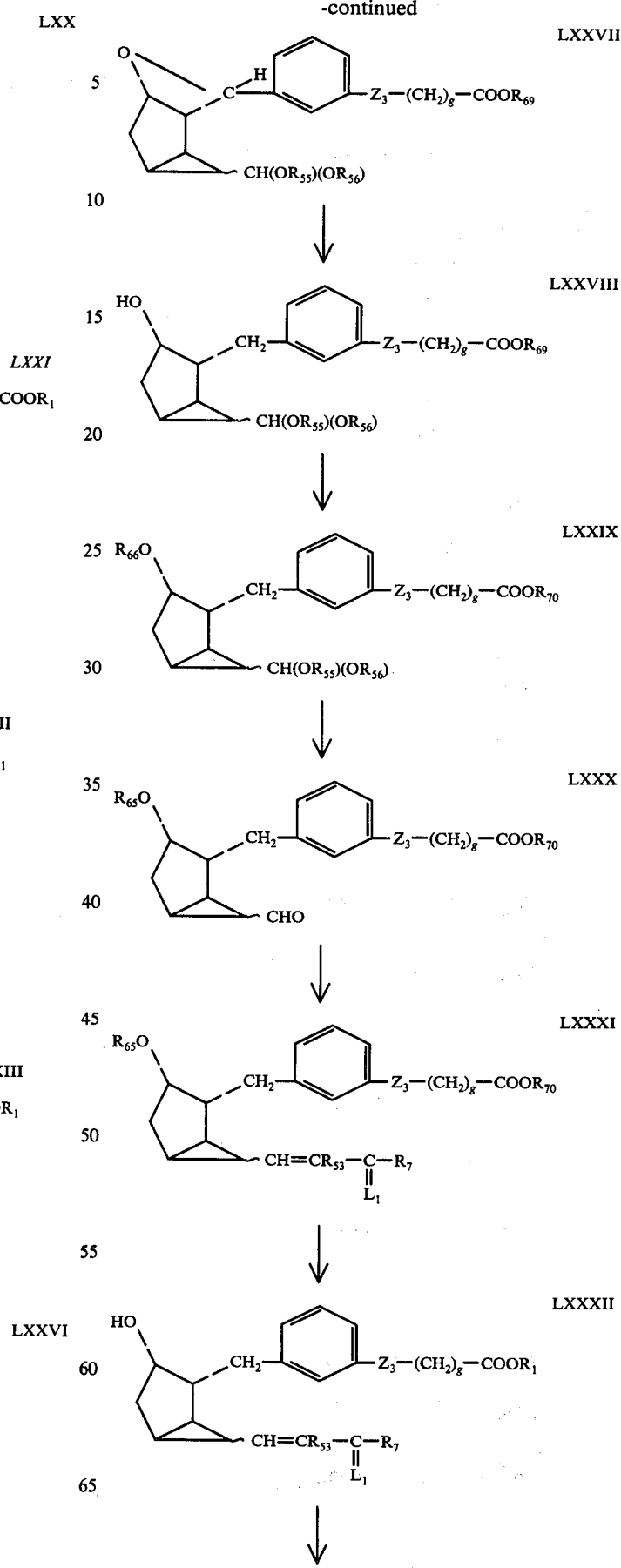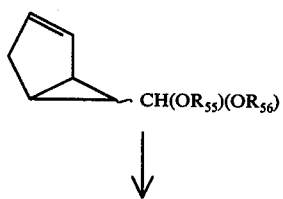
Chart D

-continued
LXXXIII
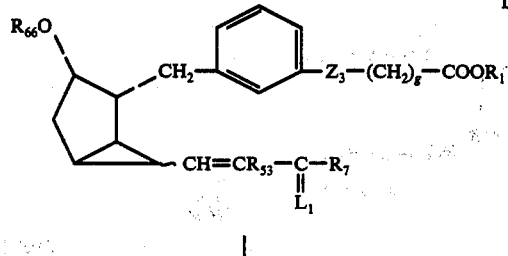
LXXXIV
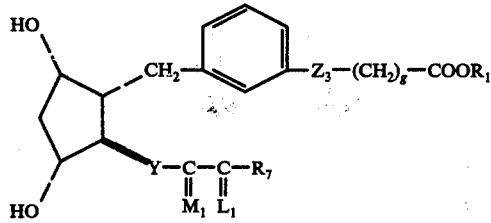
Chart E
LXXXVI
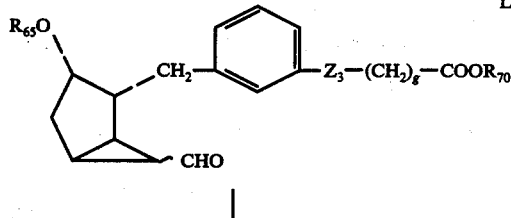
LXXXVII
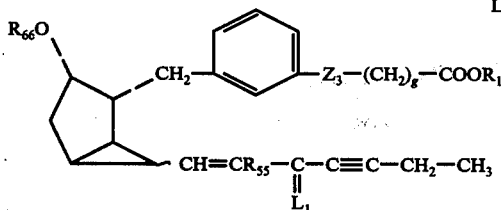
LXXXVIII
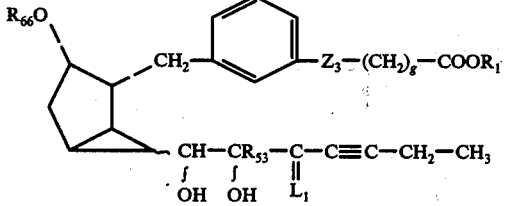
LXXXIX
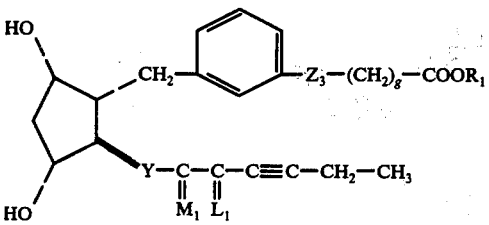
-continued
XC
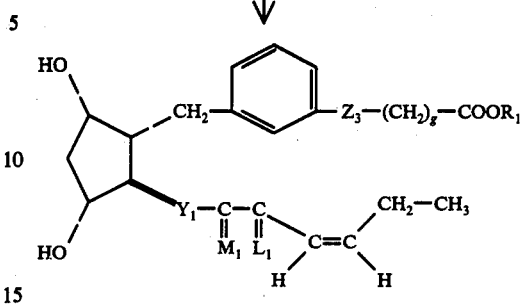
Chart F
XCI
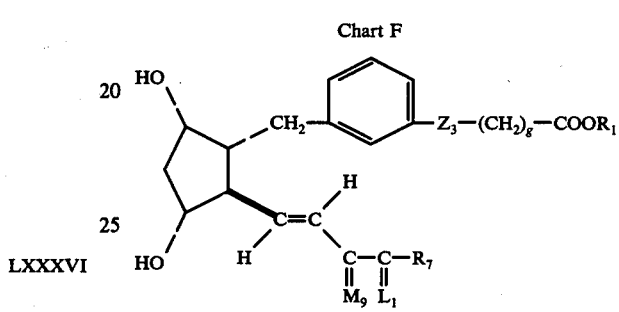
XCII
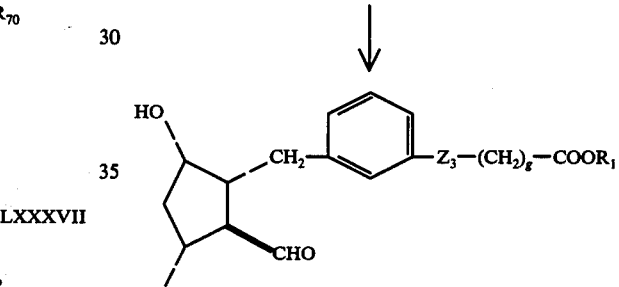
XCIII
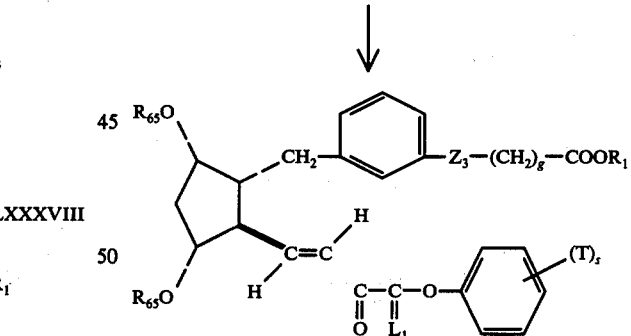
XCIV
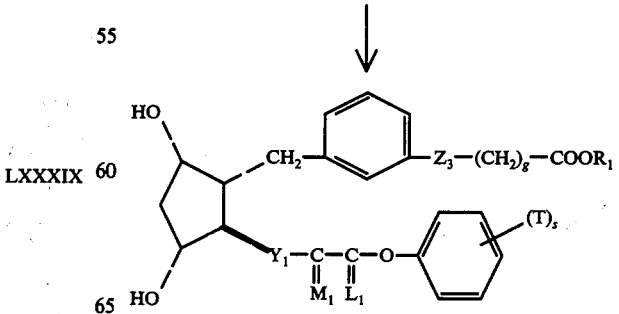
Chart G

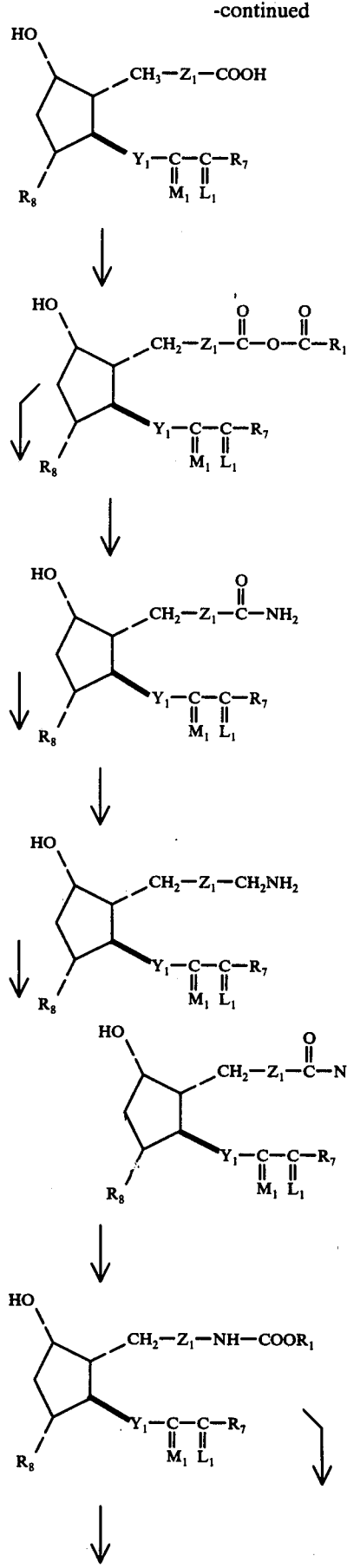
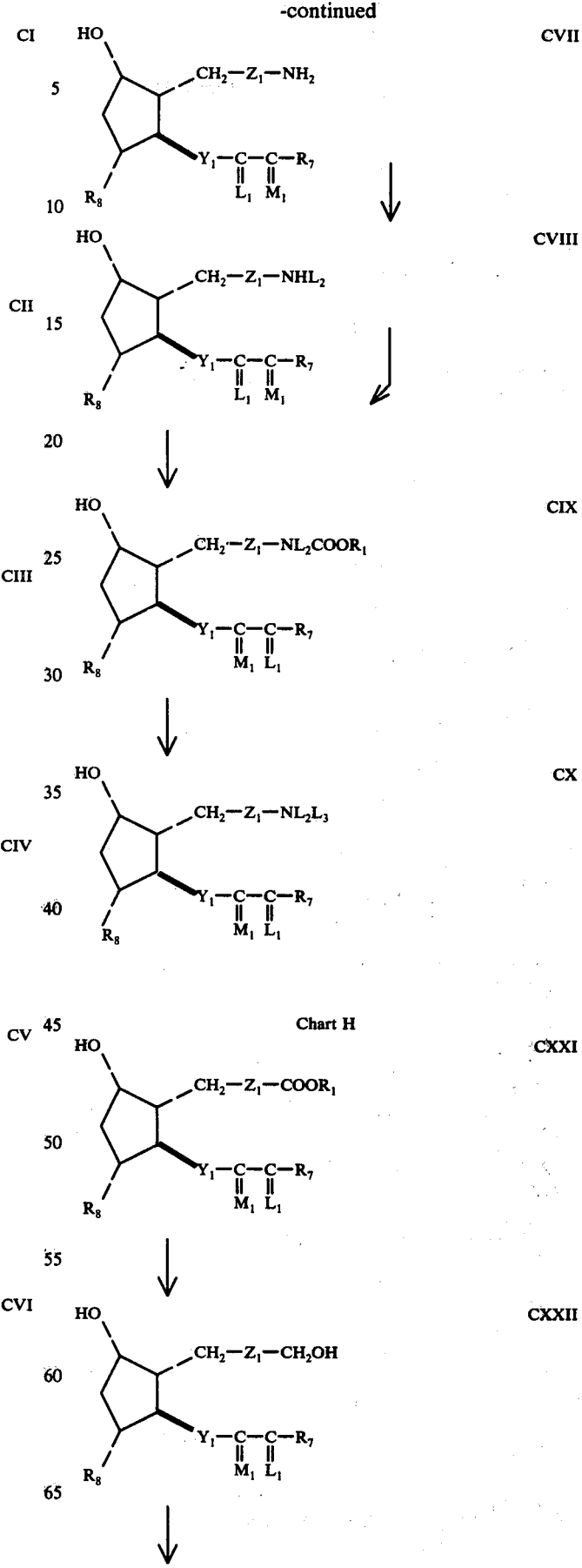
Chart H

CXXIII 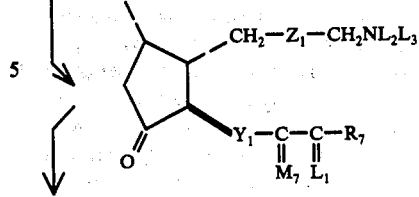

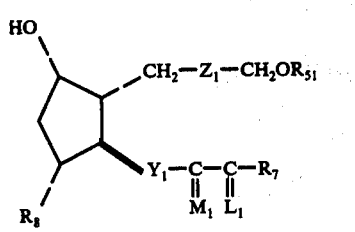

CXXXIV 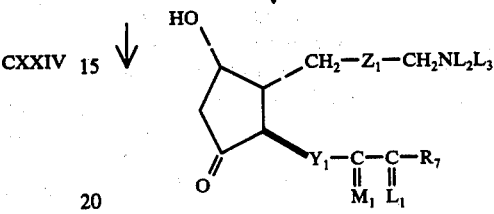

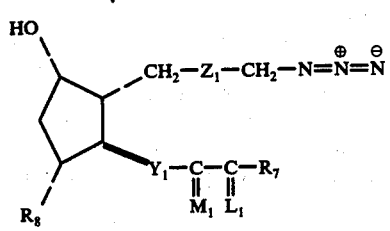

CXXIV

CXXXV 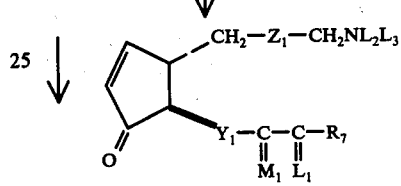

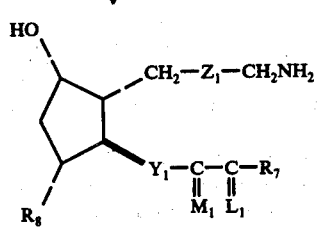

CXXV

CXXXVI 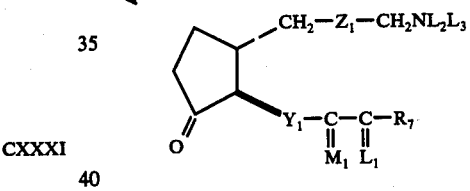

Chart I

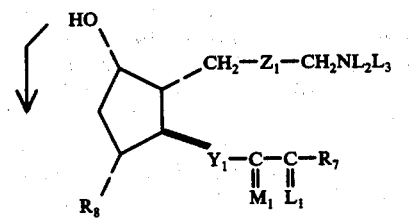

CXXXI

CXXXVII 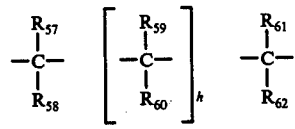

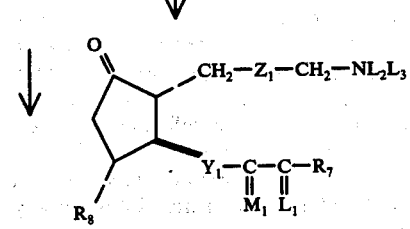

CXXXII wherein $R_{57}$, $R_{58}$, $R_{59}$, $R_{60}$, $R_{61}$, and $R_{62}$ are hydrogen, alkyl of one to 4 carbon atoms, inclusive, or phenyl, being the same or different, with the proviso that not more than one of $R_{57}$, $R_{58}$, $R_{59}$, $R_{60}$, $R_{61}$, and $R_{62}$ is phenyl and that the total number of carbon atoms in $R_{57}$, $R_{58}$, $R_{59}$, $R_{60}$, $R_{61}$, and $R_{62}$ is from 2 to 10, inclusive, and h is zero or one.

$R_{63}$ is carboxyacyl of the formula $$R_{64}\overset{O}{\underset{\|}{C}}—,$$

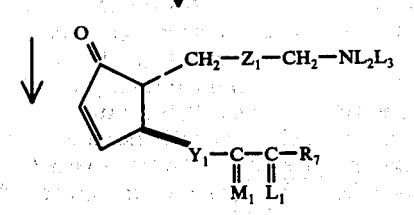

CXXXIII wherein $R_{64}$ is hydrogen, alkyl of one to 19 carbon atoms, inclusive, or aralkyl of 7 to 12 carbon atoms, inclusive, wherein the above alkyl or aralkyl are substituted with zero to 3 fluoro, chloro, bromo or iodo. $R_{66}$ is hydrogen or a blocking group, according to $R_{65}$. Blocking groups according to $R_{65}$ useful for the purposes of this invention include all blocking groups according to $R_{10}$, as enumerated herein, and additionally —Si($G_1$)$_3$, wherein $G_1$ is alkyl of one to 4 carbon atoms, inclusive, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, inclusive. In the use of these silyl blocking groups, according to $R_{65}$, methods known in the art for the preparation of the necessary reagents and appropriate reaction conditions for replacing hydroxy hydrogens with these silyl blocking groups and subsequently hydrolyzing these silyl blocking groups, are employed. $R_{68}$ is hydrogen, carboxyacyl according to $R_{63}$, or an acyl protecting group according to $R_9$. $R_{69}$ is hydrogen or alkyl of one to 4 carbon atoms inclusive. $R_{70}$ is hydrogen, alkyl of one to 4 carbon atoms, inclusive, or silyl of the formula -Si($G_1$)$_3$, wherein $G_1$ is as defined above.

$Y_1$ is as defined above. $Y_2$ is cis—CH=CH—, trans-CH=CH—, —CH$_2$CH$_2$—, or trans —CH=C(Hal)— wherein Hal is chloro or bromo.

$Z_1$ is as defined above. $Z_7$ is cis—CH=CH—CH$_2$—(CH$_2$)$_g$—C(R$_2$)$_2$—, cis—CH$_2$—CH=CH—(CH$_2$)$_g$—CH$_2$, —(CH$_2$)$_3$—(CH$_2$)$_g$—C(R$_2$)$_2$—, CH$_2$—O—CH$_2$—(CH$_2$)$_g$—CH$_2$—, or —(CH$_2$)$_2$—O—CH$_2$—(CH$_2$)$_g$—, wherein $R_2$ and g are as defined above, $Z_3$ is oxa of methylene, e.g., —O— or —CH$_2$—, respectively.

$L_1$, $L_2$, and $L_3$ are as defined above.
$M_5$ is

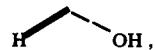

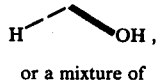

or a mixture of

and

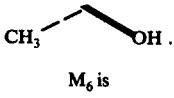

$M_6$ is

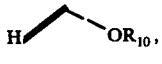

or a mixture of

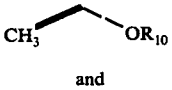

and

$M_7$ is

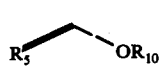

or

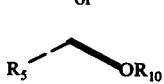

wherein $R_5$ and $R_{10}$ are as defined above.
$M_9$ is

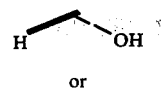

or

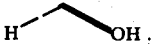

Acyl protecting groups, according to $R_9$, include:
a. benzoyl;
b. benzoyl substituted with one, 2, 3, 4, or 5 alkyl of one to 4 carbon atoms, inclusive, phenyl alkyl of 7 to 10 carbon atoms, inclusive, or nitro with the proviso that not more than 2 substitutents are other than alkyl, and that the total number of carbon atoms in the substituents does not exceed 10 carbon atoms, with the further proviso that the substituents may be the same or different;
c. benzoyl substituted with alkoxy carbonyl wherein the alkoxy carbonyl moiety is of 2 to 5 carbon atoms, inclusive;
d. naphthoyl;
e. naphthoyl substituted with one to 9, inclusive, alkyl of one to 4 carbon atoms, inclusive, phenyl alkyl of 7 to 10 carbon atoms, inclusive, or nitro, with the proviso that not more than 2 substituents on either of the naphthyl rings does not exceed 10 carbon atoms, with the further proviso that the various substituents are the same or different; or
f. alkanoyl of 2 to 12 carbon atoms, inclusive.

In preparing these alkyl derivatives of the hydroxy-containing compounds herein methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid or zinc chloride; or alternatively an anhydride of the aromatic acid of the formula ($R_9$)$_2$O (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxy-containing compound in the presence of a hydrogen chloride scavenger, e.g. a tertiary amine such as pyridine, triethylamine, or the like. The reaction is carried out under a variety of conditions, using procedures generally known in the art. Generally mild conditions are employed; 20°-60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides ($R_9$)$_2$0, or acyl chlorides ($R_9Cl$): benzoyl; substituted benzoyl, e.g., (2-, 3-, or 4-)-methylbenzoyl, (2-, 3-, or 4-)-ethylbenzoyl, (2-, 3-, or 4-)-isopropylbenzoyl, (2-, 3-, or 4-)-tert-butylbenzoyl, 2,4-dimethylenzoyl, 3,5-dimethylbenzoyl, 2-isopropyltoluyl, 2,4,5-trimethylbenzoyl, pentamethylbenzoyl, alpha-phenyl(2-, 3-, or 4-)-toluyl, (2-, 3-, or 4-)-phenethylenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9$Cl compounds corresponding to the above $R_9$ groups. If the acyl chloride is not available, it is prepared from the corresponding acid and phosphorus pentachloride as is known in the art. It is preferred that the $R_9$OH, $(R_9)_2$O, or $R_9$Cl reactant does not have bulky hindering subsitutents, e.g. tert-butyl on both of the ring carbon atoms adjacent to the carbonyl attaching site.

The acyl protecting groups, according to $R_9$, are removed by deacylation. Alkali metal carbonates are employed effectively at ambient temperature for this purpose. For example, potassium carbonate in methanol at about 25° C. is advantageously employed.

Those blocking groups within the scope of $R_{10}$ are any group which replaces a hydroxy hydrogen and is neither attacked nor is reactive to the reagents used in the transformations used herein as an hydroxy is and which is subsequently replaceable with hydrogen in the preparation of the prostaglandin-type compounds. Several blocking groups are known in the art, e.g. tetrahydropyranyl and substituted tetrahydropyranyl. See for reference E. J. Corey, Proceedings of the Robert A. Welch Foundation Conferences on Chemical Research, 12, Organic Synthesis, pgs. 51-79 (1969). Those blocking groups which have been found useful include:

a. tetrahydropyranyl;
b. tetrahydrofuranyl; and
c. a group of the formula $$-C(OR_{11})(R_{12})-CH(R_{13})(R_{14}),$$

wherein $R_{11}$ is alkyl or one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or $-(CH_2)_b-O-(CH_2)_c$, wherein a is 3, 4, or 5, or b is one, 2, or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as -toluenesulfonic acid or pyridine hydrochloride. The dihydropyran is used in large stoichiometric excess, preferably 4 to 100 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula $$-C(OR_{11})(R_{12})-CH(R_{13})(R_{14}),$$

wherein $R_{11}$, $R_{12}$, $R_{13}$, and $R_{14}$ are as defined above, the appropriate reagent is a vinyl ether, e.g. isobutyl vinyl ether or any vinyl ether of the formula $$C(OR_{11})(R_{12})=C(R_{13})(R_{14}),$$

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking groups is achieved.

The Charts herein describe the methods whereby the novel compounds disclosed in this specification are prepared. For the starting material of each of the Charts, such compounds are available in either enantiomerically pure form or as mixtures of enantiomers; or may be prepared as such by methods available in the art.

With respect to Chart A a method is provided whereby a bicyclic lactol intermediate useful in the preparation of the $PGF_{2\alpha}$-type or 11-deoxy-$PGF_{2\alpha}$-type compounds disclosed herein is prepared.

The formula XXI starting material is known in the art or readily prepared by methods known in the art.

The formula XXII compound is prepared from the formula XXI compound by a Wittig alkylation. Reagents known in the art or prepared by methods known in the art are employed. The transenone lactone is obtained stereospecifically. See for reference D. H. Wadsworth, et al., Journal of Organic Chemistry 30, 680 (1965).

In the preparation of the formula XXII compound, certain phosphonates are employed in the Wittig reaction. These phosphonates are of the general formula $$(R_{15}O)_2\overset{O}{\overset{\|}{P}}-CH_2-\overset{O}{\overset{\|}{C}}-\overset{L_1}{\overset{|}{C}}-R_7,$$

wherein $L_1$ and $R_7$ are as defined above (but $R_7$ is not cis-CH=CH-$CH_2CH_3$) and $R_{15}$ is alkyl of 1 to 8 carbon atoms, inclusive.

Phosphonates of the above general formula are prepared by methods known in the art. See Wadsworth, et al. as cited above.

Conveniently the appropriate aliphatic acid ester is condensed with the anion of dimethyl methylphosphonate as produced using n-butyllithium. For this purpose, acids of the general formula $$HOOC-\overset{L_1}{\overset{\|}{C}}-R_7$$

are employed in the form of their lower alky esters, preferably methyl or ethyl. The methyl esters for example are readily obtained by reaction of the corresponding acids with diazomethane.

For example, when $R_7$ is

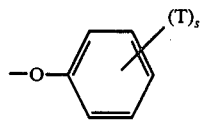

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy-, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-(o-, m-, or p-)chlorophenoxy-, (2,3-, 2,4-, 2,5-, 2,6-, 3,4-, or 3,5-)dichlorophenoxy-, (4- or 6-chloro-o-tolyloxy-, phenoxy-, (o-, m-, or p-)tolyloxy, 3,5-xylyloxy-, or m-trifluoromethylphenoxy-.

Finally there are available many 2-methyl-2-phenoxy- or (2-substituted phenoxy)propionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_7$ is: phenoxy-, (o-, m-, or p-)chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the (T)$_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is benzyl or substituted benzyl.

For example, when $R_3$ and $R_4$ of the $L_1$ moiety are both hydrogen there are available the following phenyl or substituted phenyl propionic acids: (o-, m-, or p-)-chlorophenyl-, p-fluorophenyl-, m-trifluoromethylphenyl-, (o-, m-, or p-)methylphenyl-, (o-, m-, or p-)methoxyphenyl-, (2,4-, 2,5-, or 3,4-)dichlorophenyl-, (2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl there are available, for example, the following 2-methyl-3-phenyl or substituted phenyl propionic acids: phenyl, o-chlorophenyl-, (o-, or p-methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both $R_3$ and $R_4$ are methyl there are available, for example, the following 2,2-dimethyl-3-phenyl or substituted phenyl propionic acids: phenyl- and p-methylphenyl.

When one and only one of $R_3$ and $R_4$ is fluoro, there is available, for example, 2-fluoro-3-phenyl propionic acid.

When $R_7$ is benzyl, substituted benzyl or phenylalkyl or substituted phenylaklkyl are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran) with the appropriately substituted benzyl chloride. Thus, the above acid is obtained by the following reaction: (when 1 is not zero):

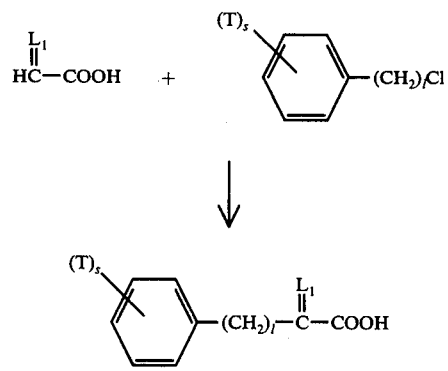

The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available the following 2-methyl alkanoic acids: butyric, pentanoic, hexanoic, heptanoic, and octanoic.

For example, when one of $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxoalkanoic acids, i.e. butyric, pentanoic, hexanoic, heptanoic, and octanoic. The transformation of these 2-oxoalkanoic acids to the corresponding 2,2-difluoroalkanoic acids proceeds by methods known in the art, using known ketonic fluorinating reagents. For example, $M_0F_6.BF_3$ is advantageously employed in the fluorination.

When $R_7$ is 1-butenyl, the formula XXII compound is prepared from the formula XXI compound by transformation of the formula XXI 2β-carboxaldehyde to a corresponding 2β-(2-formyl-trans-1-ethenyl) compound followed by a Grignard reaction employing a reagent prepared from

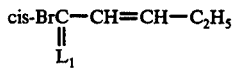

Thereupon the (3RS)-3-hydroxy compound corresponding to formula XXII is prepared, which is optionally oxidized to the formula XXII compound with the Collins reagent, or transformed to a formula XXIV compound wherein $Y_2$ is trans—CH=CH— and $R_5$ is hydrogen.

The formula XXIII compound wherein $Y_2$ is cis—CH=CH— is prepared from the formula XXII compound by photoisomerization, followed by separating the resulting trans-cis mixture of isomers. The photoisomerization proceeds by use of a conventional photon generating source which is capable of producing photons whose wave length is between about 2800 to 4000 Angstroms. It is preferred to use a conventional photon generating source which is capable of producing photons whose wave length is about 3500 Angstroms. Irradiation continues until an equilibrium mixture of cis and trans isomers is obtained. The progress of the photoisomerization is conveniently monitored by conventional methods, e.g. silica gel thin layer chromatography (TLC). The resulting equilibrium mixture of cis and trans isomers is then separated using conventional methods. For example, silica gel chromatography is advantageously employed.

The formula XXIII wherein Y is —CH$_2$CH$_2$— is advantageously prepared by catlytic hydrogenation methods.

The formula XXIII compound wherein $Y_2$ is trans—CH=C(Hal)— is prepared from the formula XXII compound by one of two methods. By the first method halogenation at C-14 -yields the formula XXIII compound directly. This method employs sulfuryl chloride in pyridine as described in C. Gandolfi, et al., II Farmaco, 27, 1125 (1972).

By a second method the formula XXIII compound is prepared from the formula XXII compound by dihalogenation, followed by dehydrohalogenation. The halogenation proceeds by methods known in the art, conveniently by reaction of the formula XXII compound with a reagent such as an N-halosuccinimide. The reaction proceeds slowly to completion, ordinarily within three to ten days. Alternatively the molecular form of the halide (Hal$_2$) in a diluent (e.g., carbon tetrachloride or a mixture of acidic acid and sodium acetate) is employed in this dihalogenation. Thereafter dehydrohalogenation proceeds by addition of an organic base, preferably amine base, to the dichloride. For example pyridine, or a diazobicycloalkene, is an especially useful amine base, although non-amine bases such as methanolic sodium acetate are likewise employed.

Optionally the formula XXIII compound is prepared directly from the formula XXI compound using a Wittig reagent derived from a 1-halophosphonate corresponding to the phosphonate described above for the preparation of the formula XXII compound. These phosphonates are known in the art or are readily prepared by methods known in the art. For example, a phosphonate as described above is transformed to the corresponding 1-halophosphonate by dripping the molecular halogen into a solution of the phosphonate and a strong organic base, e.g. sodium methoxide.

The 1-halophosphonate as prepared above is then reacted with the formula XXI compound in a manner described for the preparation of the formula XXII compound from the formula XXI compound to prepare the formula XXIII compound.

In each of the above described methods for the preparation of the formula XXIII compound, the desired formula XXIII product is often contaminated with its corresponding cis isomer. In performing the succeeding steps it is desirable to obtain isomerically pure formula XXIII product in order to avoid creation of complicated mixtures of steroisomers. Accordingly, the formula XXIII compound is subjected to conventional separation techniques, (e.g. silica gel chromatography) to obtain pure product.

The formula XXIV compound is prepared from the formula XXIII 3-oxo bicyclic lactone by transformation of the 3-oxo-moiety to the $M_5$ moiety.

The above 3-oxo bicyclic lactone is transformed to the corresponding 3α- or 3β-hydroxy bicyclic lactone, wherein $M_5$ is

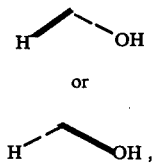

by reduction of the 3-oxo moiety, followed by separation of the 3α- and 3β-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium (tri-tert-butoxy)-aluminum hydride, metal trialkyl borohydrides, e.g. sodium trimethoxyborohydride, lithium borohydride, and the like. In those case in which carbon-carbon double bond reduction need not be avoided, the boranes, e.g. disiamylborane (bis-3-methyl-2-butyl borane) are alternatively employed.

For the production of C-15 epimerically pure prostaglandins, the 15-epi compound is separated from the mixture by methods known in the art. For example, silica gel chromatography is advantageously employed.

The 3-oxo bicyclic lactone is transformed into the corresponding (3RS)-3-methyl bicyclic lactone wherein $M_5$ is a mixture of

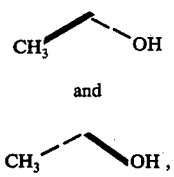

by reaction of the 3-oxo bicyclic lactone with a Grignard reagent, CH$_3$MgHal, wherein Hal is chloro, bromo or iodo. The Grignard complex is thereafter hydrolyzed, for example, using saturated aqueous ammonium chloride as is known in the art. An alternate method for transforming the 3-oxo compound to a 3(RS)-3-methyl compound is by reaction of the 3-oxo bicyclic lactone with trimethylaluminum.

The preferred method for separation of these (3RS)-3-methyl epimers is by separation of the corresponding C-15 epimers of the PG-type, methyl esters using silica gel chromatography or high pressure liquid chromatograhy (HPLC).

The formula XXV compound is prepared from the formula XXIV compound by deacylation, as described above. The formula XXVI compound is then prepared from the formula XXV compound by replacing any free hydroxy moieties with blocking groups according to $R_{10}$ by the procedure described above. The formula XXVII compound is then prepared from the formula XXVI compound by reduction of the formula XXVI lactone to a lactol. Methods known in the art are employed. For example, diisobutylaluminum hydride is employed at $-70°$ to $-80°$ C.

Thereafter the formula XXVII compound is transformed to either the formula XXVIII or XXXII compound.

The formula XXVII compound undergoes condensation to form the formula XXVIII enol. For this purpose a hydrocarbyloxy, and preferably an alkoxymethylenetriphenylphosphorane is useful. See for reference, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below $-10°$ C. The formula XXVII lactol is mixed with the above reagent and the condensation proceeds smoothly within the temperature range of $-30°$ C. $-+30°$ C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy, isobutoxy-, s-butoxy-, and t-butoxy-methylenetriphenylphosphorane. Various hydrocarbyloxymethylenetriphenylphosphoranes which are optionally substituted for the alkoxymethylenetriphenylphosphoranes and are accordingly useful for preparing the formula XXVIII intermediates wherein $R_{26}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl butyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346–348, John Wiley and Sons, New York, New York, (1965). The formula XXVIII enol intermediates are then hydrolyzed to the formula XXIX lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula XXX compound is then prepared from the formula XXIX compound by oxidation of the formula XXIX lactol to a lactone. This transformation is carried out, using for example, silver oxide as an oxidizing reagent, followed by treatment with pyridine hydrochloride.

The formula XXX lactone may then be converted to the formula XXXI ether by transformation of any free hydroxy moieties to blocking groups, according to $R_{10}$, following the procedures herein described for these transformations.

Thereafter the formula XXXII compound (wherein n is 2) is prepared from the formula XXXI compound by reduction of the formula XXXI lactone to a lactol. For example, diisobutylaluminum hydride is employed as is described above for the reduction of lactones to lactols. The formula XXXII lactol is alternately represented by the formula XXVII compound when n is one.

The formula XXXIV compound is prepared from the formula XXXII compound by a Wittig alkylation, using the appropriate (ω-carboxyalkyl)triphenylphosphonium bromide. The reaction proceeds as is generally known in the art, by first mixing the appropriate (ω-caboxyalkyl)-triphenylphosphonium bromide with sodio dimethylsulfinylcarbanide, at ambient temperature, and adding the formula XXXII lactol to this mixture. Thereafter the carboxy hydrogen of the compound so formed is transformed to an $R_1$ moiety by the methods and procedures hereinbelow described. Accordingly, there is prepared the formula XXXIV cis-4,5-didehydro-$PGF_{1\alpha}$- or 11-deoxy-$PGF_{1\alpha}$-, or 11-deoxy-$PGF_{2\alpha}$-, or $PGF_{2\alpha}$-type compound.

The formula XXXV compound is then prepared from the formula XXXIV compound by catalytic hydrogenation of the cis-5,6-double bond. Hydrogenation methods known in the art are employed. Mixtures of compounds thereby produced are conveniently separated by silica gel chromatography.

Optionally the formula XXXII lactol is transformed into the corresponding formula XXXVII 5-oxa- or 4-oxa-PG-type intermediate. First, formula XXXVI alcohol is obtained by a ring opening of the formula XXXII lactol, to its hydroxy aldehyde form, followed by reduction of the aldehyde so obtained for example, with aqueous methanolic or ethanolic sodium borohydride to the formula XXXVI primary alcohol. Alternatively and preferably, the formula XXXVI compound is obtained by a one step reduction of the formula XXVI or XXXI lactone, for example, with lithium aluminum hydride or diisobutyl aluminum hydride at a temperature ranging from 0° to 35° C. For preparing the formula XXXVII compound a Williamson synthesis is employed. For example, the formula XXXVI compound is condensed with a haloalkanoic acid or appropriate halo ester within the scope of

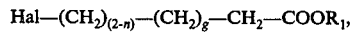

$$Hal-(CH_2)_{(2-n)}-(CH_2)_g-CH_2-COOR_1,$$

wherein Hal is chloro, bromo, or iodo and g and n are as defined above. Normally the reaction is done in the presence of a base such as n-butyllithium, phenyllithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethylsulfoxide or, especially if an organolithium compound is employed, preferably in dimethylformamide or hexamethylphosphoramide. The reaction proceeds smoothly at $-20°$ to 50° C., but is preferably performed at ambient temperature.

Accordingly, the above processes yield the formula XXXIV, XXXV, or XXVII compound which is transformed to a formula XXXVIII compound by hydrolysis of any blocking groups followed by separation of any mixed 15-epimers. Hydrolysis proceeds by above-described methods and the C-15 -epimeric mixture is separated by, for example chromatographic means. For separation of 15-methyl epimers, it is preferred that $R_1$ be methyl.

Finally the formula XXXVIII compound is transformed to the formula XXXIX compound by dehydrohalogenation with base. Amine bases are preferred, particularly 1,5-diazobicyclo-[5.4.0.]undecene-5. See Fieser and Fieser, Vol. 2, page 101 (1969).

Chart B provides a method whereby the formula LI lactol, prepared according to Chart A, is transformed into a corresponding formula LVI 3-oxa-PG-type intermediate.

The formula LII compound is obtained from the formula LI lactol by the Wittig reaction, with a (hydrocarbyloxymethylene)triphenylphosphorane $R_{22}OOC-CH=P(C_6H_5)_3$ wherein $R_{22}$ is as defined above. The reaction is conveniently carried out at 25° C., using methods and reactants known in the art.

The formula LIII compound is then obtained by reduction of the ethylenic group in the carboxyl containing side chain. For this purpose a reducing agent is used which does not reduce the $Y_2$ or $R_7$, when such reduction is not desired, for example hydrogen in the presence of a catalyst such as palladium on carbon or rhodium on alumina. Mild conditions are sufficient, and mixtures of products are conveniently separated by chromatography.

The formula LIV alcohol is obtained from the formula LIII compound by reduction, for example, with lithium aluminum hydride or lithium trimethoxy aluminum hydride. A solvent such as diethyl ether or tetrahydrofuran is conveniently used.

The formula LV compound is obtained by a Williamson synthesis, condensing the formula LIV alcohol with a haloalkanoate, $Hal(CH_2)_gCOOR_1$ wherein Hal is chloro, bromo, or iodo and $R_1$ is as above defined, in the presence of a base. For the base, there is used, for example, n-butyllithium, phenyllithium, triphenylmethyllithium, sodium hydride, or potassium t-butoxide. It is preferred that only one molecular equivalent of the base be used. The alkanoate is employed in about 100% stoichiometric excess. Instead of a haloalkanoic acid ester, a salt, for example lithium chloroacetate, is useful. After the condensation, the salt is transformed to the formula LV compound by methods known in the art. The condensation is conveniently run in a solvent such as dimethyl formamide, tetrahydrofuran, dimethyl sulfoxide, or hexamethylphosphoramide.

Finally the formula LV compound is transformed to the formula LVI compound employing the methods of Chart A for the analogous transformation (i.e., dehydrohalogenation).

Charts C, D, E, and F provide methods whereby 3-oxa-3,7-inter-m-phenylene-4,5,6-trinor- or 3,7-inter-m-phenylene-4,5,6-trinor-PGF$_\alpha$-type intermediates are prepared. With respect to Charts C and D, $R_7$ is preferred to be $-(CH_2)_m-CH_3$, or

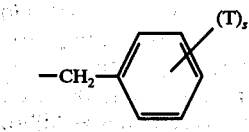

wherein m, T, and s are as defined above. In Charts E or F a method is provided for preparing those novel compounds of this specification wherein $R_7$ is preferably cis—$CH=CH-CH_2-CH_3$, or

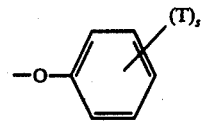

wherein T and s are as defined above, respectively. Accordingly the Charts C-F provide methods whereby intermediates useful in producing all inter-m-phenylene PG-type compounds disclosed herein are prepared.

In Chart C both the endo and exo forms of bicyclo hexene LXI are available or are made by methods known in the art, in either their racemic or enantiomerically pure forms. See U.S. Pat. No. 3,711,515. Either the endo or exo stating material will yield the ultimate intermediates of formula LXXIII by the process of Chart C.

Oxetane LXII is obtained by reaction of the formula LXI bicyclo hexene with an aldehyde of the formula

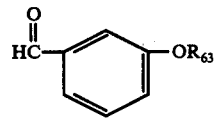

wherein $R_{63}$ is carboxyacyl of the formula

wherein $R_{64}$ is hydrogen, alkyl of one to 19 carbon atoms, inclusive, or aralkyl of 7 to 12 carbon atoms, inclusive, wherein alkyl or aralkyl are substituted with zero to 3 halo atoms.

The above benzyl aldehydes are available or readily prepared by methods known in the art. Examples of such compounds within this scope are:

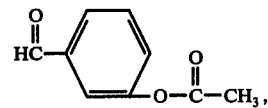

and

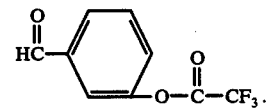

The formation of oxetane LXII is accomplished by photolysis of a mixture of the bicyclo hexene and the aldehyde in a solvent. The bicyclo hexene is preferably used in excess over the molar equivalent, for example 2 to 4 times the stoichiometric equivalent amount. The solvent is a photochemically inert organic liquid, for example liquid hydrocarbons, including benzene or hexane, 1,4-dioxane, and diethyl ether. The reaction is conveniently done at ambient conditions, for example 25° C., but may be done over a wide range of temperature, from about −78° C. to the boiling point of the solvent. The irradiation is done with mercury vapor lamps of the low or medium pressure type, for example those peaking at 3500 A. Such sources are available from The Southern New England Ultraviolet Co., Middletown, Conn. Alternatively, those lamps which emit a broad spectrum of wavelengths and which may be filtered to transmit only light of λ~3000-3700 A may also be used. For a review of photolysis see D. R. Arnold in "Advances in Photochemistry", Vol. 6, W. A. Noyes et al., Wiley-interscience, New York, 1968, pp. 301–423.

The cleavage of the oxetane ring to yield the formula LXIII compound from the formula LXII compound is accomplished with an alkali metal in the presence of a primary amine or an alcohol. Preferred is lithium in ethylamine, or sodium in butyl alcohol. See L. J. Altman et al., synthesis 129 (1974). The cleavage transformation may also be accomplished by catalytic hydrogenation over an inert metal catalyst, e.g. Pd on carbon, in ethyl acetate or ethanol.

The formula LXIV compound is prepared from the formula LXIII diol by preferably blocking the two hydroxyl groups with carboxyacyl groups according to $R_{63}$, i.e.

as defined above. For example, the diol is treated with an acid anhydride such as acetic anhydride, or with an acyl halide in a tertiary amine. Especially preferred is pivaloyl chloride in pyridine.

Other carboxyacylating agents useful for this transformation are known in the art or readily obtainable by methods known in the art, and include carboxyacyl halides, preferably chlorides, bromides, or fluorides, i.e. $R_{64}C(O)Cl$, $R_{64}C(O)Br$ or $R_{64}C(O)F$, and carboxy acid anhydrides, $(R_{64}C-)_2O$, wherein $R_{64}$ is as defined above. The preferred reagent is an acid anhydride. Examples of acid anhydrides useful for this purpose are acetic anhydride, propionic anhydride, butyric anhydride, pentanoic anhydride, nonanoic anhydride, trideconoic anhydride, steric anhydride, (mono, di, or tri)chloroacetic anhydride, 3-chlorovaleric anhydride, 3-(2-bromethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, phenoxyacetic anhydride, benzoic anhydride, (o, m, or p)bromobenzoic anhydride, 2,4 (or 3,4)-dichlorobenzoic anhydride, p-trifluoromethylbenbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3 or 5)-biphenylcarboxylic anhydride. 3-chloro-4-biphenylcarboxylic anhydride, 5-isopropyl-6-nitro-3-biphenylcarboxylic anhydride, and (1or 2)-naphthoic anhydride. The choice of anhydride depends upon the identity of $R_{64}$ in the final acylated product, for example when $R_{64}$ is to be methyl, acetic anhydride is used; when $R_{64}$ is to be 2-chlorobutyl, 3-chlorovaleric anhydride is used.

When $R_{64}$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and references cited therein. Alternatively, the formula LXIII diol is reacted with two equivalents of sodium hydride and then with excess ethyl formate.

In formula LXIV, $R_{68}$ may also represent a blocking group including benzoyl, substituted benzoyl, monoesterified phthaloyl and substituted or unsubstituted naphthoyl. For introducing those blocking groups, methods known in the art are used. Thus, an aromatic acid of the formula $R_{63}OH$, wherein $R_{63}$ is as defined above, for example benzoic acid, is reacted with the formula LXIII compound in the presence of a dehydrating agent, e.g. zinc chloride; or an anhydride of the aromatic acid of the formula $(R_{63})_2O$, for example benzoic anhydride, is used.

Preferably, however, an acyl halide e.g. $R_{63}Cl$, for example benzoyl chloride, is reacted with the formula-LXII compound in the presence of a tertiary amine such as pyridine, triethylamine, and the like. The reaction is carried out under a variety of conditions using procedures generally known in the art. Generally, mild conditions are are employed, e.g. 20°-60° C., contacting the reactants in a liquid medium, e.g. excess pyridine or an inert solvent such as benzene, toluene, or chloroform. The acylating agent is used either in stoichiometric amount or in excess.

As examples of reagents providing $R_{63}$ for the purposes of this invention, see the discussion above pertaining to the use of acyl protecting groups.

The formula LXIV acetal is converted to aldehyde LXV by acid hydrolysis, known in the art, using dilute mineral acids, acetic or formic acids, and the like. Solvents such as acetone, dioxane, and tetrahydrofuran are used.

For the conversion of LXV to LXIX, it is optional whether $R_{66}$ be hydrogen or a "blocking goup" as defined below. For efficient utilization of the Wittig reagent it is preferred that $R_{66}$ be a blocking group. If the formula LXIV compound is used wherein $R_{68}$ is hydrogen, the formula LXV intermediate will have hydrogen at $R_{66}$. If $R_{66}$ is to be a blocking group, that may be readily provided prior to conversion of LXV to LXVI by reaction with suitable reagents as discussed below.

The blocking group $R_{65}$, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_{63}$ above, i.e. acetyl, and also benzoyl, naphthoyl, and the like; (b) blocking groups according to $R_{10}$; and (c) $-Si(G_1)_3$ wherein $G_1$ is as defined above.

In replacing the hydrogen atoms of the hydroxyl groups with a carboxyacyl blocking group, methods known in the art are used. The reagents and conditions are discussed above for $R_{68}$ on the compound of formula LXIV.

When the blocking group is according to $R_{10}$ appropriate reagents and conditions are as defined above.

When the blocking group is silyl of the formula —Si($G_1$)$_3$, the formula LXV compound is transformed to a silyl derivative of formula LXV by procedures known in the art. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Silicon Compounds," Reinhold Publishing Corp., New York. N. Y. (1949). These reagents are used in the presence of a tertiary base such as pyridine at temperatures in the range of about 0° to +50° C. Examples of trisubstituted mono-chlorosilanes suitable for this purpose include chlorotrimethylsilane, chlorotriisobutylsilane, chlorotriphenylsilane, chlorotris(p-chlorophenyl)silane, chlorotrim-tolylsilane, and tribenzylchlorosilane. Alternatively, a chlorosilane is used with a corresponding disilazane. Examples of other silylating agents suitable for forming the formula LXV intermediates include pentamethylsilylaine, pentaethylsilylamine, N-trimethylsilyldiethylamine, 1,1,1-triethyl-N,N-dimethylsilylamine, N,N-diisopropyl-1,1,1,-trimethylsilylamine, 1,1,1-tributyl-N,N-dimethylsilylamine N,N-dibutyl-1,1,1-trimethylsilylamine, 1-isobutyl-N,N,1,1-tetramethylsilylamine, N-benzyl-N-ethyl-1,1,1-trimethyl-silylamine, N,N,1,1-tetramethyl-1-phenyl-silylamine, N,N-diethyl-1,1-dimethyl-1-phenylsilylamine, N,N-diethyl-1-methyl-1,1-diphenylsilylamine, N,N-dibutyl-1,1,1,-triphenylsilylamine, and 1-methyl-N,N,1,1-tetraphenylsilylamine.

In transforming the formula LXV compound to the formula LXVI compound the aldehyde group is transformed by the Wittig reaction to a moiety of the formula

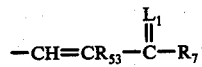

For this purpose a phosphonium salt prepared from an organic choride or bromide of the formula

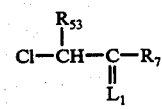

or

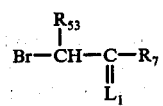

is employed, wherein $L_1$, $R_7$, and $R_{53}$ are as defined above. These organic chlorides or bromides are known in the art or are readily prepared by methods known in the art. See for example the above-identified German Offenlegungsschrift No. 2,209,990. As to the Witting reaction, see, for example, U.S. Pat. No. 3,776,941 and references cited therein.

The formula LXVII compound is obtained by deblocking if necessary. When $R_{66}$ is a hindered carboxyacyl, $R_{66}$ on the phenolic hydroxy is selectively replaced with hydrogen by hydrolysis with sodium or potassium hydroxide or carbonate ethanol-water. Other water-miscible solvents may be substituted, for example 1,4-dioxane, tetrahyrofuran, or 1,2-dimethoxyethane. The selective hyrolysis is preferably carried out at −15° to 25° C. Higher temperatures may be used but with some decrease in selectivity.

Total hydrolysis of $R_{66}$ blocking groups on the formula LXVI compound is accomplished when $R_{66}$ is carboxyacyl, with an alkali alkoxide in an alcoholic solvent, preferably sodium methoxide in methanol at a temperature from 25° C. to 50° C. When $R_{66}$ is trialkylsilyl, either aqueous acid or base are used at 25° to 50° C.

Continuing with Chart C a Williamson synthesis is employed to obtain the formula LXVIII compound. The formula LXVII phenol is condensed with a haloalkanoate within the scope of Hal-($CH_2$)$_g$—$COOR_1$, wherein Hal is chloro, bromo. or iodo and g and $R_1$ are as defined above. Normally the reaction is done in the presence of a base such as n-butyllithium, phenyllithium, triphenylmethyllithium, sodium hydride, potassium t-butoxide, sodium hydroxide, or potassium hydroxide.

The transformation of the formula LXVIII compound to the formula LXIX is accomplished by any one of several routes known in the art. See U.S. Pat. No. 3,711,515. Thus, the alkene LXVIII is hydroxylated to glycol LXIX. For this purpose osmium tetroxide is a suitable reagent, for example in conjunction with N-methylmorpholine oxidehydrogen peroxide complex (see Fieser et al., "Reagents for Organic Synthesis", p. 690, John Wiley and Sons, Inc., New York (1967)). Thereafter, several methods are available for obtaining the formula LXX product. In one method the glycol is converted to a bis(alkanesulfonic acid) ester and subsequently hydrolyzed to the formula LXX compound by methods known in the art (See, for example German Offenlegungsschrift No. 1,936,676, Derwent Farmdoc No. 6862R). Another method is by way of a diformate by formolysis of of the glycol (see U.S. Pat. No. 3,711,515).

Still another method is by way of a cyclic ortho ester. For this purpose a glycol LXIX is reacted with an ortho ester of the formula

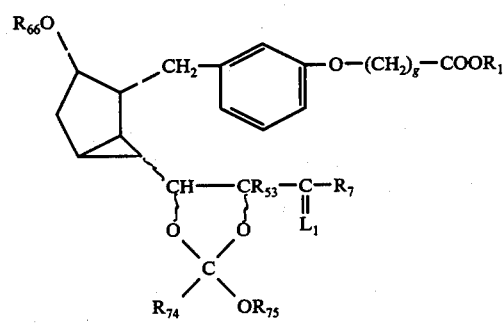

wherein $R_{74}$ is hydrogen, alkyl of one to 19 carbon atoms, inclusive, or aralkyl of 7 to 12 carbon atoms, inclusive, substituted with zero to 3 halo atoms; and $R_{75}$ is methyl or ethyl. There is then formed a cyclic orthoester of the formula

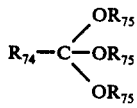

wherein g, $R_1$, $R_{53}$, $R_{66}$, $R_{74}$, $R_{75}$, $L_1$ and $R_7$ are as defined above. The reaction goes smoothly in a temperature range of −50° C. to +100° C., although for convenience 0° C. to +50° C. is generally preferred. From 1.5 to 10 molar equivalents of the ortho ester are employed, together with an acid catalyst. The amount of the catalyst is usually a small fraction of the weight of the glycol, e.g., about 1%, and typical catalysts include pyridine hydrochloride, formic acid, hydrogen chloride, p-toluenesulfonic acid, trichoroacetic acid, or trifluoroacetic acid. The reaction is preferably run in a solvent, for example benzene, dichloromethane, ethyl acetate, or diethyl ether. It is generally completed within a few minutes and is conveniently followed by TlC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:
trimethyl orthoformate,
triethyl orthoacetate,
triethyl orthopropionate,
trimethyl orthobutyrate,
trimethyl orthovalerate,
trimethyl orthooctanoate,
trimethyl orthophenylacetate, and
trimethyl ortho (2,4-dichlorophenyl)acetate.
Preferred are those ortho esters wherein $R_{74}$ is alkyl of one to 7 carbon atoms; especially preferred are those wherein $R_{74}$ is alkyl of one to 4.

Next, the cyclic orthoester depicted above is reacted with anhydrous formic acid to yield a diol diester of the formula

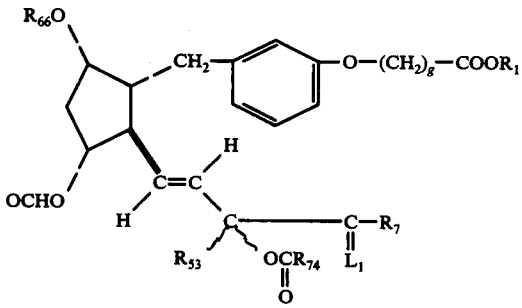

wherein g, $R_1$, $R_7$, $R_{53}$, $R_{66}$, and $L_1$ are as defined above.

Anhydrous formic acid refers to formic acid containing not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid andydrides, for example acetic anhyride, or alkyl orthoesters, for example trimethyl orthoformate, which are useful as drying agents for the formic acid. Although the reaction proceeds over a wide range of temperatures, it is conveniently run at about 20–30° C. and is usually completed with about 10 minutes.

Finally, the diol diester above is converted to product LXX by methods known in the art, for example by hydrolysis in the presence of a base in an alcoholic medium. Examples of the base are sodium or potassium carbonate or sodium or potassium akoxides includingm methoxides or ethoxides. The reaction is conveniently run in an excess of the solvolysis reagent, for example methanol or ethanol. The temperature range is from −50° C. to 100° C. The time for completion of the reaction varies with the nature of $R_{74}$ and the base, proceeding in the case of alkali carbonates in a few minutes when $R_{74}$ is hydrogen but taking up to several hours when $R_{74}$ is ethyl, for example.

When the solvolysis proceeds too long or when conditions are too severe, an ester group ($R_1$) is often removed. They are, however, readily replaced by methods known in the art. See the discussion below.

The formula LXXI compound is prepared from the formula LXX compound by oxidation of the C-15 hydroxy to a 15-oxo. Accordingly, as is known in the art, 2,3-dichloro-5,6-dicyano-1,4-benzoquinone, activated manganese dioxide, or nickel peroxide (See Fieser, et al., "Reagents for Organic Synthesis", John Wiley and Sons, New York, N.Y., pgs. 215, 637, and 731) is advantageously employed. Thereafter, the formula LXXI compound is prepared from the 15-oxo compound by transforming the C-9 and C-11 hydroxy hydrogens to silyl derivatives. Procedures known in the art are employed. See for reference Pierce, "Silylation of Organic Compunds," Pierce Chemical Company, Rockford, Ill. (1968). In employing the silylation, sufficient silylating reagent must be used so that the reaction proceeds to completion. The necessary silylating reagents for these transformations are known in the art or are prepared by methods known in the art. See for reference, Post, "Silicones and Other Silicone Compounds," Reinhold Publishing Corp., New York, N.Y. (1949).

The formula LXXII compound wherein $Y_2$ is cis—CH=CH— is then prepared from the formula LXXI compound by first optionally transforming the trans—CH=CH— moiety to the $Y_2$ moiety following the procedure of Chart A for the analogous transformation and thereafter transforming the C-15 oxo to an $M_5$ moiety, for example by use of a Grignard reagent or trimethylaluminum (when 15-methyl intermediates are to be prepared) or reduction of a carbonyl to an alcohol (when 15-hydroxy compounds are to be prepared). Thereafter, the silyl groups are hydrolyzed, using, for example, dilute aqueous acetic acid in a water miscible solvent, such as ethanol (sufficient to yield a homogeneous reaction mixture). At 25° C., the hydrolysis is ordinarily complete in 2 to 12 hr. Further, the hydrolysis is preferably carried out in an inert atmosphere, e.g., nitrogen or argon.

The formula LXXIII compound is represented by the formula LXX compound when $Y_2$ is trans—CH=CH and $M_1$ and $M_9$ are the same. Alternatively, the formula LXXIII compound is prepared from the formula LXXII compound by separation of the C-15 epimers and an optional dehydrohalogenation when $Y_1$ is —C≡C—. Such separation proceeds by methods discussed in Chart A for accomplishment of this purpose (e.g., thin layer chromatography or high pressure liquid chromatography) and dehydrohalogenation proceeds by reaction with base, as in Chart A.

Referring to Chart D there are shown process steps by which the formula LXXVI bicyclo hexene is transformed first to an oxetane (formula LXXVII) with a fully developed side chain, e.g.,

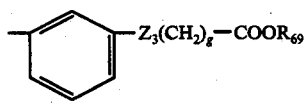

wherein $Z_3$ is oxa or methylene and ultimately to the formula LXXXIV compound. In Chart D, $R_{69}$ is hydrogen or alkyl of one to 4 carbon atoms, inclusive, and $R_{70}$ is hydrogen, alkyl of one to 4 carbon atoms, inclusive, or silyl of the formula $(G_1)_3Si-$ wherein $G_1$ is as defined herein above.

In transforming LXXVI to LXXVII in Chart D, there is employed an aldehyde of the formula

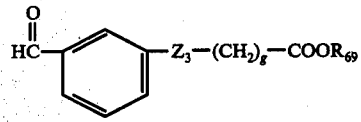

wherein $Z_3$ and $R_{69}$ are as defined above. Such aldehydes are available or are readily prepared by methods known in the art, e.g.,

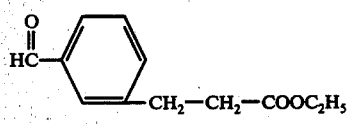

The conditions for this transformation are essentially the same as for the corresponding step of Chart C (i.e., LXI to LXII). Thereafter, the preparation of the formula LXXXI compound proceeds by methods analogous to the corresponding steps of Chart C (i.e., LXII to LXVI) with the preference that LXXVII to LXXVIII is accomplished catalytically.

The steps transforming LXXXI to LXXXIV then proceed in similar fashion, employing the same or similar reagents and conditions as the corresponding steps of Chart C discussed above.

Referring next to Chart E the process steps are shown whereby aldehyde LXXX of Chart D is transformed to a 17,18-tetradehydro-PG intermediate (formula LXXXIX) and 17,18-didehydro-PG intermediate (formula XC).

In Chart E, a Wittig reagent is employed which is prepared from a phosphonium salt of a haloalkyne of the formula

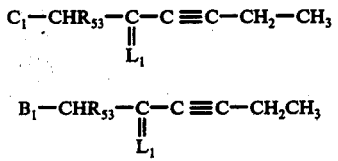

wherein $R_{53}$ and $L_1$ are as defined above, (See, for example, U. Axen et al., Chem. Comm. 1969, 303, and ibid. 1970, 602) in transforming LXXXVI to LXXXVII.

Thereafter, in subsequent transformations yielding the 17,18-tetradehydro compound LXXXIX, the reagents and conditions are similar to those employed for the corresponding reactions shown in Chart E.

Transformation of the formula LXXXIX compound to the formula XC compound is accomplished by hydrogenation of LXXXIX using a catalyst which catalyzes hydrogenation of $-C\equiv C-$ only to cis$-CH=$ CH$-$, as known in the art. See, for example, Fieser et al., "Reagents for Organic Syntheses", pp. 566–567, John Wiley and Sons, Inc., New York (1967). Preferred is Lindlar catalyst in the presence of quinoline. See Axen, references cited above.

As discussed above, Chart F provides a method whereby the formula XCI PG-type intermeidate, prepared according to Chart G or Chart D is transformed to the corresponding formula XCIV 16-phenoxy-PG-type intermediates.

The formula XCII compound is prepared from the formula XCI compound by cleavage of the 13,14-trans double bond, conveniently by ozonolysis. Ozonolysis proceeds by bubbling dry oxygen, containing about 3 percent ozone, through a mixture of a formula XCI compound in a suitable nonreactive diluent. For examle, n-hexane is advantageously employed. The ozone may be generated using methods known in the art. See, for example, Fieser, et al., "Reagents for Organic Synthesis," John Wiley and Sons, Inc. (1967), pages 773–777. Reaction conditions are maintained until the reaction is shown to be complete, for example, by silica gel thin layer chromatography or when the reaction mixture no longer rapidly decolorizes a dilute solution of bromine in acetic acid.

The formula XCIII compound is then prepared from the formula XCII compound by blocking with an $R_{65}$ blocking group and thereafter employing a phosphonate of the formula:

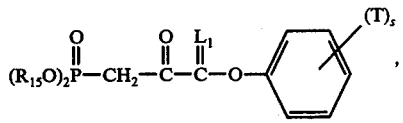

wherein $R_{15}$, $L_1$, T, and s are as defined above. Phosphonates of this general formula are prepared by methods known in the art. See the text hereinabove accompanying Chart A for discussion of the preparation and the appropriate reaction conditions by which the Wittig reaction proceeds. The formula XCIV compound is prepared from the formula XCIII compound by transformation of the 15-oxo moiety to an $M_1$ moiety. Methods hereinabove, particularly those discussed in Charts C and D above, are employed.

Optionally the method of Chart F is used to introduce the various other $R_7$ moieties to the formula XCII compound using the appropriate phosphonate.

Accordingly, the procedures of Charts A through F above provide methods whereby $PGF_\alpha$- or 11-deoxy-$PGF_\alpha$-type compounds are prepared. By the procedure described in the charts below (Charts G, H, and I) methods are provided whereby the $PGF_\alpha$-, 11-deoxy-$PGF_\alpha$-type compounds described above are transformed to the various 2-decarboxy-2-aminomethyl- or 2-(substituted amino)methyl-$PGF_\alpha$- or 11-deoxy-$PGF_\alpha$-type compounds of this invention or methods whereby the above $PGF_\alpha$- or 11-deoxy-$PGF_\alpha$-compounds are transformed to prostaglandin-type compounds of various cyclopentane ring structures (e.g., PGD-, or 11-deoxy-PGE-type compounds) and thereafter to the various novel prostaglandin analogs of the present invention.

With respect to Chart G a method is provided whereby the formula Cl $PGF_{2\alpha}$- or 11-deoxy-$PGF_{2\alpha}$-type free acid is transformed to the various 2-decarboxy-2-aminomethyl or 2-decarboxy-2-(substituted amino)methyl-$PGF_\alpha$- or 11-deoxy-$PGF_\alpha$-type compounds of formulas CIV, CVI, CVII, CVIII, CIX, or CX.

By the procedure of Chart G the formula Cl compound is transformed to a formula CII mixed acid anhydride. These mixed anhydrides are conveniently prepared from the corresponding alkyl, aralkyl, phenyl, or substituted phenyl chloroformate in the presence of an organic base (e.g., triethylamine). Reaction diluents include water in combination with water miscible organic solvents (e.g., tetrahydrofuran). This mixed anhydride is then transformed to either the formula CIII PG-type, amide or formula CV PG-type, azide.

For preparation of the $PGF_{2\alpha}$-type, amide (formula CIII) the formula CII mixed acid anhydride is reacted with liquid ammonia or ammonium hydroxide.

Alternatively, the formula CIII compound is prepared from the formula CI free acid by methods known in the art for transformation of carboxy acids to corresponding carboxyamides. For example, the free acid is transformed to a corresponding methyl ester (employing methods known in the art; e.g., excess etheral diazomethane), and a methyl ester thus prepared is transformed to the formula CIII amide employing the methods described for the transformation of the formula CII mixed acid anhydride to the formula CIII amide.

Thereafter the formula CIV 2-decarboxy-2-aminomethyl-$PGF_{2\alpha}$- or 11-deoxy-$PGF_{2\alpha}$-type compound is prepared from the formula CIII compound by carbonyl reduction. Methods known in the art art are employed in this transformation. For example, lithium aluminum hydride is conveniently employed.

The formula CII compound is alternatively used to prepare the formula CV azide. This reacton is conveniently carried out employing sodium azide by methods known in the art. See for example, Fieser and Fieser, Reagents for Organic Synthesis vol. 1, pgs. 1041–1043, wherein reagents and reaction conditions for the azide formation are discussed.

Finally, the formula CVI urethane is prepared from the formula CV azide reaction with an alkanol, aralkanol, phenol, or substituted phenol. For example, when methanol is employed the formula CVI compound is prepared wherein $R_1$ is methyl. This formula CVI PG-type product is then employed in the preparation of either the formula CVII or CVIII product.

In the preparation of the formula CVII primary amine from the formula CVI urethane, methods known in the art are employed. Thus, for example, treatment of the formula CVII urethane with strong base at temperatures above 50° C. are employed. For example, sodium potassium or lithium hydroxide is employed.

Alternatively, the formula CVI compound is employed in the preparation of the formula CVIII compound. Thus, when $L_1$ is alkyl the formula CVIII compound is prepared by reduction of the formula CVI urethane wherein $R_1$ is alkyl. For this purpose, lithium aluminum hydride is the conveniently employed reducing agent.

Thereafter, the formula CVIII product is used to prepare the corresponding CIX urethane by reaction of the formula CVIII secondary amine (wherein $L_2$ is alkyl) with an alkyl chloroformate. The reaction thus proceeds by methods known in the art for the preparation of carbamates from corresponding secondard amines. Finally, the formula CX product wherein $L_2$ and $L_3$ are both alkyl is prepared by reduction of the formula CIX carbamide. Accordingly, methods hereinabove described for the preparation of the formula CVIII compound from the formula CVI compound are used. Thus, Chart A provides a method whereby each of the various $PGF_{2\alpha}$- or 11-deoxy-$PGF_{2\alpha}$-type products of this invention is prepared. Optionally, the varius reaction steps herein may be proceeded by the employment of blocking groups according to $R_{10}$, thus necessitating their subsequent hydrolysis in preparing each of the various products above. Methods described hereinabove for the introduction and hydrolysis of blocking groups according to $R_{10}$ are employed.

Finally, the processes described above for converting the formula CII compound to the formula CV compound and the varius compounds thereafter, result in shortening the 8α-side chain of the formula CI compound by one carbon atom. Accordingly, the formula CI starting material should be selected so as to compensate for the methylene group which is consumed in the steps of the above synthesis. Thus, where a 2α-homo-product is desired a corresponding formula CI 2α,2b-dihomo starting material must be employed. Starting materials containing an additinal methylene group in the formula CI compound between the $Z_1$ moiety and the carboxyl are prepared by methods known in the art or procedures described in Charts A through F. For example, Wittig reagents containing an additional methylene are known in the art or prepared by methods described above.

Chart H provides a method which is alternatively useful for the preparation of the PG-type products of the present invention. The formula CXXI compound of Chart H is known in the art or prepared by methods herein above described. The formula CXXII primary alcohol is prepared from the formula CXXI compound by reduction of the carboxyl. This reduction is conveniently carried out employing methods known in the art. Thus, for example, lithium aluminum hydride as is known in the art, in a suitable organic solvent (e.g., tetrahydrofuran) is employed to effect this reduction. Thereafter, the CXXIII sulfonic acid ester is prepared from the formula CXXII primary alcohol by reaction with the corresponding sulfonyl chloride. For example, it is preferred to use readily available sulfonyl chlorides, such as p-toluenesulfonyl chloride. The reaction proceeds in the presence of an amine base (e.g., pyridine or triethylamine) and at temperatures at or about 0° to 5° C., so as to assure selective sulfonylation of the primary alcohol.

Thereafter, the formula CXXIII compounds is transformed to the formula CXXIV azide by reaction with a stirred suspension of sodium azide in dimethylformamide.

Thereafter, the formula CXXIV compound is transformed to the formula CXXV primary amine by lithium aluminum hydride reduction.

Accordingly, in the proceeding Charts are provided methods whereby the various novel $PGF_{60}$ or 11-deoxy-$PGF_\alpha$ analogs of the present inventon are prepared. However, for the various process steps of Charts G and H the use of lithium aluminum hydride may reduce the acetylenic triple bond at C-13 to C-14. Accordingly, when such reductions are to be employed, it is preferred that in place of the 13-acetylenic starting material that a corresponding 14-halo (e.g., chloro or bromo) compound be employed. This compound is then dehydrohalogenated following the procedure of Chart A following lithium aluminum hydride reduction.

Chart I provides a method whereby the formula CXXXI $PGF_{60}$- or 11-deoxy-$PGF_{60}$-type product herein is transformed to a corresponding PGE- or 11-deoxy-PGE-, PGA-, PGD-, 9-deoxy-PGD-, or 9-deoxy-9,10-didehydro-PGD-type product. Procedures for the transformations of Chart I are generally known in the art and comprise those methods for transforming $PGF_\alpha$-type products to PG-type products of various ring structures. In the transformations of Chart I, it is preferred that at least one $L_2$ and $L_3$ be —$COOR_1$. Accordingly, these preferred compounds wherein $R_1$ is —$COOR_1$ are transformed to PG-type products wherein $R_2$ and $R_3$ are as defined above by the transformations described in Chart G. In affecting transformation of those compounds wherein one of $L_2$ and $L_3$ is —$COOR_1$ to the more general prostaglandin analogs of the present invention, it is preferred for those compounds with a carbonyl-containing cyclopentane ring that prior to the transformation of the C-2 carboxyl that such carbonyl be protected by replacing the carbonyl with an alkylene-ketal. For example, procedures and reagents are readily available in the art for transforming carbonyl containing compounds to ethyleneketals as described in Fiester and Fieser, Reagents for Organic Synthesis, Vol. 1, page 376–377. The alkyleneketals produced are thereafter transformed to corresponding carbonyl containing prostaglandin analogs wherein $R_2$ and $R_3$ are as defined above and finally the alkyleneketals are hydrolyzed as known in the art. See, the reference immediately cited above.

Thus, the transformation of the formula CXXXI compound to the formula CXXXII compound proceeded by methods known in the art for transformation of $PGF_\alpha$- or 11-deoxy-$PGF_\alpha$-type compunds to PGE-type compounds. For example, $PGF_\alpha$- or 11-deoxy-$PGF_\alpha$-type compounds are selectively silylated at C-11 and C-15 or at C-15 in preference to silylation at C-9, and this selectively silylated compound is oxidized with a Jones or Collins reagent as is known in the art, and finally the silyl groups are hydrolyzed under acidic conditions, thereby preparing a PGE- or 11-deoxy-PGE-type product according to formula CXXXII. This formula CXXXII product is then dehydrated under acidic conditions as is known in the art for transformations of PGE-type compounds (formula CXXXII, wherein $R_8$ is hydroxy) to corresponding PGA-type compounds.

Alternatively, the formula CXXXI compound is transformed to the formula CXXXIV by selective replacement of the 15-hydroxy hydrogen with the blocking group according to $R_{10}$. This selective blocking at C-15 is accomplished by preparing a 9,11-alkylboronate of the formula CXXXI compound by methods known in the art; thereafter etherifying at C-15: hydrolyzing the 9,11-boronate; and finally selectively oxidizing the C-11 hydroxy to an oxo. This formula CXXIV compound is then transformed either to a formula CXXV compound (hydrolysis) or to the formula CXXXVII compound.

Also the formula CXXXV compound is transformed to the formula CXXXVI compound by mild acidic dehydration. Dilute organic acids, such as acetic acid, are usefully employed in this dehydration, or alternatively, the formula CXXXV compound is allowed to stand on a silica gel column, whereby the dehydration occurs spontaneously within one to 5 days.

Finally, the transformation of the formula CXXXIV compound to the formula CXXXVII compound proceeds first by dehydration of the formula CXXXIV compound (as described in the transformation of the formula CXXXV to the formula CXXXVI compound) followed by a sodium borohydride reduction of the 11-ketone and the endocyclic double bond. Thus, methods known in the art for the transformation of PGA compounds to corresponding 11-deoxy-PGF compounds are employed. Finally, the formula CXXXVII compound is prepared from the dehydrated, reduced formula CXXXV compound by oxidation of the 11-hydroxy to a ketone, and hydrolysis of the C-15 blocking group. The oxidation proceeds as in the transformation above of $PGF_\alpha$- or 11-deoxy-$PGF_\alpha$-type compound to PGE- or 11-deoxy-PGE-type compounds and the hydrolysis by methods described above for removal of blocking groups according to $R_{10}$.

In the employment of the processes above when 11-deoxy-15-tertiary alcohols are to be prepared ($R_5$ is methyl), the use of blocking groups at C-15 is not required. Accordingly, in the steps of the above charts the introduction and hydrolysis of blocking groups are thereby omitted by the preferred process.

Certain (3RS)-3-methyl lactones of chart A may be separated into their respective (3R) and (3S)-epimers by silica gel chromatographic separation or high pressure liquid chromatographic techniques. Where such separation is possible, this route is preferred. Accordingly, in these cases the separation is effected and $M_5$ is

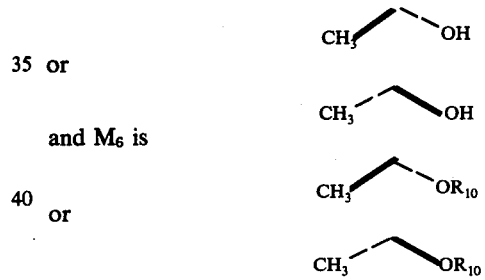

and $M_6$ is wherein $R_{10}$ is a blocking group. Accordingly, the corresponding separation procedures are omitted when the optional lactone separation is employed.

Optically active PG-type products are obtained from optically active intermediates, according to the process steps of the above charts. Likewise enantiomeric PG-type compounds are obtained from corresponding enantiomeric PG-type intermediates following the procedures in the above charts. When racemic intermediates are used in the reactions above, racemic products are obtained.

In all of the above described reactions, the products are separated by conventional means from starting material and impurities. For example, by use of silicagel chromatography monitored by thin layer chromatography the products of the various steps of the above charts are separated from the corresponding starting materials and impurities.

The acid addition salts of the 2-decarboxy-2-aminomethyl- or 2-(substituted aminomethyl)-PG analogs provided by this invention are the hydrochlorides, hydrobromides, hydriodides, sulfates, phosphates, cyclohexanesulfamates, methanesulfonates, ethanesulfonates, benzenesulfonates, toluene-sulfonates and the like, prepared by reacting the PG-analog with a stoichiometric equivalent of the acid corresponding to the pharmacologically acceptable acid addition salt.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer on an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

PREPARATION 1

Dimethyl 3,3-dimethyl-2-oxo-4-phenylbutylphosphonate, $$(C_6H_5)-CH_2-C(CH_3)_2-\overset{O}{\underset{\|}{C}}-CH_2-\overset{O}{\underset{\|}{P}}-(OCH_3)_2.$$

A. To a solution of 101.2 g. of diisopropylamine in 125 ml. of tetrahydrofuran under nitrogen at 0° C. is added dropwise with cooling (using an ice-methanol bath) 625 ml. of n-butyllithium in hexane. To the resulting solution is added dropwise with cooling 46.5 ml. of isobutyric acid. This mixture is then stirred at 0° C. for 90 min. and thereafter cooled to −15° C. Benzyl chloride (60 ml.) is added with stirring at such a rate as to maintain the reaction temperature below −5° C. The resulting mixture is thereafter stirred at ambient temperature for 4 hr. This stirred mixture is then diluted with diethyl ether and excess cold dilute hydrochloric acid. The organic layer is washed with saline and thereafter dried, concentrated, and the residue distilled under vacuum. Accordingly, there is prepared 2,2-dimethyl-3-phenyl propionic acid.

B. A mixture of 48 g. of the product of part A of this example and 82 g. of thionyl chloride are heated with stirring on a steam bath for 2 hr. The mixture is then concentrated under vacuum. Thereafter dry benzene is added and the resulting mixture is concentrated again, removing all traces of thionyl chloride. Distillation of this residue yields 48.2 g. of 2,2-dimethyl-3-phenylpropionyl chloride.

C. To a solution of 63 g. of dimethylmethylphosphonate in 600 ml. of tetrahydrofuran under nitrogen at −75° C. is added with stirring 312 ml. of 1.6 molar n-butyllithium in hexane. The addition rate is adjusted so that the reaction temperature remains below 55° C. Ten minutes after the addition is complete, 48.2 g. of the reaction product of part B of this example and 50 ml. of tetrahydrofuran are added dropwise at such rate as to maintain the reaction temperature below −60° C. The resulting mixture is then stirred at −75° C. for 2 hr. and then ambient temperture overnight. Acetic acid (20 ml.) is thereafter added and the resulting mixture distilled under vacuum, thereby removing most of the tetrahydrofuran. The residue is then shaken with diethyl ether in methylene chloride (3:1 by volume) and a cold dilute sodium bicarbonate solution. The organic layer is then washed with brine, dried, and concentrated. The residue was crystallized from diethyl ether, yielding 54 g. of dimethyl 3,3-dimethyl-2-oxo-4-phenylbutylphosphonate, the title compound. The melting point is 48°-50° C.

Following the procedure of Preparation 1, but using in place of benzyl chloride substituted benzyl chlorides of the formula wherein T is fluoro, chloro, trifluoromethyl, alkyl of one to 3 carbon atoms, inclusive, or alkoxy of one to 3 carbon atoms, inclusive, and wherein s is zero, one, 2, or 3, with the proviso that not more than two T's are other than alkyl, and with the further proviso that the various T's may be the same or different, there are prepared the corresponding dimethyl 3,3-dimethyl-2-oxo-4-(substituted phenyl)-butylphosphonates. For example, there is prepared by this procedure dimethyl 3,3-dimethyl-2-oxo-4-(p-fluorophenyl)-butylphosphonate.

Further, following the procedure of Preparation 1, but using in place of the isobutyric acid of Preparation 1, part A, propionic acid, there is prepared dimethyl 3-methyl-2-oxo-4-phenylbutylphosphonate. Following the procedure of Preparation 1, but using the substituted benzyl chlorides described above in place of benzyl chloride and propionic acid in place of isobutyric acid there are prepared the various dimethyl 3-methyl-2-oxo-4-(substituted phenyl)-butylphosphonates wherein the phenyl substitution is as described above.

Further, following the procedure of Preparation 1, but using acetic acid in place of isobutyric acid as used in Preparation 1, part A, there is prepared dimethyl 2-oxo-4-phenylbutylphosphonate. Using acetic acid in combination with the various substituted benzyl chlorides described above according to the procedure of Preparation 1, there are prepared the various dimethyl 2-oxo-4-(substituted phenyl) butyl phosphonates, wherein the phenyl substitution is as described above.

Following the procedure of Preparation 1, but using 2,2-difluoroacetic acid in place of isobutyric acid as used in part A of Preparation 1, there is prepared dimethyl 3,3-difluoro-2-oxo-4-phenylbutylphosphonate. Further, following the procedure of Preparation 1, but using 2,2-difluoro acetic acid in combination with substituted benzyl chlorides described above, there are prepared the corresponding dimethyl 3,3-difluoro-2-oxo-4-(substitutedphenyl)butylphosphonate, wherein the phenyl substitution is as described above.

Further, following the procedure of Preparation 1, but using 2-fluoro acetic acid in place of isobutyric acid there is prepared dimethyl 3-fluoro-2-oxo-4-phenylbutylphosphonate.

Using 2-fluoro acetic acid and the various substituted benzyl chlorides described above according to the procedure of Preparation 1, there are prepared the various dimethyl 3-fluoro-2-oxo-4-(substituted phenyl)butyl phosphonates, wherein the phenyl substitution is as described above.

PREPARATION 2

Triphenylphosphonium Salt of 2,2-difluoro-5-bromopentanoic acid $Br(C_6H_5)_3P—(CH_2)_3—CF_2—COOH$.

A. Methyl furoate is dissolved in 180 ml. of methanol. Thereafter 1 g. of 5 percent palladium-on-charcoal is added. This mixture is then hydrogenated at 1 to 3 atmospheres. After 45 hr. 0.79 moles of hydrogen are consumed. The black mixture is then filtered through Celite using 50 ml. of methanol to wash the reaction flask and filter. Evaporation of the filtrate under reduced pressure at 40°–45° C. bath temperature yields 51 g. of a yellow oil which is thereafter distilled, collecting that fraction boiling at 32°–35° C. Thereby, methyl tetrahydrofuroate (46.7 g.) is prepared.

B. Anhydrous hydrobromic acid is bubbled through 50 ml. of acetic anhydride with cooling until a specific gravity of 1.3 is obtained. This reagent is then added to 25 g. of the reaction product of step A of this example, with exclusion of moisture while cooling and stirring. Stirring in the ice water bath is continued for 15 min.; thereafter, the mixture is allowed to stand at room temperature overnight. The reaction mixture is then poured into 600 g. of crushed ice and water with stirring and extracted with diethyl ether. The ether extract is washed with aqueous sodium hydroxide, dried over sodium sulfate, filtered, and thereafter evaporated under reduced pressure to yield 38 g. of a pale yellow oil, which is thereafter distilled under high vacuum, yielding 31.6 g. of methyl 2-acetoxy-5-bromo-pentanoate.

C. To a solution of 60 g. of the reaction product of part B of this example in 200 ml. of methanol is added 100 ml. of methanol, which is saturated with hydrobromic acid at 0° C. and 1.3 specific gravity before the addition. The reaction mixture is then allowed to stand at room temperature overnight. The solvent is thereafter evaporated under reduced pressure at 35° C. bath temperature and 400 ml. of toluene is thereafter added. The solvent is again evaporated. This residue is then dissolved in 2 l. of ethyl acetate, washed with 5 percent aqueous sodium hydroxide solution and sodium chlorie solution before being dried over sodium sulfate. Filtration and evaporation of the solvent under reduced pressure at 45° C. yields 42 g. of oil which is distilled under high vacuum, yielding 28.8 g. of methyl 2-hydroxy-5-bromopentanoate.

D. To a solution of 34.4 g. of the reaction product of part C of this example and 400 ml. of acetone is added with stirring and cooling 75 ml. of Jones reagent (26.73 G. of $CrO_3$ in 23 ml. of concentrated sulfuric acid, diluted to 100 ml. with water) at such a rate that the reaction temperature is maintained between 30° and 40° C. The reaction is complete in approximately 20 min. Thereafter the reaction mixture is stirred for 1.5 hr. Thereafter 150 ml. of isopropyl alcohol is slowly added with stirring during 30 min. The reaction mixture is then diluted with 1.8 l. of water and extracted with 2.4 l. of methylene chloride. These extracts are washed with brine and dried with sodium sulfate. Filtration and evaporation of the solvent under reduced pressure yields 30.8 g. of a pale yellow oil, containing methyl 2-oxo-5-bromopentanoate. This oil is used in the following steps of this example without further purification.

E. With the exclusion of moisture under a nitrogen atmosphere 195 ml. of $M_0F_6·BF_3$ is cooled in a dry-ice acetone bath. A solution of 30.8 g. of the reaction product of step D of this example and 40 ml. of methylene chloride is added dropwise with stirring over a period of 15 min. The reaction temperature is maintained between −35° and −45° C. Stirring in the dry ice-acetone bath is continued for one hr., the cooling bath thereafter is removed, and the reaction mixture thereafter diluted with 200 ml. of methylene chloride and 400 ml. of water. The organic and aqueous layers are separated, the aqueous layer being extracted with methylene chloride and the combined methylene chloride extracts washed with 250 ml. of water, 250 ml. of 5 percent aqueous potassium bicarbonate, 250 ml. of brine, and thereafter dried over sodium sulfate. Filtration and evaporation of the solvent yields 31.1 g. of a dark brown oil, which when distilled under high vacuum yields methyl 2,2-difluoro-5-bromopentanoate (14 g.).

F. The reaction product of part E of this example (28 g.) is stirred in 175 ml. of aqueous hydrobromic acid (specific gravity 1.71) for 3 hr. at room temperature. The reaction mixture is then cooled in an ice bath, and diluted with 1300 ml. of diethyl ether. The organic and aqueous layers are separated and the aqueous layer is extracted with diethyl ether. The combined ethereal extracts are washed with water and the aqueous phase backwashed with 400 ml. of diethyl ether. The combined ethereal solutions are then dried over sodium sulfate. Filtration and evaporation of the solvent yields 27.7 g. of a pale yellow oil, 2,2-difluoro-5-bromopentanoic acid, which is used in the following step of this example without further purification.

G. A mixture of 15.2 g. of the reaction product of part F of this example, 80 ml. of acetonitrile and 22 g. of triphenylphosphine are heated to reflux with stirring for 30 hr. The reaction mixture is then heated to 110° C., diluted with 160 ml. of toluene, and the mixture is allowed to cool slowly at room temperature for 12 hr. with stirring. The reaction mixture is then stored at 5° C. for 24 hr. A precipitate is collected, washed with 50 ml. of toluene, and dried under vacuum at room temperature. The title compound (20.9 g.) of this example is thereby obtained.

PREPARATION 3

(6-Carboxyhexyl)triphenylphoshonium bromide.

A mixture of 63.6 g of 7-bromoheptanoic acid, 80 g. of triphenylphosphine, and 300 ml. of acetonitrile, is refluxed for 68 hr. Thereafter 200 ml. of acetonitrile is removed by distillation. After the remaining solution is cooled to room temperature, 30 ml. of benzene is added with stirring. The mixture is then allowed to stand for 12 hr. A solid separates which is collected by filtration, yielding 134.1 g. of product, melting point 185°–187° C.

Following the procedure of Preparation 3, but using 3-bromopropionic acid, 4-bromobutanoic acid, 5-bromopentanoic acid, or 6-bromohexanoic acid, in place of 7-bromoheptanoic acid, there are prepared the corresponding (ω-carboxyalkyl)triphenylphosphonium bromides.

PREPARATION 4

3α-Benzoyloxy-5α-hydroxy-2β-(3-oxo-4,4-difluoro-trans-1-octenyl)-1α-cyclopentaneacetic acid, γ lactone (Formula XXII: $R_7$ is n-butyl, $R_{16}$ is benzoyloxy, and $R_3$ and $R_4$ of the $L_1$ moiety are fluoro.

Refer to Chart A.

A. A solution of 24.3 g. of thallous ethoxide in 125 ml. of dry benzene is cooled in an ice bath, and thereafter a solution of 25.3 g. of dimethyl 3,3-difluoro-2-oxo-heptylphosphonate in 75 ml. of benzene is added and thereafter rinsed with 50 ml. of benzene. The solution is stirred for 30 min. at 5° C. and thereafter 22.1 g. of crystalline 3α-benzoyloxy-5α-hydroxy-2β-carboxaldehyde-1α-cyclopentaneacetic acid, γ lactone is added rapidly. This reaction mixture is then stirred for 13 hr. at ambient temperature yielding a brown solution of pH 9–10. Acetic acid (6 ml.) is added and the mixture is transferred to a beaker with 600 ml. of diethyl ether. Celite and 500 ml. of water is added, followed by the addition of 30 ml. (about 33 g.) of saturated potassium iodide. The mixture (containing a bright yellow precipitate of thallous iodide) is stirred for about 45 min., and thereafter filtered through a bed of Celite. The organic layer is then washed with water, aqueous potassium bicarbonate, and brine. Thereafter the resulting mixture is dried over magnesium sulfate and evaporated at reduced pressure, yielding 33.6 g. of an oil, which is then chromatographed on 600 g. of silica gel packed in 20 percent ethyl acetate in cyclohexane. Elution, collecting 500 ml. fractions, with 2 l. of 20 percent, 2 l. of 25 percent, and 4 l. of 30 percent ethyl acetate in cyclohexane yields 20.3 g. of crude product, which upon recrystallization from 240 ml. of diethyl ether in pentane (2:1) yields 13.3 g. of 3α-benzoyloxy-5αhydroxy-2β-(3-oxo-4,4-difluoro-trans-1-octenyl)-1α-cyclopentaneacetic acid, γ lactone.

Alternatively this product is prepared by adding 3α-benzoyloxy - 2β - carboxyaldehyde - 5α - hydroxy - 1α-cyclopentaneacetic acid γ lactone (3 g.) in 30 ml. of dichloromethane to a solution of dimethyl 2-oxo-3,3-difluoroheptylphosphonate (6.69 g.) and sodium hydride (1.35 g.) in 15 ml. of tetrahydrofuran. The resulting reaction mixture is then stirred for 2 hr. at about 25° C., acidified with acetic acid, and concentrated under reduced pressure. The residue is partitioned between dichloromethane and water, and the organic phase is concentrated. The residue is chromatographed on silica gel, eluting with ethyl acetate in Skellysolve B (1:1).

Following the procedure of Example 4, but using in place of 3α-benzoyloxy-5α-hydroxy-2βcarboxalehyde-1α-cyclopentaneacetic acid γ lactone, 5α-hydroxy-2β-carboxaldehyde-1αcyclopentaneacetic acid γ lactone, there is obtained 5α-hydroxy-2β-(3-oxo-4,4-difluoro-trans-1-ocetnyl)-1α-cyclopentaneacetic acid γ lactone.

Further, following the procedure of Preparation 4, but using place of dimethyl 2-oxo-3,3-difluoroheptylphosphonate, any of the various dimethyl phosphonates described hereinabove there are prepared the corresponding 3α-benzoyloxy-5α-hydroxy-1α-cyclopentaneacetic acid α lactones or 5α-hydroxy-1α-cyclopentaneacetic acid γ lactones with a 2β-(3-oxo-trans-1-alkenyl)-substituent, optionally substituted, as follows:
4,4-difluorohexenyl; 4,4-difluoroheptenyl; 4,4-difluorononenyl; 4,4-difluorodecencyl; 4-fluorohexenyl; 4-fluoroheptenyl; 4-fluoroocentyl; 4-fluorononenyl; 4-fluorodecenyl; 4,4-dimethylhexenyl; 4,4-dimethylheptenyl, 4,4-dimethyloctenyl; 4,4-dimethylnonenyl; 4,4dimethyldecenyl; 4-methylhexenyl; 4-methylheptenyl; 4-methyloctenyl, 4-methylnonenyl; 4-methyldecenyl; hexenyl; heptenyl; octenyl; nonenyl; decenyl; 5-phenylpentenyl; 5-(m-trifluoromethylphenyl)-pentenyl; 5-(m-fluorophenyl)-pentenyl; 5-(m-chlorophenyl)-pentenyl; 5-(p-trifluoromethylphenyl)-pentenyl; 5-(p-fluorophenyl)-pentenyl; 5-(p-chlorophenyl)-pentenyl; 4-methyl-5-phenylpentenyl; 4-methyl-5-(m-trifluoromethylphenyl)pentenyl; 4-methyl-5-(m-fluorophenyl)-pentenyl; 4-methyl-5-(p-trifluoromethylphenyl)-pentenyl; 4-methyl-5-(p-fluorophenyl)-pentenyl;-4-methyl-5-(p-chlorophenyl)-pentenyl; 4,4-dimethyl-5-(m-trifluoromethylphenyl)-pentenyl; 4,4-dimethyl-5-(m-fluorophenyl)-pentenyl; 4,4-difluoro-5-(m-chlorophenyl)-pentenyl; 4,4-dimethyl-5-(p-trifluoromethylphenyl)-pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)-pentenyl; 4-fluoro-5-(m-fluorophenyl)-pentenyl; 4-fluoro-5-(m-chlorophenyl)-pentenyl; 4-fluoro-5-(p-trifluoromethylphenyl)-pentenyl; 4-fluoro-5-(p-fluorophenyl)-pentenyl; 4-fluoro-5-(p-chlorophenyl)-pentenyl; 4,4-difluoro-5-phenylpentenyl; 4,4-difluoro-5-(m-trifluoromethylphenyl)-pentenyl; 4,4-difluoro-5-(m-fluorophenyl)-pentenyl; 4,4-difluoro-5-(m-chlorophenyl)-pentenyl; 4,4-difluoro-5-(p-trifluoromethylphenyl)-pentenyl; 4,4-difluoro-5-(p-fluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4-(p-fluorophenoxy)-butenyyl; 4-(p-chlorophenoxy)-butenyl; 4-methyl-4-phenoxybutenyl; 4-methyl-4-(m-trifluoromethylphenoxy)-butenyl; 4-methyl-4-(m-fluorophenoxy)-butenyl; 4-methyl-4-(m-chlorophenoxy)-butenyl; 4-methyl-4-(p-trifluoromethylphenoxy)-butenyl; 4-methyl-4-(p-fluorophenoxy)-butenyl; 4-methyl-4-(p-chlorophenoxy)-butenyl; 4,4-dimethyl-4-phenoxybutenyl; 4,4-dimethyl-4-(trifluoromethylphenoxy)-butenyl; 4,4-dimethyl-4-(m-fluorophenoxy)-butenyl; 4,4-dimethyl-4-(m-chlorophenoxy)-butenyl; 4,4-dimethyl-4-(p-trifluoromethylphenoxy)-butenyl; 4,4-dimethyl-4-(p-fluorophenoxy)-butenyl; 4,4-dimethyl-4-(p-chlorophenoxy)-butenyl; and the like.

PREPARATION 5

3α-(Benzoyloxy)-5α-hydroxy-2β-(3-oxo-cis-1-octenyl)-1α-cyclopentaneactic acid γ-lactone (Formula XXIII: $R_3$ and $R_4$ of the $L_1$ moiety are hydrogen, Rhd 7 is n-butyl, $R_{16}$ is benzoyloxy, and $Y_2$ is cis—CH═CH—).

Refer to Chart A.

A solution of 16.3 g. of the reaction product of Preparation 4 in one 1. of acetone (agitated by bubbling nitrogen through the solution) is irradiated for 3 hr. in a Raynot Photochemical Reactor (RPR-208, using 8 lamps) wherein the photo emission spectrum shows substantial intensity at a wave length at or around 3500 Angstroms. The solvent is then evaporated and the residue chromatographed on 1.5 kg. of silica gel packed in 10 percent ethyl acetate in cyclohexane. Elution, collecting 1.5 l. fractions, with 4.5 l. each of 10 percent, 15 percent, 20 percent, 25 percent, 30 percent, 35 percent, and 40 percent ethyl acetate in cyclohexane yields starting material and crude 3αbenzoyloxy-5α-hydroxy-2β-(3-oxo-cis-1-octenyl)-1α-cycopentaneacetic acid γ lactone. Further, chromatographic purification yields pure cis isomer.

Following the procedure of Preparation 4 and Preparation 5 but using in place of dimethyl 2-oxo-heptylphosphonate employed according to the procedure of Preparation 4 any of the various dimethyl phosphonates described hereinabove there are prepared the corresponding 3α-benzoyloxy-5α-hydroxy-1α-cyclopentaneacetic acid γ lactones with a 2β-(3-oxo-cis-1-alkenyl)-substituent, optionally substituted, as follows:

4,4difuorohexenyl; 4,4-difluoroheptenyl; 4,4-difluorooctenyl; 4,4-difluorononenyl; 4,4-difluorodecenyl; 4-fluorohexenyl; 4-fluoroheptenyl; 4-fluorooctenyl; 4-;fluorononenyl; 4-fluorodecenyl; 4,4-dimethylhexenyl; 4,4-dimethylheptenyl, 4,4-dimethyloctenyl; 4,4-dimethylnonenyl; 4,4-dimethyldecenyl; 4-methylhexenyl; 4-methylheptenyl; 4-methyloctenyl; 4-methylnonenyl; 4-methyldecenyl; hexenyl; nonenyl; decenyl; 5-phenylpentenyl 5-(m-trifluoromethylphenyl)-pentenyl 5-(m-fluorophenyl)-pentenyl; 5-(m-chlorophenyl)-pentenyl; 5-(p-trifluoromethylphenyl)-pentenyl; 5-(p-fluorophenyl)-pentenyl; 5-(p-chlorophenyl)-pentenyl; 4-methyl-5-phenylpentenyl; 4-methyl-5-(m-trifluoromethylphenyl)pentenyl; 4-methyl-5-(m-fluorophenyl)pentenyl; 4-methyl-5-(p-trifluoromethylphenyl)-pentenyl; 4-methyl-5-(p-fluorophenyl)-pentenyl; 4-methyl-5-(p-chlorophenyl)-pentenyl; 4,4-dimethyl-5-(m-trifluoromethylphenyl)-pentenyl; 4,4dimethyl-5-(m-fluorophenyl)-pentenyl; 4,4-dimethyl-5-(m-fluorophenyl)-pentenyl; 4,4-difluoro-5-(m-chlorophenyl)-pentenyl; 4,4-dimethyl-5-(p-trifluoromethylphenyl)-pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)-pentenyl; 4-fluoro-5-(m-fluorophenyl)-pentenyl; 4-fluoro-5-(m-chlorophenyl)-pentenyl; 4-fluoro-5-(p-trifluoromethylphenyl)-pentenyl 4-fluoro-5-fluorophenyl)-pentenyl; 4-fluoro-5-(p-chlorophenyl)-pentenyl; 4,4-difluoro-5-phenylpentenyl; 4,4-difluoro-5-(m-trifluoromethylphenyl)-pentenyl; 4,4-difluoro-5(m-fluorophenyl)-pentenyl; 4,4-difluoro-5-(m-chlorophenyl)-pentenyl; 4,4-difluoro-5-(p-trifluromethylphenyl)-pentenyl; 4,4-difluoro-5-(p-trifluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4-(p-fluorophenoxy)-butenyl; 4-(p-chlorophenoxy)-butenyl; 4-methyl-4-phenoxybutenyl; 4-methyl-4-(m-trifluoromethylphenoxy)-butenyl; 4-methyl-4-(m-fluorophenoxy)-butenyl; 4-methyl-4-(m-chlorophenoxy)-butenyl; 4-methyl-4-(p-trifluoromethylphenoxy)-butenyl; 4-methyl-4-(p-fluorophenoxy)-butenyl; 4-methyl-4-(p-chlorophenoxy)-butenyl; 4,4-dimethyl-4-phenoxybutenyl; 4,4-dimethyl-4-(trifluoromethylphenoxy)-butenyl; 4,4-dimethyl-4-(m-fluorophenoxy)-butenyl; 4,4-dimethyl-4-(m-chlorophenoxy)-butenyl; 4,4-dimethyl-4-(p-trifluoromethylphenoxy)-butenyl; 4,4-dimethyl-4-(p-fluorophenoxy)-butenyl; 4,4-dimethyl-4-(p-chlorophenoxy)-butenyl; and the like.

Following the procedure of Preparation 5, but using 2β-(3-oxo-trans-1, cis-5-octadienyl)-containing bicyclic lactones in places of the starting material of Preparation 5, there is prepared 3α-benzoyloxy-5α-hydroxy-2β-(3-oxo-cis,cis-1,5-octadienyl)-1α-cyclopentaneacetic acid γ lactone. This cis,cis-1,5-octadienyl compound is separated from the mixture of cis,cis-1,5-and trans-1-cis-5-geometric isomers produced by the photoiosmerization described in Preparation 5, by the chromatogaphic separation method described therein. The various other 3α-benzoyloxy-5α-hydroxy-1α-cyclopentaneactic acid γ-lactones with 2β-(3-oxo-cis, cis-1,5-octadienyl)substituents are likewise prepared, e.g. 4-fluoro; 4-methyl; 4,4-dimethyl; and 4,4-difluoro.

PREPARATION 6

3α-benzoyloxy-5α-hydroxy-2β-(3-oxo-4,4-difluorooctyl)-1α-cyclopentaneacetic acid γ-lactone (Formula XXIII: $R_3$ and $R_4$ of the $L_1$ moiety are fluoro, $R_7$ is n-butyl, $Y_2$ is $-CH_2CH_2-$, and $R_{16}$ is benzoyloxy).

Refer to Chart A.

A mixture of the reaction product of Preparation 4, a 5 percent palladium-on-charcoal catalyst and 400 ml. of ethyl acetate are stirred under hydrogen for one hour, when hydrogen uptake ceases, the mixture is filtered and the filtrate evaporated to yield title compound.

Following the procedure of Preparation 6 but using any of the various products described following Preparation 5 there are prepared the corresponding 3α-benzoyloxy-5α-hydroxy-1α-cyclopentaneacetic acid γ lactones with a 2β-(3-oxoalkyl)-substituent, optionally substituted, as follows:

4,4-diflurorheptyl; 4,4-difluorooctyl; 4,4-difluorononyl; 4,4-difluorodecyl; 4-fluorohexyl; 4-fluoroheptyl; 4,-fluorooctyl; 4-fluorononyl; 4-fluorodecyl; 4,4-dimethylhexyl; 4,4-dimethylheptyl; 4,4-dimethyloctyl; 4,4-dimethylnonyl; 4,4-dimethyldecyl; 4-methylhexyl; 4-methylheptyl, 4-methyloctyl, 4-methylnonyl; 4-methyldecyl; hexyl; heptyl; nonyl; decyl; 5-phenylpentyl; 5-(m-trifluoromethylphenyl)-pentyl; 5-(m-fluorophenyl)-pentyl; 5-(m-chlorophenyl)-pentyl; 5-(p-trifluoromethylphenyl):pentyl; 5-(p-fluorophenyl)-pentyl; 5-(p-chlorophenyl)-pentyl; 4-methyl-5-phenylpentyl; 4-methyl-5-(m-trifluoromethylphenyl)pentyl; 4-methyl-5-(m-fluorophenyl)-pentyl; 4-methyl-5-(p-trifluoromethylphenyl)-pentyl; 4-methyl-5-(p-fluorophenyl)-pentyl; 4-methyl-5-(p-chlorophenyl)-pentyl; 4,4-dimethyl-5-(m-trifluoromethylphenyl)-pentyl; 4,4-dimethyl-5-(m-fluorophenyl)-pentyl; 4,4-difluoro-5-(m-chlorophenyl)-pentyl; 4,4-dimethyl-5-(p-trifluoromethylphenyl)-pentyl; 4,4-dimethyl-5-(p-fluorophenyl)-pentyl; 4,4-dimethyl-5-(p-chlorophenyl)-pentyl; 4-fluoro-5-phenylpentyl; 4-fluoro-5-(m-trifluoromethylphenyl)-pentyl; 4-fluoro-5-(m-fluorophenyl)-pentyl; 4-fluoro-5-(m-chlorphenyl)-pentyl; 4-fluoro-5-(p-trifluoromethylphenyl)-pentyl; 4-fluoro-5-(p-fluorophenyl)-pentyl; 4-fluoro-5-(p-chlorphenyl)-pentyl; 4,4-difluoro-5-phenylpentyl; 4,4-difluoro-5-(m-trifluoromethylphenyl)-pentyl; 4,4-difluoro-5-(m-fluorophenyl)-pentyl; 4,4-difluoro-5-(m-chlorphenyl)-pentyl; 4,4-difluoro-5-(p-trifluoromethylphenyl)-pentyl; 4,4-difluoro-5-(p-fluorophenyl)-pentyl; 4,4-difluoro-5-(p-chlorphenyl)-pentyl; 4-phenoxybutyl;

4-(m-trifluoromethylphenoxy)-butyl; 4-(p-fluorophenoxy)-butyl; 4-(m-chlorophenoxy)-butyl; 4-(m-trifluoromethylphenoxy)-butyl; 4-(p-fluorophenoxy)-butyl; 4-(p-chlorophenoxy)-butyl; 4-methyl-4-phenoxybutyl; 4-methyl-4-(m-trifluoromethylphenoxy)-butyl; 4-methyl-4-(m-fluorophenoxy)-butyl; 4-methyl-4-(m-chlorophenoxy)-butyl; 4-methyl-4-(p-trifluoromthylphenoxy)-butyl; 4-methyl-4-(p-fluorophenoxy)-butyl; 4-methyl-4-(p-chlorophenoxy)-butyl; 4,4-dimethyl-4-phenoxybutyl; 4,4-dimethyl-4-(trifluoromethylphenoxy)-butyl; 4,4-dimethyl-4-(m-fluorophenoxy(-butyl; 4,4-dimethyl-4-(m-chlorphenoxy)-butyl; 4,4-dimethyl-4-(p-trifluoromethylphenoxy)-butyl; 4,4-dimethyl-4-(p-fluorophenoxy)-butyl; 4,4-dimethyl-4-(p-chlorophenoxy)-butyl; and the like.

Following the procedure of Prepration 5, but using the 2$\beta$-(3-oxo-trans-1,cis-5-octadienyl)-compounds described above, there is prepared 3$\alpha$-benzoyloxy-5$\alpha$-hydroxy-2$\beta$-(3-oxo-cis-5-octenyl)-1$\alpha$-cyclopentaneacetic acid $\gamma$ lactone. This cis-5-octenyl compound is separated from the mixture of unsaturated lactones which are produced by the hydrogenation described in Preparation 6, by chromatogrphic separation. The varius 5$\alpha$-hydroxy-1$\alpha$-cyclopentaneacetic acid $\gamma$ lactones wich 2$\beta$-(3-oxo-cis-5-octenyl) substitutes are likewise prepared, e.g. 4-fluoro-4-methyl-4,4-dimethyl- and the unsubstituted 2$\beta$-(3-oxo-cis-5-octenyl) compound from the formula XXII compound wherein $R_{16}$ is hydrogen.

PREPARATION 7

3$\alpha$-benzoyloxy-5$\alpha$-hydroxy-2$\beta$-(2-chloro-3-oxo-4,4-dimethyl trans-1-octenyl)-1$\alpha$-cyclopentaneacetic acid $\gamma$ lactone (Formula XXIII: $R_{16}$ is benzoyloxy, $R_3$ and $R_4$ of the $L_1$ moiety are methyl, $R_7$ is n-butyl, and $Y_2$ is trans—CH=CCl—).

A solution of 3$\alpha$-benzoyloxy-5$\alpha$-hydroxy-2$\beta$-(3-oxo-4,4-dimethyl-trans-1-octenyl)-1$\alpha$-cyclopentaneacetic acid $\gamma$ lactone prepared according to Preparation 4 (1.15 g.) in dioxane (35 ml.) is treated with N-chlorosuccinimide (9.7 g.) and stirred for 6 days. The resulting solution is then diluted with methylene chloride, washed with saline and a sodium sulfate solution, dried, and evaporated to yield a viscous residue. The residue in benzene is subjected to silica gel chromatography, eluting with hexane and ethyl acetate (9:1) whereupon pure 3$\alpha$-benzoyloxy-5$\alpha$-hydroxy-2$\beta$-(1,2-dichloro-3-oxo-4,4-dimethyl-octyl)-1$\alpha$-cyclopentane-acetic acid $\gamma$ lactone is recovered (as a mixture of isomers). Thereafter the dichlorides so obtained are diluted with pyridine (20 ml.) and heated at 100° C. for 4.5 hr. The resulting solution is then diluted with diethyl ether and washed with ice cold dilute hydrochloric acid and brine. The resulting mixture is then dried and subject to silica gel chromatography, eluting with hexane and ethyl acetate (9:1), yielding 0.765 g. of pure product. NMR absorptions are observd 0.85, 1.22, 1.0–1.9, 1.9–3.5, 4.8–5.1, 5.35, 5.28, 7.2–7.6, and 7.8–8.1 $\delta$. The mass spectrum shows peaks at 432, 396, 376, 378, 254, and 256.

Alternatively, the above starting material (0.190 g.) in dry pyridine (5 ml.) at 0° C. is treated with freshly distilled sulfuryl chloride (0.386 g.) and the reaction is maintained for 5 hr. Thereafter additional sulfuryl chloride (0.667 g.) and pyridine (5 ml.) is added and the reaction continued for 12 hr. at ambient temperature. A resulting dark solution is then diluted with methylene chloride, washed with ice cold dilute phosphoric acid, sodium becarbonate solution, dried, and evaporated.

The residue is chromatographed on silica gel eluting with hexane and ethyl acetate (9:1). Pure product identical with that recovered in the preceeding paragraph is obtained.

Further following the procedure of Preparation 7, there are prepared corresponding 3$\alpha$-benzoyloxy-5$\alpha$-hydroxy-1$\alpha$-cyclopentaneacetic acid $\gamma$ lactones or 5$\alpha$-hydroxy-1$\alpha$-cyclopentaneacetic $\gamma$ lactones with a 2$\beta$-(2-chloro-3-oxo-trans-1-alkenyl)-substituent, optionally substituted as indicated in Preparation 4 or in the text following Preparation 4.

PREPARATION 8

3$\alpha$-benzoyloxy-5$\alpha$-hydroxy-2$\beta$-(3-oxo-4,4-difluoro-trans-1, cis-5-octadienyl)- or 2$\beta$-[(3R)- or (3S)-3-hydroxy-4,4-difluro -trans-1, cis-5-octadienyl]-1$\alpha$-cyclopentaneacetic acid $\gamma$ lactone (Formula XXIII or XXIV: $R_{16}$ is benzoyloxy, $R_3$ and $R_4$ of the $L_1$ moiety are fluoro, $R_7$ is butenyl, $Y_2$ is trans—CH=CH—, and $R_5$ of the $M_5$ moiety of formula XXIV is hydrogen).

Refer to Chart A.

A. Following the procedure of Japanese Patent Appl. Number 0018-459, 3$\alpha$-benzoyloxy-5$\alpha$-hydroxy-2$\beta$-carboxaldehyde-1$\alpha$-cyclopentaneacetic acid $\gamma$-lactone is transformed to 3$\alpha$-benzoyloxy-5$\alpha$-hydroxy-2$\beta$-(2-formyl-trans-1-ethenyl)-1$\alpha$-cyclopentaneacetic acid $\gamma$-lactone.

B. Grignard reagents are prepared by reacting magnesium turnings with 1-iodo-1,1-difluro -cis-2-pentene. 1-iodo-1,1-difluoro-cis-2-pentene is prepared as follows:

2,2-difluoro-acetic acid is esterified with excess ethereal diazomethane. Thereafter the resulting methyl 2,2-difluoro-acetate is iodinized to methyl 2,2-difluoro-2-iodo-acetate by the procedure of Tetrahedron Lett. 3995 (1971) (e.g., addition of lithium diisopropylamine to the starting material, followed by treatment with iodine). This product is then reduced to a corresponding aldehyde 2,2-difluoro-2-iodo-acetaldehyde, employing diisobutyl aluminum hydride at −78° C. This aldehyde is then alkylated by a Wittig alkylation, employing the ylid ethyl triphenylphosphorane, $(C_6H_5)_3P$=CH—CH$_3$, thereby yielding the title iodide.

C. The Grignard reagent of part B is reacted with 3$\alpha$-benzoyloxy-5$\alpha$-hydroxy-2$\beta$-(2-formyl-trans-1-ethenyl)-1$\alpha$-cyclopentaneacetic acid $\gamma$ lactone, thereby preparing a corresponding 2$\beta$-[(3RS)-3-hydroxy-trans-1, cis-5-octandienyl] compound which is separated into title formula XXIV (3R) and (3S) epimers by silica gel chromatography.

D. The reaction product of part B of this Example is oxidized with Collins reagent to prepare the formula XXIII title compound.

Following the procedure of Preparation 8, but employing the following Grignard reagents in part A;
1-bromo-cis-2-pentene;
1-bromo-1-methyl-cis-2-pentene;
1-bromo-1,1-dimethyl-cis-2-pentene; or
1-bromo-1-fluoro-cis-2-pentene
there are prepared respectively the corresponding 3$\alpha$-benzoyloxy-5$\alpha$-hydroxy-1$\alpha$-cyclopentaneacetic acid $\gamma$ lactones or 5$\alpha$-hydroxy-1$\alpha$-cyclopentaneacetic acid $\gamma$ lactones with 2$\beta$-[3 oxo- or (3R)- or (3S)-3-hydroxy-trans-1, cis-5-octadienyl]side chains unsubstituted or optionally substituted as follows:
4-methyl;
4,4dimethyl; or
4-fluoro.

When 5α-hydroxy-1α-cycloentaneactic acid γ lactones are to be prepared, a corresponding 5α-hydroxy-b 2β-(2-formyl-transethenyl)-1α-cycloentaneactic acid γ lactone is employed.

Further using the oxo-substituted lactones described in and following Preparation 8 there are prepared optionally-substituted 2β-(3-oxo-cis-1,cis-5-octadienyl); 2β-(3-oxo-cis-5-octenyl); or 2β-(2-chloro-trans 1,cis-5-octadienyl) lactones corresponding to lactones described in and following Preparation 8 following the procedure of Preparations 5, 6, and 7 respectively.

PREPARATION 9

3α-Benzoyloxy-5α-hydroxy-2β-[(3S)-3-hydroxy-trans-1-octenyl]-1α-cyclopentaneacetic acid γ lactone (Formula XXIV: $R_3$ and $R_4$ of the $L_1$ moiety are hydrogen, $R_5$ and $R_6$ of the $M_5$ moiety are hydrogen, $R_7$ is n-butyl, $R_{16}$ is benzoyloxy, and Y is trans —CH=CH—) or its (3R)-hydroxy epimer.

Sodium borohydride (2.86 g.) is slowly added to a stirred suspension of 12.6 g. of anhydrous zinc chloride in 78 m. of dimethyl ether of ethylene glycol (glyme) with ice bath cooling. The mixture is stirred for 20 hr. at ambient temperature and thereafter cooled to −20° C. A solution of 8.0 g. of 3α-benzoyloxy-5α-hydroxyy-2α-(3-oxo-cis-1-octenyl)-1α-cyclopentaneacetic acid γ lactone (prepared according to Preparation 4) in 80 ml. of glyme is added over a period of 15 min. Stirring is continued for 24 hour at −20° C. and thereafter 60 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield an oil, which when chromatographed on 900 g. of silica gel packed in one percent acetone and methylene chloride, eluting with one to 15 percent acetone in methylene chloride yields the epimermically pure title product and its pure epimer.

Following the procedure of Preparation 9, but using in place of the 3α-benzoyloxy-5α-hydroxy-2β-(3-oxo-trans-1-octenyl)-cyclopentaneacetic acid γ lactone starting material employed therein, the various 5α-hydroxy- or 3α-benzoyloxy-5α-hydroxy-2β-(3-oxo-cis-1- or trans-1-alkenyl or substituted alkenyl)-, 2β-(3-oxo-alkyl or substituted alkyl)-, or 2β-(3-oxo-trans-1, cis-5-actadienyl or substituted octadienyl)-1α-cyclopentaneacetic acid γ lactones there are prepared the corresponding (3R)- or (3S) hydroxy products.

For example, there are obtained the above 3α-benzoyloxy-5α-hydroxy- or 5α-hydroxy-1α-cyclopentaneactic acid γ lactones wherein the 2β-side chain in either the 3R or 3S form consists of 2-chloro-3-hydroxy-trans-1-hexenyl; 2-chloro-3-hydroxy-trans-1-heptenyl; 2-chloro-3-hydroxy-trans-1-nonenyl; 2-chloro-3-hydroxy-trans-1decenyl; 2-chloro-3-hydroxy-4-methyl-trans-1-octenyl; 2-chloro-3-hydroxy-4,4-dimethyl-trans-1-octenyl 2-chloro-3-hydroxy-4-fluoro-trans-1-octenyl; 2-chloro-3-hydroxy-4,4difluoro-trans-1-octenyl; 2-chloro-3-hydroxy-5-phenyl-trans-1-pentenyl; 2-chloro-3-hydroxy-5-(p-fluorophenyl)-trans-1-pentenyl; 2-chloro-3-hydroxy-5-(m-chlorophenyl)-trans-1-pentenyl; 2-chloro-3-hydroxy-(m-trifluoromethylphenyl)-trans-1-pentenyl; 2-chloro-3-hydroxy-4,4-dimethyl-5-phenyl-trans-1-pentenyl, 2-chloro-3-hydroxy-4,4-dimethyl-5-(p-fluorophenyl)-trans-1-pentenyl; 2-chloro-3-hydroxy-4,4-dimethyl-5-(m-chlorophenyl)-trans-1-pentenyl; 2-chloro-3-hydroxy-4,4-dimethyl-5-(m-trifluoromethylphenyl)-trans-1-pentenyl; 2-chloro-3-hydroxy-4,4-difluoro-5-phenyl-trans-1-pentenyl; 2-chloro-3-hydroxy-4,4-difluoro-5-(p-fluorophenyl)-trans-1-pentenyl; 2-chloro-3-hydroxy-4,4-difluoro-5-(m-chlorophenyl)-trans-1-pentenyl; 2-chloro-b 3-hydroxy-4,4-difluoro-5-(m-trifluoromethylphenyl)-trans-1-pentenyl; 2-chloro-3-hydroxy-4-phenoxy-trans-1-butenyl; 2-chloro-3-hydroxy-4-(p-fluorophenoxy)-trans-1-butenyl; 2-chloro-3-hydroxy-4-(m-chlorophenoxy)-trans-1-butenyl; 2-chloro-3-hydroxy-4-(m-trifluoromethylphenoxy)-trans-1-butenyl; 2-chloro-3-hydroxy-4,4-dimethyl-4-phenoxy-trans-1-butenyl; 2-chloro-3-hydroxy-4,4-dimethyl-4-(p-fluorophenoxy)-trans-1-butenyl; 3-hydroxy-trans-1-hexenyl; 3-hydroxy-trans-1-heptenyl 3-hydroxy-trans-1-nonenyl; 3-hydroxy-trans-1-decenyl; 3-hydroxy-trans-1, cis-5-octadienyl; 3-hydroxy-4-methyl-trans-1-octenyl; 3-hydroxy-4,4-dimethyl-trans-1, cis-5-octadienyl; 3-hydroxy-4,4-difluoro-trans-1, cis-5-octadienyl; 3-hydroxy-4-fluoro-trans-1-octenyl; 3-hydroxy-4,4-difluoro-trans-1-octenyl; 3-hydroxy-5-phenyl-trans-1-pentenyl; 3-hydroxy-5-(p-fluorophenyl)-trans-1-pentenyl; 3-hydroxy-5-(m-chlorophenyl)-trans-1-pentenyl; 3-hydroxy-5-(m-trifluoromethylphenyl)-trans-1-pentenyl; 3-hydroxy-4,4-dimethyl-5-phenyl-trans-11 -pentenyl; 3-hydroxy-4,4-dimethyl-5-(p-fluorophenyl)-trans-1-pentenyl; 3-hydroxy-4,4-dimethyl-5-(m-chlorophenyl)-trans-1-pentenyl; 3-hydroxy-4,4-dimethyl-5-(m-trifluoromethylphenyl)-trans-1-pentenyl; 3-hydroxy-4,4-difluoro-5-phenyl-trans-1-pentenyl; 3-hydroxy-4,4-difluoro-5-(p-fluorophenyl)-trans-11 -pentenyl; 3-hydroxy-4,4-difluoro-5-(m-chlorophenyl)-trans-1-pentenyl; 3-hydroxy-4,4-difluoro-5-(m-trifluoromethylphenyl)-trans-1- pentenyl; 3-hydroxy-4-phenoxy-trans-1-butenyl; 3-hydroxy-4-(p-fluorophenoxy)-trans-1-butenyl; 3-hydroxy-4-m-chlorophenoxy)-trans-1-butenyl; 3-hydroxy-4-(m-trifluoromethylphenoxy)-trans-1-butenyl; 3-hydroxy-4,4-dimethyl-4-phenoxy-trans-1-butenyl; 3-hydroxy4,4-dimethyl-4-(p-fluorophenoxy)-trans-1-butenyl; 3-hydroxy-4,4-dimethyl:4-(m-chlorophenoxy)-trans-1-butenyl; 3-hydroxy-4,4-dimethyl-4-(m-trifluoromethoxyphenoxy)-trans-1-butenyl; 3-hydroxy-cis-1-hexenyl; 3-hydroxy-cis-1-heptenyl; 3-hydroxy-cis-1-octenyl 3-hydroxy-cis-1-nonenyl; 3-hydroxy-cis-1-decenyl; 3-hydroxy-cis,cis-1,5-octadienyl; 3-hydroxy-4-methyl-cis-1-octenyl 3-hydroxy-4,4-dimethyl-cis-1-octenyl; 3-hydroxy-4-fluoro-cis-1octenyl 3-hydroxy-4,4-difluoro-cis-1-octenyl 3-hydroxy-5-phenyl-cis-1-pentenyl; 3-hydroxy-5-(p-fluorophenyl)-cis-1-pentenyl; 3-hydroxy-5-(m-chlorophenyl)-cis-1-pentenyl; 3-hydroxy-5-(m-trifluoromethylphenyl)-cis-1-pentenyl; 3-hydroxy-4,4-dimethyl-5-phenyl-cis-1-pentenyl; 3-hydroxy-4,4-dimethyl-5-(p-fluorophenyl)-cis-1-pentenyl; 3-hydroxy-4,4-dimethyl-5-(m-chlorohenyl)-cis-1-pentenyl; 3-hydroxy-4,4-dimethyl-5-(m-trifluoromethylphenyl)-cis-1-pentenyl; 3-hydroxy-4,4-difluoro-5-phenyl-cis-1-pentenyl; 3-hydroxy-4,4-difluoro-5-(p-fluorophenyl)-cis-1-pentenyl; 3-hydroxy-4,4-difluoro-5-(m-chlorophenyl)-cis-1-pentenyl; 3-hydroxy-4,4-difluoro-5-(m-trifluoromethylphenyl)-cis-1-pentenyl; 3-hydroxy-4-phenoxy-cis-1-butenyl; 3-hydroxy-4-(p-fluorophenoxy)-cis-1-butenyl; 3-hydroxy-4-(m-chlorophenoxy)-cis-1-butenyl; 3hydroxy-4-(m-trifluoromethylphenoxy)-cis-1-butenyl; 3-hydroxy-4,4-dimethyl-4-phenoxy-cis-1-butenyl; 3-hydroxy-4,4-dimethyl-4-(p-fluorophenoxy)-cis-1-butenyl; 3-hydroxy-4,4-dimethyl-4-(m-chlorophenoxy)-cis-1-butenyl; 3-hydroxy-4,4-dimethyl-4-(m-trifluoromethylphenoxy)-cis-1-butenyl;

3-hydroxy-hexyl; 3-hydroxy-heptyl; 3-hydroxy-octyl; 3-hydroxy-nonyl;; 3-hydroxy-decyl; 3-hydroxy-cis-5-octenyl; 3-hydroxy-4-methyl-octyl; 3-hydroxy-4,4-dimethyl-cis-5-octenyl; 3-hydroxy-4,4-difluoro-cis-5-octenyl; 3-hydroxy-4,4-dimethyl-octyl; 3-hydroxy-4-fluoro-octyl; 3-hydroxy-4,4-difluoro-octyl; 3-hydroxy-5-phenyl-pentyl; 3-hydroxy-5-(p-fluorophenyl)-pentyl; 3-hydroxy-5-(m-chlorophenyl)-pentyl; 3-hydroxy-5-(m-trifluoromethylphenyl)-pentyl; 3-hydroxy-4,4-dimethyl-5-phenyl-pentyl; 3-hydroxy-4,4-dimethyl-5-(p-fluorophenyl)-pentyl; 3-hydroxy-4,4-dimethyl-5-(m-chlorophenyl)-pentyl; 3-hydroxy-4,4-dimethyl-5-(m-trifluoromethylphenyl)pentyl; 3-hydroxy-4,4-difluoro-5-phenyl-pentyl; 3-hydroxy-4,4-difluoro-5-(p-fluorophenyl)-pentyl; 3-hydroxy-4,4-difluoro-5-(m-chlorophenyl)-pentyl; 3-hydroxy-4,4-difluoro-5-(m-trifluoromethylphenyl)-pentyl; 3-hydroxy-4-phenoxybutyl; 3-hydroxy-4-(p-fluorophenoxy)-butyl; 3-hydroxy-4-(m-chlorophenoxy)-butyl; 3-hydroxy-4-(m-trifluoromethylphenoxy)-butyl; 3-hydroxy-4,4-dimethyl-4-phenoxy-butyl; 3-hydroxy-4,4-dimethyl-4-(p-fluorophenoxy)-butyl; 3-hydroxy-4,4-dimethyl-4-(m-chlorophenoxy)-butyl; 3-hydroxy-4,4-dimethyl-4-(m-trifluoromethylphenoxy)-butyl; 2-chloro-3-hydroxy-4,4-dimethyl-4-(m-chlorophenoxy)-trans-1-butenyl; 2-chloro-3-hydroxy-4,4-dimethyl-4-(m-trifluoromethylphenoxy)-trans-1-butenyl; and the like.

PREPARATION 10

3α-Benzoyloxy-5α-hydroxy-2β-[(3RS)-3-hydroxy-3-methyl-trans-1-octenyl]-1α-cyclopentaneacetic acid γ lactone.

Refer to Chart A.

A solution of 18 g. of 3α-benzoyloxy-5α-hydroxy-2β-(3-oxo-trans-1-octenyl)-1α-cyclopentaneacetic acid γ lactone in 890 ml. of dry benzene is cooled to 9° C. under a nitrogen atmosphere. A toluene solution of trimethylaluminum (60 ml.) is added over a period of 4 min. to the resulting mixture. This mixture is then stirred for 1.5 hr. at 20°-25° C. then cooled to 10° C. Thereupon 370 ml. of saturated ammonium chloride is slowly added at such a rate so as to maintain the reaction mixture at ambient temperature. After 0.5 hr. the reaction mixture is diluted with ethyl acetate and water and filtered, the filter cake being washed with the ethyl acetate-water solvent. The aqueous layer is extracted with ethyl acetate and the combined organic extracts are washed with brine, dried over magnesium sulfate, and evaporated to yield an oil, which is chromatographed on one kg. of silica gel packed in 10 percent ethyl acetate and Skellysolve B. Elution with 10 to 16 percent ethyl acetate in Skellysolve B (18 l.), 28 percent ethyl acetate in Skellysolve B (8 l.) yields title compound. Fractions as shown by thin layer chromatography to contain pure product are combined. Rechromatography, in the fashion described above, yields (3S)- or (3R)-epimer.

Omitting the chromatographic separation described above, the 3RS-epimeric mixture obtained on trimethylaluminum alkylation are separated in high yield as prostaglandin-type products.

Following the procedure of Preparation 10, but using in place of the 3-oxo lactone starting material therein, the various lactones described following Preparation 4, 5, 6, or 7, there are obtained 3-hydroxy-3-methyl compounds corresponding to each of the 3-hydroxy compounds named following Preparation 9.

PREPARATION 11

5α-Hydroxy-2β-[(3S)-3-hydroxy-trans-1-octenyl]-1α-cyclopentaneacetaldehyde, γ lactol, bis(tetrahydropyranyl ether) (Formula XXVII or XXXII: $R_3$ and $R_4$ of the $L_1$ moiety are hydrogen, $M_6$ is

$R_7$ is n-butyl, $R_{18}$ is tetrahydropyran-2-yloxy, and $Y_2$ is trans—CH=CH— and n is one in formula XXXII), or its (3R) epimer.

Refer to Chart A.

A. A solution of 5 g. of the reaction product of Preparation 9 in 150 ml. of methanol is purged with nitrogen. Thereafter, potassium carbonate (2.02 g.) is added and the resulting mixture is stirred at ambient temperature until thin layer chromatographic analysis shows the solvolysis to be complete (about 1.5 hr.). The methanol is then evaporated under reduced pressure. The residue is then shaken with ethyl acetate (250 ml.), brine (250 ml.), and 8 g. of potassium bisulfate. The aqueous layer is then extracted twice with 125 ml. of ethyl acetate and the organic extracts are dried over magnesium sulfate, and evaporated to yield an oil. This oil is then dissolved in chloroform and a few crystals of p-toluenesulfonic acid are added. When thin layer chromatography indicates the action is complete (about 2 hr.), the reaction mixture is then washed with aqueous potassium bicarbonate, dried, and evaporated to yield an oil which is then chromatographed using silica gel packed in one percent ethanol in methylene chloride for purification. Accordingly, the formula XXV deacylated lactone is prepared.

B. A solution of 1.57 g. of the reaction product of part A above, in 35 ml. of methylene chloride (containing 2.5 ml. of dihydropyran and 100 mg. of pyridine hydrochloride) is allowed to stand for 23 hr. at ambient temperature. The reaction mixture is then washed with water, aqueous potassium bicarbonate, dried over magnesium sulfate, and evaporated, yielding an oil which is thereafter chromatographed on 200 g. of silica gel packed in one percent acetone in methylene chloride. Elution with from one to ten percent acetone in methylene chloride yields the formula XXVI bis-tetrahydropyranyl ether lactone corresponding to the lactone reaction product of part A above.

C. A solution of the reaction product of part B above in 20 ml. of toluene is cooled to −70° C. and thereafter 10 ml. of 10 percent diisobutylaluminum hydride in toluene is slowly added. The reaction mixture is then stirred at −70° C. until thin layer chromatographic analysis indicates that the reduction is complete (about 30 min.). Thereafter the cooling bath is removed and 9 ml. of a mixture of tetrahydrofuran and water (2:1) is added slowly. The reaction mixture is then stirred and allowed to warm to room temperature, and is then filtered through Celite. The filter cake is rinsed with benzene, combined organic extracts are then dried over magnesium sulfate and evaporated to yield the title compound.

Following the procedure of Preparation 11, but using as starting material 3α-benzoyloxy-5α-hydroxy-2β-[(3R) or (3S)-3-hydroxy-3-methyl-trans-1-octenyl]-1α- cyclopentaneacetic acid γ lactone, there is obtained the corresponding bis-tetrahydropyranyl ether.

Following the procedure of Preparation 11, each 5α-hydroxy or 3α-benzoyloxy-5α-hydroxy-1α-cyclopentaneacetic acid γ lactone described in and following Preparations 9 and 10 are transformed into the corresponding lactol.

PREPARATION 12

3α,5α-Dihydroxy-2α-[(3S)-3-hydroxy trans-1-octenyl]-1α-cyclopropionaldehyde δ-lactol bis tetrahydropyranyl ether) (Formula XXXII: n is 2, R$_3$ and R$_4$ of the L$_1$ moiety are hydrogen, M$_8$ is

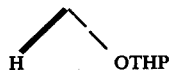

R$_7$ is n-butyl, R$_{18}$ is tetrahydropyranyloxy, and Y is trans—CH=CH—).

Refer to Chart A.

A. A suspension of methoxymethyltriphenylphosphonium chloride (32.4 g.) in 150 ml. of tetrahydrofuran is cooled to −15° C. To the suspension is added 69.4 ml. of n-butyl-lithium in hexane (1.6 molar) in 45 ml. of tetrahydrofuran. After 30 min. There is added a solution of 3α,5α-dihydroxy-2β-[(3S)-3-hydroxy-trans-1-octenyl]-1α-cyclopentaneacetaldehyde γ lactol bis-(tetrahydropyranyl)ether, Preparation 11 (10 g.), in 90 ml. of tetrahydrofuran. The mixture is stirred for 1.5 hr. while warming to 25° C. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula XXVIII product are combined.

B. The reaction product of part A above in 20 ml. of tetrahydrofuran is hydrolyzed with 50 ml. of 66 percent aqueous acetic acid at about 57° C. for 2.5 hr. The resulting mixture is then concentrated under reduced pressure. Toluene is added to the residue and the solution is again concentrated. Finally the residue is subjected to chromatography on silica gel, eluting with chloroform and methanol (6:1). The title compound is thereby obtained by combining and concentrating fractions as shown by thin layer chromatography to contain pure product. Accordingly, there is obtained the corresponding formula XXIX δ-lactol.

C. Silver oxide is prepared by the addition of silver nitrate (1.14 g.) in water (3 ml.) dropwise to a 2 normal sodium hydroxide solution (6.8 ml.). A precipitate is formed. Added to the precipitate in ice water bath is the δ lactol of part B above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol), (9:1), the mixture is filtered. The filtrate is then extracted with diethyl ether. The aqueous layer is then chilled in an ice bath and acidified with 10 percent potassium bisulfate solution to pH less than 2. This aqueous mixture is then extracted with diethyl ether. The ethereal extracts are then combined, washed with brine, dried over magnesium sulfate, filtered, and evaporated under reduced pressure to yield the formula XXX lactone.

D. The formula XXX lactone prepared in part C above is then transformed to its bis-tetrahydropyranyl ether derivative following the procedure described in Preparation 11 part B.

E. The formula XXXI compound prepared in part D above is then reduced to the corresponding title δ lactol bis-tetrahydropyranyl ether by the procedure described in Preparation 11, part C.

Following the procedure of Preparation 12, but using the corresponding (3R) starting material in place of the (3S) starting material there is obtained the corresponding (3R)-γ-lactol product Following the procedure of Preparation 12, but using in place of the formula XXVII lactol, the various formula XXVII lactols described following Preparation 11, there are obtained the corresponding formula XXXII lactols wherein n is 2.

PREPARATION 13 cis-4,5-Didehydro-PGF$_{1α}$11,15-bis(tetrahydropyranyl ether) (Formula XXXIV: g is one, n is two, R$_3$ and R$_4$ of the L$_1$ moiety are hydrogen, M$_6$ is

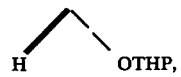

R$_1$ is hydrogen, R$_7$ is n-butyl, R$_{18}$ is tetrahydropyranyloxy, and Y$_2$ is trans—CH=CH—) or its 15-epimer.

Refer to Chart A.

3-Carboxypropyltriphenylphosphonium bromide (prepared by heating 4-bromobutyric acid and triphenylphosphine in benzene at reflux for 18 hr., and thereafter purifying), 106 g., is added to sodiomethylsulfinylcarbanide prepared from sodium hydride (2.08 g., 57 percent) and 30 ml. of dimethylsulfoxide. The resulting Wittig reagent is combined with the formula XXXII lactol of Preparation 12 and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate.

Following the procedure of Preparation 13, but employing 4-carboxybutyltriphenylphosphonium bromide and the product of Preparation 11, there is prepared PGF$_{2α}$, 11,15-bis(tetrahydropyranyl ether).

Following the procedure of Preparation 13, but using the (3R)-lactol of Preparation 11 there is obtained 15-epi-PGF$_{2α}$-11,15-bis-tetrahydropyranyl ether.

Following the procedure of Preparation 13 but using 5-carboxypentyltriphenylphosphonium bromide or 6-carboxyhexyltriphenylphosphonium bromide or 4-carboxybutyltriphenylphosphonium bromide in optional combination with the product of Preparation 11 there is obtained 2α-homo- or 2α,2β-dihomo-PGF$_{2α}$-11,15-bis(-tetrahydropyranyl ether) or its cis-4,5-didehydro isomer.

Finally following the procedure of Preparation 13, and employing each of the γ- or δ-lactols described following Preparation 11 or 12, there are prepared each of the corresponding 11-deoxy-PGF$_{2\alpha}$- or PGF$_{2\alpha}$- or cis-4,5-didehydro-11-deoxy-PGF$_{1\alpha}$-or cis-4,5-didehydro-PGF$_{1\alpha}$-type products, respectively.

PREPARATION 14

PGF$_{1\alpha}$, 11,15-bis(tetrahydropyranyl ether).

A. solution of PGF$_{2\alpha}$, 11,15-bis(tetrahydropyranyl ether in ethyl acetate is shaken with hydrogen at about one atmosphereic pressure at ambient temperature in the presence of a 5 percent palladium-on-charcoal catalyst. Hydrogenation is stopped when one equivalent of hydrogen per equivalent of starting material is absorbed. Catalyst is removed by filtration and the filtrate is then concentrated under reduced pressure and the residue chromatographed on silica gel, eluting with ethyl acetate and Skellysolve B. Fractions shown to contain pure product are combined yielding the title compound.

Following the procedure of Preparation 14, but using 2α-homo- or 2α,2β-dihomo-PGF$_{2\alpha}$, 11,15-bis(tetrahydropyranyl ether, there is prepared 2α-homo- or 2α,2β-dihomo-PGF$_{1\alpha}$1, 11,15-bis(tetrahydropyranyl ether).

Further, following the procedure of Preparation 14 but using the various PGF$_{2\alpha}$- or 11-deoxy-PGF$_{2\alpha}$- type compounds described following Preparation 14, there is prepared each of the corresponding 11-deoxy-PGF$_{1\alpha}$ or PGF$_{1\alpha}$-type compounds.

PREPARATION 15

5-Oxa-PGF$_{1\alpha}$, methyl ester, 11,15-bis-(tetrahydropyranyl ether), (Formula XXXVII: q and n are one, R$_3$ and R$_4$ of the L$_1$ moiety are hydrogen, M$_6$ is

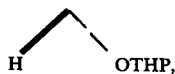

R$_{18}$ is tetrahydropyranyloxy, R$_1$ is methyl, R$_7$ is n-butyl, and Y$_2$ is trans—CH=CH—), or its 15-epimer.

Refer to Chart A.

A. A mixture of α,5α-dihydroxy-2β-[(3S)-3-hydroxy-trans-1-octenyl]-1α-cyclopentaneacetaldehyde δ lactol bis(tetrahydropyranyl ether or its (3R) epimer (6.3 g.) and 50 ml. of 95 percent ethanol is treated at 0° C. with stirring with a solution of sodium borohydride in 10 ml. of water (added over a period of one min.). The resulting mixture is then stirred at 0° C. for 10 min. and then shaken with 10 ml. of water, 250 ml. of ethyl acetate, and 150 ml. of brine. The organic phase is then washed with brine, dried, and concentrated under reduced pressure to yield 2-decarboxy-2-hydroxymethyl-2,3,4,5,6-pentanor-PGF$_{1\alpha}$, 11,15-bis-(tetrahydropyranyl ether), a formula XXXVI compound, or its (15R)-epimer.

B. A solution of potassium tert-butoxide (1.77 g.) in 30 ml. of tetrahydrofuran is mixed at 0° C., with stirring, with a solution of the reaction product of part A (5.8 g.) in 30 ml. of tetrahydrofuran. The resulting mixture is then stirred at 0° C. for 5 min. and thereafter 5 ml. of trimethyl ortho-4-bromobutyrate is added. Stirring is continued at 0° C. for 2 hr. and at about 25° C. for 16 hr. To this mixture is added 30 ml. of dimethylformamide and 0.5 g. of potassium-t-butoxide. The resulting mixture is then stirred for 20 hr. Some of the solvent is then removed under reduced pressure and the residue is then shaken with water diethyl ether and dichloromethane (3:1). The organic phase is then washed with water and brine, dried, and concentrated. The residue, containing the ortho ester, is dissolved in 60 ml. of methanol at 0° C. and treated with 15 ml. of cold water containing 2 drops of acetic acid. The resulting mixture is then stirred at 0° C. for 5 min., shaken with 200 ml. of diethyl ether, 50 ml. of dichloromethane, and 200 ml. of brine. The organic phase is then washed with brine, dried, and concentrated under reduced pressure. The residue is subjected to silica gel chromatography, yielding the title methyl esters.

C. Trimethyl ortho-4-butyrate is prepared as follows:

Refer to S. M. McElvain, et al., Journal of the American Chemical Society 64, 1825 (1942). A mixture of 4-bromobutyronitrile (74 g. ), 21 ml. of methanol, and 150 ml. of diethyl ether is treated at 0° C. with stirring, with hydrogen bromide (40 g.). The mixture is then stirred for an additional 4 hr. at 0° C. and 100 ml. of hexane is added. The precipitated imino ester hydrobromide is separated from the liquid by filtration and washed with 400 ml. of diethyl ether in hexane (1:1). The imino ester salt is treated in 250 ml. of diethyl ether with 150 ml. of methanol and 25 ml. of methylorthoformate, with stirring, at about 25° C. for 24 hr. The resulting mixture is then cooled to about 10° C. and the organic solution is separated from the ammonium bromide thereby formed. Diethyl ether (100 ml.) is then added. The resulting solution is then immediately and quickly washed an ice cold solution prepared from potassium carbonate (20 g.) and 300 ml. of brine. The organic phase is washed with brine, treated with 3 drops of pyridine, and dried over anhydrous magnesium sulfate. The solution is then concentrated under reduced pressure, diluted with 150 ml. of benzene, and again concentrated. The residue is then distilled to yield the title ortho-4-bromobutyrate.

Following the procedure of part C of Preparation 15 but using 4-bromo butanonitrile-5-bromo pentanonitrile or 6-bromohexanonitrile there is prepared trimethylortho-4-bromobutanoate trimethylortho-5-bromopentanoate or trimethylortho-6-bromohexanonate.

Following the procedure of Preparation 15 but using each of the various lactols described in or following Preparations 11 or 12, there is prepared a corresponding 5-oxa- or 4-oxa PGF$_{1\alpha}$- or 11-deoxy-PFG$_{1\alpha}$-type, methyl ester, 11,15-bis- or 15-(tetrahydropyranyl ether).

Further, following the procedure of Preparation 15, but using trimethylortho-6-bromohexanoate there is prepared in (15R) or (15S) form the corresponding 4-oxa- or 5-oxa-PGF$_{1\alpha}$-11-deoxy-PGF$_{1\alpha}$-type methyl ester, 11,15-bis- or 15-(tetrahydropranyl ether) wherein g is 2 or 3.

PREPARATION 16

3-Oxa-PGF$_{1\alpha}$, 11,15-bis(tetrahydropranylether), methyl ester (Formula LV: R$_1$ is methyl, g is one, R$_3$ and R$_4$ of the L$_1$ moiety are hydrogen, M$_6$ is

R$_7$ is n-butyl, R$_8$ is tetrahydropyranyloxy and Y$_2$ is trans-CH=CH—), or its 15-epimer, or the corresponding free acids.

Refer to Chart B.

A. 3α,5α-dihydroxy-2β-[(3S)-3-hydroxy-trans-1-octenyl]-1α-cyclopentaneacetaldehyde α-lactol bis-(tetrahydropyranyl ether) (10.0 g.) is dissolved in 150 ml. of absolute ethanol (containing 3 drops of acetic acid). To this solution is added carbethoxymethylenetriphenylphosphorane (10 g.) and the mixture is stirred at ambient temperature for 72 hr. The resulting mixture is concentrated under reduced pressure to a volume of about 35 ml., mixed with ice, and dilute sodium bicarbonate solution, and shaken with ethyl acetate. The organic phase is washed with brine, dried over magnesium sulfate, and concentrated to yield a residue. The residue is slurried in 100 ml. of diethyl ether and filtered. The filtrate is concentrated to a residue which is subject to silica gel chromatography, eluting with 20 to 40 percent ethyl acetate in Skellysolve B. There is obtained 2,3,4-trinor-$PGF_{2\alpha}$ethyl ester, 11,15-bis-(tetrahydropyranyl ether), a formula LII compound.

B. The reaction product of step A above is mixed with the 5 percent palladium-on-charcoal catalyst (0.3 g.) in 30 ml. of ethyl acetate and hydrogenated at atmospheric pressure. When about 41 ml. of hydrogen is consumed, the catalyst is filtered off and the filtrate concentrated under reduced pressure to yield 2,3,4-trinor-$PGF_{1\alpha}$, ethyl ester, 11,15-bis(tetrahydropyranyl ether), a formula LIII compound.

C. The reaction product of step B above (1.1 g.) in 30 ml. of diethyl ether is added with stirring to a mixture of lithium aluminum hydride (0.3 g.) in 60 ml. of diethyl ether at 0° C. The addition continues over a 10 min. period. The mixture is warmed to room temperature for 2 hr. then cooled to 0° C., and treated with 0.35 ml. of water cautiously added. Thereafter 0.35 ml. of 15 percent aqueous sodium hydroxide solution is added, and thereafter one ml. of water. The solids are removed by filtration and the filtrate is concentrated under reduced pressure to yield 2-decarboxy-2-hydroxymethyl-2,3,4-trinor-$PGF_{1\alpha}$, 11,15-bis(tetrahydropyranyl ether).

D. The reaction product of part C above (1.7 g.) together with 15 ml. of dimethylsulfoxide and 5 ml. of tetrahydrofuran is treated with 2.28 ml. of 1.6 molar n-butyllithium in hexane, with stirring and cooling. After 5 min. there is added 5 ml. of dimethylformamide. The resulting solution is then stirred and cooled to 0° C. Thereafter lithium chloroacetate (0.7 g.) is added. The mixture is then stirred at 0° C. for 2 hr. and at about 25° C. for 22 hr. Thereafter the resulting solution is diluted with 200 ml. of ice-water, acidified with a cold solution of 3 ml. of dilute acetic acid in 50 ml. of water, and extracted thereafter with dichloromethane. The organic phase is washed with cold water and brine and dried over magnesium sulfate. Accordingly, there is prepared 3-oxa-$PGF_{1\alpha}$,11,15-bis(tetrahydropyranyl ether).

E. To the above solution (part D) is added excess ethereal diazomethane and after a few min. the excess reagent is destroyed with acetic acid. The mixture is then washed with a mixture of sodium bicarbonate solution and brine and thereafter with brine. The resulting solution is then dried and concentrated under reduced pressure. The residue so obtained is subjected to silica gel chromatography eluting with ethyl acetate and Skellysolve B to yield the title methyl ester.

Following the procedure of Preparation 16, but using the (3R)- starting material there are obtained the corresponding 15-epi products.

Finally, following the procedure of Preparation 16, but using each of the various lactols described following Preparations 11, or 12, there are prepared 3oxa-$PFG_{1\alpha}$- or 11-deoxy-$PGF_{1\alpha}$-type compounds.

PREPARATION 17

3-Oxa-3,7-inter-m-phenylene-4,5,6-trinor-$PGF_{1\alpha}$ or 3,7-inter-m-phenylene-4,5,6-trinor-$PGF_{1\alpha}$ (Formula LXXIII or LXXXIV: $R_1$, $R_3$, and $R_4$ of the $L_1$ moiety, and $R_5$ of the $M_1$ moiety are all hydrogen; $R_7$ is n-butyl, $Z_3$ of formula LXXXIV is methylene; and $Y_1$ is trans—CH=CH—) or the corresponding cis-13-; 13,14-dihydro-; or 14-chloro-compounds.

Refer to Charts C, D, E, and F.

A. Optically Active Bicyclo[3.1.0]-hex-2-ene-6-endocarboxyaldehyde.

Following the procedure of Preparation of 1 of U.S. Pat. No. 3,711,515, racemic bicyclo[3.1.0] hex-2-ene-6-endo-carboxyaldehyde is prepared from bicyclo[2.2.1]-hepta-2,5-diene and peracetic acid.

The racemic compound is resolved by the procedure of Example 13 of U.S. Pat. No. 3,711,515, forming an oxazolidine as follows:

Racemic bicyclo[3.1.0]hex-2-ene-6-endo-carboxaldehyde (12.3 g.) and 1-ephedrine (16.5 g.) are dissolved in about 150 ml. of benzene. The benzene is removed under vacuum and the residue taken up in about 150 ml. of isopropyl ether. The solution is filtered, then cooled to −13° C. to yield crystals of 2-endo-bicyclo-[3.1.0]hex-2-ene-6-yl-3,4-dimethyl-5-phenyl-oxazolidine, 11.1 g., m.p. 90° -92° C. Three recrystallizations from isopropyl ether, cooling each time to about −2° C., yield crystals of the oxazolidine, 2.2 g., m.p. 100°–103° C., now substantially a single isomeric form as shown by NMR.

The above re-crystallized oxazolidine (1.0 g.) is dissolved in a few ml. of dichloromethane, charged to a 20 g. silica gel column and eluted with dichloromethane. The silica gel is chromatograph-grade (Merck), 0.05–0.2 mm. particle size, with about 4–5 g. of water per 100 g. Fractions of the eluate are collected, and those shown by thin layer chromatography (TLC) to contain the desired compound are combined and evaporated to an oil (360 mg.). This oil is shown by NMR to be the desired title compound, substantially free of the ephedrine, in substantially a single optically-active isomeric form. Points on the circular dichroism curve are ($\lambda$ in nm., $\theta$): 350, 0; 322.5, 4,854; 312, −5,683; 302.5, −4,854; 269, 0; 250, 2,368; 240, 0; and 210, −34,600.

B. 1-Bicyclo[3.1.0]hex-2-ene-6-endo-carboxaldehyde Neopentyl Glycol Acetal (Formula LXI: $R_{55}$ and $R_{56}$ taken together are —$CH_2$—$C(CH_3)_2$—$CH_2$— and ~ is endo).

A mixture of 2,2-dimethyl-1,3-propanediol (900 g.), 5 l. of benzene, and 3 ml. of 85 percent phosphoric acid is heated at reflux. To it is added, in 1.5 hr., a solution of optically active bicyclo[3.1.0]hex-2-ene-6-endocarbox-aldehyde (part A, 500 g.) in one liter of benzene. Provision is made to take off azeotropically distilled water with a Dean-Stark trap. After 3 hr. the mixture is cooled and extracted with 2 liters of 5 percent sodium bicarbonate. The organic phase is dried over sodium sulfate and concentrated under reduced pressure. The resulting semisolid residue is taken up in methanol and recrystallized, using a total of 1200 ml. of methanol to which 600 ml. of water is added, then chilled to −13° C. to yield 300 g. of the title compound, m.p. 52°-55° C., and and having NMR peaks at 0.66, 1.20, 0.83–2.65, 3.17–3.8, 3.96, and 5.47-5.88 δ, $[\alpha]_D$−227° (C=0.8976 in methanol). and $R_f$0.60 (TLC on silica gel in 25 percent ethyl acetate in mixed isomeric hexanes). Further work-up of the mother liquors yields 50-100 g. of additional product.

C. d-8-(m-Acetoxyphenyl)-7-oxa-tricyclo-[4.2.0.0²,⁴]octane-6-endo-carboxyaldehyde Neopentyl Glycol Acetal (Formula LXII: $R_{55}$ and $R_{56}$ taken together are —CH$_2$—C(CH$_3$)$_2$—CH$_2$—, $R_{63}$ is

and ~ is endo).

A solution of the formula LXI 1-bicyclo[3.1.0]hex-2-ene-6-endo-carboxaldehyde neopentyl glycol acetal (Part B, 5.82 g.) and m-acetoxy-benzaldehyde (1.64 g.) in 25 ml. of benzene is charged to a Pyrex photolysis vessel equipped with an immersible water-cooled coldfinger and a fritted gas inlet tube. Dissolved oxygen is removed by bubbling nitrogen through the solution. The mixture is then irradiated at 350 nm. with a Rayonet Type RS Preparative Photochemical Reactor (The Southern New England Ultraviolet Co., Middletown, Conn.) equipped with six RUl 3500 A lamps. After 24 hrs the photolysate is concentrated under reduced pressure to a pale yellow oil, 10 g., which is subjected to silica gel chromatography. Elution with 10-70 percent ethyl acetate in Skellysolve B (mixture of isomeric hexanes) yields separate fractions of the recovered starting materials and the formula LXII title compound, a pale yellow oil 0.86 g., having NMR peaks at 0.68, 1.20, 0.8;14 2.5, 2.28, 2.99, 3.12–3.88, 3.48, 4.97–5.52, and 6.78–7.60 δ; infrared absorption bands at 3040, 2950, 2860, 2840, 1765, 1610, 1590, 1485, 1470, 1370, 1205, 1115, 1020, 1005, 990, 790, and 700 cm.$^{-1}$; mass spectral peaks at 358, 357, 116, 115, 108, 107, 79, 70, 69, 45, 43, and 41; $[\alpha]_D$ +55° (C=0.7505 in 95 percent ethanol); and $R_f$ 0.18 (TLC on silica gel in 25 percent ethyl acetate in mixed isomeric hexanes).

D. d-2-Exo-[m-(pivaloyloxy)benzl]-3-exo-pivaloyloxy)-bicyclo-[3.1.0]hexane-6-endo-carboxaldehyde Neopentyl Glycol Acetal (Formula LXIV: $R_{55}$ and $R_{56}$ taken together are -CH$_2$—C(CH$_3$)$_2$—CH$_2$—, $R_{68}$ is

and ~ is endo).

A mixture of lithium (0.25 g.) in 70 ml. of ethylamine is prepared at 0° C. and cooled to −78° C. A solution of the formula LXII d-8-(m-acetoxyphenyl)-7-oxa-tricyclo-[4.2.0.0²,⁴]-octane-6-endo-carboxaldehyde neopentyl glycol acetal (part C 1.83 g.) in 10 ml. of tetrahydrofuran is added dropwise in about 5 min. After stirring at −78° C. for about 3.5 hr. the reaction is quenched with solid ammonium chloride and water-tetrahydrofuran. The mixture is warmed slowly to about 25° C., and ethylamine is removed. The residue is neutralized with dilute acetic acid, mixed with 200 ml. of brine, and extracted with ethyl acetate. The organic phase is washed with brine and a mixture of brine and saturated aqueous sodium bicarbonate (1:1), and dried over sodium sulfate. Concentration under reduced pressure yields the formula LXIII diol as a pale tan oil, 1.64 g., having $R_f$ 0.03 (TLC on silica gel in 25 percent ethyl acetate in mixed isomeric hexanes).

The product of the preceeding paragraph is dissolved in 30 ml. of pyridine and treated with 1.5 ml. of pivaloyl chloride over a period of 22 hr. at about 25° C. The reaction mixture is mixed with water, then brine and extracted with ethyl acetate. The organic phase is washed successively with brine, water, saturated aqueous copper (II) sulfate, saturated aqueous sodium bicarbonate, and brine, and dried over sodium sulfate. Concentration under reduced pressure yields a residue, 2.53 g., which is subjected to silica gel chromatography to yield the formula LXIV title compound, 1.87 g., having NMR peaks at 0.71, 1.20, 1.33, 0.9–3.1, 3.28–4.00, 4.17, 4.7–5.2, and 6.77–7.53 δ; mass spectral peaks at 486, 485, 115, 73, 72, 57, 44, 43, 42, 41, 30, 29, 15; $[\alpha]_D$ +19° (C=0.9340 in ethanol); and $R_f$ 0.50 (TLC on silica gel in 25 percent ethyl acetate in mixed isomeric hexanes).

E. 2-Exo-[m-(pivaloyloxy)benzyl]-3-exo-(pivaloyloxy)-bicyclo[3.1.0]hexane-6-endo-carboxaldehyde (Formula LXV: $R_{66}$ is

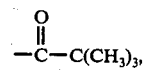

and ~ is endo).

The formula LXIV acetal, i.e. d-2-exo-[(m-pivaloyloxy)-benzyl]-3-exo-(pivaloyloxy)-bicyclo[3.1.0]-hexane-6-endocarboxaldehyde neopentyl glycol acetal (part D, 0.48 g.) is treated at 0° C. with 25 ml. of 88 percent formic acid for 4 hr. The mixture is diluted with 200 ml. of brine and extracted with ethyl acetate. The organic phase is washed with brine and saturated aqueous sodium bicarbonate, and dried over magnesium sulfate. Concentration under reduced pressure yields an oil, 0.55 g., which is subjected to silica gel chromatography. Elution with 5-15 percent ethyl acetate in Skellysolve B yields the formula LXV title compound as an oil, 0.37 g., having NMR peaks at 1.20, 1.33, 0.6–3.2, 5.1–5.5, 6.6–7.5, and 9.73 δ; and $R_f$ 0.50 (TLC on silica gel in 25 percent ethyl acetate in mixed isomeric hexanes).

F. 2-Exo-[m-(pivaloyloxy)benzyl]-3-exo-(pivaloyloxy)-6-endo-(cis-1-heptenyl)-bicyclo[3.1.0]hexane. (Formula LXVI: $R_3$ and $R_4$ of the $L_1$ moiety are both hydrogen, $R_7$ is n-butyl, $R_{66}$ is

$R_{53}$ is hydrogen, and ~ is endo); and 2-Exo-(m-hydroxybenzyl)-3-exo-hydroxy-6-endo-(cis-1-heptenyl)bicyclo[3.1.0]-hexane (Formula LXVII: $R_3$ and $R_4$ of the $L_1$ moiety are both hydrogen, $R_7$ is n-butyl, $R_{53}$ and $R_{66}$ are hydrogen, and ~ is endo).

A Wittig ylid reagent is prepared in 10 ml. of benzene from n-hexyltriphenylphosphoniumbromide (0.79 g.) and n-butyllithium (0.6 ml. of 2.32 M. solution in hexane) at about 25° C. for 0.5 hr. After the precipitated lithium bromide has settled, the solution is removed and added to a cold (0° C.) slurry of the formula LXV aldehyde (part E, 0.37 g.). After 15 min. there is added 1.0 ml. of acetone and the mixture is heated to 60° C. for 10 min. The mixture is concentrated under reduced pressure. The residue is washed with 10 percent ethyl acetate in Skellysolve B and these washings are concentrated to the formula LXVI title compound, an oil, 0.33 g. having NMR peaks at 1.18, 1.33, 0.6–3.2, 4.5–6.0, and 6.67–7.62 δ; and $R_f$ 0.78 (TLC on silica gel in 25 percent ethyl acetate in Skellysolve B).

The above product of the preceeding paragraph is transformed to the formula LXVII diol by treatment with sodium methoxide (2.5 ml. of a 25 percent solution in methanol) for 4 hrs., followed by addition of 0.5 g. of solid sodium methoxide and further stirring for 15 hr. at 25° C., then at reflux for 6 hr. The mixture is cooled, mixed with 300 ml. of brine, acidified, and extracted with ethyl acetate. The organic phase is washed with brine, dried over magnesium sulfate, and concentrated under reduced pressure to a residue, 0.27 g. The residue is subjected to silica gel chromatography, eluting with 25-35 percent ethyl acetate in Skellysolve B, to yield the formula-LXVII title compound as an oil, 0.21 g., having NMR peaks at 0.87, 0.6-3.25, 3.88-4.35, 4.82-5.92, and 6.47-7.33 δ; and $R_f$ 0.13 (TLC on silica gel in 25 percent ethyl acetate in Skellysolve B).

G. 2-Exo-{m-[(carboxy)methoxy]}-3-exo-hydroxy-6-endo-(cis-1-heptenyl)bicyclo[3.1.0]hexane (Formula LXVIII: $R_3$ and $R_4$ of the $L_1$ moiety are both hydrogen, g is one, $R_7$ is n-butyl, $R_1$, $R_{53}$ and $R_{66}$ are hydrogen, and ~ is endo).

The formula-LXVII diol, i.e. 2-exo(m-hydroxybenzyl)-3-exo-hydroxy-6-endo-(cis-1-heptenyl)bicyclo[3.1.0]hexane (part F, 0.19 g.) is treated in 8 ml. of dioxane with bromoacetic acid (0.61 g.) and 6 ml. of 1N aqueous sodium hydroxide. After the mixture has been heated at reflux for 3 hr., with sodium hydroxide solution added when necessary to maintain a pH of about 10, the mixture is cooled, diluted with 100 ml. of water, and extracted with diethyl ether. The aqueous phase is acidified to pH 1-2 and extracted with ethyl acetate to yield the formula-LXVIII title compound, a pale yellow oil, 0.20 g. Recovered formula LXVIII diol is obtained from the diethyl ether organic phase on drying and concentrating, 0.025 g.

H. 3-Oxa-3,7-inter-m-phenylene-4,5,6-trinor-$PGF_{1\alpha}$ (Formula LXXIII: $R_3$ and $R_4$ of the $L_1$ moiety and $R_5$ and $R_6$ of the $L_1$ moiety ar all hydrogen, $R_7$ is n-butyl, g is one, $Y_1$ is trans —CH=CH— and $R_1$ is hydrogen).

The formula LXVIII alkene is transformed to the title compound applying the procedures disclosed in U.S. Pat. No. 3,711,515. Thus, compound LXVIII (part G) is hydroxylated by the procedures of Example 6 of that patent to the formula LXIX glycol of Chart G, using osmium tetroxide either alone or in combination with N-methylmorpholine oxide-hydrogen peroxide complex.

The glycol is then either (1) sulfonated, for example to yield the bismesylate, and then hydrolyzed to a mixture of the title compound and its 15-epimer, applying the procedures of Example 7 of that patent, or (2) treated with substantially 100 percent formic acid to form the diformate of LXIX and thereafter hydrolyzed to a mixture of the title compound and its 15 epimer, applying the procedures of Examples 20 and 21 of that patent. The epimers are separated by silica gel chromatography to yield the title compound and its 15-epimer.

A third route from glycol LXIX to compound LXXIII is by way of a cyclic ortho ester

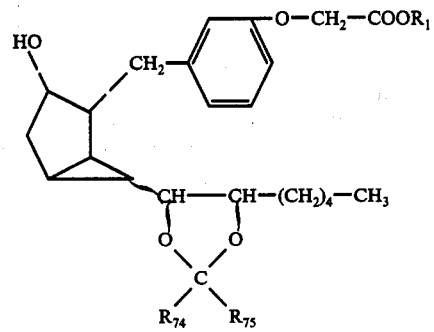

wherein $R_{74}$, $R_{75}$, and ~ are as defined above. The glycol is treated as a 1-20 percent solution in benzene with trimethyl orthoformate (1.5-10 molar equivalents) and a catalytic amount (1 percent of the weight of the glycol) of pyridine hydrochloride at about 25° C. The reaction is followed by TLC (thin layer chromatography) and is complete in a few minutes. There is thus obtained the cyclic ortho ester in 100 percent yield.

The cyclic ester is then treated with 20 volumes of 100 percent formic acid at about 25° C. In about 10 min. the reaction mixture is quenched in water or aqueous alkaline bicarbonate solution and extracted with dichloromethane. The organic phase is shaken with 5 percent aqueous sodium bicarbonate, dried over sodium sulfate, and concentrated to yield the corresponding diester. The diester is contacted with 10-50 volumes of anhydrous methanol and 10-20 percent of its weight of potassium carbonate at about 25° C. until the ester groups are removed. The mixture of 15-epimers thus obtained is then separated to yield the formula LXXIII compound or its 15-epimer.

I. 2-Exo-[m-(2-carboxyethyl)benzyl]-3-exo-hydroxy-6-endo(cis-1-heptenyl)bicyclo-[3.1.0]hexane (Formula LXXXII, $Z_3$ is methylene, q is one, $R_3$ and $R_4$ of the $L_1$ moiety are hydrogen, $R_7$ is n-butyl, $R_1$ and $R_{53}$ are hydrogen and ~ is endo).

With respect to Chart D, there is first prepared the formula LXXVI oxetane. Following the procedures of parts C, but replacing the m-acetoxybenzaldehyde of part C with the aldehyde of the formula

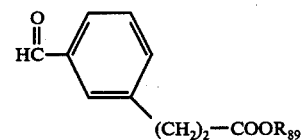

wherein $R_{69}$ is as defined above, the corresponding formula LXXVII oxetanes are obtained with a fully developed side chain.

Thereafter, following the procedures of parts D, E, and F, but replacing the formula LXII oxetane of part D with the oxetane obtained by the procedure of the preceeding paragraph of this part, there are obtained the corresponding formula LXXXI products.

Finally, the blocking groups on each LXXXI compound are removed by methods disclosed herein or known in the art to yield the formula LXXXII compound.

J. 3,7-inter-m-phenylene-4,5,6-trinor-$PGF_{1\alpha}$(Formula LXXXIV: $R_1$ is hydrogen $R_2$ and $R_3$ of the $L_1$ moiety and $R_5$ and $R_6$ of the $M_1$ moiety are hydrogen, $R_7$ is n-butyl, g is one, $Y_1$ is trans—CH═CH— and $Z_3$ is —$CH_2$—).

Following the procedures of part H, the formula LXXXII alkene is transformed in several steps to the formula LXXXIV compound.

Following the procedure of Preparation 17, but employing in the transformation of the formula LXV compound to the formula LXVI compond the various phosphonium salts described in the text accompanying Chart C, or optionally employing the procedure of Chart E or F, there are prepared each of the various 3-oxa-3,7-inter-m-phenylene- or 3,7-inter-m-phenylene-4,5,6-trinor-$PGF_{1\alpha}$-type compounds corresponding to each of the 3-oxa-$PGF_{1\alpha}$-type, 11,15-bis-(tetrahydropyranyl ethers) described following Preparation 16.

K. The formula LXX reaction product of part H is oxidized selectively at C-15 to a corresponding formula LXXI compound employing 2,3-dichloro-5,6-dicyano-benzoquinone.

L. Following the procedure of Preparation 5, the reaction product of part K is photoisomerized to the corresponding 13-cis-$PGF_{1\alpha}$-type compound.

M. Following the procedure of Preparation 6, the reaction product of part K is hydrogenated to the corresponding 13,14-dihydro-$PGF_{1\alpha}$-type compound.

N. Following the procedure of Preparation 7, the reaction product of part K is halogenated to the corresponding 14-chloro-$PGF_{1\alpha}$-type product.

O. Following the procedure of Preparation 9, the reaction products of parts L, M, and N are reduced to corresponding (15S)- or (15)R- 15-hydroxy-$PGF_{1\alpha}$-type compounds wherein $Y_2$ of formula LXXII is cis—CH═CH—; —$CH_2CH_2$—; or trans—CH═CCl—, respectively.

PREPARATION 18

15-methyl-$PGF_{2\alpha}$, Methyl Ester.

A. (15RS)-15-methyl-$PGF_{2\alpha}$, methyl ester, 11,15-bis-(tetrahydropyranyl ether), prepared by esterification of (15RS)-15-methyl-$PGF_{2\alpha}$, 11,15-bis(tetrahydropyranyl ether) with excess ethereal diazomethane separated into its separate (15S)- and (15R)-epimers by silica gel chromatography.

B. 15-methyl-$PGF_{2\alpha}$, Methyl ester-bis(tetrahydropyranyl ether) (0.60 g.) is reacted with 30 ml. of tetrahydrofuran, water, and acetic acid (1:3:6) at 40° C. for 4 hr. Thereafter, the resulting mixture is diluted with 60 ml. of water and freeze dried. The residue is then extracted with diethyl ether and washed with aqueous potassium bicarbonate and brine. The diethyl ether extract is then dried using magnesium sulfate and evaporated to yield an oil which is chromatographed to yield pure product.

Using corresponding (15R) starting material in part B the corresponding 15-epimeric product is prepared.

Following the procedure of Preparation 18, but optionally omitting the chromatographic separation, and employing each of the variously $PGF_\alpha$-type, 11,15-bis- or 15-(tetrahydropyranyl ethers), described following Preparations 13, 14, 15, or 16, there are obtained the corresponding $PGF_\alpha$-type products.

PREPARATION 19

13,14-Didehydro-$PGF_{2\alpha}$or its 15-epimer.
Refer to Chart A.

Potassium t-butoxide (6.79 g.) in tert-butanol (45 ml.) and methanol (8 ml.) is treated with 14-chloro-$PGF_{2\alpha}$, 11,15-bis(tetrahydropyranyl ether) and the reaction is allowed to proceed for 25 hr. The resulting mixture is then diluted with diethyl ether, washed with ice cold 8 percent phosphoric acid, and the phases are separated. The aqueous phase is then extracted with benzene, and thereafter extracted with ethyl acetate. The combined organic extracts are then washed with sodium chloride solution, dried, and evaporated to yield title product.

Following the procedure of Preparation 19, each of the compounds described in and following Preparation 18, wherein $Y_2$ is trans—CH═CCl- is transformed to a corresponding 13,14-didehydro-$PGF_{1\alpha}$- or 11-deoxy-$PGF_\alpha$-type compound wherein $Y_1$ is —C≡C—.

Accordingly the above Preparations provide $PGF_\alpha$- starting material useful in the Example below in preparing each of the novel 2-decarboxy-2-aminomethyl or 2-(substituted amino)-methyl-PG-type products of the present invention.

EXAMPLE 1

15-Methyl-$PGF_{2\alpha}$, amide (Formula CIII: $Z_1$ is cis—CH═CH—$CH_2CH_2$—$CH_2$—, $R_8$ is hydroxy, $Y_1$ is trans—CH═CH—, $R_3$ and $R_4$ of the $L_1$ moiety and $R_5$ of the $M_1$ moiety are all hydrogen, and $R_7$ is n-butyl).

Refer to Chart G.

A. To a cold (0° C.) mixture of 3.68 g. of 15-methyl-$PGF_{2\alpha}$, tetrahydrofuran (60 ml.), water (5 ml.), and triethylamine (1.11 g.) is added with stirring isobutylchloroformate (1.5 g.) over a 5 min. period. Accordingly, there is prepared the formula CII mixed acid anhydride wherein $R_1$ is isobutyl, corresponding to the formula Cl starting material.

B. The reaction mixture of part A is stirred at 0° C. for 25 min. and thereafter liquid ammonia is added. The temprature of this mixture is then allowed to rise to 0° C. and the mixture is stirred at 0° C. for 3 hr. The resulting mixture is then concentrated under vacuum (at temperatures below 30° C.). The residue is then dissolved in 125 ml. of ethyl acetate and 7.5 ml. of ethanol, washed with saturated brine, and the organic phase dried over magnesium sulfate and concentrated under reduced pressure. This residue is then diluted with toluene and the solution concentrated under required pressure to yield 3.6 g. of 15-methyl-$PGF_{2\alpha}$, amide. Characteristic NMR absorptions are observed at 5.3–5.6, 6.3, and 5.59 δ.

Following the procedure of Example 1, but employing each of the various $PGF_\alpha$-type compounds described following preparation 18 or 19, there are prepared each of the corresponding $PGF_{2\alpha}$- or 11-deoxy-$PGF_{2\alpha}$-type, amides. Likewise, following the procedure of Example 1, part A, there are prepared each of the corresponding $PGF_\alpha$- or 11-deoxy-$PGF_\alpha$-isobutyric anhydrides.

EXAMPLE 2

2-Decarboxy-2-azidomethyl-$PGF_{2\alpha}$, or 2-nor-$PGF_{2\alpha}$, azide (Formula CV: $Z_1$ is CH═CH—$(CH_2)_3$ or CH═CH—$(CH_2)_2$, respectively, $R_8$ is hydroxy, $Y_1$ is trans—CH═CH—, $R_3$ and $R_4$ of the $L_1$ moiety and $R_5$ of the $M_1$ moiety are all hydrogen, and $R_7$ is n-butyl).

A. To a cold solution (0° C.) of $PGF_{2\alpha}$(7.1 g.), 125 ml. of acetone, 10 ml. of water, and 2.2 g. of triethylamine is added with stirring 3.01 g. of isobutylchloroformate. The mixture is stirred at 0° C. for about 30 min. at which time a cold solution of 7 g. of sodium azide on 35 ml. of water is added. The mixture is then stirred at 0° C. for one hr. at which time it is diluted with 300 ml. of water and extracted with diethyl ether. The organic layers are then combined; washed with water, dilute carbonate solution, saturated saline; dried; and concentrated under reduced pressure, maintaining bath temperature below 30° C., to yield 2-nor-PGF$_{2\alpha}$, azide.

B. 2-Decarboxy-2-azidomethyl-PGF$_{2\alpha}$ is prepared by the following reaction sequence:

1. A solution of t-butyldimethylsilyl chloride (10 g.), imidazole (9.14 g.), and PGF$_{2\alpha}$(3 g.) in 12 ml. of dimethylformamide are magnetically stirred under nitrogen atmosphere for 24 hr. The resulting mixture is then cooled in an ice bath and the reaction quenched by addition of ice water. The resulting mixture is then diluted with 150 ml. of water and extracted with diethyl ether. The combined ethereal extracts are then washed with water, saturated ammonium chloride, a sodium chloride solution, and thereafter dried over sodium sulfate. Solvent is removed under vacuum yielding PGF$_{2\alpha}$, t-butyldimethylsilyl ester, 9,11,15-tris-(t-butyldimethylsilyl ether). NMR absorptions are observed at 0.20, 0.30, 0.83, 0.87, 0.89, 1.07-2.50, 3.10-4.21, and 5.38 δ. Characteristic infrared absoprtions are observed at 970, 1000, 1060, 1250, 1355, 1460, 1720, and 2950 cm.$^{-1}$.

2. To a magnetically stirred suspension of lithium aluminum hydride (7.75 g.) in 18 ml. of diethyl ether is added dropwise at room temperature over a period of 12 min. 8.71 g. of the reaction product of part (1) above in 40 ml. of diethyl ether. After stirring at ambient temperature for one hr., the resulting product is cooled in an ice water bath and saturated sodium sulfate is added dropwise until the appearance of a milky suspension. The resulting product is coagulated with sodium sulfate, triturated with diethyl ether, and the solvent is removed by suction filtration. Concentration of the diethyl ether under vacuum yields 7.014 g. of 2-decarboxy-2-hydroxymethyl-PGF$_{2\alpha}$, 9,11,15-tris-(t-butyldimethylsilyl ether). NMR absorptions are observed at 0.03, 0.82, 0.87, 1.10-2.60, 3.30-4.30, and 5.37 δ. Characteristic infrared absorptions are observed at 775, 840, 970, 1065, 1250, 1460, 2895, 2995, and 3350 cm$^{-1}$.

3. p-Toluenesulfonyl chloride (3.514 g.), pyridine (44 ml.), and the reaction product of subpart (2), 7.014 g., are placed in a freezer at −20° C. for 3 days. Thereafter, 7.200 g. of 2-decarboxy-2-p-toluenesulfonyloxymethyl-PGF$_{2\alpha}$, 9,11,15-tris-(t-butyldimethylsilyl ether), is recovered. NMR absorptions are observed at 0.10, 0.94, 0.97, 1.10, 2.50, 2.50, 4.03, 3.80-4.80, 5.45, 7.35, and 7.80 δ. Infrared absorptions are observed at 775, 970, 1180, 1190, 1250, 1360, 1470, 2900, and 2995 cm.$^{-1}$.

4. The reaction product of subpart (3) (2.13 g.) is placed in 42 ml. of acetic acid, tetrahydrofuran, and water (3:1:1) containing 0.25 ml. of 10 percent aqueous hydrochloric acid. The reaction mixture becomes homogeneous after vigorous stirring for 16 hr. at room temperature. The resulting solution is then diluted with 500 ml. of ethyl acetate; washed with saturated sodium chloride and ethyl acetate; dried over sodium sulfate; and evaporated under reduced pressure, yielding 1.301 g. of an oil. Crude product is chromatographed on 150 g. of silica gel packed with ethyl acetate. Eluting with ethyl acetate yields 0.953 g. of 2-decarboxy-2-p-toluenesulfonyloxymethyl-PGF$_{2\alpha}$.

5. The reaction product of subpart (4), (0.500 g.) in 5.0 ml. of dimethylformamide was added to a stirred suspension of sodium azide (1.5 g.) in 20 ml. of dimethylformamide. Stirring is continued at ambient temperature for 3 hr. The reaction mixture is then diluted with water (75 ml.), extracted with diethyl ether (500 ml.), and the the etheral extracts washed successively with water, saturated sodium chloride, and dried over sodium sulfate. Removal of the diethyl ether under reduced pressure yields 0.364 g. of 2-decarboxy-2-azidomethyl-PGF$_{2\alpha}$. A characteristic azido infrared absorption is observed at 2110 cm.$^{-1}$.

Following the procedure of Example 2, but employing any of the PGF$_\alpha$- or 11-deoxy-PGF$_\alpha$-type compounds described following preparation 18 or 19, there are prepared corresponding 2-decarboxy-2-azidomethyl-PGF$_{2\alpha}$ or 11-deoxy-PGF$_{2\alpha}$-type compounds.

EXAMPLE 3

2-Decarboxy-2-aminomethyl-PGF$_{1\alpha}$(Formula CIV: Z$_1$ is —(CH$_2$)$_5$—, R$_8$ is hydroxy, Y$_1$ is trans—CH= CH—, R$_3$ and R$_4$ of the L$_1$ moiety and R$_5$ of the M$_1$ moiety are all hydrogen and R$_7$ is n-butyl).

A. PGF$_{1\alpha}$(150 mg.) is treated with excess ethereal diazomethane and evaporated yielding PGF$_{1\alpha}$, methyl ester. This residue is then dissolved in 1 ml. of 95 percent ethanol. The resulting mixture is then transferred to a steel Parr bomb rinsed with 2 one-half ml. aliquots of 95 percent ethanol and 200 mg. of ammonium chloride are added. Then the mixture is cooled in a dry ice acetone bath and ammonia is added until about 5 to 10 ml. has condensed. The bomb is then sealed and allowed to warm to room temperature. Thereafter the bomb is placed in an oven at 50° C. for 2 days cooled in a dry-ice acetone bath, and opened. Thereafter residual ammonia is evaporated with nitrogen and the product extracted with ethyl acetate, washed with water and saturated brine, dried over sodium sulfate, and evaporated to yeild PGF$_{1\alpha}$amide.

B. Lithium aluminum hydride (100 mg.) in 5 ml. of dry tetrahydrofuran under nitrogen is prepared. A solution of the reaction product of part A is then slowly added (being dissolved in a small amount of fry tetrahydrofuran). The resulting mixture is then stirred at room temperature for 48 hr. and thereafter one-tenth ml. of water is added while cooling the mixture in an ice bath. Thereafter 0.1 ml. of 15 percent sodium hydroxide and 0.3 ml. of water is added. The suspension is then filtered; dried over magnesium sulfate; washed with ethyl acetate; and evaporated to yield a crystalline residue, 40 mg. of title product. The infrared absorption spectrum shows a characteristic absorption at 2700–3400 cm.$^{-1}$. The mass spectrum shows peaks at 450, 449, 407, 390, 389, 348, 347, and 329.

EXAMPLE 4

2-Decarboxy-2-aminomethyl-PGF$_{2\alpha}$(Formula CXXV: Z$_1$ is cis—CH=CH—(CH$_2$)$_3$—, R$_8$ is hydroxy, Y$_1$ is trans—CH=CH—, R$_3$ and R$_4$ of the L$_1$ moiety and R$_5$ of the M$_1$ moiety are all hydrogen, and R$_7$ is n-butyl).

Refer to Chart H. Crude 2-decarboxy-2-azidomethyl-PGF$_{2\alpha}$(Example 2, 0.364 g.) in 12 ml. of diethyl ether is added to a magnetically stirred suspension of lithium aluminum hydride (0.380 g.) in 20 ml. of diethyl ether. Reaction temprature is maintained at about 0° C. and addition of lithium aluminum hydride proceeds dropwise over a 4 min. period. After addition is complete, the resulting mixture is stirred at ambient temperature for 1.5 hr. and thereafter placed in an ice bath (0°-5° C.). Excess reducing agent is then destroyed by addition of saturated sodium sulfate. After cessation of gas evolution, the resulting product is coagulated with sodium sulfate, triturated with diethyl ether, and solid salts removed by filtration. The filtrate is then dried with sodium sulfate, and evaporated under reduced pressure to yield 0.304 g. of a slightly yellow oil. This oil (100 mg.) is then purified by preparative thin layer chromatography, yielding 42 g. of title product. NMR absorptions are observed at 0.90, 1.10–2.80, 3.28, 3.65–4.25, and 5.45 $\delta$. Characteristic infrared absorptions are observed at 970, 1060, 1460, 2995, and 3400 cm.$^{-1}$. The mass spectrum shows parent peak at 699.4786 and other peaks at 628, 684, 595, 217, and 274.

Following the procedures of Examples 2 and 4, each of the various PGF$_\alpha$- or 11-deoxy-PGF$_\alpha$-type compounds described in the preparations are transformed to corresponding 2-decarboxy-2-aminomethyl-PGF$_\alpha$- or 11-deoxy-PGF$_\alpha$-type products.

EXAMPLE 5

2-Decarboxy-2-carbomethoxyaminomethyl-2-nor-PGF$_{2\alpha}$(Formula CVT: R$_1$ is methyl, Z$_1$ is cis—CH=CH—(CH$_2$)$_3$—, R$_8$ is hydroxy, Y$_1$ is trans—CH=CH—, R$_3$ and R$_4$ of the L$_1$ moiety and R$_5$ of the M$_1$ moiety are all hydrogen, and R$_7$ is n-butyl).

Refer to Chart G.

A solution of -PGF$_{2\alpha}$, azide (the product of Example 2, part A) in 200 ml. of methanol is heated at reflux for 2 hr. and thereafter concentrated under reduced pressure to yield 7.7 g. of 2-decarboxy-2-carbomethoxyamino-methyl-2-nor-PGF$_{2\alpha}$ contaminated with a trace of less polar material. This crude product is then chromatographed on a dry packed column of silica gel deactivated by addition of about 8 percent water. The column is eluted with acetone in methylene chloride (1:1) and 4.92 g. of pure title compound is recovered. The NMR absorption spectrum indicate characteristic absorptions at 5.2–5.7, 3.0, and 3.63 $\delta$. The mass spectrum show a parent peak at 599.3864 and other peaks at 584, 527, 509, 438, 217, 173, and 88.

Following the procedure of Examples 2 and 5, each of the various PGF$_{2\alpha}$compounds described in the preparations above is transformed to a corresponding 2-decarboxy-2-carbomethoxyaminomethyl-2-nor-PGF$_{2\alpha}$- or 11-deoxy-PGF$_{2\alpha}$-type product. Further, employing the procedure of the above Examples, but using various other alkanols in place of methanol in Example 5, there are prepared the corresponding 2-decarboxy-2-carboalkoxyaminomethyl-PGF$_{2\alpha}$- or 11-deoxy-PGF$_{2\alpha}$-type products. Accordingly, employing for example a 2a-homo-PGF$_\alpha$- or 11-deoxy-PGF$_\alpha$-type formula Cl starting material in Chart G, there is prepard a corresponding 2-decarboxy-2-carbalkoxyaminomethyl-PGF$_{2\alpha}$- or 11-deoxy-PGF$_{2\alpha}$-type product wherein the 8$\alpha$-side chain contains 7 carbon atoms (exclusive of any carbon atoms contained in the carboalkoxy moiety).

EXAMPLE 6

2-Decarboxy-2-aminomethyl-2-nor-PGF$_{2\alpha}$ (Formula CVII: Z$_1$ is cis—CH=CH—(CH$_2$)$_3$—, R$_8$ is hydroxy, Y$_1$ is trans—CH=CH—, R$_3$ and R$_4$ of the L$_1$ moiety and R$_5$ of the M$_1$ moiety are all hydrogen, and R$_7$ is n-butyl).

Refer to Chart G.

A mixture of 2-decarboxy-2-carbomethoxyaminomethyl-2-nor-PGF$_{2\alpha}$ (Example 5, 900 mg.) in 10 ml. of methanol and 5 ml. of 50 percent aqueous sodium hydroxide solution are heated at reflux for 8 hr. The mixture is thereafter cooled and shaken with water and ethyl acetate. The organic layer is then washed with brine, dried, and concentrated under reduced pressure to yield 0.75 g. of a residue. This residue is then chromatographed on 100 g. of dry packed silica gel conditioned with 5 ml. of water and 5 ml. of 5 percent ammonium hydroxide in methanol. The column is eluted with one percent ammonium hydroxide in methanol and fractions containing pure product are combined and concentrated under reduced pressure. The residue thus obtained is treated with ethyl acetate and filtered to remove traces of silica gel. Finally, concentration under reduced pressure yields 0.25 g. of title product. Characteristic NMR absorptions are observed at 5.25–5.60, 3.22, and 2.55–2.84 $\delta$. The mass spectrum shows a parent peak at 685.4607 and other peaks at 614, 217, and 174.

Following the procedure of Example 6, but employing each of the various 2-decarboxy-2-carbomethoxyaminomethyl-PGF$_{2\alpha}$- or 11-deoxy-PGF$_{2\alpha}$-type products described following Example 5, there are prepared each of the corresponding 2-decarboxy-2-aminomethyl-PGF$_{2\alpha}$- or 11-deoxy-PGF$_{2\alpha}$-type products. For example, 2-decarboxy-2-carbomethoxyaminomethyl-PGF$_{2\alpha}$ yields 2-decarboxy-2-aminomethyl-PGF$_{2\alpha}$.

EXAMPLE 7

2-Decarboxy-2-methylaminomethyl-2-nor-PGF$_{2\alpha}$ (Formula CVII: L$_2$ is methyl, Z$_1$ is cis—CH=CH—(CH$_2$)$_3$—, R$_8$ is hydroxy, Y$_1$ is trans—CH=CH—, R$_3$ and R$_4$ of the L$_1$ moiety and R$_5$ of the M$_1$ moiety are all hydrogen, and R$_7$ is n-butyl).

Refer to Chart G.

A. A mixture of 2-carbomethoxyaminomethyl-2-decsarboxy-2-nor-PGF$_{2\alpha}$(Example 5, 3.17 g.), 30 ml. of methylene chloride, 10 ml. of dihydropyran (redistilled), in 2 ml. of methylene chloride saturated with pyridine hydrochloride are allowed to stand for 16 hr. at room temperature. The mixture is thereafter diluted with diethyl ether and washed quickly with an ice cold solution of dilute aqueous hydrochloric acid, dilute potassium carbonate, and brine. Thereafter, the resulting mixture is dried over magnesium sulfate and concentrated under reduced pressure to yield 5.3 g. of a residue. The residue is then chromatographed on a dry pack column of silica gel (500 g.) and 100 ml. of 30 percent ethyl acetate in Skellysolve B. The column is thereafer eluted with 30 to 50 percent ethyl acetate in Skellysolve B. Thereby, pure 2-decarboxy-2-carbomethoxyaminomethyl-2-nor-PGF$_{2\alpha}$, tris-(tetrahydropyranyl ether), 4.4 g., is thereby obtained. Characteristic NMR absorptions are observed at 5.26–5.69, 4.52–4.8, 3.64, and 2.97–2.38 $\delta$.

B. To a slurry of 5 g. of lithium aluminum hydride in 250 ml. of tetrahydrofuran is added 12 g. of the reaction product of part A in 50 ml. of benzene. The resulting mixture is stirred and heated at reflux for 24 hr. and thereafter cooled. A solution of 5 ml. of water in 20 ml. of tetrahydrofuran is then cautiously added with stirring followed by addition of 20 ml. of a 10 percent aqueous sodium hydroxide solution. The resulting mixture is then filtered and the filtrate concentrated under reduced pressure to yield 10.7 g. of 2-decarboxy-2-methylaminomethyl-2-nor-PGF$_{2\alpha}$, tris-(tetrahydropyranyl ether).

C. A mixture of the reacton product of part B (0.6 g.), 7 ml. of acetic acid, and 3 ml. of water are stirred and heated to 45° C. for about 20 hr. The resulting mixture is then cooled and shaken with 50 ml. of ethyl acetate and a mixture of 7 ml. of 50 percent aqueous sodium hydroxide and 30 ml. of ice water. The organic layer is then washed with brine, dried, and concentrated under reduced pressure to yield 0.3 g. of a residue. The residue is then chromatographed on a column of silica gel wet packed with a solution of one percent ammonium hydroxide in methanol. Eluting with the same solvent (one percent ammonium hydroxide in methanol) and concentrating fractions containing pure product under reduced pressure, a residue is obtained. This residue is then mixed with ethyl acetate, filtered to remove traces of silica gel, and the filtrate concentrated under reduced pressure to yield 2 g. of 2-decarboxy-2-methylaminomethyl-2-nor-PGF$_{2\alpha}$. Characteristic NMR absorptions are observed at 5.23–5.61, 3.4–3.7, 2.45–2.73 and 2.38 $\delta$. The mass spectrum shows a parent peak at 627.4370 and other peaks at 555, 484, 466, 394, 217, and 173.

Following the procedure of Example 7, but using in place of 2-decarboxy-2-carbomethoxyaminomethyl-2-nor-PGF$_{2\alpha}$, the various other 2-decarboxy-2-carbomethoxyaminomethyl-2-nor-PGF$_\alpha$-, or 11-deoxy-PGF$_\alpha$-type compounds described following Example 5, there are prepared the corresponding 2-decarboxy-2-methylaminomethyl-PGF$_\alpha$- or 11-deoxy-PGF$_\alpha$-type products corresponding to each of the 2-decarboxy-2-aminomethyl-PGF$_\alpha$- or 11-deoxy-PGF$_\alpha$-type compounds described following Example 6.

Further, following the procedure of Example 7, but using each of the various 2-decarboxy-2-carboalkoxyaminomethyl-PGF$_\alpha$- or 11-deoxy-PGF$_\alpha$-type products described following Example 5, there are prepared each of the corresponding 2-decarboxy-2-alkylaminomethyl-PGF$_\alpha$- or 11-deoxy-PGF$_\alpha$-type products.

EXAMPLE 8

2-Decarboxy-2-carbomethoxymethylaminomethyl-2-nor-PGF$_{2\alpha}$(Formula CIX: R$_1$ is methyl, L$_2$ is methyl, Z$_1$ is cis—CH=CH—(CH$_2$)$_3$—, R$_8$ is hydrogen, Y$_1$ is trans—CH=CH—, R$_3$ and R$_4$ of the L$_1$ moiety and R$_5$ of the M$_1$ moiety are all hydrogen, and R$_7$ is n-butyl).

Refer to Chart G.

A. To a stirred mixture of 2-decarboxy-2-methylaminomethyl-2-nor-PGF$_{2\alpha}$, tris-(tetrahydropyranyl ether) 2.17 g. obtained by Example 7, part B, 25 ml. of acetone, 3 ml. of water, and 3 ml. of triethylamine are combined at 0° C. Thereafter, during a 5 min. period 2.0 ml. of methyl chloroformate is added. The resulting mixture is then stirred at 0° C. for one hr. and thereafter shaken with ethyl acetate and water. The organic layer is then washed with cold dilute hydrochloric acid, dilute aqueous potassium hydroxyide, and brine. The mixture is then dried over magnesium sulfate and concentrated to yield 2.3 g. of a material containing a less polar impurity. The material is chromatographed on a dry pack column of silica gel (200 g.) conditioned with 25 ml. of 30 percent ethyl acetate in Skellysolve B. The column is then eluted with the same solvent. Thereupon, the tris-(tetrahydropyranyl ether) of the title product (2.08 g.) is obtained. Characteristic NMR absorptions are observed at 5.22–5.7, 4.54–4.83, 3.67, 3.10–3.60, and 2.88 $\delta$.

B. The reaction product of part A (1.3 g.), 20 ml. of acetic acid, 10 ml. of water, and 5 ml. of tetrahydrofuran are heated at 40° C. for 16 hr. The mixture is then cooled, diluted with ethyl acetate, and shaken with a mixture of 20 ml. of 50 percent aqueous sodium hydroxide and 100 ml. of water and ice. The organic layer is then washed with brine, dried, anc concentrated under reduced pressure to yield 0.95 g. of a residue. The residue is then chromatographed on 125 g. of silica gel, 5 ml. of water, and 25 ml. of 50 percent acetone and chloroform yielding 0.55 g. of title product. Characteristic NMR absorptions are observed 5.28–5.26, 3.67, 3.10–3.42, and 2.88 $\delta$. The mass spectrum shows a parent peak at 613.4013, and other peaks at 582, 542, 523, 452, 433, 217, and 173 $\delta$.

Following the procedure of Example 8 and employing in place of the starting material of Example 7, part B, the various other tetrahydropyranyl ethers of PGF$_\alpha$- or 11-deoxy-PGF$_\alpha$-type compounds described following Example 7, there are prepared the corresponding 2-decarboxy-2-carbomethoxymethylaminomethyl-PGF$_\alpha$- or 11-deoxy-PGF$_\alpha$-type products.

EXAMPLE 9

2-Decarboxy-2-dimethylaminomethyl-2-nor-PGF$_{2\alpha}$-(Formula CX: L$_2$ and L$_3$ are methyl, Z$_1$ is cis—CH=CH—(CH$_2$)$_3$—, R$_8$ is hydroxy, Y$_1$ is trans—CH=CH—, R$_3$ and R$_4$ of the L$_1$ moiety and R$_5$ of the M$_1$ moiety are all hydrogen, and R$_7$ is n-butyl).

Refer to Chart G.

A. To a mixture of 1.0 g. of lithium aluminum hydride in 100 ml. of tetrahydrofuran there is added with stirring a solution of 2.08 g. of the reaction product of Example 8, part A in 10 ml. of benzene. The mixture is then heated at reflux for 20 hr. and thereafter cooled. A solution of one ml. of water and 10 ml. of tetrahydrofuran is then cautiously added with stirring followed by addition of 4 ml. of a 10 percent aqueous sodium hydroxide solution. The mixture is then filtered and the filtrate concentrated under reduced pressure to yield 1.95 g. of essentially pure 2-decarboxy-2-dimethylaminomethyl-2-nor-PGF$_{2\alpha}$, tris-(tetrahyropyranyl ether). Characteristic NMR absorptions are observed at 5.25–5.67, 4.52–4.80, and 2.18 $\delta$.

B. A mixture of 8.6 g. of the reaction product of part A, 90 ml. of acetic acid, 45 ml. of water, and 20 ml. of methanol are stirred at 40° C. for 20 hr. The mixture is then cooled, diluted with ethyl acetate (800 ml.) and the resulting mixture shaken with a mixture of 90 ml. of 50 percent sodium hydroxide solution, and 400 ml. of ice and water. The organic layer is then washed with brine, dried, and concentrated to yield 5.3 g. of a residue. This residue is then chromatographed on a dry-pack column of 500 g. of silica gel conditoned with a solution of 10 ml. of concentrated ammonium hydroxide, 50 ml. of methanol, and 50 ml. of chloroform. The column is then eluted with one percent concentrated ammonium hydroxide, and 15 percent methanol in chloro, then one percent aqueous ammonium hydroxide and 25 percent methanol in chloroform. Thereupon, pure title product (3.85 g.) is obtained. Characteristic NMR absorptions are observed at 5.23–5.60, 4.48, and 2.21 $\delta$. Mass spectrum shows a parent peak at 569.4130 and other peaks at 498, 479, 217, 173, and 58.

Following the procedure of Example 9, but employing each of the various tetrahydropyranyl ethers of the PGF$_\alpha$- or 11-deoxy-PGF$_\alpha$-type compounds described following Example 8, there are prepared each of the corresponding 2-decarboxy-2-dimethylaminomethyl-PGF$_\alpha$- or 11-deoxy-PGF$_\alpha$-type products.

Accordingly, following the procedure of the above Examples, there are prepared each of the corresponding 2-decarboxy-2-aminomethyl- or 2-decarboxy-2-(substituted amino)methyl-PGF$_\alpha$- or 11-deoxy-PGF$_\alpha$-type products of this invention.

However, in the above Example which employ lithium aluminum hydride reagents, reduction of acetylenic moieties (Y$_1$ is —C≡C—) is avoided by following the procedure of each of the above Examples, employing the 14-chloro-PGF$_\alpha$- or 11-deoxy-PGF$_\alpha$ intermediates described above, and thereafter dehydrohalogenating with base the 2-decarboxy-2-aminomethyl- or 2-decarboxy-2-(substituted amino) methyl- -chloro- PGF$_\alpha$- or 11-deoxy-PGF$_\alpha$-type intermediate as described in Preparation 19.

Further, the products of the above example wherein tetrahydropyranyl blocking groups are employed, are optionally prepared by the procedures described above, except that the introduction and subsequent hydrolysis of the blocking groups is omitted.

EXAMPLE 10

2-Decarboxy-2-aminomethyl-2-nor-16,16-dimethyl-PGF$_{2\alpha}$ (Formula CVII: Z$_1$ is cis—CH=CH—(CH$_2$)$_3$—, R$_8$ is hydroxy, Y$_1$ is trans—CH=CH—, R$_3$ and R$_4$ of the L$_1$ moiety are both methyl, R$_5$ is hydrogen, and R$_7$ is n-butyl).

A. 16,16-Dimethyl-PGF$_{2\alpha}$ (750 mg.) is dissolved in 12.5 ml. of acetone. Water (1.0 ml.) and triethylamine (0.23 g.) in 1 ml. of acetone is added. The mixture is then cooled to 0° C. with an ice bath and 0.311 g. of isobutylchlorormate in 1 ml. of acetone is added. The reaction mixture is then stirred for 30 min. at 0° C. An ice cold solution of 0.73 g. of sodium azide in 3.5 ml. of water is then added and the reaction mixture is stirred at 0° for one hr. and then diluted with 30 ml. of water and the product extracted with ethyl acetate. The ethyl acetate extract is then washed with ice, cold dilute sodium bicarbonate, brine, and dried over magnesium sulfate. The resulting mixture is then concentrated under reduced pressure at 28° C. and the residue is taken up in 20 ml. of methanol and refluxed for 2 hr. This solution is then partially cooled and concentrated at reduced pressure to a solution which is azeotroped with benzene to remove traces of water. Accordingly, there is recovered 2-decarboxy-2-carbomethoxyaminomethyl-2-nor-16,16-dimethyl-PGF$_{2\alpha}$-tris-(tetrahydropyranyl ether), 670 mg. Characteristic NMR absorptions are observed at 3.65, 3.33, 3.21, 3.09, 3.98, 0.90, and 0.86 $\delta$.

B. The reaction product of part A (670 mg.) is dissolved in 15 ml. of methanol and the resulting solution purged of air with nitrogen. A solution of 7 ml. of 30 percent aqueous sodium hydroxide which has been purged in a like manner is then added to the mixture and the result refluxed in a nitrogen atmosphere for 6 hr. Thereafter, the reaction mixture is allowed to stand over night at room temperature under nitrogen. The resulting mixture is then diluted with 100 ml. of ethyl acetate and washed with deionized water and brine. The mixture is thereafter dried over magnesium sulfate and concentrated under reduced pressure to yield 0.49 g. of crude product which is chromatographed over 75 g. of silica gel mixed with 3 ml. of water and 15 ml. of 5 percent ammonium hydroxide in methanol. The column is dry packed and wet with methanol containing one percent concentrated ammonium hydroxide solution. The column is then eluted with methanol containing one percent concentrated ammonium hydroxide solution. Thereupon there are obtained 240 g. of pure title product. Characteristic NMR absorptions are observed at 5.63–5.28, 3.49, 0.86, and 0.83 $\delta$. The mass spectrum shows parent peak at 713.4939.

EXAMPLE 11

2-Decarboxy-2-aminomethyl-16,16-dimethyl-PGF$_{2\alpha}$ (Formula CXXV: Z$_1$ is cis—CH=CH—(CH$_2$)$_3$—, R$_8$ is hydroxy, Y$_1$ is trans—CH=CH—, R$_3$ and R$_4$ of the L$_1$ moiety are both methyl, R$_5$ of the M$_1$ moiety is hydrogen, and R$_7$ is n-butyl).

Refer to Chart H.

A. 16,16-Dimethyl-PGF$_{2\alpha}$, 11,15-(bis-tetrahydropyranyl ether), 5 g. is dissolved in 16 ml. of methylene chloride and treated with 5 ml. of freshly redistilled dihydroryan and 300 mg. of pyridine hydrochloride at room temperature for 8 hr. The reaction mixture is then washed with ice-cold dilute aqueous sodium bicarbonate, dried over anhydrous magnesium sulfate, and concentrated under reduced pressure to yield 6.2 g. of 16,16-dimethyl-PGF$_{2\alpha}$, tris-(tetrahydropyranyl ether), tetrahydropyranyl ester. Characteristic NMR absorptions are observed at 5.63–5.33, 4.67, 0.90, 0.86, and 0.83 $\delta$.

B. The reaction product of Part A (6.2 g.) in 100 ml. of anhydrous diethyl ether is added dropwise to a mixture of 1.5 g. of lithium aluminum hydride in 15 ml. of diethyl ether. The reaction mixture is stirred at ambient temperature for about 30 min. and thereafter excess reducing agent is decomposed by cautious addition of approximately 25 ml. of ethyl acetate and 30 ml. of water, respectively. The organic salts are then filtered and the residue rinsed with ethyl acetate. The filtrate is then concentrated under reduced pressure to yield 5.95 g. of essentially pure 2-decarboxy-2-hydroxymethyl-16,16-dimethyl-PGF$_{2\alpha}$, tris-(tetrahydropyranyl ether). Characteristic NMR absorptions are observed at 5.67–5.33, 0.93, 0.88, and 0.84 $\delta$.

C. The reaction product of part B (2.28 g.) is dissolved in 50 ml. of pyridine and cooled to $-18°$ C. in an ice methanol bath. p-Toluenesulfonyl chloride, 1.26 g., is added and the mixture is stirred at $-18°$ C. for 5 min. The resulting mixture is then cooled at $-12°$ C. for 20 hr. The reaction mixture is then poured into ice and water and the product extracted with dimethyl ether. The ethereal extract is then washed with ice cold dilute aqueous potassium bisulfate until the aqueous phase is acidic (pH 3). The extract is then washed with water and brine, and dried over magnesium sulfate, and concentrated under reduced pressure to yield 2.42 g. of crude 2-decarboxy-2-p-toluenesulfonyloxymethyl-16,16-dimethyl-PGF$_{2\alpha}$, tris-(tetrahydropyranyl ether). This crude material is then purified by chromatography using 240 g. of silica gel partially deactivated with 90 ml. of ethyl acetate (dry packed and wet with 15 percent ethyl acetate and Skellysolve B). Eluting with 25–30 percent ethyl acetate in Skellysolve B, there is obtained 1.74 g. of purified product. Characteristic NMR absorptions are observed at 7.95, 7.72, 7.39, 7.23, 5.67, 5.22, 4.69, 2.48, 0.93, 0.88, and 0.85 $\delta$.

D. The reaction product of part C (1.74 g.) is dissolved in 25 ml. of dimethylformamide. A slurry of 5.2 g. of sodium azide and 61 ml. of dimethylformamide is added. The reaction mixture is then stired for 3.5 hr. at ambient temperature, being protected from atmospheric humidity. The reaction mixture is then poured into 300 ml. of water and extracted 5 times with 150 ml. portions of diethyl ether. This ethereal extract is then washed with deionized water and brine before drying over magnesium sulfate. The dry extract is then concentrated under reduced pressure yielding 1.22 g. of 2-decarboxy-2-azidomethyl-16,16-dimethyl-PGF$_{2\alpha}$, tris-(tetrahydropyranyl ether ). Characteristic infrared absorptions are observed at 2130 and 1500–1600 cm.$^{-1}$.

E. A suspension of 0.5 g. of lithium aluminum hydride in 20 ml. of diethyl ether is prepared by stirring the mixture in a nitrogen atmosphere for several minutes.

The azide prepared in part D is dissolved in 30 ml. of diethyl ether and slowly added dropwise to the reducing agent prepared above. The reaction mixture is then stirred for an hour at ambient temperature and excess reducing agent thereafter decomposed by cautious addition of water. The inorganic salts are then removed by filtration and the residue rinsed well with diethyl ether. The combined filtrate is then concentrated under reduced pressure to yield crude product (1.28 g.). This crude product is then chromatographed over 200 g. of silica gel pretreated with 3 ml. of water, 15 ml. of 5 percent ammonium hydroxide in methanol, and thereafter dry-packed and wet with methanol in methylene chloride (1:1) mixture. 1.27 g. of 2-decarboxy-2-aminomethyl-16,16-dimethyl-PGF$_{2\alpha}$, 9,11,15-tris-(tetrahydropyranyl ether) is obtained.

F. The reaction product of part E (1.27 g.) is taken up in 15 ml. of acetic acid and 7.5 ml. of water. The resulting mixture is then warmed to 40° C. under a nitrogen atmosphere. The reaction mixture is then diluted with 40 ml. of ethyl acetate and cooled to −15° C. in an ice methanol bath. The solution is then made basic by addition of 14 ml. of a 50 percent aqueous sodium hydroxide solution in 30 ml. of crushed ice and water. The ethyl acetate layer is then separated and the aqueous layer extracted 3 times with ethyl acetate. The combined ethyl acetate extracts are then dried over magnesium sulfate and concentrated under reduced pressure to yield 0.78 g. of crude product. This material is then purified by chromatography over 100 g. of silica gel pretreated with 5 ml. of water and 20 ml. of a 5 percent concentrated ammonium hydroxide in methanol. The column is then dry-packed and wetted with a mixture of methanol and methylene chloride (1:1). The column is then eluted in 10 ml. fractions employing the following solvent mixtures; 100 ml. of methanol in methylene chloride (1:1); 200 ml. of methanol; 200 ml. of a one percent ammonium hydroxide in methanol solution; and 200 ml. of a two percent ammonium hydroxide in methanol solution. Thereupon 200 mg. of pure title product is obtained. Characteristic NMR absorptions are observed at 5.70–5.27, 3.35, 0.96, 0.86, and 0.83 δ. The mass spectrum of the trimethylsilyl derivative shows a parent peak at 527.5032.

EXAMPLE 12

2-Decarboxy-2-aminomethyl-15-methyl-PGF$_{2\alpha}$.

Refer to Chart G.

A. To a cold mixture (0° C.) of 3.68 g. of 15-methyl-PGF$_{2\alpha}$, 16 ml. of tetrahydrofuran, 5 ml. of water, and 1.11 g. of triethylamine is added with stirring 1.50 g. of isobutyl chloroformate over a 5 min. period. After stirring the mixture at 0° C. for an additional 25 min., excess liquid ammonia is added. The temperature of the reaction mixture is then allowed to rise to 0° C. and the mixture is stirred for an additional 3 hr. The resulting mixture is then concentrated under reduced pressure, maintaining bath temperature below 30° C., and the residue, taken up in 125 ml. of ethyl acetate and 7.5 ml. of ethanol, is washed with brine, dried, and concentrated under reduced pressure. The resulting residue is then diluted with toluene and the solution concentrated under vacuum to yield 3.6 g. of 15-methyl-PGF$_{2\alpha}$ amide. Characteristic NMR absorptions are observed at 3.6, 3.59, and 5.3–5.6 δ.

B. To a mixture of 5.0 g. of lithium aluminum hydride in 400 ml. of dry tetrahydrofuran is added dropwise with stirring a solution of 3.6 g. of the reaction product of part A in 50 ml. of tetrahydrofuran. The mixture is then heated at reflux for 16 hr. and thereafter cooled to 0° C. A solution of 5 ml. of water and 40 ml. of tetrahydrofuran is then added cautiously (dropwise) with stirring, followed by addition of 20 ml. of 10 percent aqueous sodium hydroxide. The mixture is then filtered and the filter cake washed with tetrahydrofuran and concentrated under reduced pressure. The residue (3.9 g.) is then chromatographed and a dry pack column of 300 g. of silica gel pretreated with 10 ml. of water and 40 ml. of 5 percent concentrated ammonium hydroxide in methanol. Eluting with one percent concentrated ammonium hydroxide in methanol, there is obtained 2.91 g. of 2-decarboxy-2-aminomethyl-15-methyl-PGF$_{2\alpha}$. Melting point is 66–67° C. An analytical sample, crystallized from diethyl ether, had a melting point at 68°–69° C. The mass spectrum shows a parent peak at 713.4943 and other peaks at 698, 642, 608, 217, and 174. NMR absorptions are observed at 5.2–5.7, 3.7–4.25, 3.0, 2.5–2.8, and 1.26 δ.

Following the procedure of Example 12, part A, 3.1 g. of 16-phenoxy-17,18,19,20-tetranor-PGF$_{2\alpha}$ and 15 ml. of tetrahydrofuran, 4.5 ml. of water, and 0.885 g. of triethylamine at 0° C. is treated with 1.19 g. of isobutyl chloroformate followed by excess liquid ammonia. Thereby there is obtained 16-phenoxy-17,18,19,20-tetranor-PGF$_{2\alpha}$, amide (3.13 g.). Further, following the procedure of Example 12, part B, the reaction product of the preceding sentence (3.13 g.) is reduced with 4.0 g. of lithium aluminum hydride and 340 ml. of dry tetrahydrofuran and purified, yielding 2.25 g. of 2-decarboxy-2-aminomethyl-16-phenoxy-17,18,19,20-tetranor-PGF$_{2\alpha}$ as an oil. The mass spectrum shows a parent peak 735.4359 and NMR absorptions are observed at 6.75, 7.15, 5.2–5.73, 4.30–4.60, 3.70–4.20, and 3.60 δ.

EXAMPLE 13

2-Decarboxy-2-aminomethyl-15-methyl-PGE$_2$ (Formula CXXXII: R$_3$ and R$_4$ of the L$_1$ moiety are hydrogen, L$_2$ and L$_3$ are hydrogen, R$_5$ of the M$_1$ moiety is methyl, R$_7$ is n-butyl, Y$_1$ is trans—CH═CH (CH$_2$)$_3$—, and R$_8$ is hydroxy.

Refer to Chart 1.

A. Following the procedure of Examples 1, 2, and 3 of U.S. Pat. No. 3,822,303, 15-methyl-PGF$_{2\alpha}$, methyl ester is transformed to 15-methyl-PGE$_2$, methyl ester. The methyl ester is then hydrolyzed by enzymatic methods known in the art.

B. The free acid prepared above (1.0 g.) 20 ml. of freshly distilled ethylene glycol, and 100 ml. of benzene are heated at reflux under a nitrogen atmosphere with vigorous stirring for 24 hr. The reaction mixture is then cooled to room temperature, diluted with water, and extracted thoroughly with ethyl acetate. The combined organic layers are then washed with water, brine, and dried over sodium sulfate and evaporated under reduced pressure. The crude product is taken up in 50 ml. of methanol and treated under nitrogen with 20 ml. of 3N aqueous potassium hydroxide solution. The mixture is then allowed to stand for 2 hr. at room temperature and then concentrated under reduced pressure, removing most of the methanol. The residue is then diluted with ice and water, acidified with 35 ml. of 1 2N aqueous potassium bisulfate solution, and extracted thoroughly with ethyl acetate. The combined ethyl acetate extracts are then washed with water and brine, dried over sodium sulfate, and concentrated under reduced pressure yielding a residue which is chromatographed on 90 g. of silica gel, eluting with 50–80 percent ethyl acetate in Skellysolve B. Pure product, 15-methyl-PGE$_2$, ethylene ketal, is thereby obtained.

C. Following the procedure of Example 12, the reaction product of part B is transformed to 2-decarboxy-2-aminomethyl-15-methyl-PGE$_2$, ethylene ketal.

D. The reaction product of part C is then deketalized with mild aqueous acetic acid yielding title product. This product is then optionally transformed to an amine salt (e.g. hydrochloride) so as to enhance stability.

Following the procedure of Example 13, but employing each of the various PGE or 11-deoxy-PGE compounds, prepared according to the procedure of Example 13, part A, or prepared by methods known in the art from each of the corresponding PGF$_\alpha$ of 11-deoxy-PGF$_\alpha$-type compounds described above, there are prepared each of the corresponding 2-decarboxy-2-aminomethyl- or 2-(substituted amino)methyl-PGE- or 11-deoxy-PGE-type products according to formula CXXXII.

Further, following the procedure of the above Example, but employing each of the various PG-type compounds with a carbonyl containing cyclopentane ring, there are prepared each of the various 2-aminomethyl-PG analogs of the present invention. Each of the various PGA-type compounds are prepared from the respective PGE-type compounds (R$_8$ is hydroxy) by acidic hydration, employing methods known in the art. Each of the PGD, 9-deoxy-9,10-didehydro-PGD- or 9-deoxy-PGD-type compounds are prepared by methods described in Procedures 1, 2, or 3, respectively, as indicated below:

Procedure 1

PGD$_2$ or PGD$_2$, methyl ester
Refer to Chart 1.

A. PGF$_{2\alpha}$ (2.0 g.) and methylene chloride (50 ml.) is treated with 688 mg. of n-butylboronic acid. The reaction mixture is then stirred vigorously and heated at reflux, adding 5 ml. aliquots of methylene chloride to replace amounts lost through evaporation. The procedure is continued for about 25 min. adding about 20 to 25 ml. of methylene chloride. The resulting distillate becomes clear. Thereafter 10 ml. of dihydropyrane is added to the mixture followed by addition of pyridine hydrochloride (150 mg.). After 20 hr. the reaction is complete and the methylene chloride is removed under reduced pressure and the residue combined with 30 ml. of methanol and 13 ml. of a 3N aqueous potassium hydroxide solution. The resulting solution is allowed to stand for 2 hr. and thereafter treated with 5 ml. of 30 percent sodium peroxide and 30 ml. of water. The methanol is then removed under reduced pressure and the aqueous residue diluted with 100 ml. of water and extracted twice with diethyl ether. The aqueous layer is then acidified with 25 ml. of 2N aqueous potassium bisulfate and extracted with ethyl acetate. The combined organic extracts are then combined, washed with brine, and dried over anhydrous sodium sulfate. Removal of solvent under reduced pressure yields 3.3 g. of an oil which is chromatographed on 100 g. of acid washed silica gel. The column is packed with and eluted with 75 percent ethyl acetate in hexane. PGF$_{2\alpha}$, 15-(tetrahydropyranyl ether) is thereby obtained.

B. PGF$_{2\alpha}$, 15-(tetrahydropyranyl ether) (2 g.) in acetone (75 ml.) is cooled to −45° C. and thereafter treated with 1.2 ml. of the Jones reagent. The mixture is stirred for 30 min. at −35° to −45° C. and thereafter treated with 0.5 ml. of isopropanol and stirred an additional 15 min. The reaction mixture is then poured into a mixture of ice, water, and diethyl ether. The mixture is then extracted with diethyl ether and the combined ethereal extracts washed with brine, and dried over sodium sulfate. After filtration, removal of solvent proceeds by rotary evaporation. Crude product (1.8 g.) thereby obtained is chromatographed on 360 g. of silica gel eluting with 45 percent ethyl acetate in hexane. PGD$_2$, 15-tetrahydropyranyl ether (800 mg.) is thereby obtained.

C. PGD$_2$, 15-(tetrahydropyranyl ether) (800 mg.) in 20 ml. of acetic acid and 10 ml. of water is heated at 40° C. for 2 hr. and then diluted with 100 ml. of 45 percent ethyl acetate in hexane (800 mg.). Upon purification pure title product is obtained.

Procedure 2

9-Deoxy-9,10-didehydro-PGD$_2$
Refer to Chart 1.

Quantities of PGD$_2$ are subject to silica gel chromatography until about 3.9 g. of less polar (than PGD$_2$) impurities are obtained from eluant fractions.

The 3.9 g. of less polar impurities are then chromatographed on 11.2 g. of silica gel packed with 5 percent acetone in methylene chloride eluting with 10 to 15 percent acetone in methylene chloride. Partially purified title product (1.2 g.), thereby obtained, is chromatographed on 200 g. of neutral silica gel packed with ethyl acetate, methanol, and chloroform (1:1:18). This column is washed with 800 ml. of ethyl acetate, methanol, and chloroform (1:1:48) and the above partially purified product thereafter added to the column. Eluting with ethyl acetate, methanol, and chloroform (1:1:48) yields pure title product.

Procedure 3

9-Deoxy-PGD$_2$
Refer to Chart 1.

A. Following Procedure 2 above, the reaction product of Procedure 1, part A is dehydrated to yield 9,10-didehydro-9-deoxy-PGD$_2$, 15-tetrahydropyranyl ether.

B. To a stirred solution of the reaction product of step A dissolved in methanol at −20° C. under a nitrogen atmosphere there is added a solution of sodium borohydride in water and methanol. The resulting mixture is stirred for 20 min. and thereafter acetic acid is added cautiously. The resulting mixture is then concentrated and water is added and the pH is adjusted to about 3 with the addition of citric acid. The mixture is extracted with dichloromethane and the combined organic extracts are washed with water and brine and dried and concentrated to yield 9-deoxy-PGF$_{2\alpha}$, 15-tetrahydropyranyl ether.

C. To a solution of the reaction product of step B dissolved in acetone at −20° C., there is added dropwise with stirring over one min. the Jones reagent (chromium trioxide, water, and concentrated sulfuric acid). The resulting mixture is then stirred at −20° C. for 20 min. and thereafter isopropanol is added and the mixture is stirred at −20° C. for an additional 10 min. The mixture is then diluted with water and extracted with diethyl ether. The ethereal extracts are then washed with water and brine, dried, and concentrated.

The residue is then chromatograhed on silica gel yielding pure 9-deoxy-PGD$_2$, 15-tetrahydropyranyl ether.

D. The title compound is then prepared by hydrolysis of the C-15 blocking group by the procedures of given above.

Following the procedure of the above examples there are obtained each of the various 2-decarboxy-PGF$_\alpha$-type compounds described in the following Tables. Further, following the procedure of the above Examples there are obtained 11-deoxy-PGF$_\alpha$-, PGE-, 11-deoxy-PGE-, PGA-, PGD-, 9-deoxy-PGD-, and 9-deoxy-9,10-didehydro-PGD-type compounds corresponding to each of the PGF$_\alpha$-type compounds of the Tables.

In interpreting these Tables, each formula listed in the Table represents a prostaglandin-type product whose complete name is given by combining the name provided in the respective legends below the formula with the prefix found in the "Name" column in the tabular section of the Tables for each example.

Table A

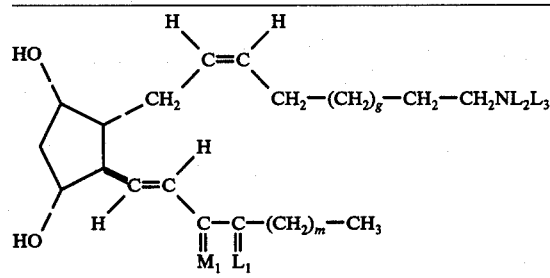

2-decarboxy-PGF$_{2\alpha}$-type compounds

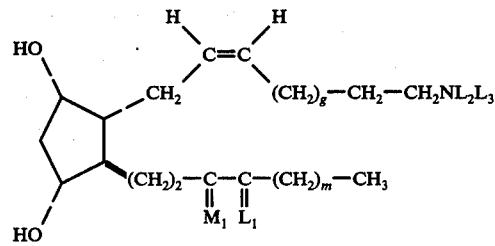

2-decarboxy-13,14-dihydro-PGF$_{2\alpha}$-type compounds

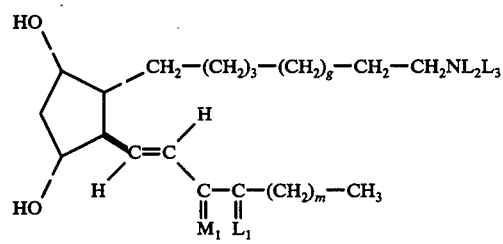

2-decarboxy-PGF$_{1\alpha}$-type compounds

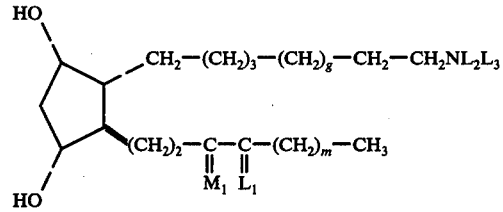

2-decarboxy-13,14-dihydro-PGF$_{1\alpha}$-type compounds

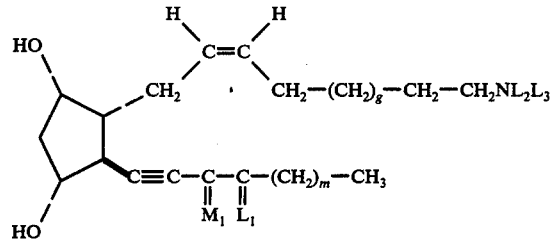

2-decarboxy-13,14-didehydro-PGF$_{2\alpha}$-type compounds

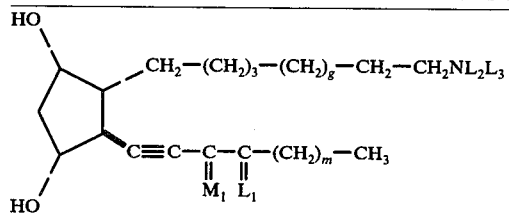
2-decarboxy-13,14-didehydro-PGF$_{1\alpha}$-type compounds
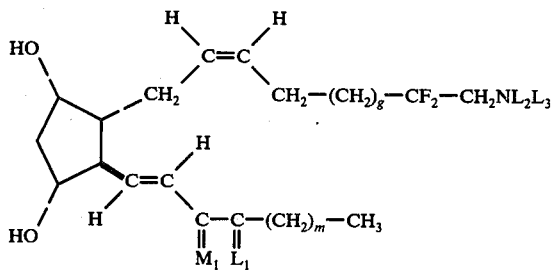
2-decarboxy-2,2-difluoro-PGF$_{2\alpha}$-type compounds
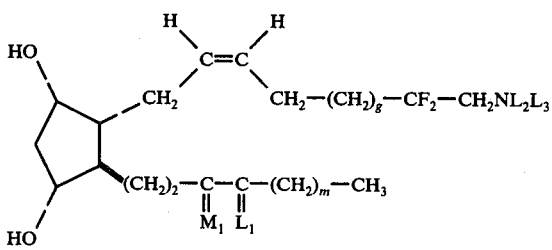
2-decarboxy-2,2-difluoro-13,14-dihydro-PGF$_{2\alpha}$-type compounds
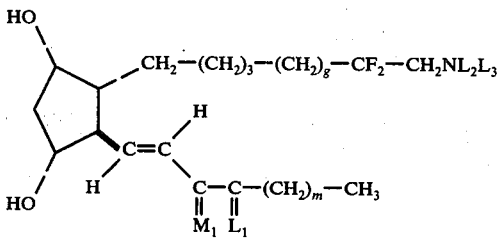
2-decarboxy-2,2-difluoro-PGF$_{1\alpha}$-type compounds
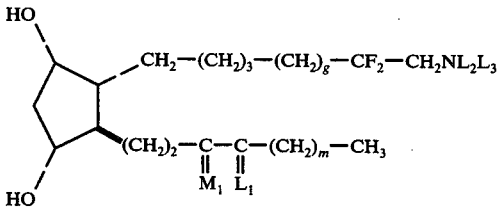
2-decarboxy-2,2-difluoro-13,14-dihydro-PGF$_{1\alpha}$-type compounds
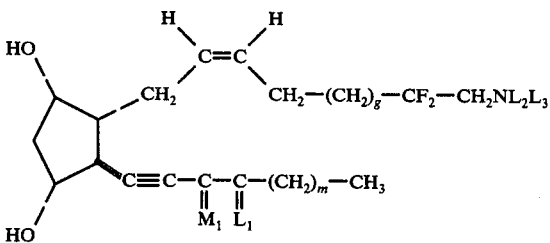
2-decarboxy-13,14-didehydro-2,2-difluoro-PGF$_{2\alpha}$-type compounds Table A-continued
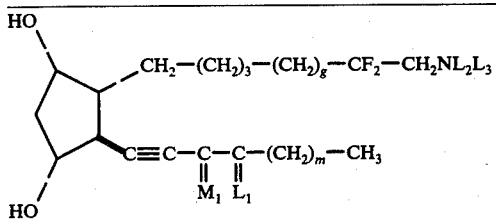
2-decarboxy-13,14-didehydro-2,2-difluoro-PGF$_{1\alpha}$-type compounds
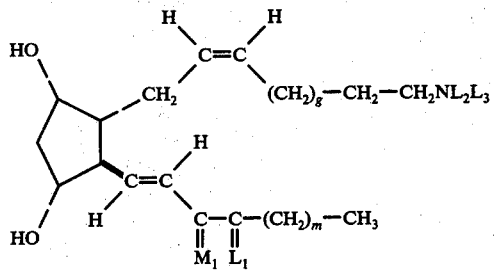
2-decarboxy-cis-4,5-didehydro-PGF$_{1\alpha}$-type compounds
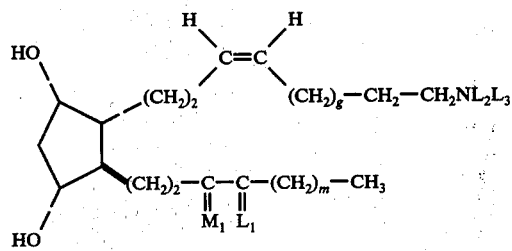
2-decarboxy-cis-4,5-didehydro-13,14-dihydro-PGF$_{1\alpha}$-type compounds
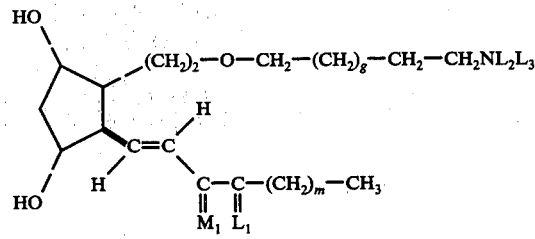
2-decarboxy-5-oxa-PGF$_{1\alpha}$-type compounds
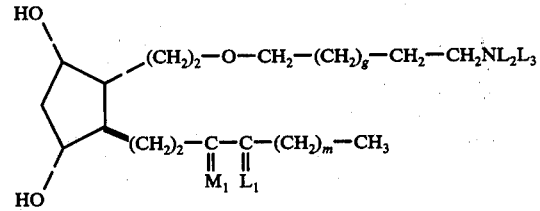
2-decarboxy-5-oxa-13,14-dihydro-PGF$_{1\alpha}$-type compounds
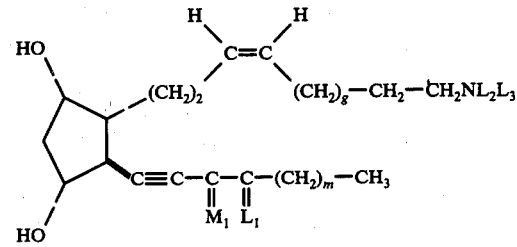
2-decarboxy-13,14-didehydro-cis-4,5-didehydro-PGF$_{1\alpha}$-type compounds

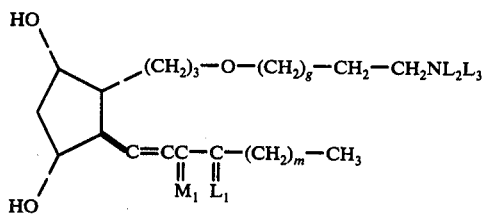
2-decarboxy-13,14-didehydro-5-oxa-PGF$_{1\alpha}$-type compounds
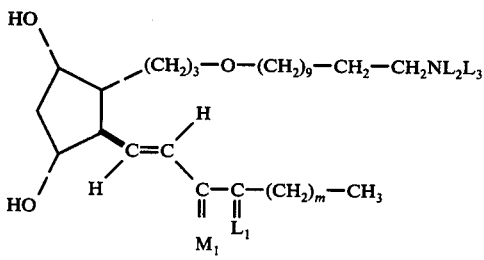
2-decarboxy-4-oxa-PGD$_{1\alpha}$-type compounds
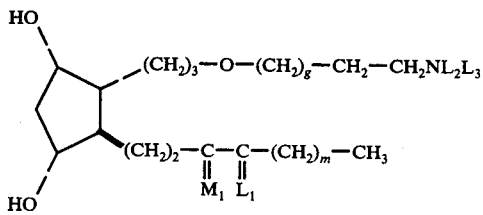
2-decarboxy-4-oxa-13,14-dihydro-PGF$_{1\alpha}$-type compounds
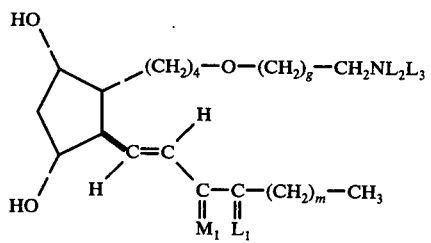
2-decarboxy-3-oxa-PGF$_{1\alpha}$-type compounds
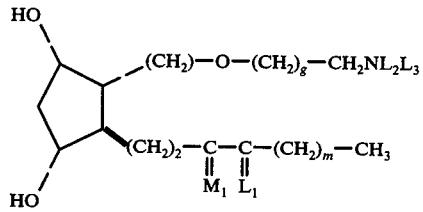
2-decarboxy-3-oxa-13,14-dihydro-PGF$_{1\alpha}$-type compounds
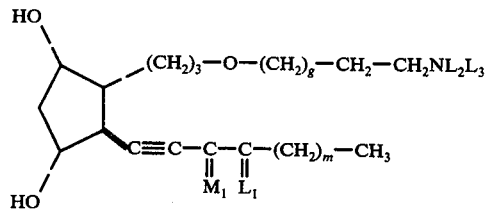
2-decarboxy-13,14-didehydro-4-oxa-PGF$_{1\alpha}$-type compounds Table A-continued
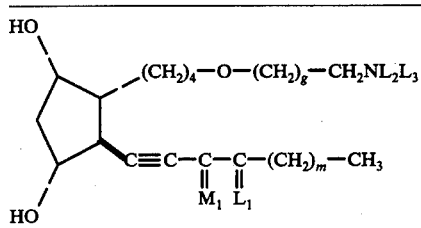
2-decarboxy-13,14-didehydro-3-oxa-PGF$_{1\alpha}$-type compounds
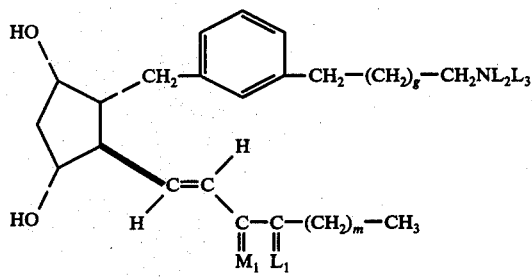
2-decarboxy-3,7-inter-m-phenylene-4,5,6-trinor-PGF$_{1\alpha}$-type compounds
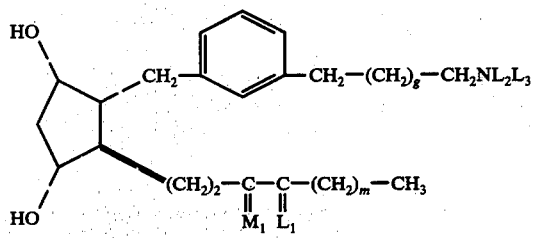
2-decarboxy-3,7-inter-m-phenylene-4,5,6-trinor-13,14-dihydro-PGF$_{1\alpha}$-type compounds
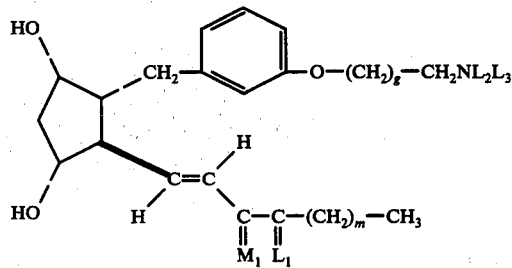
2-decarboxy-3,7-inter-m-phenylene-3-oxa-4,5,6-trinor-PGF$_{1\alpha}$-type compounds
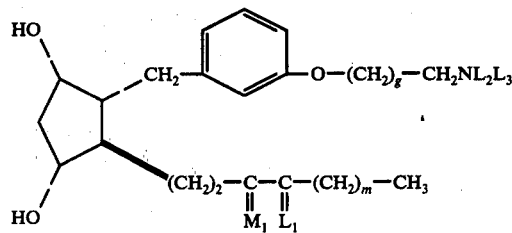
2-decarboxy-3,7-inter-m-phenylene-3-oxa-4,5,6-trinor-13,14-dihydro-PGF$_{1\alpha}$-type compounds Table A-continued

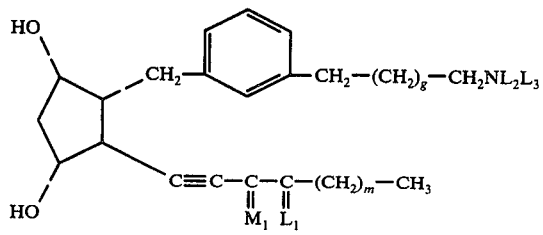

2-decarboxy-13,14-didehydro-3,7-inter-m-phenyl-ene-4,5,6-trinor-PGF$_{1\alpha}$-type compounds

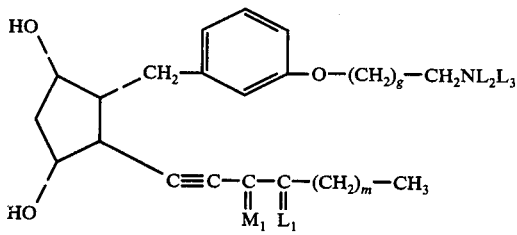

2-decarboxy-13,14-didehydro-3,7-inter-m-phenyl-ene-3-oxa-4,5,6-trinor-PGF$_{1\alpha}$-type compounds

| Exam- | | | L$_1$ | | M$_1$ | | | | |
|---|---|---|---|---|---|---|---|---|---|
| ple | g | m | R$_3$ | R$_4$ | R$_5$ | ~OH | L$_2$ | L$_3$ | Name |
| A-1 | 1 | 3 | methyl | hydrogen | hydrogen | α | hydrogen | hydrogen | 2-aminomethyl-16-methyl |
| A-2 | 1 | 3 | methyl | hydrogen | methyl | α | hydrogen | hydrogen | 2-aminomethyl-15,16-dimethyl |
| A-3 | 1 | 3 | methyl | hydrogen | hydrogen | α | methyl | hydrogen | 2-methylaminomethyl-16-methyl |
| A-4 | 1 | 3 | methyl | methyl | hydrogen | α | hydrogen | hydrogen | 2-aminomethyl-16,16-dimethyl |
| A-5 | 1 | 3 | methyl | methyl | methyl | α | hydrogen | hydrogen | 2-aminomethyl-15,16,16-trimethyl |
| A-6 | 1 | 3 | methyl | methyl | hydrogen | α | methyl | hydrogen | 2-methylaminomethyl-16,16-dimethyl |
| A-7 | 1 | 3 | fluoro | hydrogen | hydrogen | α | hydrogen | hydrogen | 2-aminomethyl-16-fluoro |
| A-8 | 1 | 3 | fluoro | hydrogen | methyl | α | hydrogen | hydrogen | 2-aminomethyl-15-methyl-16-fluoro |
| A-9 | 1 | 3 | fluoro | hydrogen | hydrogen | α | methyl | hydrogen | 2-methylaminomethyl-16-fluoro |
| A-10 | 1 | 3 | fluoro | fluoro | hydrogen | α | hydrogen | hydrogen | 2-aminomethyl-16,16-difluoro |
| A-11 | 1 | 3 | fluoro | fluoro | methyl | α | hydrogen | hydrogen | 2-aminomethyl-15-methyl-16,16-difluoro |
| A-12 | 1 | 3 | fluoro | fluoro | hydrogen | α | methyl | hydrogen | 2-methylaminomethyl-16,16-difluoro |
| A-13 | 1 | 3 | hydrogen | hydrogen | hydrogen | α | hydrogen | hydrogen | 2-aminomethyl |
| A-14 | 1 | 3 | hydrogen | hydrogen | hydrogen | α | methyl | hydrogen | 2-methylaminomethyl |
| A-15 | 3 | 3 | hydrogen | hydrogen | hydrogen | α | hydrogen | hydrogen | 2-aminomethyl-2a,2b-dihomo |
| A-16 | 3 | 3 | methyl | methyl | hydrogen | α | hydrogen | hydrogen | 2-aminomethyl-2a,2b-dihomo-16,16-dimethyl |
| A-17 | 3 | 3 | methyl | methyl | methyl | α | hydrogen | hydrogen | 2-aminomethyl-2a,2b-dihomo-15,16,16-trimethyl |
| A-18 | 3 | 3 | fluoro | fluoro | hydrogen | α | hydrogen | hydrogen | 2-aminomethyl-2a,2b-dihomo-16,16-difluoro |
| A-19 | 3 | 3 | fluoro | fluoro | methyl | α | hydrogen | hydrogen | 2-aminomethyl-2a,2b-dihomo-15-methyl-16,16-difluoro |

Table B

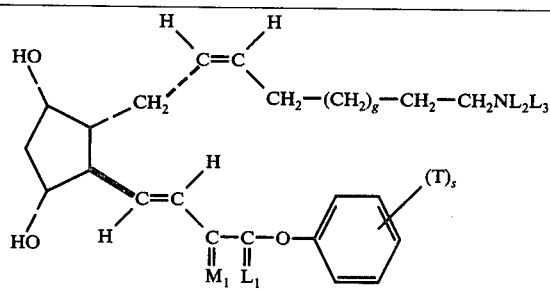

2-decarboxy-PGF$_{2\alpha}$-type compounds

Table B-continued
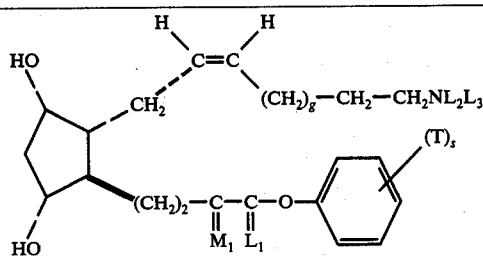
2-decarboxy-13,14-dihydro-PGF$_{2\alpha}$-type compounds
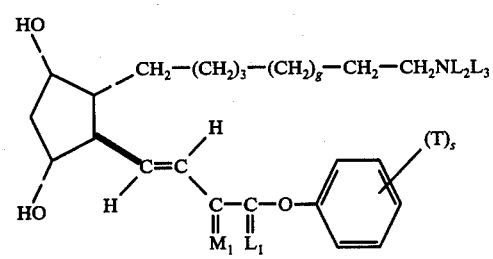
2-decarboxy-PGF$_{1\alpha}$-type compounds
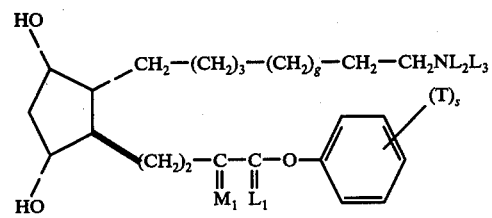
2-decarboxy-13,14-dihydro-PGF$_{1\alpha}$-type compounds
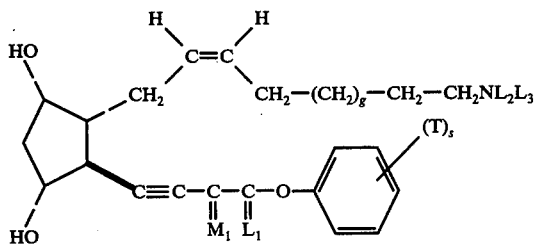
2-decarboxy-13,14-didehydro-PGF$_{2\alpha}$-type compounds
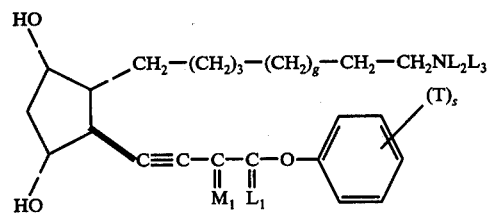
2-decarboxy-13,14-didehydro-PGF$_{1\alpha}$-type compounds
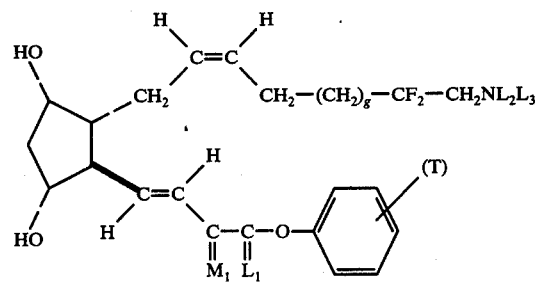
2-decarboxy-2,2-difluoro-PGF$_{2\alpha}$-type compounds Table B-continued
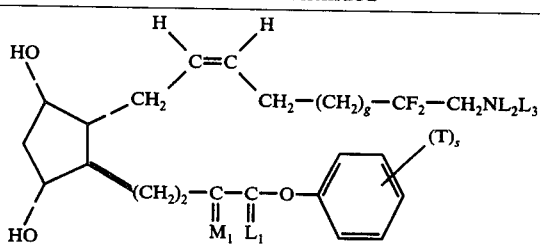
2-decarboxy-2,2-difluoro-13,14-dihydro-PGF$_{2\alpha}$-type compounds
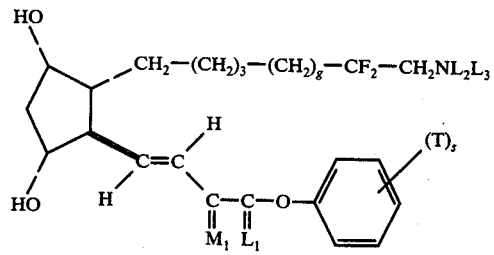
2-decarboxy-2,2-difluoro-PGF$_{1\alpha}$-type compounds
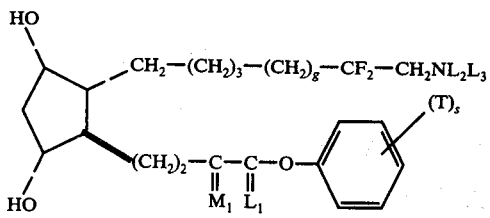
2-decarboxy-2,2-difluoro-13,14-dihydro-PGF$_{1\alpha}$-type compounds
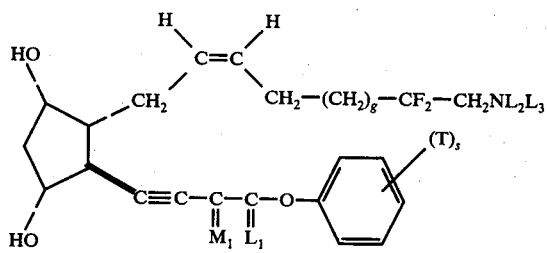
2-decarboxy-13,14-didehydro-2,2-difluoro-PGF$_{2\alpha}$-type compounds
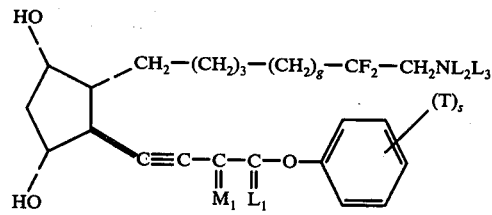
2-decarboxy-13,14-didehydro-2,2-difluoro-PGF$_{1\alpha}$-type compounds
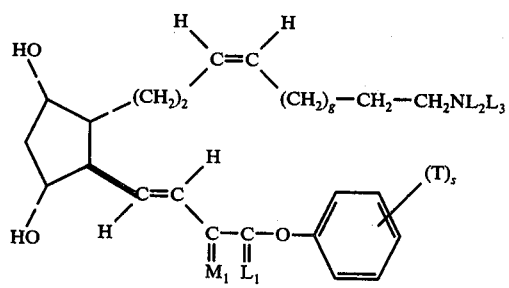
2-decarboxy-cis-4,5-didehydro-PGF$_{1\alpha}$-type compounds Table B-continued
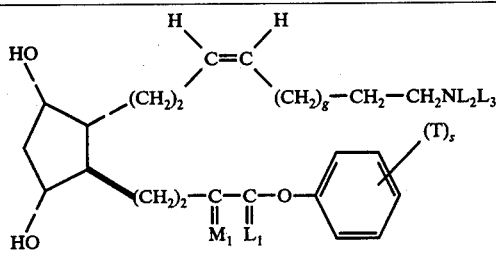
2-decarboxy-cis-4,5-didehydro-13,14-dihydro-PGF$_{1\alpha}$-type compounds
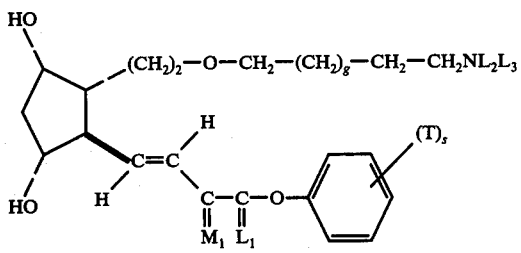
2-decarboxy-5-oxa-PGF$_{1\alpha}$-type compounds
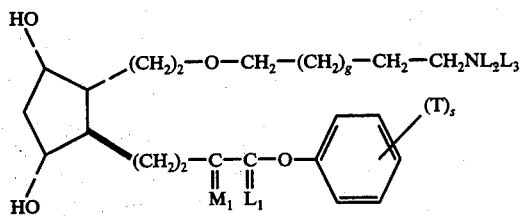
2-decarboxy-5-oxa-13,14-dihydro-PGF$_{1\alpha}$-type compounds
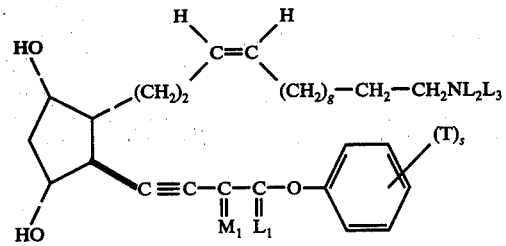
2-decarboxy-13,14-didehydro-cis-4,5-didehydro-PGF$_{1\alpha}$-type compounds
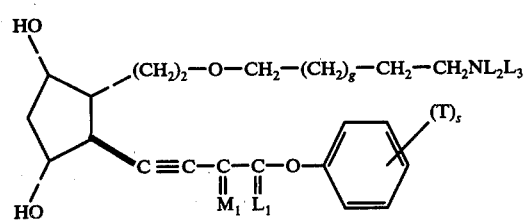
2-decarboxy-13,14-didehydro-5-oxa-PGF$_{1\alpha}$-type compounds
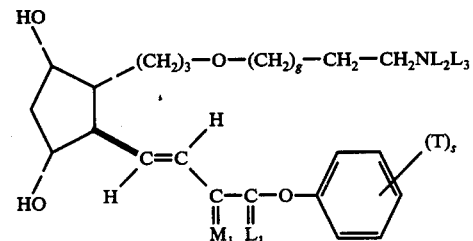
2-decarboxy-4-oxa-PGF$_{1\alpha}$-type compounds Table B-continued
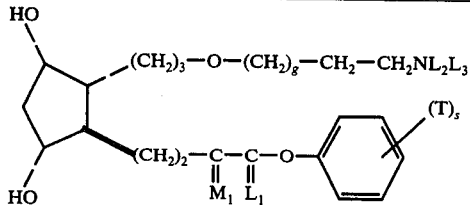
2-decarboxy-4-oxa-13,14-dihydro-PGF$_{1\alpha}$-type compounds
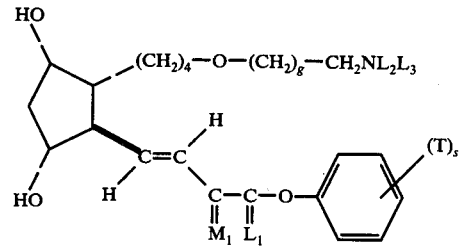
2-decarboxy-3-oxa-PGF$_{1\alpha}$-type compounds
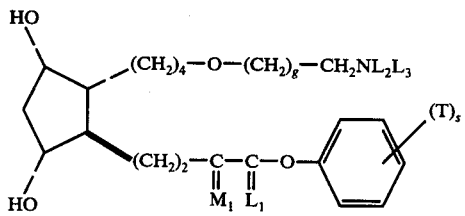
2-decarboxy-3-oxa-13,14-dihydro-PGF$_{1\alpha}$-type compounds
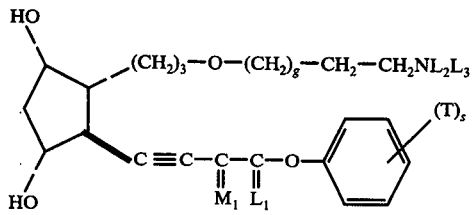
2-decarboxy-13,14-didehydro-4-oxa-PGF$_{1\alpha}$-type compounds
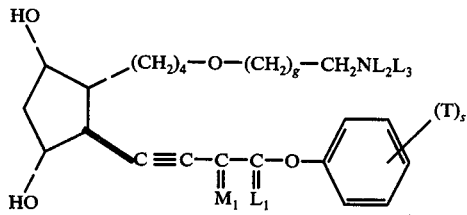
2-decarboxy-13,14-didehydro-3-oxa-PGF$_{1\alpha}$-type compounds
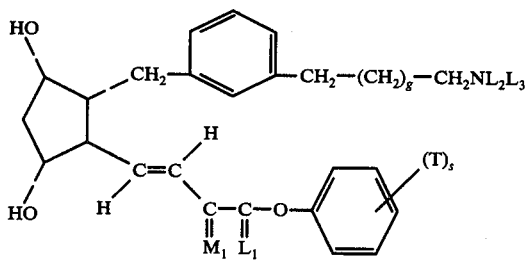
2-decarboxy-3,7-inter-m-phenylene-4,5,6-trinor-PGF$_{1\alpha}$-type compounds Table B-continued

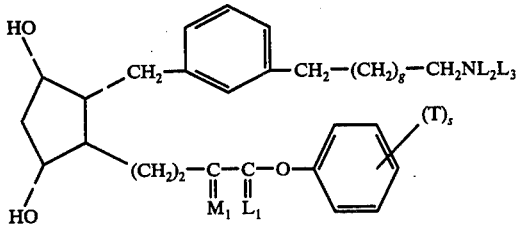

2-decarboxy-3,7-inter-m-phenylene-4,5,6-trinor-13,14-dihydro-PGF$_{1\alpha}$-type compounds

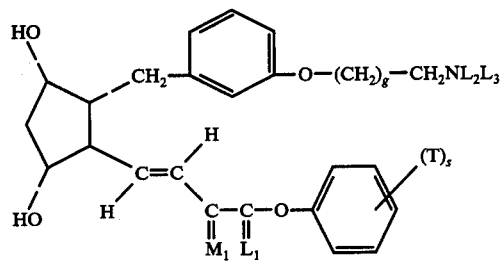

2-decarboxy-3,7-inter-m-phenylene-3-oxa-4,5,6-trinor-PGF$_{1\alpha}$-type compounds

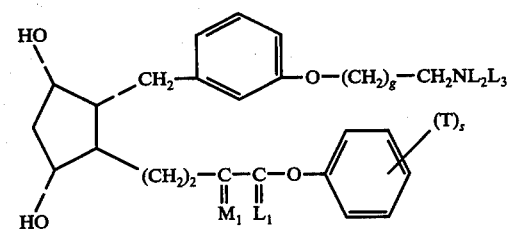

2-decarboxy-3,7-inter-m-phenylene-3-oxa-4,5,6-trinor-13,14-dihydro-PGF$_{1\alpha}$-type compounds

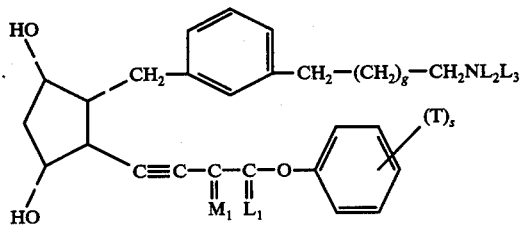

2-decarboxy-13,14-didehydro-3,7-inter-m-phenylene-4,5,6-trinor-PGF$_{1\alpha}$-type compounds

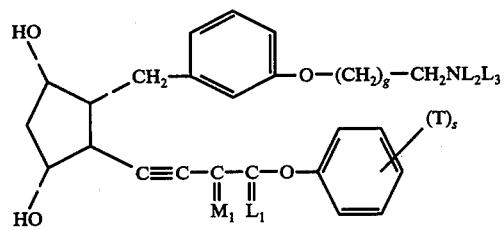

2-decarboxy-13,14-didehydro-3,7-inter-m-phenylene-3-oxa-4,5,6-trinor-PGF$_{1\alpha}$-type compounds

| Example | g | s | T | L$_1$ R$_3$ | R$_4$ | M$_1$ R$_5$ | ~OH | L$_2$ | L$_3$ | Name |
|---|---|---|---|---|---|---|---|---|---|---|
| B-1 | 1 | 0 |  | hydrogen | hydrogen | hydrogen | α | hydrogen | hydrogen | 2-aminomethyl-16-phenoxy-17,18,19,20-tetranor |
| B-2 | 1 | 1 | p-fluoro | hydrogen | hydrogen | hydrogen | α | hydrogen | hydrogen | 2-aminomethyl-16-(p-fluorophenoxy)-17,18,19,20-tetranor |
| B-3 | 1 | 1 | m-chloro | hydrogen | hydrogen | hydrogen | α | hydrogen | hydrogen | 2-aminomethyl-16-(m-chlorophenoxy)-17,18,19,20-tetranor |
| B-4 | 1 | 1 | m-trifluoromethyl | hydrogen | hydrogen | hydrogen | α | hydrogen | hydrogen | 2-aminomethyl-16-(m-trifluoromethylphenoxy)-17,18,19,20- |

Table B-continued

| | | | | | | | | | | |
|---|---|---|---|---|---|---|---|---|---|---|
| B-5 | 1 | 0 | | hydrogen | hydrogen | methyl | α | hydrogen | hydrogen | tetranor 2-aminomethyl-15-methyl-16-phenoxy-17,18,19,20-tetranor |
| B-6 | 1 | 1 | p-fluoro | hydrogen | hydrogen | methyl | α | hydrogen | hydrogen | 2-aminomethyl-15-methyl-16-(p-fluorophenoxy)-17,18,19,20-tetranor |
| B-7 | 1 | 1 | m-chloro | hydrogen | hydrogen | methyl | α | hydrogen | hydrogen | 2-aminomethyl-15-methyl-16-(m-chlorophenoxy)-17,18,19,20-tetranor |
| B-8 | 1 | 1 | m-trifluoro- | hydrogen | hydrogen | methyl | α | hydrogen | hydrogen | 2-aminomethyl-15-methyl-16-(m-trifluoromethylphenoxy) |
| B-9 | 1 | 0 | | hydrogen | hydrogen | hydrogen | α | methyl | hydrogen | 2-methylaminomethyl-16-phenoxy-17,18,19,20-tetranor |
| B-10 | 1 | 1 | p-fluoro | hydrogen | hydrogen | hydrogen | α | methyl | hydrogen | 2-methylaminomethyl-16-(p-fluorophenoxy)-17,18,19,20-tetranor |
| B-11 | 1 | 1 | m- | hydrogen | hydrogen | hydrogen | α | methyl | hydrogen | 2-methylaminomethyl-16-(m-chlorophenoxy)-17,18,19,20-tetranor |
| B-12 | 1 | 1 | m-tri- | hydrogen | hydrogen | hydrogen | α | methyl | hydrogen | 2-methylaminomethyl-16-(m-trifluoromethylphenoxy)-17,18,19,20-tetranor |
| B-13 | 1 | 0 | | methyl | methyl | hydrogen | α | hydrogen | hydrogen | 2-aminomethyl-16-methyl-16-phenoxy-18,19,20-trinor |
| B-14 | 1 | 1 | p-fluoro | methyl | methyl | hydrogen | α | hydrogen | hydrogen | 2-aminomethyl-16-methyl-16(p-fluorophenoxy-18,19,20-trinor |
| B-15 | 1 | 1 | m-chloro | methyl | methyl | hydrogen | α | hydrogen | hydrogen | 2-aminomethyl-16-methyl-16-(m-chlorophenoxy)-18,19,20-trinor |
| B-16 | 1 | 1 | m-trifluoromethyl | methyl | methyl | hydrogen | α | hydrogen | hydrogen | 2-aminomethyl-16-methyl-16-(m-trifluoromethylphenoxy)-18,19,20-trinor |
| B-17 | 1 | 0 | | methyl | methyl | methyl | α | hydrogen | hydrogen | 2-aminomethyl-15,16-dimethyl-16-phenoxy-18,19,20-trinor |
| B-18 | 1 | 1 | p-fluoro | methyl | methyl | methyl | α | hydrogen | hydrogen | 2-aminomethyl-15,16-dimethyl-16-(p-fluorophenoxy)-18,19,20-trinor |
| B-19 | 1 | 1 | m-chloro | methyl | methyl | methyl | α | hydrogen | hydrogen | 2-aminomethyl-15,16-dimethyl-16-(m-chlorophenoxy)-18,19,20-trinor |
| B-20 | 1 | 1 | m-trifluoromethyl | methyl | methyl | methyl | α | hydrogen | hydrogen | 2-aminomethyl-15,16-dimethyl-16-(m-trifluoromethylphenoxy)-18,19,20-trinor |
| B-21 | 1 | 0 | | methyl | methyl | hydrogen | α | methyl | hydrogen | 2-methylaminomethyl-16-methylaminomethyl-18,19,20-trinor |
| B-22 | 1 | 1 | p-fluoro | methyl | methyl | hydrogen | α | methyl | hydrogen | 2-methylaminomethyl-16-methyl-16-(p-fluorophenoxy)-18,19,20-trinor |
| B-23 | 1 1 | 1 1 | m-chloro | methyl | methyl | hydrogen | α | methyl | hydrogen | 2-methylaminomethyl-16-methyl-16-(m-chlorophenoxy)-18,19,20-trinor |
| B-24 | 1 | 1 | m-trifluoro- | methyl- | methyl | hydrogen | α | methyl | hydrogen | 2-methylaminomethyl-16-methyl-16-(m-trifluoromethylphenoxy)-18,19,20-trinor |
| B-25 | 3 | 0 | | hydrogen | hydrogen | hydrogen | α | hydrogen | hydrogen | 2-aminomethyl-2a,2b-dihomo-16-phenoxy-17,18,19,20-tetranor |
| B-26 | 3 | 1 | p-fluoro | hydrogen | hydrogen | hydrogen | α | hydrogen | hydrogen | 2-aminomethyl-2a,2b-cihomo-16-(p-fluorophenoxy)-17,18,19,20-tetranor |
| B-27 | 3 | 1 | m-chloro | hydrogen | hydrogen | hydrogen | α | hydrogen | hydrogen | 2-aminomethyl-2a,2b-dihhomo-16-(m-chlorophenoxy)-17,18,19,20-tetranor |
| B-28 | 3 | 1 | m-trifluoromethyl | hydrogen | hydrogen | hydrogen | α | hydrogen | hydrogen | 2-aminomethyl-2a,2b-dihomo-16-(m-trifluoromethylphenoxy)-17,18,19,20-tetranor |
| B-29 | 3 | 0 | | hydrogen | hydrogen | methyl | α | hydrogen | hydrogen | 2-aminomethyl-22a,2b-dihomo-16-(m-trifluorophenoxy-17,18,19,20-tetranor |
| B-30 | 3 | 1 | p- | hydrogen | hydrogen | methyl | α | hydrogen | hydrogen | 2-aminomethyl-2a,2b- |

Table B-continued

| | | | | | | | | | |
|---|---|---|---|---|---|---|---|---|---|
| | | | fluoro | | | | | | dihomo-15-methyl-16-(p-fluorophenoxy)-17,18,19,20-tetranor |
| B-31 | 3 | 1 | m-chloro | hydrogen | hydrogen | methyl | α | hydrogen | hydrogen | 2-aminomethyl-2a,2b-dihomo-15-methyl-16-(m-chlorophenoxy)-17,18,19,20-tetranor |
| B-32 | 3 | 1 | m-trifluoromethyl | hydrogen | hydrogen | methyl | α | hydrogen | hydrogen | 2-aminomethyl-2a,2b-dihomo-15-methyl-16-(m-trifluoromethylphenoxy-17,18,19,20-tetranor |

Table C

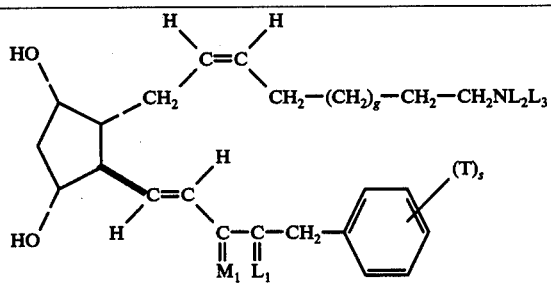

2-decarboxy-18,19,20-trinor-PGF$_{2\alpha}$-type compounds

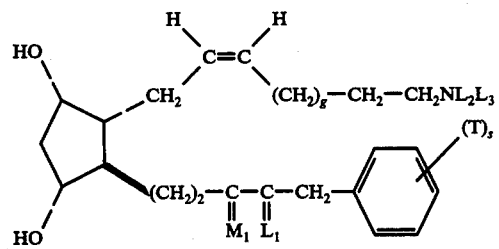

2-decarboxy-18,19,20-trinor-13,14-dihydro-PGF$_{2\alpha}$-type compounds

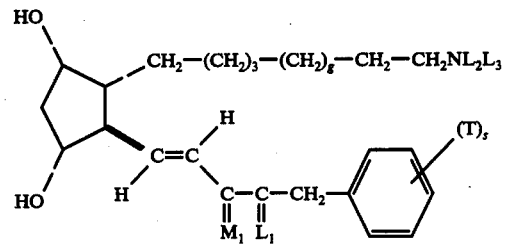

2-decarboxy-18,19,20-trinor-PGF$_{1\alpha}$-type compounds

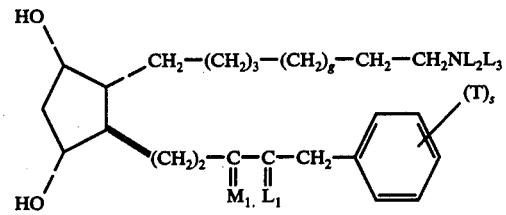

2-decarboxy-18,19,20-trinor-13,14-dihydro-PGF$_{1\alpha}$-type compounds

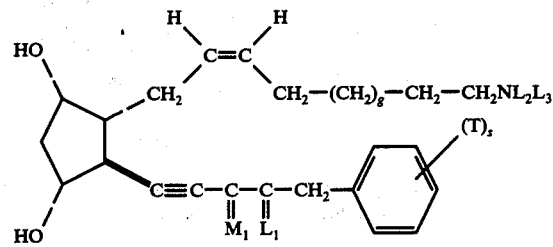

Table C-continued 2-decarboxy-13,14-didehydro-18,19,20-trinor-
PGF$_{2\alpha}$-type compounds

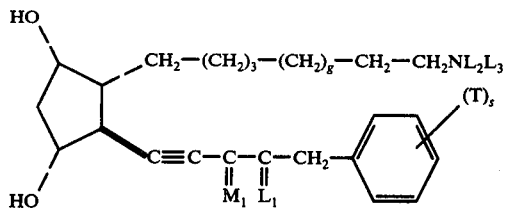

2-decarboxy-13,14-didehydro-18,19,20-trinor-
PGF$_{1\alpha}$-type compounds

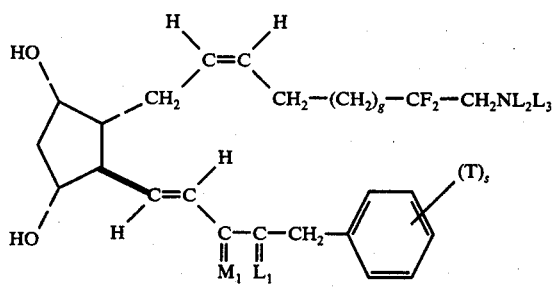

2-decarboxy-18,19,20-trinor-2,2-difluoro-
PGF$_{2\alpha}$-type compounds

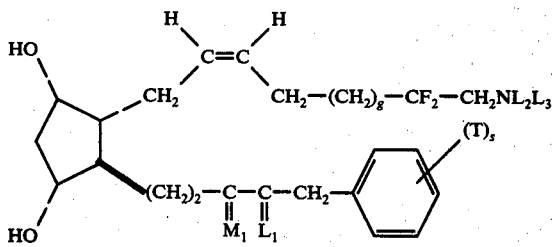

2-decarboxy-18,19,20-trinor-2,2-difluoro-
13,14-dihydro-PGF$_{2\alpha}$-type compounds

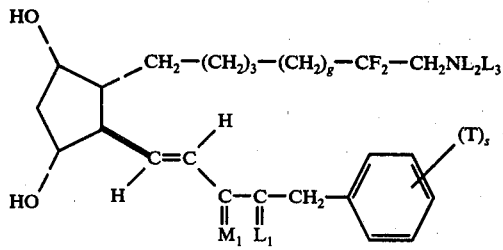

2-decarboxy-18,19,20-trinor-2,2-difluoro-PGF$_{1\alpha}$-
type compounds

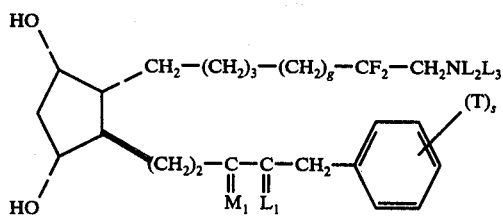

2-decarboxy-18,19,20-trinor-2,2-difluoro-13,14-
dihydro-PGF$_{1\alpha}$-type compounds

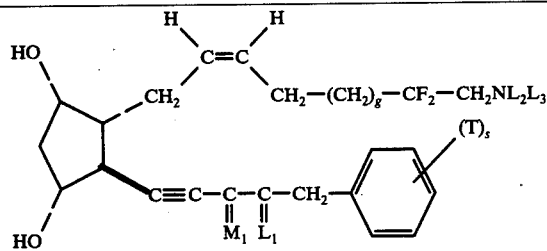
2-decarboxy-13,14-didehydro-18,19,20-trinor-
2,2-difluoro-PGF$_{2\alpha}$-type compounds
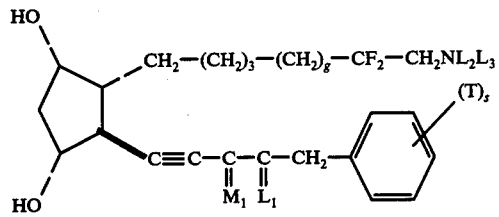
2-decarboxy-13,14-didehydro-18,19,20-trinor-
2,2-difluoro-PGF$_{1\alpha}$-type compounds
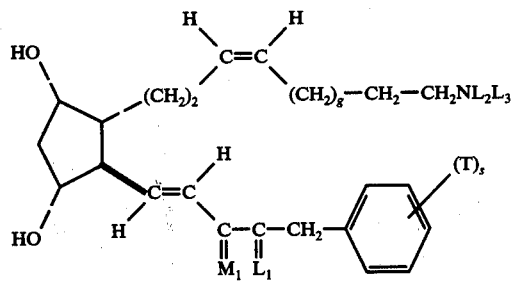
2-decarboxy-18,19,20-trinor-cis-4,5-didehydro-
PGF$_{1\alpha}$-type compounds
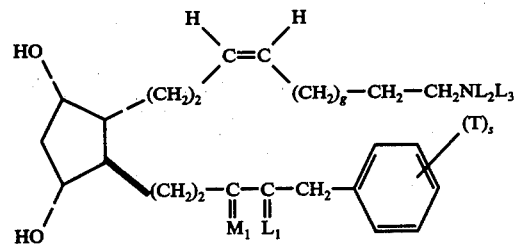
2-decarboxy-18,19,20-trinor-cis-4,5-didehydro-
13,14-dihydro-PGF$_{1\alpha}$-type compounds
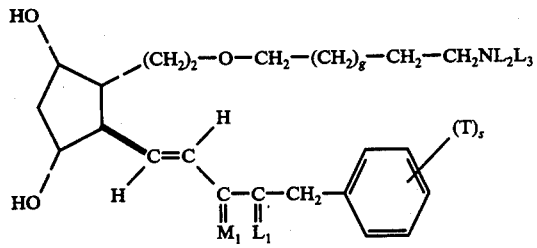
2-decarboxy-18,19,20-trinor-5-oxa-PGF$_{1\alpha}$-type
compounds
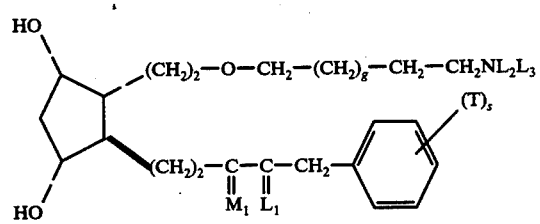

Table C-continued 2-decarboxy-18,19,20-trinor-5-oxa-13,14-dihydro-PGF$_{1\alpha}$-type compounds

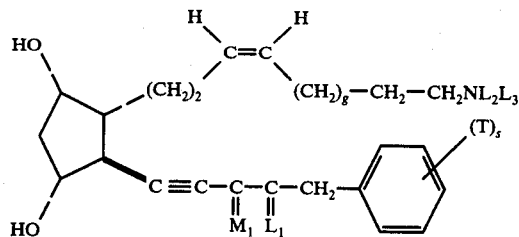

2-decarboxy-13,14-didehydro-18,19,20-trinor-cis-4,5-didehydro-PGF$_{1\alpha}$-type compounds

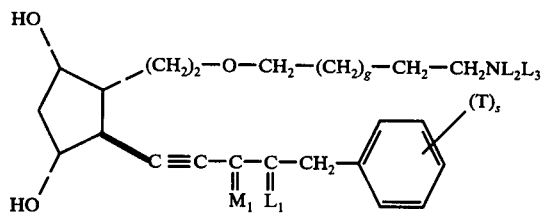

2-decarboxy-13,14-didehydro-18,19,20-trinor-5-oxa-PGF$_{1\alpha}$-type compounds

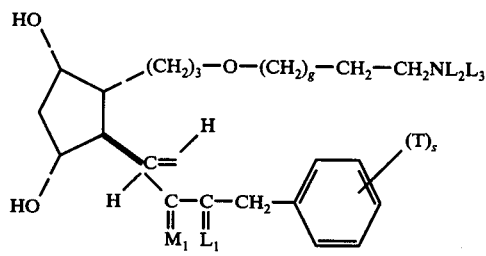

2-decarboxy-18,19,20-trinor-4oxa-PGF$_{1\alpha}$-type compounds

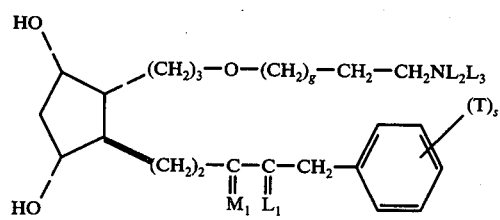

2-decarboxy-18,19,20-trinor-4-oxa-13,14-dihydro-PGF$_{1\alpha}$-type compounds

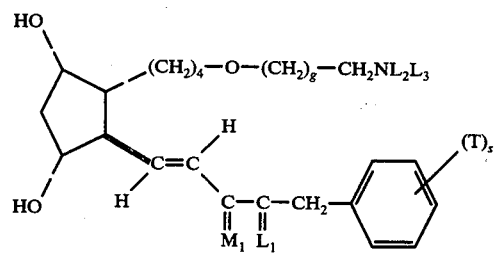

2-decarboxy-18,19,20-trinor-3-oxa-PGF$_{1\alpha}$-type compounds

Table C-continued

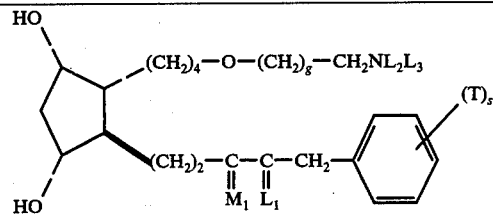

2-decarboxy-18,19,20-trinor-3-oxa-13,14-dihydro-PGF$_{1\alpha}$-type compounds

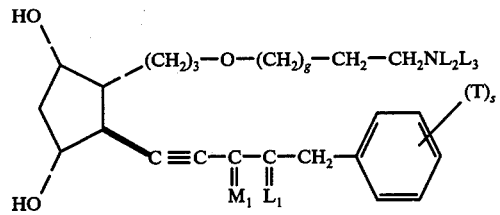

2-decarboxy-13,14-didehydro-18,19,20-trinor-4-oxa-PGF$_{1\alpha}$-type compounds

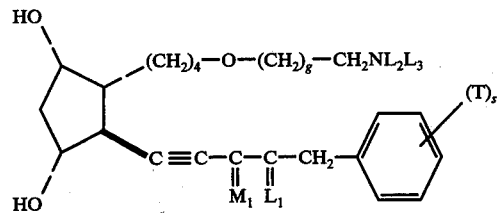

2-decarboxy-13,14-didehydro-18,19,20-trinor-3-oxa-PGF$_{1\alpha}$-type compounds

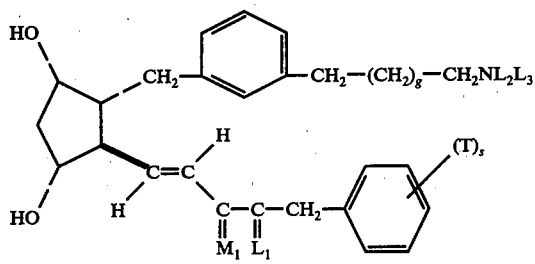

2-decarboxy-3,7-inter-m-phenylene-4,5,6,18,19,20-hexanor-PGF$_{1\alpha}$-type compounds

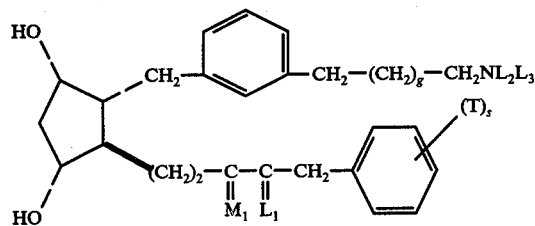

2-decarboxy-3,7-inter-m-phenylene-4,5,6,18,19,20-hexanor-13,14-dihydro-PGF$_{1\alpha}$-type compounds

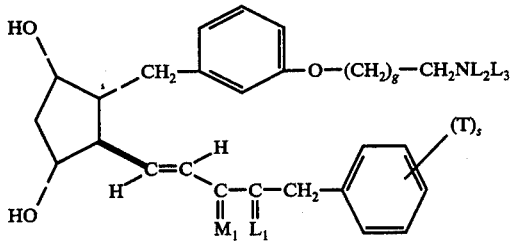

2-decarboxy-3,7-inter-m-phenylene-3-oxa-4,5,6,18,19,20-hexanor-PGF$_{1\alpha}$-type compounds Table C-continued

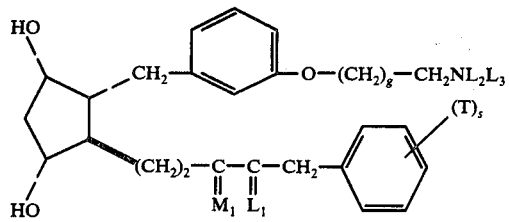

3,7-inter-m-phenylene-3-oxa-4,5,6,18,19,20-hexa-anor-13,14-dihydro-PGF$_{1\alpha}$-type compounds

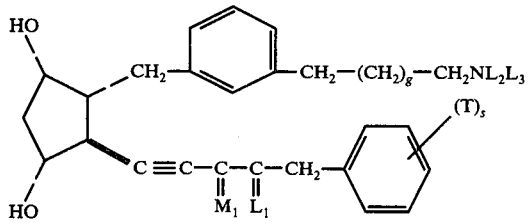

2-decarboxy-13,14-didehydro-3,7-inter-m-phenyl-ene-4,5,6,18,19,20-hexanor-PGF$_{1\alpha}$-type compounds

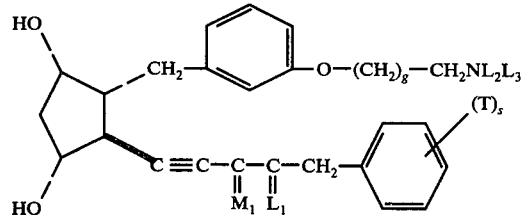

2-decarboxy-13,14-didehydro-3,7-inter-m-phenyl-ene-3-oxa-4,5,6,18,19,20-hexanor-PGF$_{1\alpha}$-type compounds

| Example | g | s | T | L$_1$ R$_3$ | R$_4$ | M$_1$ R$_5$ | ~OH | L$_2$ | L$_3$ | Name |
|---|---|---|---|---|---|---|---|---|---|---|
| C-1 | 1 | 0 | | hydrogen | hydrogen | hydrogen | α | hydrogen | hydrogen | 2-aminomethyl-17-phenyl |
| C-2 | 1 | 1 | p-fluoro | hydrogen | hydrogen | hydrogen | α | hydrogen | hydrogen | 2-aminomethyl-17-(p-fluorophenyl) |
| C-3 | 1 | 1 | m-chloro | hydrogen | hydrogen | hydrogen | α | hydrogen | hydrogen | 2-aminomethyl-17-(m-chlorophenyl) |
| C-4 | 1 | 1 | m-trifluoromethyl | hydrogen | hydrogen | hydrogen | α | hydrogen | hydrogen | 2-aminomethyl-17-(m-trifluoromethylphenyl) |
| C-5 | 1 | 0 | | hydrogen | hydrogen | methyl | α | hydrogen | hydrogen | 2-aminomethyl-15-methyl-17-phenyl |
| C-6 | 1 | 1 | p-fluoro | hydrogen | hydrogen | methyl | α | hydrogen | hydrogen | 2-aminomethyl-15-methyl-17-(p-fluorophenyl) |
| C-7 | 1 | 1 | m-chloro | hydrogen | hydrogen | methyl | α | hydrogen | hydrogen | 2-aminomethyl-15-methyl-17-(m-chlorophenyl) |
| C-8 | 1 | 1 | m-trifluoromethyl | hydrogen | hydrogen | methyl | α | hydrogen | hydrogen | 2-aminomethyl-15-methyl-17-(m-trifluoromethylphenyl) |
| C-9 | 1 | 0 | | hydrogen | hydrogen | hydrogen | α | methyl | hydrogen | 2-methylaminomethyl-17-phenyl |
| C-10 | 1 | 1 | p-fluoro | hydrogen | hydrogen | hydrogen | α | methyl | hydrogen | 2-methylaminomethyl-17-(p-fluorophenyl) |
| C-11 | 1 | 1 | m-chloro- | hydrogen | hydrogen | hydrogen | α | methyl | hydrogen | 2-methylaminomethyl-17-(m-chlorophenyl) |
| C-12 | 1 | 1 | m-trifluoromethyl | hydrogen | hydrogen | hydrogen | α | methyl | hydrogen | 2-methylaminomethyl-17-(m-trifluoromethylphenyl) |
| C-13 | 1 | 0 | | methyl | methyl | hydrogen | α | hydrogen | hydrogen | 2-aminomethyl-16,16-dimethyl-17-phenyl |
| C-14 | 1 | 1 | p-fluoro | methyl | methyl | hydrogen | α | hydrogen | hydrogen | 2-aminomethyl-16,16-dimethyl-17-(p-fluorophenyl) |
| C-15 | 1 | 1 | m-chloro | methyl | methyl | hydrogen | α | hydrogen | hydrogen | 2-aminomethyl-16,16-dimethyl-17-(m-chlorophenyl) |
| C-16 | 1 | 1 | m-trifluoromethyl | methyl | methyl | hydrogen | α | hydrogen | hydrogen | 2-aminomethyl-16,16-dimethyl-17-(m-trifluoromethylphenyl) |
| C-17 | 1 | 0 | | methyl | methyl | methyl | α | hydrogen | hydrogen | 2-aminomethyl-15,16,16-trimethyl-17-phenyl |

Table C-continued

| | | | | | | | | | |
|---|---|---|---|---|---|---|---|---|---|
| C-18 | 1 | 1 | p-fluoro | methyl | methyl | methyl | α | hydrogen | hydrogen | 2-aminomethyl-15,16,16-trimethyl-17-(p-fluorophenyl) |
| C-19 | 1 | 1 | m-chloro | methyl | methyl | methyl | α | hydrogen | hydrogen | 2-aminomethyl-15,16,16-trimethyl-17-(m-chlorophenyl) |
| C-20 | 1 | 1 | m-trifluoromethyl | methyl | methyl | methyl | α | hydrogen | hydrogen | 2-aminomethyl-15,16,16-trimethyl-17-(m-trifluoromethylphenyl) |
| C-21 | 1 | 0 | | methyl | methyl | hydrogen | α | methyl | hydrogen | 2-methylaminomethyl-16,16-dimethyl-17-phenyl |
| C-22 | 1 | 1 | p-fluoro | methyl | methyl | hydrogen | α | methyl | hydrogen | 2-methylaminomethyl-16,16-dimethyl-17-(p-fluorophenyl) |
| C-23 | 1 | 1 | m-chloro | methyl | methyl | hydrogen | α | methyl | hydrogen | 2-methylaminomethyl-16,16-dimethyl-17-(m-chlorophenyl) |
| C-24 | 1 | 1 | m-trifluoromethyl | methyl | methyl | hydrogen | α | methyl | hydrogen | 2-methylaminomethyl-16,16-dimethyl-17-(m-trifluoromethylphenyl) |
| C-25 | 3 | 0 | | hydrogen | hydrogen | hydrogen | α | hydrogen | hydrogen | 2-aminomethyl-2a,2b-dihomo-17-phenyl |
| C-26 | 3 | 1 | p-fluoro | hydrogen | hydrogen | hydrogen | α | hydrogen | hydrogen | 2-aminomethyl-2a,2b-dihomo-17-(p-fluorophenyl) |
| C-27 | 3 | 1 | m-chloro | hydrogen | hydrogen | hydrogen | α | hydrogen | hydrogen | 2-aminomethyl-2a,2b-dihomo-17-(m-chlorophenyl) |
| C-28 | 3 | 1 | m-trifluoromethyl | hydrogen | hydrogen | hydrogen | α | hydrogen | hydrogen | 2-aminomethyl-2a,2b-dihomo-17-(m-trifluoromethylphenyl) |
| C-29 | 3 | 0 | | hydrogen | hydrogen | methyl | α | hydrogen | hydrogen | 2-aminomethyl-2a,2b-dihomo-15-methyl-17-phenyl |
| C-30 | 3 | 1 | p-fluoro | hydrogen | hydrogen | methyl | α | hydrogen | hydrogen | 2-aminomethyl-2a,2b-dihomo-15-methyl-17-(p-fluorophenyl) |
| C-31 | 3 | 1 | m-chloro | hydrogen | hydrogen | methyl | α | hydrogen | hydrogen | 2-aminomethyl-2a,2b-dihomo-15-methyl-17-(m-chlorophenyl) |
| C-32 | 3 | 1 | m-trifluoromethyl | hydrogen | hydrogen | methyl | α | hydrogen | hydrogen | 2-aminomethyl-2a,2b-dihomo-15-methyl-17-(m-trifluoromethylphenyl) |
| C-33 | 1 | 0 | | fluoro | fluoro | hydrogen | α | hydrogen | hydrogen | 2-aminomethyl-16,16-difluoro-17-phenyl |
| C-34 | 1 | 1 | p-fluoro | fluoro | fluoro | hydrogen | α | hydrogen | hydrogen | 2-aminomethyl-16,16-difluoro-17-(p-fluorophenyl) |
| C-35 | 1 | 1 | m-chloro | fluoro | fluoro | hydrogen | α | hydrogen | hydrogen | 2-aminomethyl-16,16-difluoro-17-(m-chlorophenyl) |
| C-36 | 1 | 1 | m-trifluoromethyl | fluoro | fluoro | hydrogen | α | hydrogen | hydrogen | 2-aminomethyl-16,16-difluoro-17-(m-trifluoromethylphenyl) |
| C-37 | 1 | 0 | | fluoro | fluoro | methyl | α | hydrogen | hydrogen | 2-aminomethyl-15-methyl-16,16-difluoro-17-phenyl |
| C-38 | 1 | 1 | p-fluoro | fluoro | fluoro | methyl | α | hydrogen | hydrogen | 2-aminomethyl-15-methyl-16,16-difluoro-17-(p-fluorophenyl) |
| C-39 | 1 | 1 | m-chloro | fluoro | fluoro | methyl | α | hydrogen | hydrogen | 2-aminomethyl-15-methyl-16,16-difluoro-17-(m-chlorophenyl) |
| C-40 | 1 | 1 | m-trifluoromethyl | fluoro | fluoro | methyl | α | hydrogen | hydrogen | 2-aminomethyl-15-methyl-16,16-difluoro-17-(m-trifluoromethylphenyl) |
| C-41 | 1 | 0 | | fluoro | fluoro | hydrogen | α | methyl | hydrogen | 2-aminomethyl-16,16-difluoro-17-phenyl |
| C-42 | 1 | 1 | p-fluoro | fluoro | fluoro | hydrogen | α | methyl | hydrogen | 2-methylaminomethyl-16,16-difluoro-17-(p-fluorophenyl) |
| C-43 | 1 | 1 | m-chloro | fluoro | fluoro | hydrogen | α | methyl | hydrogen | 2-methylaminomethyl-16,16-difluoro-17-(m-chlorophenyl) |
| C-44 | 1 | 1 | m-trifluoromethyl | fluoro | fluoro | hydrogen | α | methyl | hydrogen | 2-methylaminomethyl-16,16-difluoro-17-(m-trifluoromethylphenyl) |

Table D
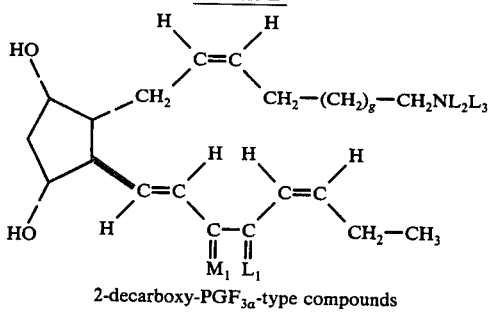
2-decarboxy-PGF$_{3\alpha}$-type compounds
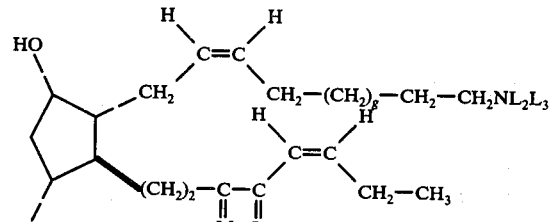
2-decarboxy-13,14-dihydro-PGF$_{3\alpha}$-type compounds
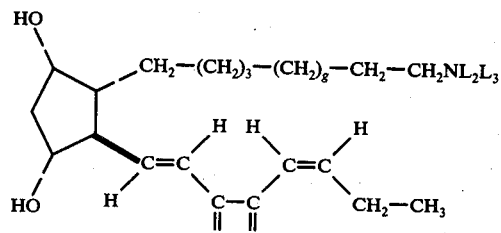
2-decarboxy-5,6-dihydro-PGF$_{3\alpha}$-type compounds
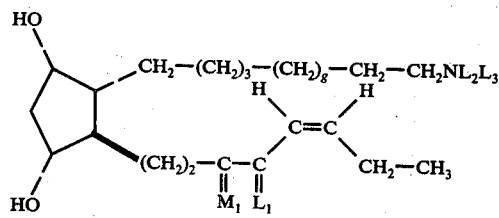
2-decarboxy-5,6,13,14-tetrahydro-PGF$_{3\alpha}$-type compounds
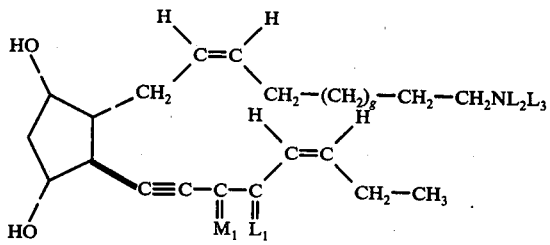
2-decarboxy-13,14-didehydro-PGF$_{3\alpha}$-type compounds
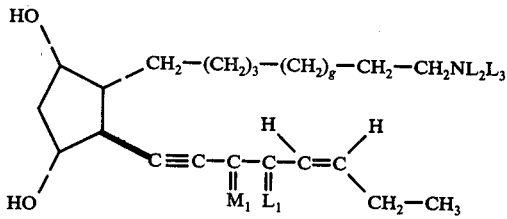
2-decarboxy-13,14-didehydro-5,6-dihydro-PGF$_{3\alpha}$-type compounds -continued
Table D

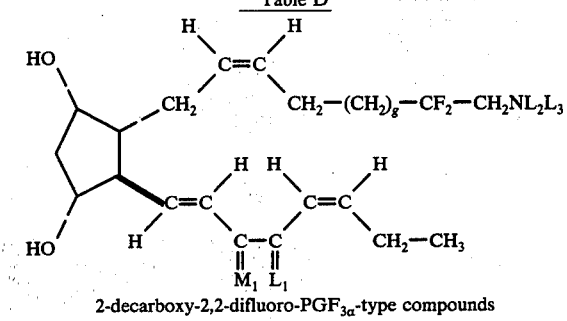
2-decarboxy-2,2-difluoro-PGF$_{3\alpha}$-type compounds

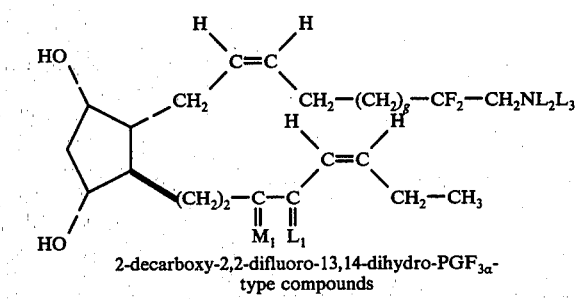
2-decarboxy-2,2-difluoro-13,14-dihydro-PGF$_{3\alpha}$-type compounds

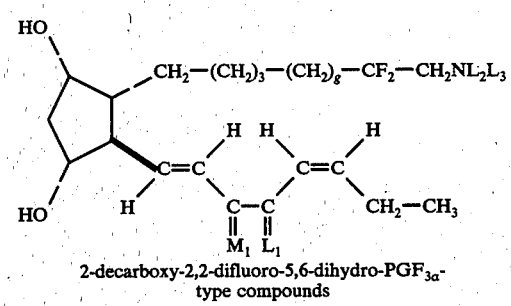
2-decarboxy-2,2-difluoro-5,6-dihydro-PGF$_{3\alpha}$-type compounds

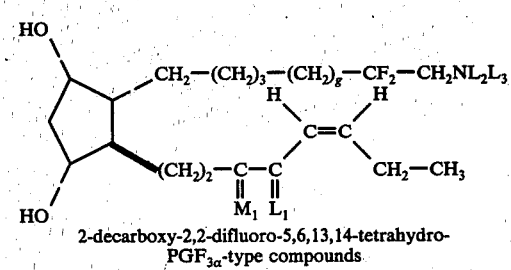
2-decarboxy-2,2-difluoro-5,6,13,14-tetrahydro-PGF$_{3\alpha}$-type compounds

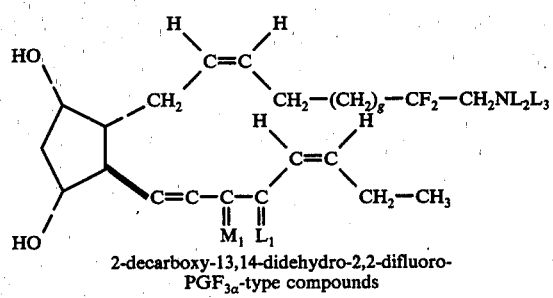
2-decarboxy-13,14-didehydro-2,2-difluoro-PGF$_{3\alpha}$-type compounds

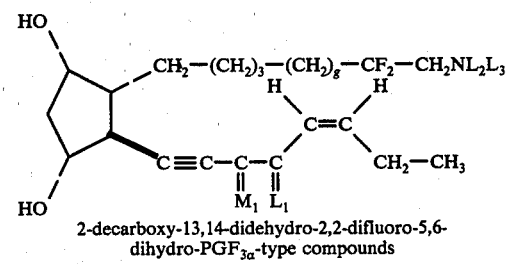
2-decarboxy-13,14-didehydro-2,2-difluoro-5,6-dihydro-PGF$_{3\alpha}$-type compounds Table D

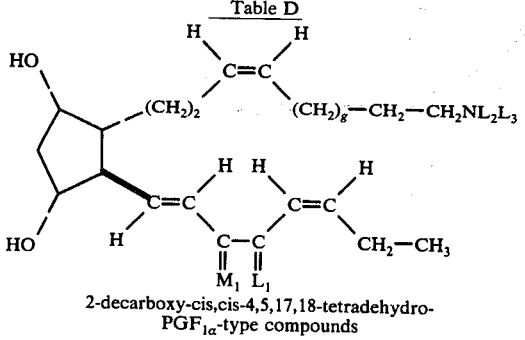
2-decarboxy-cis,cis-4,5,17,18-tetradehydro-
PGF$_{1\alpha}$-type compounds

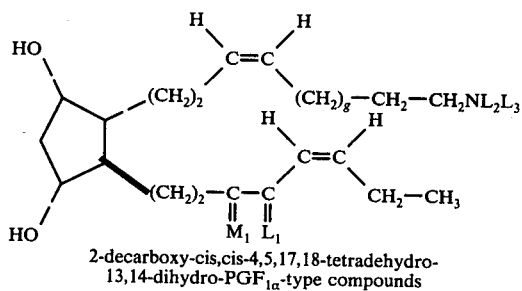
2-decarboxy-cis,cis-4,5,17,18-tetradehydro-
13,14-dihydro-PGF$_{1\alpha}$-type compounds

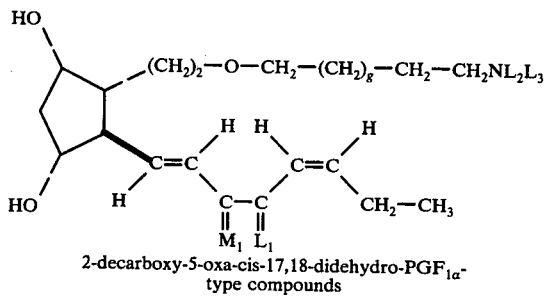
2-decarboxy-5-oxa-cis-17,18-didehydro-PGF$_{1\alpha}$-
type compounds

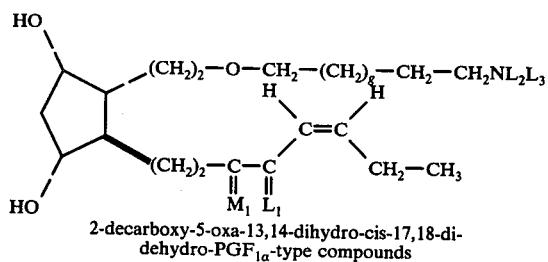
2-decarboxy-5-oxa-13,14-dihydro-cis-17,18-di-
dehydro-PGF$_{1\alpha}$-type compounds

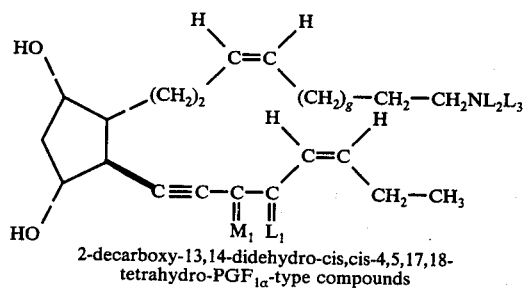
2-decarboxy-13,14-didehydro-cis,cis-4,5,17,18-
tetrahydro-PGF$_{1\alpha}$-type compounds

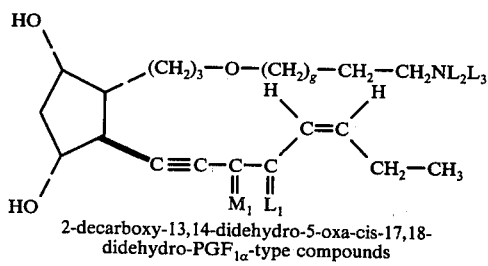
2-decarboxy-13,14-didehydro-5-oxa-cis-17,18-
didehydro-PGF$_{1\alpha}$-type compounds -continued Table D

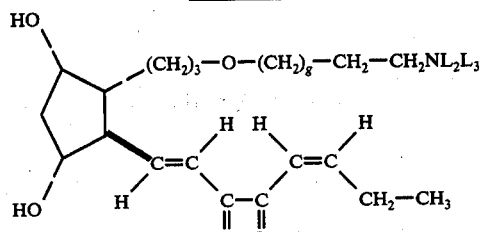

2-decarboxy-4-oxa-cis-17,18-didehydro-PGF$_{1\alpha}$-
type compounds

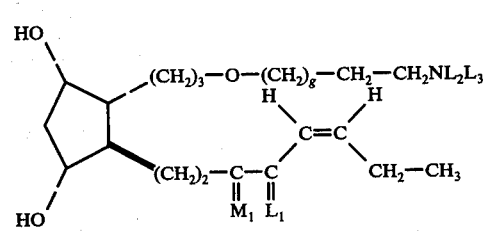

2-decarboxy-4-oxa-13,14-dihydro-17,18-didehy-
dro-PGF$_{1\alpha}$ type compounds

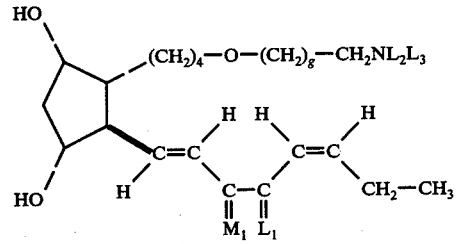

2-decarboxy-3-oxa-cis-17,18-didehydro-PGF$_{1\alpha}$-
type compounds

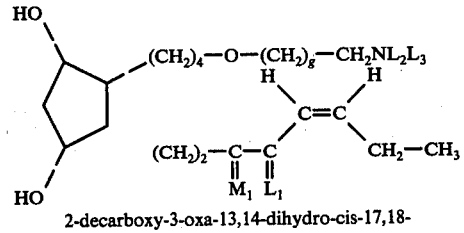

2-decarboxy-3-oxa-13,14-dihydro-cis-17,18-
didehydro-PGF$_{1\alpha}$-type compounds

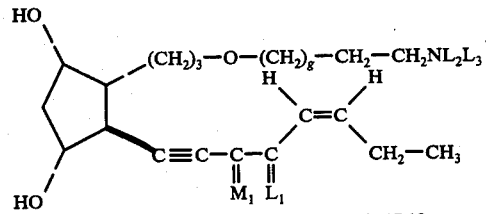

2-decarboxy-13,14-didehydro-4-oxa-cis-17,18-
didehydro-PGF$_{1\alpha}$-type compounds

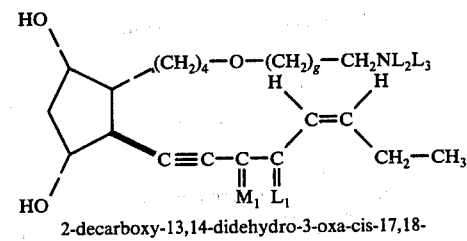

2-decarboxy-13,14-didehydro-3-oxa-cis-17,18-
didehydro-PGF$_{1\alpha}$-type compounds

Table D

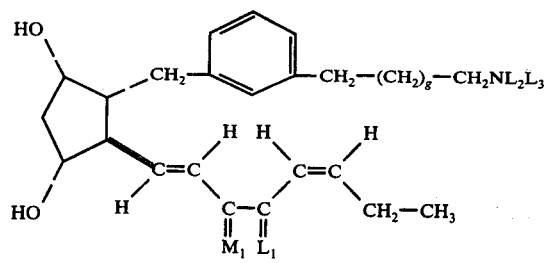

2-decarboxy-3,7-inter-m-phenylene-4,5,6-trinor-
cis-17,18-didehydro-PGF$_{1\alpha}$-type compounds

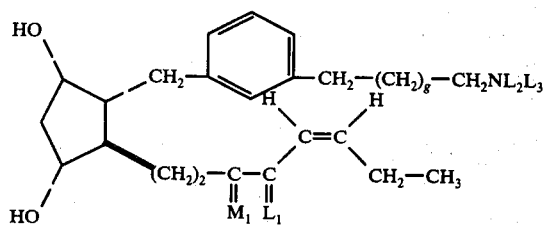

2-decarboxy-3,7-inter-m-phenylene-4,5,6-trinor-
13,14-dihydro-17,18-didehydro-PGF$_{1\alpha}$-type
compounds

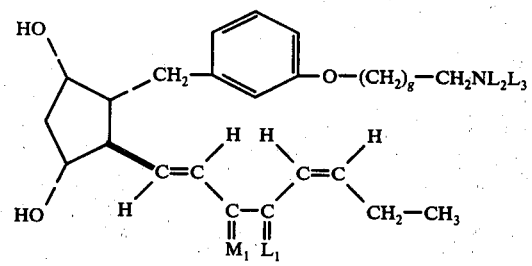

2-decarboxy-3,7-inter-m-phenylene-3-oxa-4,5,6-
trinor-cis-17,18-didehydro-PGF$_{1\alpha}$-type compounds

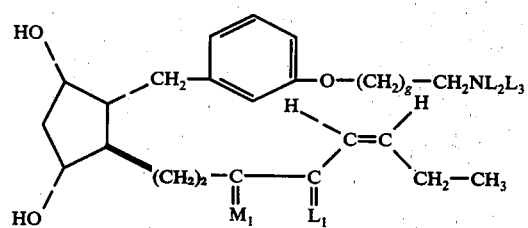

2-decarboxy-3,7-inter-m-phenylene-3-oxa-4,5,6-
trinor-13,14-dihydro-cis-17,18-didehydro-PGF$_{1\alpha}$-
type compounds

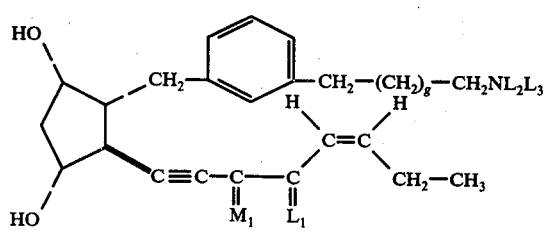

2-decarboxy-13,14-didehydro-3,7-inter-m-phenylene-
4,5,6-trinor-cis-17,18-didehydro-PGF$_{1\alpha}$-type-
compounds -continued

Table D

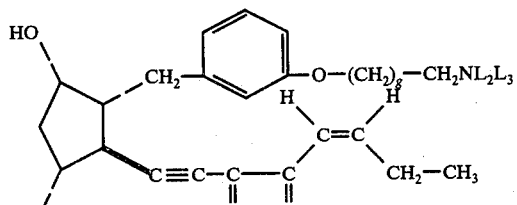

2-decarboxy-13,14-didehydro-3,7-inter-m-phenyl-
ene-3-oxa-4,5,6-trinor-cis-17,18-didehydro-
PGF$_{1\alpha}$-type compounds

| Example | g | L$_1$ R$_3$ | R$_4$ | M$_1$ R$_5$ | ~OH | L$_2$ | L$_3$ | Name |
|---|---|---|---|---|---|---|---|---|
| D-1 | 1 | methyl | hydrogen | hydrogen | α | hydrogen | hydrogen | 2-aminomethyl-16-methyl |
| D-2 | 1 | methyl | hydrogen | methyl | α | hydrogen | hydrogen | 2-aminomethyl-15,16-dimethyl |
| D-3 | 1 | methyl | hydrogen | hydrogen | α | methyl | hydrogen | 2-methylaminomethyl-16-methyl |
| D-4 | 1 | methyl | methyl | hydrogen | α | hydrogen | hydrogen | 2-aminomethyl-16,16-dimethyl |
| D-5 | 1 | methyl | methyl | methyl | α | hydrogen | hydrogen | 2-aminomethyl-15,16,16-trimethyl |
| D-6 | 1 | methyl | methyl | hydrogen | α | methyl | hydrogen | 2-methylaminomethyl-16,16-dimethyl |
| D-7 | 1 | fluoro | hydrogen | hydrogen | α | hydrogen | hydrogen | 2-aminomethyl-16-fluoro |
| D-8 | 1 | fluoro | hydrogen | methyl | α | hydrogen | hydrogen | 2-aminomethyl-15-methyl-16-fluoro |
| D-9 | 1 | fluoro | hydrogen | hydrogen | α | methyl | hydrogen | 2-methylaminomethyl-16-fluoro |
| D-10 | 1 | fluoro | fluoro | hydrogen | α | hydrogen | hydrogen | 2-aminomethyl-16,16-difluoro |
| D-11 | 1 | fluoro | fluoro | methyl | α | hydrogen | hydrogen | 2-aminomethyl-15-methyl-16,16-difluoro |
| D-12 | 1 | fluoro | fluoro | hydrogen | α | methyl | hydrogen | 2-methylaminomethyl-16,16-difluoro |
| D-13 | 1 | hydrogen | hydrogen | hydrogen | α | hydrogen | hydrogen | 2-aminomethyl |
| D-14 | 1 | hydrogen | hydrogen | methyl | α | hydrogen | hydrogen | 2-aminomethyl-15-methyl |
| D-15 | 3 | hydrogen | hydrogen | hydrogen | α | hydrogen | hydrogen | 2-aminomethyl-2a,2b-dihomo |
| D-16 | 3 | hydrogen | hydrogen | methyl | α | hydrogen | hydrogen | 2-aminomethyl-2a,2b-dihomo-15-methyl |
| D-17 | 3 | methyl | methyl | hydrogen | α | hydrogen | hydrogen | 2-aminomethyl-2a,2b-dihomo-16,16-dimethyl |
| D-18 | 3 | methyl | methyl | methyl | α | hydrogen | hydrogen | 2-aminomethyl-2a,2b-dihomo-15,16,16-trimethyl |
| D-19 | 3 | fluoro | fluoro | hydrogen | α | hydrogen | hydrogen | 2-aminomethyl-2a,2b-dihomo-16,16-difluoro |
| D-20 | 3 | fluoro | fluoro | methyl | α | hydrogen | hydrogen | 2-aminomethyl-2a,2b-dihomo-15-methyl-16,16-difluoro |

Table E

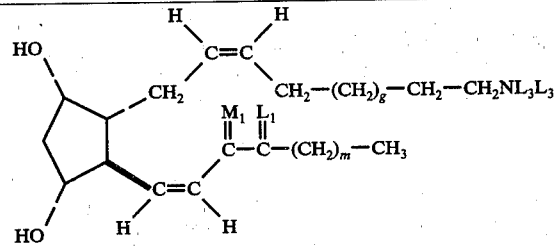

cis-13-PGF$_{2\alpha}$-type compounds

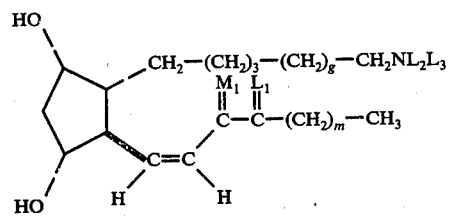

cis-13-PGF$_{1\alpha}$-type compounds

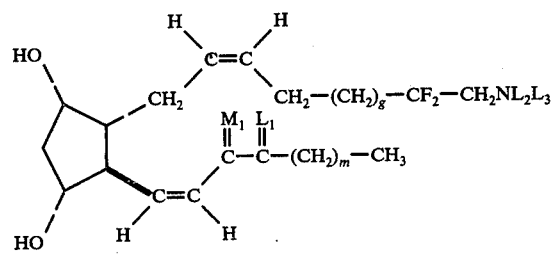

Table E-continued 2,2-difluoro-cis-13-PGF$_{2\alpha}$-type compounds

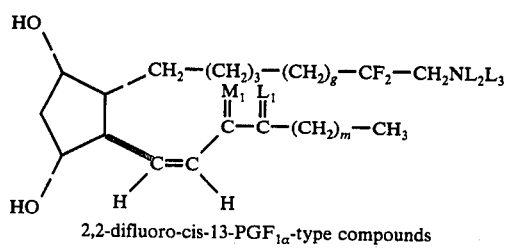

2,2-difluoro-cis-13-PGF$_{1\alpha}$-type compounds

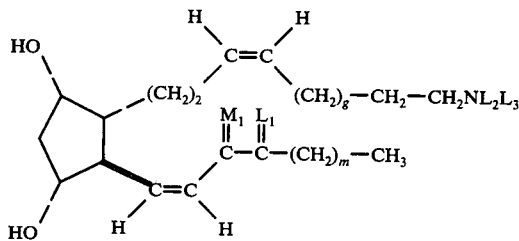

2-decarboxy-cis-4,5-didehydro-cis-13-PGF$_{1\alpha}$-type Compounds

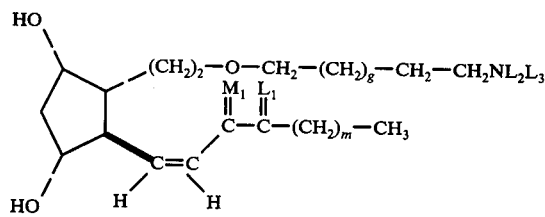

2-decarboxy-5-oxa-cis-13-PGF$_{1\alpha}$-type compounds

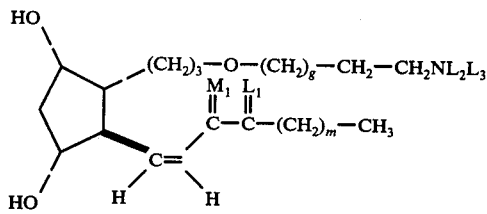

2-decarboxy-4-oxa-cis-13-PGF$_{1\alpha}$-type compounds

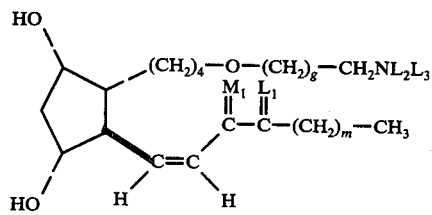

2-decarboxy-3-oxa-cis-13-PGF$_{1\alpha}$-type compounds

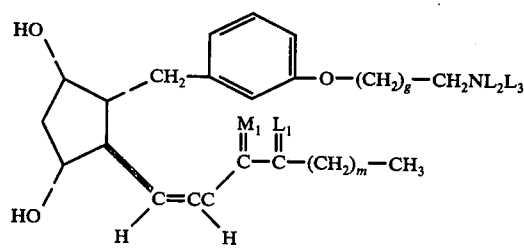

2-decarboxy-3,7-inter-m-phenylene-4,5,6-trinor-cis-13-PGF$_{1\alpha}$-type compounds

Table E-continued

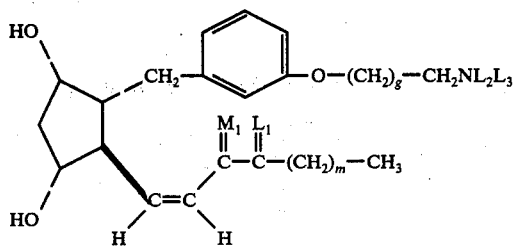

2-decarboxy-3,7-inter-m-phenylene-3-oxa-4,5,6-trinor-cis-13-PGD$_1$-type compounds

| Example | g | m | L$_1$ R$_3$ | R$_4$ | M$_1$ R$_5$ | ~OH | L$_2$ | L$_3$ | Name |
|---|---|---|---|---|---|---|---|---|---|
| E-1 | 1 | 3 | methyl | hydrogen | hydrogen | α | hydrogen | hydrogen | 2-aminomethyl-15-epi-16-methyl |
| E-2 | 1 | 3 | methyl | hydrogen | methyl | α | hydrogen | hydrogen | 2-aminomethyl-15-epi-15,16-dimethyl |
| E-3 | 1 | 3 | methyl | hydrogen | hydrogen | α | methyl | hydrogen | 2-aminomethylaminomethyl-15-epi-16-methyl |
| E-4 | 1 | 3 | methyl | methyl | hydrogen | α | hydrogen | hydrogen | 2-aminomethyl-15-epi-16,16-dimethyl |
| E-5 | 1 | 3 | methyl | methyl | methyl | α | hydrogen | hydrogen | 2-aminomethyl-15-epi-15,16,16-trimethyl |
| E-6 | 1 | 3 | methyl | methyl | hydrogen | α | methyl | hydrogen | 2-methylaminomethyl-15-epi-16,16-dimethyl |
| E-7 | 1 | 3 | fluoro | hydrogen | hydrogen | α | hydrogen | hydrogen | 2-aminomethyl-15-epi-16-fluoro |
| E-8 | 1 | 3 | fluoro | hydrogen | methyl | α | hydrogen | hydrogen | 2-aminomethyl-15-epi-15-methyl-16-fluoro |
| E-9 | 1 | 3 | fluoro | hydrogen | hydrogen | α | methyl | hydrogen | 2-aminomethyl-15-epi-16-fluoro |
| E-10 | 1 | 3 | fluoro | fluoro | hydrogen | α | hydrogen | hydrogen | 2-aminomethyl-15-epi-16,16-difluoro |
| E-11 | 1 | 3 | fluoro | fluoro | methyl | α | hydrogen | hydrogen | 2-aminomethyl-15-epi-15-methyl-16,16-difluoro |
| E-12 | 1 | 3 | fluoro | fluoro | methyl | α | hydrogen | hydrogen | 2-aminomethyl-15-epi-15-methyl-16,16-difluoro |
| E-13 | 1 | 3 | hydrogen | hydrogen | hydrogen | α | methyl | hydrogen | 2-methylaminomethyl-15-epi |
| E-14 | 3 | 3 | hydrogen | hydrogen | hydrogen | α | hydrogen | hydrogen | 2-aminomethyl-15-epi-2a,2b-dihomo |
| E-15 | 3 | 3 | methyl | methyl | hydrogen | α | hydrogen | hydrogen | 2-aminomethyl-15-epi-2a,2b-dihomo-16,16-dimethyl |
| E-16 | 3 | 3 | methyl | methyl | methyl | α | hydrogen | hydrogen | 2-aminomethyl-15-epi-2a,2b-dihomo-15,16,16-trimethyl |
| E-17 | 3 | 3 | fluoro | fluoro | hydrogen | α | hydrogen | hydrogen | 2-aminomethyl-15-epi-2a,2b-dihomo-16,16-difluoro |
| E-18 | 3 | 3 | fluoro | fluoro | methyl | α | hydrogen | hydrogen | 2-aminomethyl-15-epi-2a,2b-dihomo-15-methyl-16,16-difluoro |

Table F

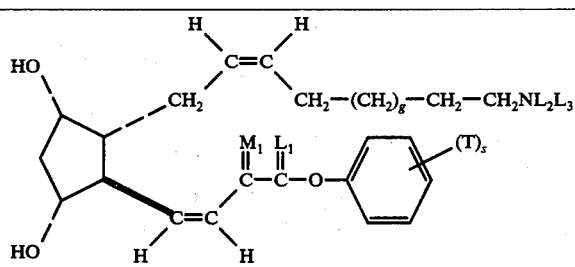

2-decarboxy-cis-13-PGF$_{2\alpha}$-type compounds

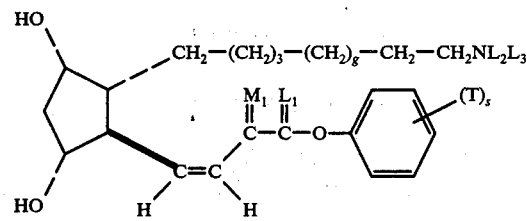

2-decarboxy-cis-13-PGF$_{1\alpha}$-type compounds

Table F-continued
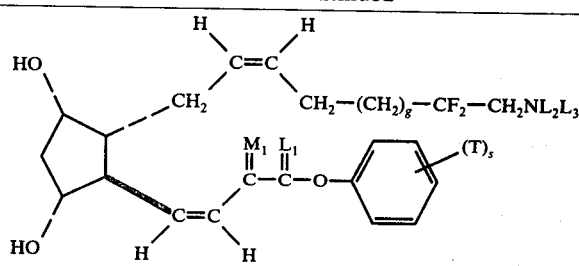
2-decarboxy-2,2-difluoro-cis-13-PGF$_{2\alpha}$-type
compounds
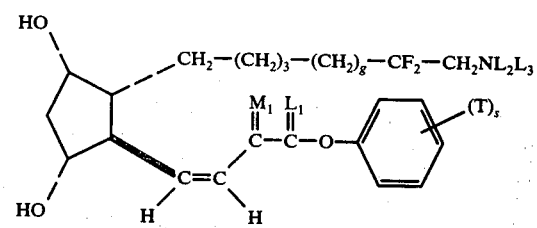
2-decarboxy-2,2-difluoro-cis-13-PGF$_{1\alpha}$-type
compounds
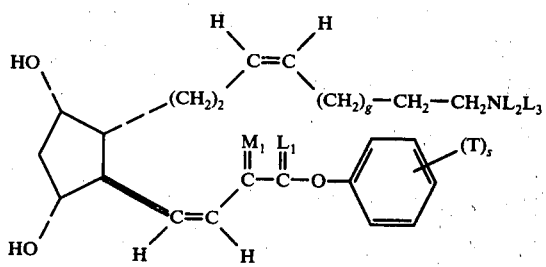
2-decarboxy-cis-4,5-didehydro-cis-13-PGF$_{1\alpha}$-
type compounds
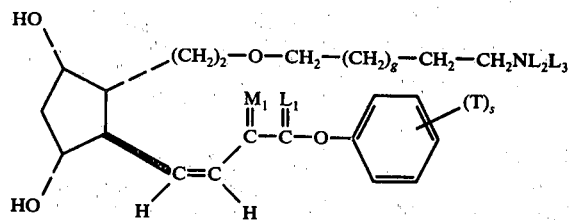
2-decarboxy-5-oxa-cis-13-PGF$_{1\alpha}$-type compounds
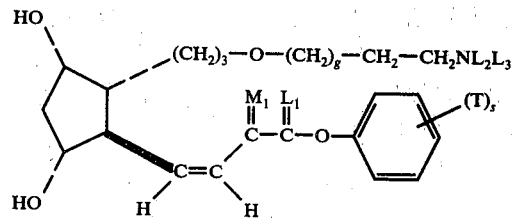
2-decarboxy-4-oxa-cis-13-PGF$_{1\alpha}$-type compounds
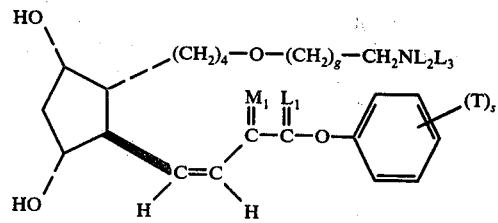
2-decarboxy-3-oxa-cis-13-PGF$_{1\alpha}$-type compounds

Table F-continued

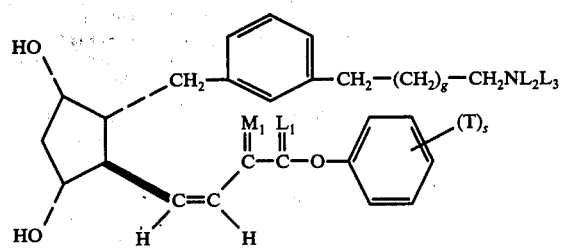

3,7-inter-m-phenylene-4,5,6-trinor-cis-13-PGF$_{1\alpha}$-type compounds

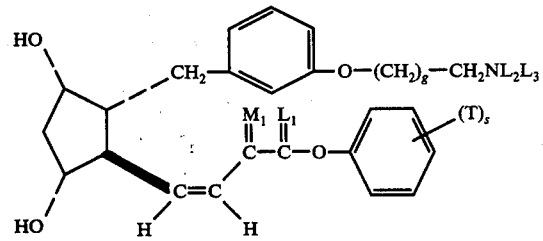

3,7-inter-m-phenylene-3-oxa-4,5,6-trinor-cis-13-PGF$_{1\alpha}$-type compounds

| Example | g | s | T | L$_1$ R$_3$ | R$_4$ | M$_1$ R$_5$ | ~OH | L$_2$ | L$_3$ | Name |
|---|---|---|---|---|---|---|---|---|---|---|
| F-1 | 1 | 0 | | hydrogen | hydrogen | hydrogen | α | hydrogen | hydrogen | 2-aminomethyl-15-epi-16-phenoxy-17,18,19,20-tetranor |
| F-2 | 1 | 1 | p-fluoro | hydrogen | hydrogen | hydrogen | α | hydrogen | hydrogen | 2-aminomethyl-15-epi-16-(p-fluorophenoxy)-17,18,19,20-tetranor |
| F-3 | 1 | 1 | m-chloro | hydrogen | hydrogen | hydrogen | α | hydrogen | hydrogen | 2-aminomethyl-15-epi-16-(m-chlorophenoxy)-17,18,19,20-tetranor |
| F-4 | 1 | 1 | m-trifluoro- | hydrogen | hydrogen | hydrogen | α | hydrogen | hydrogen | 2-aminomethyl-15-epi-16-(m-trifluoromethylphenoxy)-17,18,19,20-tetranor |
| F-5 | 1 | 0 | | hydrogen | hydrogen | methyl | α | hydrogen | hydrogen | 2-aminomethyl-15-epi-15-methyl-16-phenoxy-17,18,19,20-tetranor |
| F-6 | 1 | 1 | p-fluoro | hydrogen | hydrogen | methyl | α | hydrogen | hydrogen | 2-aminomethyl-15-epi-15-methyl-16-(p-fluorophenoxy)-17,18,19,20-tetranor |
| F-7 | 1 | 1 | m-chloro | hydrogen | hydrogen | methyl | α | hydrogen | hydrogen | 2-aminomethyl-15-epi-15-methyl-16-(m-chlorophenoxy)-17,18,19,20-tetranor |
| F-8 | 1 | 1 | m-trifluoromethyl | hydrogen | hydrogen | methyl | α | hydrogen | hydrogen | 2-aminomethyl-15-epi-15-methyl-16-(m-trifluoromethylphenoxy)-17,18,19,20-tetranor |
| F-9 | 1 | 0 | | hydrogen | hydrogen | hydrogen | α | methyl | hydrogen | 2-methylaminomethyl-15-epi-16-phenoxy-17,18,19,20-tetranor |
| F-10 | 1 | 1 | p-fluoro | hydrogen | hydrogen | hydrogen | α | methyl | hydrogen | 2-methylaminomethyl-15-epi-16-(p-fluorophenoxy)-17,18,19,20-tetranor |
| F-11 | 1 | 1 | m-chloro | hydrogen | hydrogen | hydrogen | α | methyl | hydrogen | 2-methylaminomethyl-15-epi-16-(m-chlorophenoxy)-17,18,19,20-tetranor |
| F-12 | 1 | 1 | m-trifluoromethyl | hydrogen | hydrogen | hydrogen | α | methyl | hydrogen | 2-methylaminomethyl-15-epi-16-(m-trifluoromethylphenoxy)-17,18,19,20-tetranor |
| F-13 | 1 | 0 | | methyl | methyl | hydrogen | α | hydrogen | hydrogen | 2-aminomethyl-15-epi-16-methyl-16-phenoxy-18,19,20-trinor |
| F-14 | 1 | 1 | p-fluoro | methyl | methyl | hydrogen | α | hydrogen | hydrogen | 2-aminomethyl-15-epi-16-methyl-16-(p-fluorophenoxy)-18,19,20-trinor |
| F-15 | 1 | 1 | m-chloro | methyl | methyl | hydrogen | α | hydrogen | hydrogen | 2-aminomethyl-15-epi-16-methyl-16-(m-chlorophenoxy)-18,19,20-trinor |
| F-16 | 1 | 1 | m-trifluoromethyl | methyl | methyl | hydrogen | α | hydrogen | hydrogen | 2-aminomethyl-15-epi-16-methyl-16-(m-trifluoromethylphenoxy)- |

Table F-continued

| | | | | | | | | | | |
|---|---|---|---|---|---|---|---|---|---|---|
| F-17 | 1 | 0 | | methyl | methyl | methyl | α | hydrogen | hydrogen | 2-aminomethyl-15-epi-15,16-dimethyl-16-phenoxy-18,19,20-trinor |
| F-18 | 1 | 1 | p-fluoro | methyl | methyl | methyl | α | hydrogen | hydrogen | 2-aminomethyl-15-epi-15,16-dimethyl-16-(p-fluorophenoxy)-18,19,20-trinor |
| F-19 | 1 | 1 | m-chloro | methyl | methyl | methyl | α | hydrogen | hydrogen | 2-aminomethyl-15-epi-15,16-dimethyl-16-(m-chlorophenoxy)-18,19,20-trinor |
| F-20 | 1 | 1 | m-trifluoro | methyl | methyl | methyl | α | hydrogen | hydrogen | 2-aminomethyl-15-epi-15,16-dimethyl-16-(m-trifluoromethylphenoxy)-18,19,20-trinor |
| F-21 | 1 | 0 | | methyl | methyl | hydrogen | α | methyl | hydrogen | 2-methylaminomethyl-15-epi-16-methyl-16-phenoxy-18,19,20-trinor |
| F-22 | 1 | 1 | p-fluoro | methyl | methyl | hydrogen | α | methyl | hydrogen | 2-methylaminomethyl-15-epi-16-methyl-16-(p-fluorophenoxy)-18,19,20-trinor |
| F-23 | 1 | 1 | m-chloro | methyl | methyl | hydrogen | α | methyl | hydrogen | 2-methylaminomethyl-15-epi-16-methyl-16-(m-chlorophenoxy)-18,19,20-trinor |
| F-24 | 1 | 1 | m-trifluoromethyl | methyl | methyl | hydrogen | α | methyl | hydrogen | 2-methylaminomethyl-15-epi-16-methyl-16-(m-trifluoromethylphenoxy)-18,19,20-trinor |
| F-25 | 3 | 0 | | hydrogen | hydrogen | hydrogen | α | hydrogen | hydrogen | 2-aminomethyl-15-epi-2a,2b-dihomo-16-phenoxy-17,18,19,20-tetranor |
| F-26 | 3 | 1 | p-fluoro | hydrogen | hydrogen | hydrogen | α | hydrogen | hydrogen | 2-aminomethyl-15-epi-2a,2b-dihomo-16-(p-fluorophenoxy)-17,18,19,20-tetranor |
| F-27 | 3 | 1 | m-chloro | hydrogen | hydrogen | hydrogen | α | hydrogen | hydrogen | 2-aminomethyl-15-epi-2a,2b-dihomo-16-(m-chlorophenoxy)-17,18,19,20-tetranor |
| F-28 | 3 | 1 | m-trifluoromethyl | hydrogen | hydrogen | hydrogen | α | hydrogen | hydrogen | 2-aminomethyl-15-epi-2a,2b-dihomo-16-(m-trifluoromethylphenoxy)-17,18,19,20-tetranor |
| F-29 | 3 | 0 | | hydrogen | hydrogen | methyl | α | hydrogen | hydrogen | 2-aminomethyl-15-epi-2a,2b-dihomo-15-methyl-16-phenoxy-17,18,19,20-tetranor |
| F-30 | 3 | 1 | p-fluoro | hydrogen | hydrogen | methyl | α | hydrogen | hydrogen | 2-aminomethyl-15-epi-2a,2b-dihomo-15-metyl-16-(p-fluorophenoxy)-18,19,20-tetranor |
| F-31 | 3 | 1 | m-chloro | hydrogen | hydrogen | methyl | α | hydrogen | hydrogen | 2-aminomethyl-15-epi-2a,2b-dihomo-15-methyl-16-(m-chlorophenoxy)-17,18,19,20-tetranor |
| F-32 | 3 | 1 | m-trifluoro- | hydrogen | hydrogen | methyl | α | hydrogen | hydrogen | 2-aminomethyl-15-epi-2a,2b-dihomo-15-methyl-16-(m-trifluoromethylphenoxy)-17,18,19,20-tetranor |

Table G

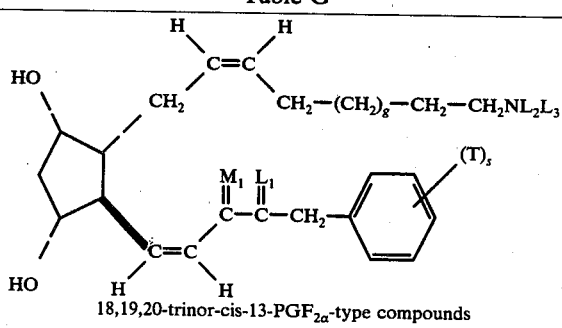

18,19,20-trinor-cis-13-PGF$_{2\alpha}$-type compounds

Table G-continued
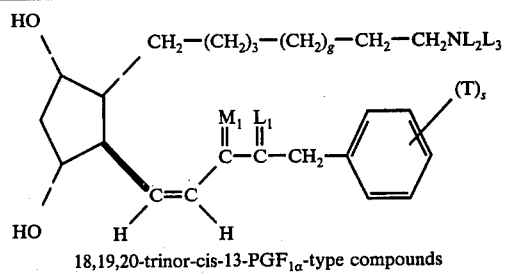
18,19,20-trinor-cis-13-PGF$_{1\alpha}$-type compounds
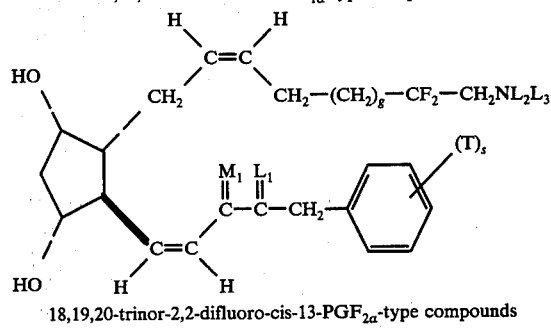
18,19,20-trinor-2,2-difluoro-cis-13-PGF$_{2\alpha}$-type compounds
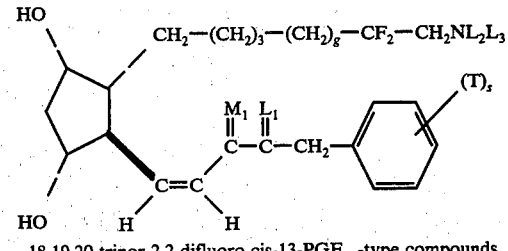
18,19,20-trinor-2,2-difluoro-cis-13-PGF$_{1\alpha}$-type compounds
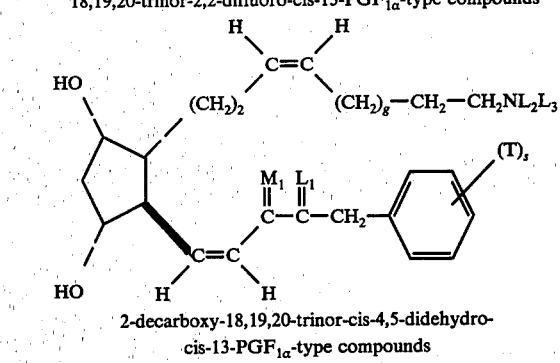
2-decarboxy-18,19,20-trinor-cis-4,5-didehydro-cis-13-PGF$_{1\alpha}$-type compounds
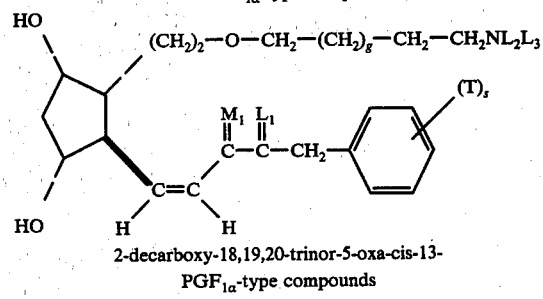
2-decarboxy-18,19,20-trinor-5-oxa-cis-13-PGF$_{1\alpha}$-type compounds
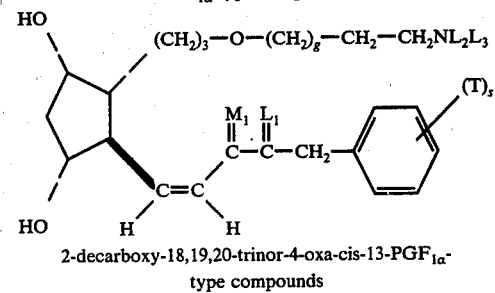
2-decarboxy-18,19,20-trinor-4-oxa-cis-13-PGF$_{1\alpha}$-type compounds Table G-continued

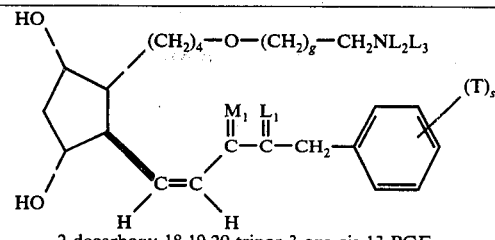

2-decarboxy-18,19,20-trinor-3-oxa-cis-13-PGF$_{1\alpha}$-type compounds

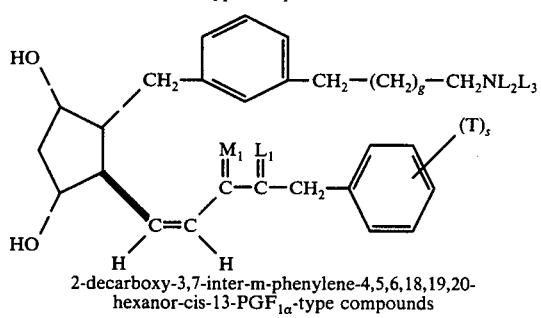

2-decarboxy-3,7-inter-m-phenylene-4,5,6,18,19,20-hexanor-cis-13-PGF$_{1\alpha}$-type compounds

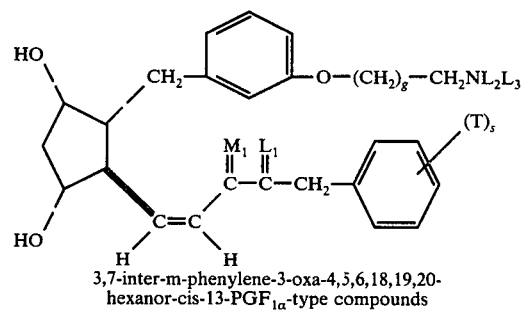

3,7-inter-m-phenylene-3-oxa-4,5,6,18,19,20-hexanor-cis-13-PGF$_{1\alpha}$-type compounds

| Example | g | s | T | L$_1$ R$_3$ | R$_4$ | M$_1$ R$_5$ | ~OH | L$_2$ | L$_3$ | Name |
|---|---|---|---|---|---|---|---|---|---|---|
| G-1 | 1 | 0 |  | hydrogen | hydrogen | hydrogen | α | hydrogen | hydrogen | 2-aminomethyl-15-epi-17-phenyl |
| G-2 | 1 | 1 | p-fluoro | hydrogen | hydrogen | hydrogen | α | hydrogen | hydrogen | 2-aminomethyl-15-epi-17-(p-fluorophenyl) |
| G-3 | 1 | 1 | m-fluoro | hydrogen | hydrogen | hydrogen | α | hydrogen | hydrogen | 2-aminomethyl-15-epi-17-(m-fluorophenyl) |
| G-4 | 1 | 1 | m-trifluoromethyl | hydrogen | hydrogen | hydrogen | α | hydrogen | hydrogen | 2-aminomethyl-15-epi-17-(m-trifluoromethyl)phenyl) |
| G-5 | 1 | 0 |  | hydrogen | hydrogen | methyl | α | hydrogen | hydrogen | 2-aminomethyl-15-epi-15-methyl-17-phenyl |
| G-6 | 1 | 1 | p-fluoro | hydrogen | hydrogen | methyl | α | hydrogen | hydrogen | 2-aminomethyl-15-epi-15-methyl-17-(p-fluorophenyl) |
| G-7 | 1 | 1 | m-chloro | hydrogen | hydrogen | methyl | α | hydrogen | hydrogen | 2-aminomethyl-15-epi-15-methyl-17-(m-chlorophenyl) |
| G-8 | 1 | 1 | m-trifluoromethyl | hydrogen | hydrogen | methyl | α | hydrogen | hydrogen | 2-aminomethyl-15-epi-15-methyl-17-(m-trifluoromethylphenyl) |
| G-9 | 1 | 0 |  | hydrogen | hydrogen | hydrogen | α | methyl | hydrogen | 2-methylaminomethyl-15-epi-17-phenyl |
| G-10 | 1 | 1 | p-fluoro | hydrogen | hydrogen | hydrogen | α | methyl | hydrogen | 2-methylaminomethyl-15-epi-17-(p-fluorophenyl) |
| G-11 | 1 | 1 | m-chloro | hydrogen | hydrogen | hydrogen | α | methyl | hydrogen | 2-methylaminomethyl-15-epi-17-(m-chlorophenyl) |
| G-12 | 1 | 1 | m-trifluoromethyl | hydrogen | hydrogen | hydrogen | α | methyl | hydrogen | 2-methylaminomethyl-15-epi-17-(m-trifluoromethylphenyl) |
| G-13 | 1 | 0 |  | methyl | methyl | hydrogen | α | hydrogen | hydrogen | 2-aminomethyl-15-epi-16,16-dimethyl-17-phenyl |
| G-14 | 1 | 1 | p-fluoro | methyl | methyl | hydrogen | α | hydrogen | hydrogen | 2-aminomethyl-15-epi-16,16-dimethyl-17-p-fluorophenyl |
| G-15 | 1 | 1 | m-chloro | methyl | methyl | hydrogen | α | hydrogen | hydrogen | 2-aminomethyl-15-epi-16,16-dimethyl-17-(m-chlorophenyl |
| G-16 | 1 | 1 | m-trifluoromethyl | methyl | methyl | hydrogen | α | hydrogen | hydrogen | 2-aminomethyl-15-epi-16,16-dimethyl-17-(m-trifluoromethylphenyl |

Table G-continued

| | | | | | | | | | |
|---|---|---|---|---|---|---|---|---|---|
| G-17 | 1 | 0 | | methyl | methyl | methyl | α | hydrogen | hydrogen | 2-aminomethyl-15-epi-15,16,16-trimethyl-17-phenyl |
| G-18 | 1 | 1 | p-fluoro | methyl | methyl | methyl | α | hydrogen | hydrogen | 2-aminomethyl-15-epi-15,16,16-trimethyl-17-(p-fluorophenyl) |
| G-19 | 1 | 1 | m-chloro | methyl | methyl | methyl | α | hydrogen | hydrogen | 2-aminomethyl-15-epi-15,16,16-trimethyl-17-(m-chlorophenyl) |
| G-20 | 1 | 1 | m-trifluoromethyl | methyl | methyl | methyl | α | hydrogen | hydrogen | 2-aminomethyl-15-epi-15,16,16-trimethyl-(m-trifluoromethylphenyl) |
| G-21 | 1 | 0 | | methyl | methyl | hydrogen | α | methyl | hydrogen | 2-methylaminomethyl-15-epi-16,16-dimethyl-17-phenyl |
| G-22 | 1 | 1 | p-fluoro | methyl | methyl | hydrogen | α | methyl | hydrogen | 2-methylaminomethyl-15-epi-16,16-dimethyl-17-(p-fluorophenyl) |
| G-23 | 1 | 1 | m-chloro | methyl | methyl | hydrogen | α | methyl | hydrogen | 2-methylaminomethyl-15-epi-16,16-dimethyl-17-(m-chlorophenyl) |
| G-24 | 1 | 1 | m-trifluoromethyl | methyl | methyl | hydrogen | α | methyl | hydrogen | 2-methylaminomethyl-15-epi-16,16-dimethyl-17-(m-trifluoromethylphenyl) |
| G-25 | 3 | 0 | | hydrogen | hydrogen | hydrogen | α | hydrogen | hydrogen | 2-aminomethyl-13-epi-2a,2b-dihomo-17-phenyl |
| G-26 | 3 | 1 | p-fluoro | hydrogen | hydrogen | hydrogen | α | hydrogen | hydrogen | 2-aminomethyl-13-epi-2a,2b-dihomo-17-(p-fluorophenyl) |
| G-27 | 3 | 1 | m-chloro | hydrogen | hydrogen | hydrogen | α | hydrogen | hydrogen | 2-aminomethyl-13-epi-2a,2b-dihomo-17-(m-chlorophenyl) |
| G-28 | 3 | 1 | m-trifluoromethyl | hydrogen | hydrogen | hydrogen | α | hydrogen | hydrogen | 2-aminomethyl-13-epi-2a,2b-dihomo-17-(m-trifluoromethylphenyl) |
| G-29 | 3 | 0 | | hydrogen | hydrogen | methyl | α | hydrogen | hydrogen | 2-aminomethyl-15-epi-2a,2b-dihomo-15-methyl-17-phenyl |
| G-30 | 3 | 1 | p-fluoro | hydrogen | hydrogen | methyl | α | hydrogen | hydrogen | 2-aminomethyl-15-epi-2a,2b-dihomo-15-methyl-17-(p-fluorophenyl) |
| G-31 | 3 | 1 | m-chloro | hydrogen | hydrogen | methyl | α | hydrogen | hydrogen | 2-aminomethyl-15-epi-2a,2b-dihomo-15-methyl-17-(m-chlorophenyl) |
| G-32 | 3 | 1 | m-trifluoromethyl | hydrogen | hydrogen | methyl | α | hydrogen | hydrogen | 2-aminomethyl-15-epi-2a,2b-dihomo-15-methyl-17-(m-trifluoromethylphenyl |
| G-33 | 1 | 0 | | fluoro | fluoro | hydrogen | α | hydrogen | hydrogen | 2-aminomethyl-15-epi-16,16-difluoro-17-phenyl |
| G-34 | 1 | 1 | p-fluoro | fluoro | fluoro | hydrogen | α | hydrogen | hydrogen | 2-aminomethyl-15-epi-16,16-difluoro-17-(p-fluorophenyl) |
| G-35 | 1 | 1 | m-chloro | fluoro | fluoro | hydrogen | α | hydrogen | hydrogen | 2-aminomethyl-15-epi-16,16-difluoro-17-(m-chlorophenyl) |
| G-36 | 1 | 1 | m-trifluoromethyl | fluoro | fluoro | hydrogen | α | hydrogen | hydrogen | 2-aminomethyl-15-epi-16,16-difluoro-17-(m-trifluoromethylphenyl) |
| G-37 | 1 | 0 | | fluoro | fluoro | methyl | α | hydrogen | hydrogen | 2-aminomethyl-15-epi-15-methyl-16,16-difluoro-17-phenyl |
| G-38 | 1 | 1 | p-fluoro | fluoro | fluoro | methyl | α | hydrogen | hydrogen | 2-aminomethyl-15-epi-15-methyl-16,16-difluoro-17-(p-fluorophenyl) |
| G-39 | 1 | 1 | m-chloro | fluoro | fluoro | methyl | α | hydrogen | hydrogen | 2-aminomethyl-15-epi-15-methyl-16,16-difluoro-17-(m-chlorophenyl) |
| G-40 | 1 | 1 | m-trifluoromethyl | fluoro | fluoro | methyl | α | hydrogen | hydrogen | 2-aminomethyl-15-epi-15-methyl-16,16-difluoro-17-(m-trifluoromethylphenyl) |
| G-41 | 1 | 0 | | fluoro | fluoro | hydrogen | α | methyl | hydrogen | 2-methylaminomethyl-15-epi-16,16-difluoro-17-phenyl |
| G-42 | 1 | 1 | p-fluoro | fluoro | fluoro | hydrogen | α | methyl | hydrogen | 2-methylaminomethyl-15-epi-16,16-difluoro-17-(p-fluorophenyl) |
| G-43 | 1 | 1 | m-chloro | fluoro | fluoro | hydrogen | α | methyl | hydrogen | 2-methylaminomethyl-15-epi-16,16-difluoro-17-(m-chlorophenyl) |
| G-44 | 1 | 1 | m-trifluoromethyl | fluoro | fluoro | hydrogen | α | methyl | hydrogen | 2-methylaminomethyl-15-epi-16,16-difluoro-17-(m-fluoromethylphenyl) |

Table H
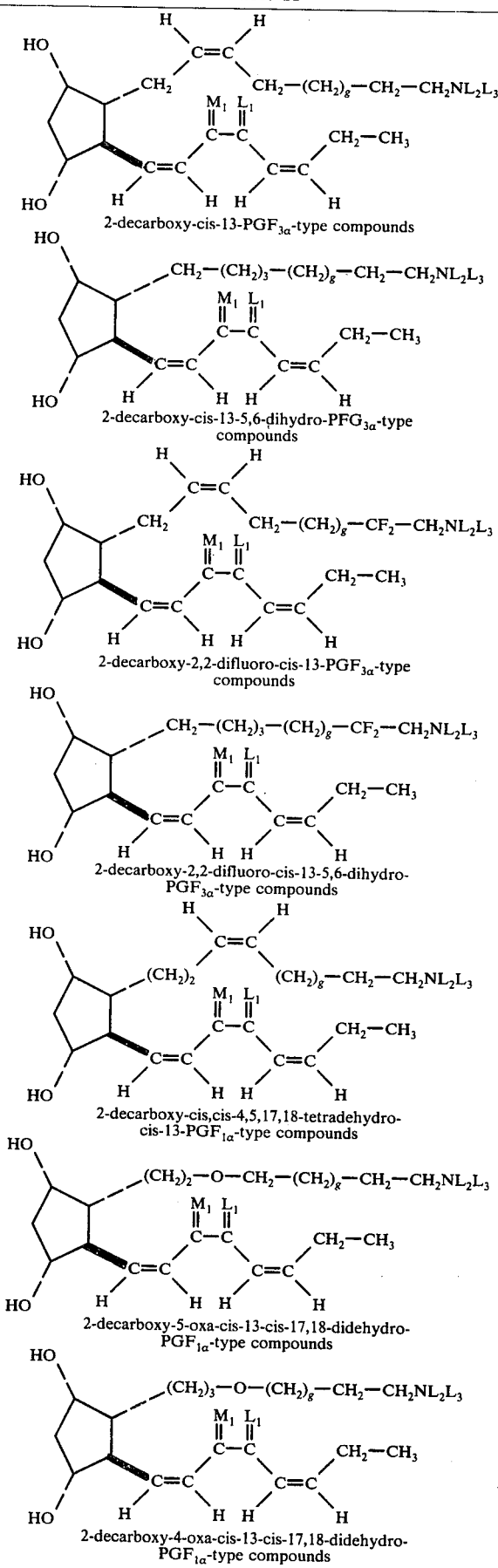

Table H-continued

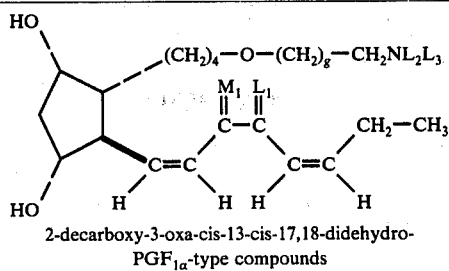

2-decarboxy-3-oxa-cis-13-cis-17,18-didehydro-
PGF$_{1\alpha}$-type compounds

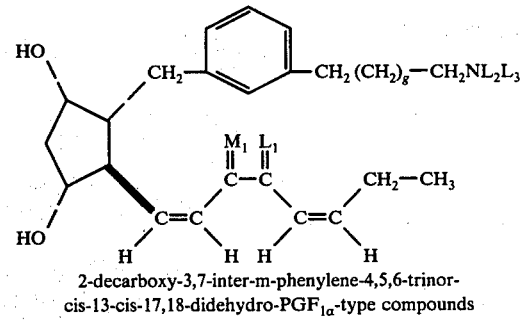

2-decarboxy-3,7-inter-m-phenylene-4,5,6-trinor-
cis-13-cis-17,18-didehydro-PGF$_{1\alpha}$-type compounds

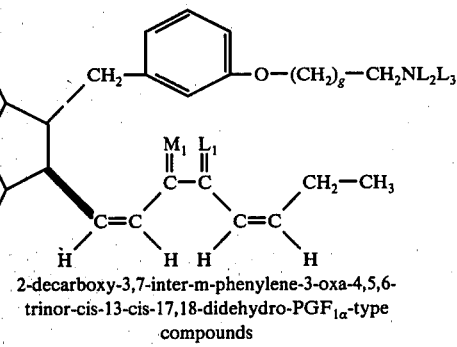

2-decarboxy-3,7-inter-m-phenylene-3-oxa-4,5,6-
trinor-cis-13-cis-17,18-didehydro-PGF$_{1\alpha}$-type
compounds

| Example | g | L$_1$ R$_3$ | R$_4$ | M$_1$ R$_5$ | ~OH | L$_2$ | L$_3$ | Name |
|---|---|---|---|---|---|---|---|---|
| H-1 | 1 | methyl | hydrogen | hydrogen | α | hydrogen | hydrogen | 2-aminomethyl-15-epi-16-methyl |
| H-2 | 1 | methyl | hydrogen | methyl | α | hydrogen | hydrogen | 2-aminomethyl-15-epi-15,16-dimethyl |
| H-3 | 1 | methyl | hydrogen | hydrogen | α | methyl | hydrogen | 2-methylaminomethyl-15-epi-16-methyl |
| H-4 | 1 | methyl | methyl | hydrogen | α | hydrogen | hydrogen | 2-aminomethyl-15-epi-16,16-dimethyl |
| H-5 | 1 | methyl | methyl | methyl | α | hydrogen | hydrogen | 2-aminomethyl-15-epi-15,16,16-trimethyl |
| H-6 | 1 | methyl | methyl | hydrogen | α | methyl | hydrogen | 2-methylaminomethyl-15-epi-16,16-dimethyl |
| H-7 | 1 | fluoro | hydrogen | hydrogen | α | hydrogen | hydrogen | 2-aminomethyl-15-epi-16-fluoro |
| H-8 | 1 | fluoro | hydrogen | methyl | α | hydrogen | hydrogen | 2-aminomethyl-15-epi-15-methyl-16-fluoro |
| H-9 | 1 | fluoro | hydrogen | hydrogen | α | methyl | hydrogen | 2-methylaminomethyl-15-epi-16-fluoro |
| H-10 | 1 | fluoro | fluoro | hydrogen | α | hydrogen | hydrogen | 2-aminomethyl-15-epi-16,16-difluoro |
| H-11 | 1 | fluoro | fluoro | methyl | α | hydrogen | hydrogen | 2-aminomethyl-15-epi-15-methyl-16,16-difluoro |
| H-12 | 1 | fluoro | fluoro | hydrogen | α | methyl | hydrogen | 2-methylaminomethyl-15-epi-16,16-difluoro |
| H-13 | 1 | hydrogen | hydrogen | hydrogen | α | hydrogen | hydrogen | 2-aminomethyl-15-epi |
| H-14 | 1 | hydrogen | hydrogen | methyl | α | hydrogen | hydrogen | 2-aminomethyl-15-epi-15-methyl |
| H-15 | 3 | hydrogen | hydrogen | hydrogen | α | hydrogen | hydrogen | 2-aminomethyl-15-epi-2a,2b-di-homo |
| H-16 | 3 | hydrogen | hydrogen | methyl | α | hydrogen | hydrogen | 2-aminomethyl-15-epi-2a,2b-dihomo-15-methyl |
| H-17 | 3 | methyl | methyl | hydrogen | α | hydrogen | hydrogen | 2-aminomethyl-15-epi-2a,2b-di-homo-16,16-dimethyl |
| H-18 | 3 | methyl | methyl | methyl | α | hydrogen | hydrogen | 2-aminomethyl-15-epi-2a,2b-dihomo-15,16,16-trimethyl |
| H-19 | 3 | fluoro | fluoro | hydrogen | α | hydrogen | hydrogen | 2-aminomethyl-15-epi-2a,2b-dihomo-16,16-difluoro |
| H-20 | 3 | fluoro | fluoro | methyl | α | hydrogen | hydrogen | 2-aminomethyl-15-epi-2a,2b-dihomo-16,16-difluoro |

Table I
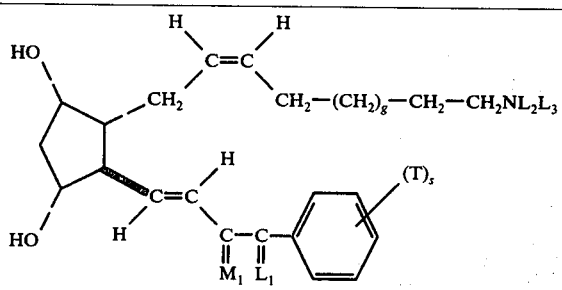
2-decarboxy-PGF$_{2\alpha}$-type compounds
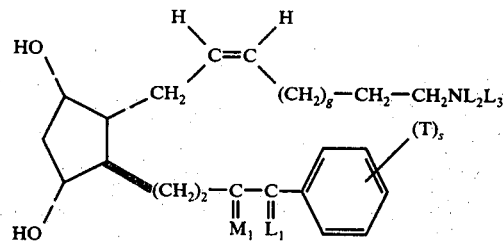
2-decarboxy-13,14-dihydro-PGF$_{2\alpha}$-type compounds
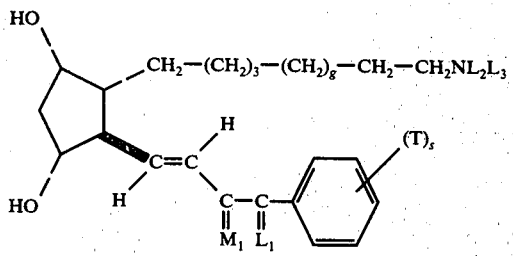
2-decarboxy-PGF$_{1\alpha}$-type compounds
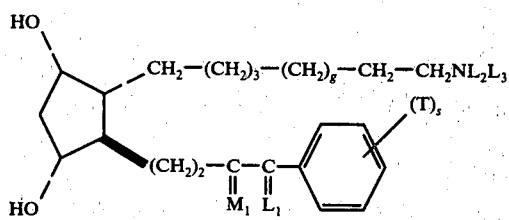
2-decarboxy-13,14-dihydro-PGF$_{1\alpha}$-type compounds
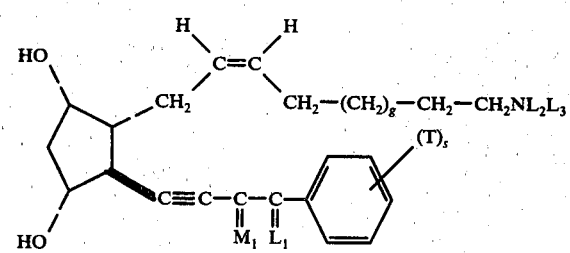
2-decarboxy-13,14-didehydro-PGF$_{2\alpha}$-type compounds
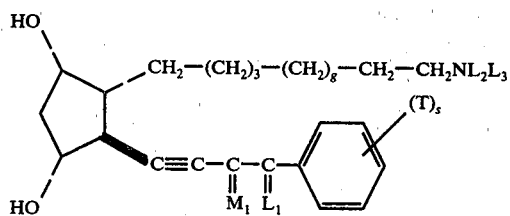
2-decarboxy-13,14-didehydro-PGF$_{1\alpha}$-type compounds Table I-continued
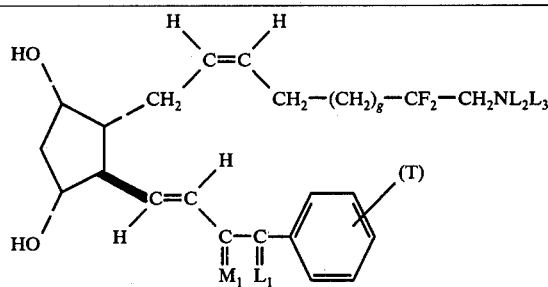
2-decarboxy-2,2-difluoro-PGF$_{2\alpha}$-type compounds
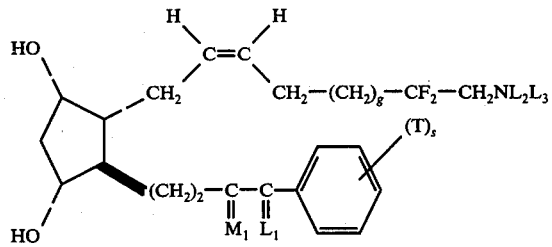
2-decarboxy-2,2-difluoro-13,14-dihydro-PGF$_{2\alpha}$-type compounds
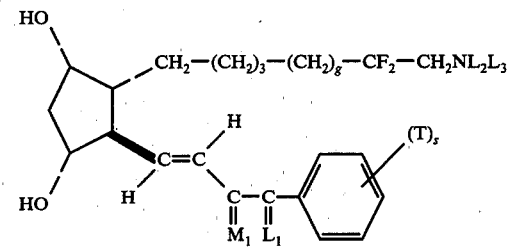
2-decarboxy-2,2-difluoro-PGF$_{1\alpha}$-type compounds
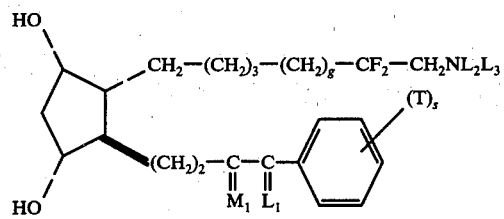
2-decarboxy-2,2-difluoro-13,14-dihydro-PGF$_{1\alpha}$-type compounds
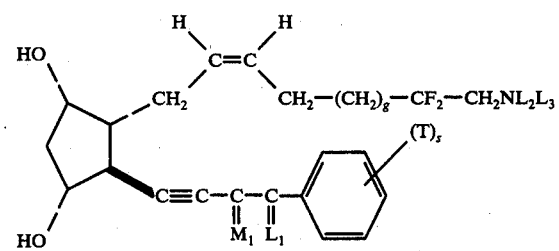
2-decarboxy-13,14-didehydro-2,2-difluoro-PGF$_{2\alpha}$-type compounds
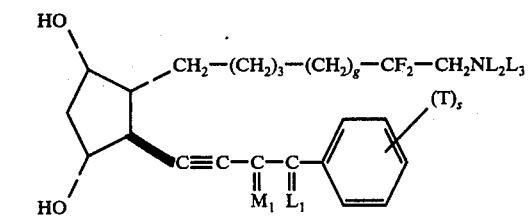
2-decarboxy-13,14-didehydro-2,2-difluoro-PGF$_{1\alpha}$-type compounds Table I-continued
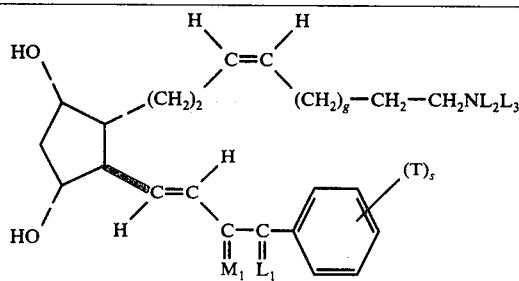
2-decarboxy-cis-4,5-didehydro-PGF$_{1\alpha}$-type compounds
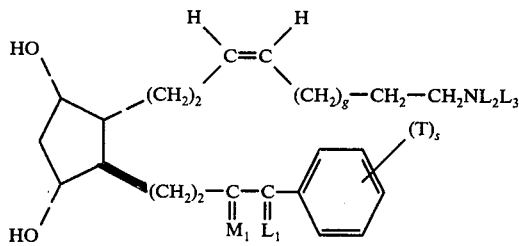
2-decarboxy-cis-4,5-didehydro-13,14-dihydro-PGF$_{1\alpha}$-type compounds
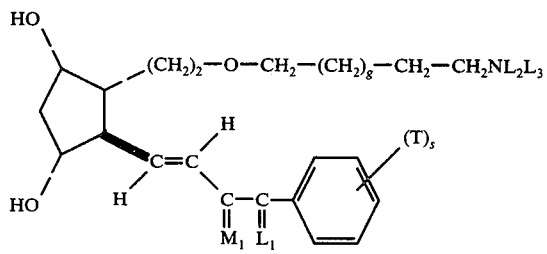
2-decarboxy-5-oxa-PGF$_{1\alpha}$-type compounds
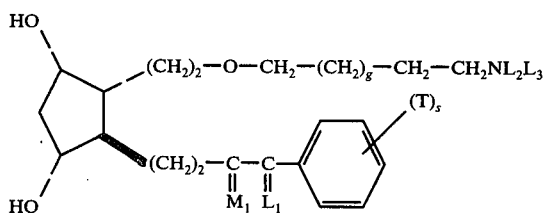
2-decarboxy-5-oxa-13,14-dihydro-PGF$_{1\alpha}$-type compounds
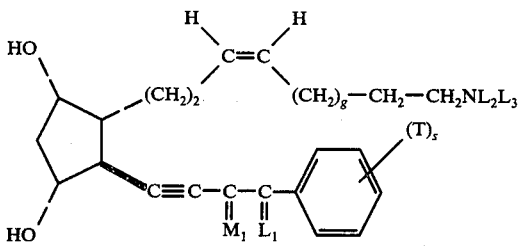
2-decarboxy-13,14-didehydro-cis-4,5-didehydro-PGF$_{1\alpha}$-type compounds
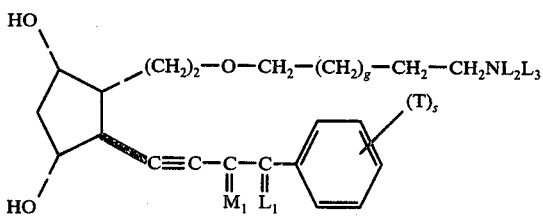
2-decarboxy-13,14-didehydro-5-oxa-PGF$_{1\alpha}$-type compounds Table I-continued
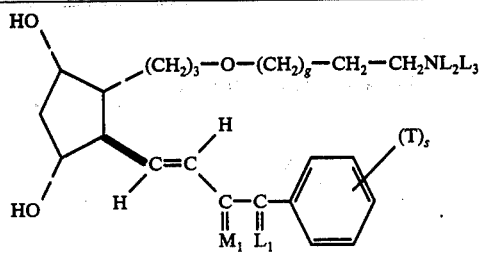
2-decarboxy-4-oxa-PGF$_{1\alpha}$-type compounds
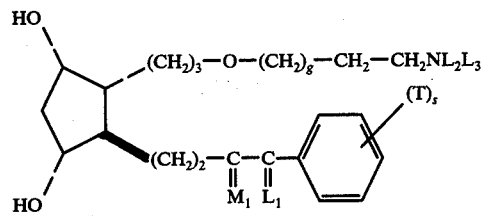
2-decarboxy-4-oxa-13,14-dihydro-PGF$_{1\alpha}$-type compounds
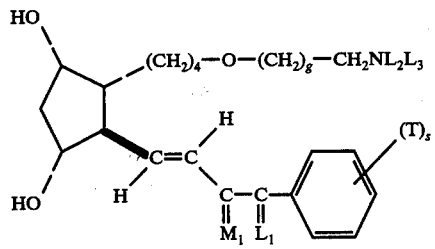
2-decarboxy-3-oxa-PGF$_{1\alpha}$-type compounds
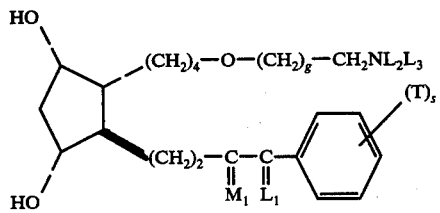
2-decarboxy-3-oxa-13,14-dihydro-PGF$_{1\alpha}$-type compounds
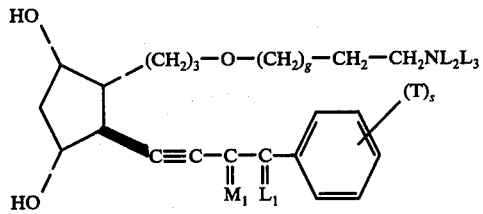
2-decarboxy-13,14-didehydro-4-oxa-PGF$_{1\alpha}$-type compounds
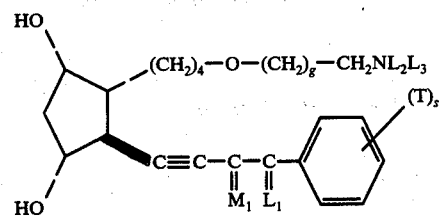
2-decarboxy-13,14-didehydro-3-oxa-PGF$_{1\alpha}$-type compounds

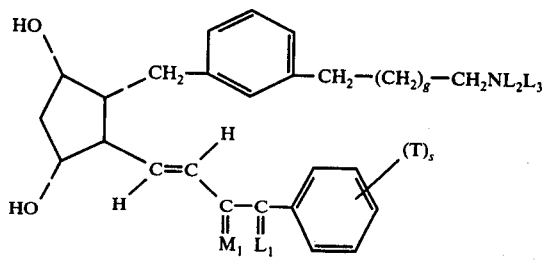

2-decarboxy-3,7-inter-m-phenylene-4,5,6-trinor-PGF$_{1\alpha}$-type compounds

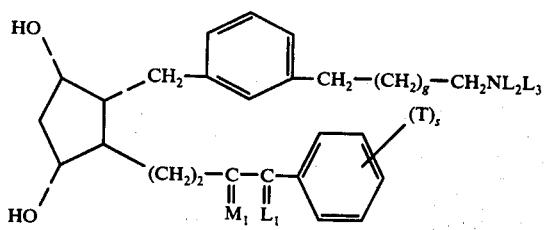

2-decarboxy-3,7-inter-m-phenylene-4,5,6-trinor-13,14-dihydro-PGF$_{1\alpha}$-type compounds

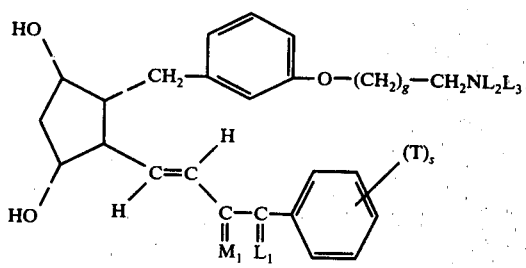

2-decarboxy-3,7-inter-m-phenylene-3-oxa-4,5,6-trinor-PGF$_{1\alpha}$-type compounds

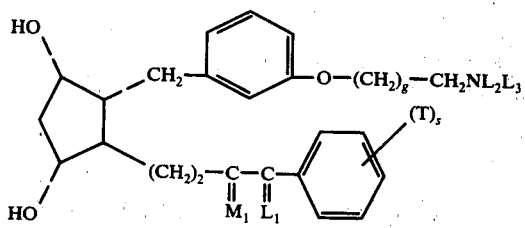

2-decarboxy-3,7-inter-m-phenylene-3-oxa-4,5,6-trinor-13,14-dihydro-PGF$_{1\alpha}$-type compounds

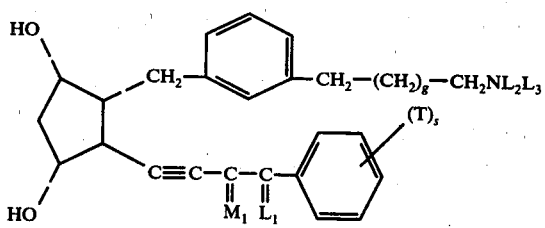

2-decarboxy-13,14-didehydro-3,7-inter-m-phenylene-4,5,6-trinor-PGF$_{1\alpha}$-type compounds

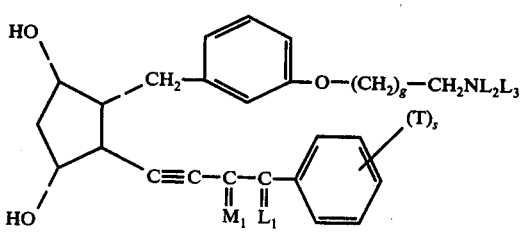

2-decarboxy-13,14-didehydro-3,7-inter-m-phenylene-3-oxa-4,5,6-trinor-PGF$_{1\alpha}$-type compounds Table I-continued

| Example | g | s | T | L₁ R₃ | R₄ | M₁ R₅ | ~OH | L₂ | L₃ | Name |
|---|---|---|---|---|---|---|---|---|---|---|
| B-1 | 1 | 0 | | hydrogen | hydrogen | hydrogen | α | hydrogen | hydrogen | 2-amino-16-phenyl-17,18,19,20-tetranor |
| B-2 | 1 | 1 | p-fluoro | hydrogen | hydrogen | hydrogen | α | hydrogen | hydrogen | 2-aminomethyl-16-(p-fluorophenyl)-17,18,19,20-tetranor |
| B-3 | 1 | 1 | m-chloro | hydrogen | hydrogen | hydrogen | α | hydrogen | hydrogen | 2-aminomethyl-16-(m-chlorophenyl)-17,18,19,20-tetranor |
| B-4 | 1 | 1 | m-trifluoromethyl | hydrogen | hydrogen | hydrogen | α | hydrogen | hydrogen | 2-aminomethyl-16-(m-trifluoromethylphenyl)-17,18,19,20-tetranor |
| B-5 | 1 | 0 | | hydrogen | hydrogen | methyl | α | hydrogen | hydrogen | 2-aminomethyl-15-methyl-16-phenyl-17,18,19,20-tetranor |
| B-6 | 1 | 1 | p-fluoro | hydrogen | hydrogen | methyl | α | hydrogen | hydrogen | 2-aminomethyl-15-methyl-16-(p-fluorophenyl)-17,18,19,20-tetranor |
| B-7 | 1 | 1 | m-chloro | hydrogen | hydrogen | methyl | α | hydrogen | hydrogen | 2-aminomethyl-15-methyl-16-(m-chlorophenyl)-17,18,19,20-tetranor |
| B-8 | 1 | 1 | m-trifluoro | hydrogen | hydrogen | methyl | α | hydrogen | hydrogen | 2-aminomethyl-15-methyl-16-(m-trifluoromethylphenyl) |
| B-9 | 1 | 0 | | hydrogen | hydrogen | hydrogen | α | methyl | hydrogen | 2-methylaminomethyl-16-phenyl-17,18,19,20-tetranor |
| B-10 | 1 | 1 | p-fluoro | hydrogen | hydrogen | hydrogen | α | methyl | hydrogen | 2-methylaminomethyl-16-(p-fluorophenyl)-17,18,19,20-tetranor |
| B-11 | 1 | 1 | m- | hydrogen | hydrogen | hydrogen | α | methyl | hydrogen | 2-methylaminomethyl-16-(m-chlorophenyl)-17,18,19,20-tetranor |
| B-12 | 1 | 1 | m-tri- | hydrogen | hydrogen | hydrogen | α | methyl | hydrogen | 2-methylaminomethyl-16-(m-trifluoromethylphenyl)-17,18,19,20-tetranor |
| B-13 | 1 | 0 | | methyl | methyl | hydrogen | α | hydrogen | hydrogen | 2-aminomethyl-16-methyl-16-phenyl-18,19,20-trinor |
| B-14 | 1 | 1 | p-fluoro | methyl | methyl | hydrogen | α | hydrogen | hydrogen | 2-aminomethyl-16-methyl-16-(p-fluorophenyl-18,19,20-trinor |
| B-15 | 1 | 1 | m-chloro | methyl | methyl | hydrogen | α | hydrogen | hydrogen | 2-aminomethyl-16-methyl-16-(m-chlorophenyl)-18,19,20-trinor |
| B-16 | 1 | 1 | m-trifluoromethyl | methyl | methyl | hydrogen | α | hydrogen | hydrogen | 2-aminomethyl-16-methyl-16-(m-trifluoromethylphenyl)-18,19,20-trinor |
| B-17 | 1 | 0 | | methyl | methyl | methyl | α | hydrogen | hydrogen | 2-aminomethyl-15,16-dimethyl-16-phenyl-18,19,20-trinor |
| B-18 | 1 | 1 | p-fluoro | methyl | methyl | methyl | α | hydrogen | hydrogen | 2-aminomethyl-15,16-dimethyl-16-(p-fluorophenyl)-18,19,20-trinor |
| B-19 | 1 | 1 | m-chloro | methyl | methyl | methyl | α | hydrogen | hydrogen | 2-aminomethyl-15,16-dimethyl-16-(m-chlorophenyl)-18,19,20-trinor |
| B-20 | 1 | 1 | m-trifluoromethyl | methyl | methyl | methyl | α | hydrogen | hydrogen | 2-aminomethyl-15,16-dimethyl-16-(m-trifluoromethylphenyl)-18,19,20-trinor |
| B-21 | 1 | 0 | | methyl | methyl | hydrogen | α | methyl | hydrogen | 2-methylaminomethyl-16-methyl-16-phenyl-18,19,20-trinor |
| B-22 | 1 | 1 | p-fluoro | methyl | methyl | hydrogen | α | methyl | hydrogen | 2-methylaminomethyl-16-methyl-16-(p-fluorophenyl)-18,19,20-trinor |
| B-23 | 1 | 1 | m-chloro | methyl | methyl | hydrogen | α | methyl | hydrogen | 2-methylaminomethyl-16-methyl-16-(m-chlorophenyl)-18,19,20-trinor |
| B-24 | 1 | 1 | m-trifluoro- | methyl | methyl | hydrogen | α | methyl | hydrogen | 2-methylaminomethyl-16-methyl-16-(m-trifluoromethylphenyl)-18,19,20-trinor |
| B-25 | 3 | 0 | | hydrogen | hydrogen | hydrogen | α | hydrogen | hydrogen | 2-aminomethyl-2a,2b-dihomo-16-phenyl-17,18,19,20-tetranor |
| B-26 | 3 | 1 | p-fluoro | hydrogen | hydrogen | hydrogen | α | hydrogen | hydrogen | 2-aminomethyl-2a,2b-dihomo-16-(p-fluorophenyl)-17,19,20- |

Table I-continued

| | | | | | | | | | |
|---|---|---|---|---|---|---|---|---|---|
| B-27 | 3 | 1 | m-chloro | hydrogen | hydrogen | hydrogen | α | hydrogen | hydrogen | tetranor 2-aminomethyl-2a,2b-dihomo-16-(m-chlorophenyl)-17,18,19,20-tetranor |
| B-28 | 3 | 1 | m-trifluoromethyl | hydrogen | hydrogen | hydrogen | α | hydrogen | hydrogen | 2-aminomethyl-2a,2b-dihomo-16-(m-trifluoro-17,18,19,20-tetranor |
| B-29 | 3 | 0 | | hydrogen | hydrogen | methyl | α | hydrogen | hydrogen | 2-aminomethyl-2a,2b-dihomo-15-methyl-16-phenyl-17,18,19,20-tetranor |
| B-30 | 3 | 1 | p-fluoro | hydrogen | hydrogen | methyl | α | hydrogen | hydrogen | 2-aminomethyl-2a,2b-dihomo-15-methyl-16-(p-fluorophenyl)-17,18,19,20-tetranor |
| B-31 | 3 | 1 | m-chloro | hydrogen | hydrogen | methyl | α | hydrogen | hydrogen | 2-aminomethyl-2a,2b-dihomo-15-methyl-16-(m-chlorophenyl)-17,18,19,20-tetranor |
| B-32 | 3 | 1 | m-trifluoromethyl | hydrogen | hydrogen | methyl | α | hydrogen | hydrogen | 2-aminomethyl-2a,2b-dihomo-15-methyl-16-(m-trifluoromethylphenyl)-17,18,19,20-tetranor |

I claim:
1. A prostaglandin analog of the formula

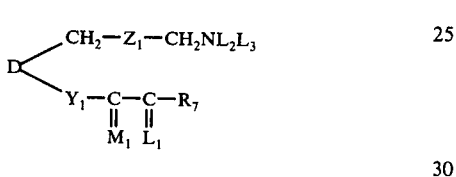

wherein D is

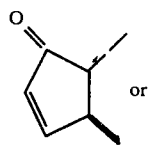

or

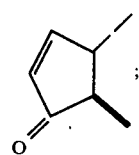

;

wherein $L_1$ is

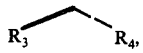

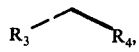

or a mixture of

and

wherein $R_3$ and $R_4$ are hydrogen, methyl, or fluoro, being the same or different, with the proviso that one of $R_3$ and $R_4$ is methyl only when the other is hydrogen or methyl;
wherein $L_2$ and $L_3$ are hydrogen or alkyl of one to 4 carbon atoms, inclusive;
wherein $M_1$ is

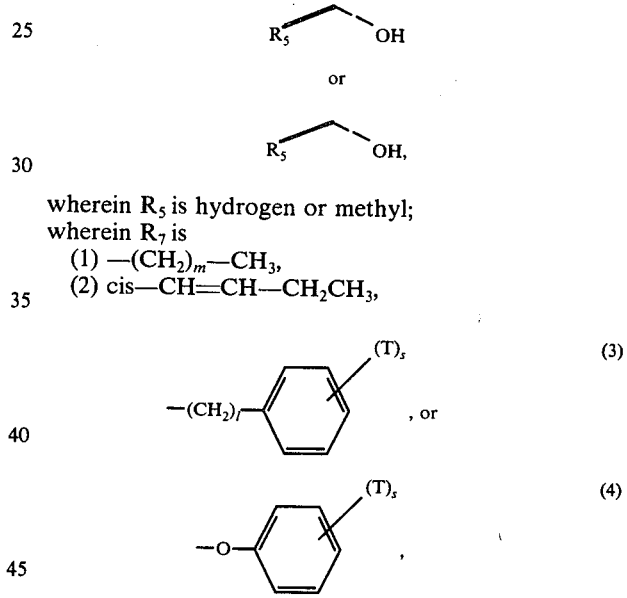

wherein $R_5$ is hydrogen or methyl;
wherein $R_7$ is
(1) $-(CH_2)_m-CH_3$,
(2) cis$-CH=CH-CH_2CH_3$, wherein $l$ is zero to three, inclusive, wherein $m$ is one to 5, inclusive, s is zero, one, 2, or 3 and T is chloro, fluoro, trifluoromethyl, alkyl of one to 3 carbon atoms, or alkoxy of one to 3 carbon atoms, the various T's being the same or different, with the proviso that not more than two T's are other than alkyl;
wherein $Y_1$ is
(1) trans$-CH=CH-$,
(2) cis$-CH=CH-$,
(3) $-CH_2CH_2-$, or
(4) $-C\equiv C-$; and
wherein $Z_1$ is
(1) cis$-CH=CH-CH_2-(CH_2)_g-CH_2-$,
(2) cis$-CH=CH-CH_2-(CH_2)_g-CF_2-$,
(3) cis$-CH_2-CH=CH-(CH_2)_g-CH_2-$,
(4) $-(CH_2)_3-(CH_2)_g-CH_2-$,
(5) $-(CH_2)_3-(CH_2)_g-CF_2-$,
(6) $-CH_2-O-CH_2-(CH_2)_g-CH_2-$,
(7) $-(CH_2)_2-O-(CH_2)_g-CH_2-$,
(8) $-(CH_2)_3-O-(CH_2)_g-$,

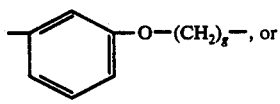 (9)

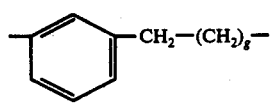 (10)

wherein g is zero, one, two, or three.

2. A prostaglandin analog according to claim 1, wherein

D is

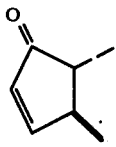

3. A compound according to claim 1, wherein at least one of $R_2$ and $R_3$ is methyl.

4. 2-Decarboxy-2-methylaminomethyl-PGA$_2$, a prostaglandin analog according to claim 3.

5. A prostaglandin analog according to claim 2, wherein $L_2$ and $L_3$ are both hydrogen.

6. 2-Decarboxy-2-aminomethyl-PGA$_2$, a prostaglandin analog according to claim 5.

7. A prostaglandin analog according to claim 1, wherein

D is

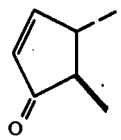

8. A prostaglandin analog according to claim 7, wherein at least one of $L_2$ and $L_3$ is methyl.

9. 2-Decarboxy-2-methylaminomethyl-9-deoxy-9,10-didehydro-PGD$_2$, a prostaglandin analog according to claim 8.

10. A prostaglandin analog according to claim 7, wherein $L_2$ and $L_3$ are both hydrogen.

11. 2-Decarboxy-2-aminomethyl-9-deoxy-9,10-didehydro-PGD$_2$, a prostaglandin analog according to claim 10.

* * * * *

UNITED STATES PATENT OFFICE
CERTIFICATE OF CORRECTION

Patent No. __4,073,808__                    Dated __14 February 1978__

Inventor(s) __Norman A. Nelson__

It is certified that error appears in the above-identified patent and that said Letters Patent are hereby corrected as shown below:

Column 188, lines 24-30,

" 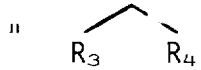 and 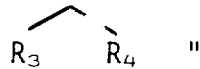 " should read -- 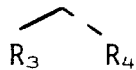 and 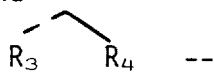 --

Column 189, line 24, "$R_2$ and $R_3$ is methyl" should read -- $L_2$ and $L_3$ is methyl --.

Signed and Sealed this

Seventeenth Day of November 1981

[SEAL]

Attest:

Attesting Officer

GERALD J. MOSSINGHOFF

Commissioner of Patents and Trademarks